United States Patent
Zhao et al.

(10) Patent No.: US 10,450,316 B2
(45) Date of Patent: Oct. 22, 2019

(54) CERTAIN PROTEIN KINASE INHIBITOR

(71) Applicants: Chongqing Fochon Pharmaceutical Co., Ltd., Chongqing (CN); Shanghai Fochon Pharmaceutical Co., Ltd., Shanghai (CN)

(72) Inventors: Xingdong Zhao, Chongqing (CN); Tongshuang Li, Surrey (CA); Haohan Tan, Chongqing (CN); Zhifang Chen, Chongqing (CN); Ling Chen, Chongqing (CN); Qihong Liu, Chongqing (CN); Yue Rong, Chongqing (CN); Lijun Yang, Chongqing (CN); Xianlong Wang, Chongqing (CN); Rui Tan, Chongqing (CN); Zuwen Zhou, Chongqing (CN); Bin Liu, Chongqing (CN); Min Lin, Chongqing (CN); Lihua Jiang, Chongqing (CN); Yanxin Liu, Chongqing (CN); Li Linghu, Chongqing (CN); Jing Sun, Chongqing (CN); Weibo Wang, Moraga, CA (US)

(73) Assignees: CHONGQING FOCHON PHARMACEUTICAL CO., LTD., Chongqing (CN); SHANGHAI FOCHON PHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 15/569,709

(22) PCT Filed: Apr. 28, 2016

(86) PCT No.: PCT/CN2016/080475
§ 371 (c)(1),
(2) Date: Oct. 26, 2017

(87) PCT Pub. No.: WO2016/173505
PCT Pub. Date: Nov. 3, 2016

(65) Prior Publication Data
US 2018/0291027 A1    Oct. 11, 2018

Related U.S. Application Data

(60) Provisional application No. 62/154,082, filed on Apr. 28, 2015.

(51) Int. Cl.
| | | |
|---|---|---|
| *C07D 487/04* | (2006.01) |
| *C07D 401/14* | (2006.01) |
| *C07D 403/14* | (2006.01) |
| *A61K 45/06* | (2006.01) |
| *A61K 31/506* | (2006.01) |
| *C07D 487/10* | (2006.01) |
| *C07D 471/14* | (2006.01) |
| *C07D 519/00* | (2006.01) |
| *A61P 35/00* | (2006.01) |
| *A61K 31/5383* | (2006.01) |

(52) U.S. Cl.
CPC .......... *C07D 487/04* (2013.01); *A61K 31/506* (2013.01); *A61K 31/5383* (2013.01); *A61K 45/06* (2013.01); *A61P 35/00* (2018.01); *C07D 401/14* (2013.01); *C07D 403/14* (2013.01); *C07D 471/14* (2013.01); *C07D 487/10* (2013.01); *C07D 519/00* (2013.01)

(58) Field of Classification Search
CPC ... C07D 401/14; C07D 403/14; C07D 487/04
See application file for complete search history.

(56) References Cited

U.S. PATENT DOCUMENTS

2018/0305363 A1*  10/2018  Liu .................. A61K 31/506

FOREIGN PATENT DOCUMENTS

| CN | 104910137 | 9/2015 |
|---|---|---|
| WO | WO 2010/020675 | 2/2010 |
| WO | WO 2010/075074 | 7/2010 |
| WO | WO 2014/160017 | 10/2014 |
| WO | WO 2015/086525 | 6/2015 |
| WO | WO 2015/101293 | 7/2015 |

OTHER PUBLICATIONS

International Search Report and Written Opinion for PCT/CN2016/080475 dated Jul. 25, 2016.

* cited by examiner

*Primary Examiner* — Brian E McDowell
(74) *Attorney, Agent, or Firm* — Foley & Lardner LLP

(57) ABSTRACT

Provided are certain CDK4/6 inhibitors with the structure of formula (I), pharmaceutical compositions thereof, and methods of use therefor. The compounds are of the class of pyrimidin-2 amine derivatives, useful for the treatment of hyper-proliferative diseases.

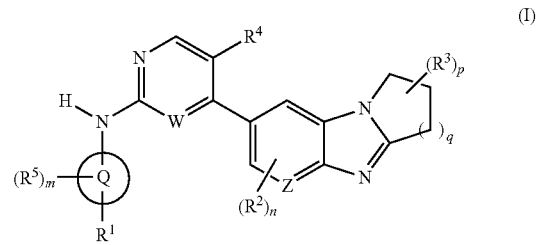

16 Claims, No Drawings

CERTAIN PROTEIN KINASE INHIBITOR

CROSS REFERENCE TO RELATED APPLICATIONS

The present application is a national stage application, filed under 35 U.S.C. § 371, of PCT Application No. PCT/CN2016/080475, filed Apr. 28, 2016 entitled "CERTAIN PROTEIN KINASE INHIBITORS," which claims priority to U.S. Provisional Patent Application 62/154,082, filed Apr. 28, 2015, all of which are hereby incorporated by reference in their entireties.

FIELD OF THE INVENTION

Provided are certain compounds and/or pharmaceutically acceptable salts thereof which can inhibit kinase activity of CDK4/6 and may be useful for the treatment of hyper-proliferative diseases like cancer and inflammation.

BACKGROUND OF THE INVENTION

Hyper-proliferative diseases like cancer and inflammation are attracting the scientific community to provide therapeutic benefits. In this regard efforts have been made to identify and target specific mechanisms which play a role in proliferating the diseases.

Tumor development is closely associated with genetic alteration and deregulation of cyclin-dependent kinases (CDKs) and their regulators, suggesting that inhibitors of CDKs may be useful anti-cancer therapeutics.

CDKs are serine/threonine protein kinases, which are the driving force behind the cell cycle and cell proliferation. CDKs regulate initiation, progression, and completion of mammalian cell cycle, and they are critical for cell growth. Most of the known CDK's, including CDK1 through CDK9, are involved either directly or indirectly in cell cycle progression. Those directly involved with cell cycle progression, such as CDK1-4 and 6, can be classified as G1, S, or G2M phase enzymes. Uncontrolled proliferation is a hallmark of cancer cells and the alteration of CDK function occurs with high frequency in many solid tumors.

The pivotal roles of CDKs, and their associated proteins, in coordinating and driving the cell cycle in proliferating cells have been outlined. The development of monotherapies for the treatment of proliferative disorders, such as cancers, using therapeutics targeted generically at CDKs, or at specific CDKs, is therefore potentially highly desirable. CDK inhibitors could conceivably also be used to treat other conditions such as viral infections, autoimmune diseases and neuro-degenerative diseases, amongst others. CDKs targeted therapeutics may also provide clinical benefits in the treatment of the previously described diseases when used in combination therapy with either existing, or new, therapeutic agents.

Therefore, a compound having an inhibitory activity on CDK will be useful for the prevention or treatment of cancer. Although CDK4/6 inhibitors were disclosed in the arts, e.g., WO2010075074, many suffer from having short half-life or toxicity. Therefore, there is a need for new CDK4/6 inhibitors that have at least one advantageous property selected from potency, stability, selectivity, toxicity and pharmaco-dynamics properties as an alternative for the treatment of hyper-proliferative diseases. In this regard, a novel class of CDK4/6 inhibitors is provided herein.

DISCLOSURE OF THE INVENTION

Disclosed herein are certain novel fused tricyclic ring derivatives and pharmaceutical compositions thereof, and their use as pharmaceuticals.

In one aspect, disclosed herein is a compound of formula (I):

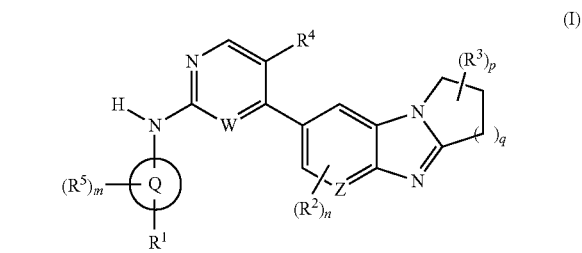

or a pharmaceutically acceptable salt thereof, wherein:
Q is selected from aryl and heteroaryl;
W is selected from N and $CR^6$;
Z is selected from N and $CR^6$;
$R^1$ is selected from hydrogen, halogen, hydroxyl, CN, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkylamino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from $R^X$;

each $R^2$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —$NO_2$, —$NR^{A1}R^{B1}$, —$OR^{A1}$, —$SR^{A1}$, —$S(O)_rR^{A1}$, —$S(O)_2OR^{A1}$, —$OS(O)_2R^{B1}$, —$S(O)_rNR^{A1}R^{B1}$, —$P(O)R^{A1}R^{B1}$, —$P(O)(OR^{A1})(OR^{B1})$, —$(CR^{C1}R^{D1})_tNR^{A1}R^{B1}$, —$(CR^{C1}R^{D1})_tOR^{B1}$, —$(CR^{C1}R^{D1})_t$ $SR^{B1}$, —$(CR^{C1}R^{D1})_tS(O)_rR^{B1}$, —$(CR^{C1}R^{D1})_t$ $P(O)R^{A1}R^{B1}$, —$(CR^{C1}R^{D1})_tP(O)(OR^{A1})(OR^{B1})$, —$(CR^{C1}R^{D1})_tCO_2R^{B1}$, —$(CR^{C1}R^{D1})_tC(O)NR^{A1}R^{B1}$, —$(CR^{C1}R^{D1})_tNR^{A1}C(O)R^{B1}$, —$(CR^{C1}R^{D1})_tNR^{A1}CO_2R^{B1}$, —$(CR^{C1}R^{D1})_tOC(O)NR^{A1}R^{B1}$, —$(CR^{C1}R^{D1})_tNR^{A1}CONR^{A1}R^{B1}$, —$(CR^{C1}R^{D1})_t$ $NR^{A1}SO_2NR^{A1}R^{B1}$, —$NR^{A1}(CR^{C1}R^{D1})_tNR^{A1}R^{B1}$, —$O(CR^{C1}R^{D1})_tNR^{A1}R^{B1}$, —$S(CR^{C1}R^{D1})_tNR^{A1}R^{B1}$, —$S(O)_r(CR^{C1}R^{D1})_tNR^{A1}R^{B1}$, —$C(O)R^{A1}$, —$C(O)$ $(CR^{C1}R^{D1})_tNR^{A1}R^{B1}$, —$C(O)(CR^{C1}R^{D1})_tOR^{B1}$, —$C(O)$ $(CR^{C1}R^{D1})_tSR^{B1}$, —$C(O)(CR^{C1}R^{D1})_tS(O)_rR^{B1}$, —$CO_2R^{B1}$, —$CO_2(CR^{C1}R^{D1})_tC(O)NR^{A1}R^{B1}$, —$OC(O)R^{A1}$, —CN, —$C(O)NR^{A1}R^{B1}$, —$NR^{A1}C(O)R^{B1}$, —$NR^{A1}CO_2R^{B1}$, —OC $(O)NR^{A1}R^{B1}$, —$NR^{A1}C(O)NR^{A1}R^{B1}$, —$NR^{A1}S(O)_rR^{B1}$, —$CR^{A1}(=N—OR^{B1})$, —$C(=NR^{E1})R^{A1}$, —$C(=NR^{E1})$ $NR^{A1}R^{B1}$, —$NR^{A1}C(=NR^{E1})NR^{A1}R^{B1}$, —$CHF_2$, —$CF_3$, —$OCHF_2$, and —$OCF_3$, wherein alkyl, alkenyl, alkynyl, cycloalkyl, heterocyclyl, aryl and heteroaryl are each unsubstituted or substituted with at least one substituent, such as one, two, three, or four substituents, independently selected from $R^X$;

each $R^3$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —$NO_2$, —$NR^{A2}R^{B2}$, —$OR^{A2}$, —$SR^{A2}$, —$S(O)_rR^{A2}$, —$S(O)_2OR^{A2}$, —$OS(O)_2R^{B2}$, —$S(O)_rNR^{A2}R^{B2}$, —$P(O)R^{A2}R^{B2}$, —$P(O)(OR^{A2})(OR^{B2})$, —$(CR^{C2}R^{D2})_tNR^{A2}R^{B2}$, —$(CR^{C2}R^{D2})_tOR^{B2}$, —$(CR^{C2}R^{D2})_t$SR^{B2}$, —$(CR^{C2}R^{D2})_tS(O)_rR^{B2}$, —$(CR^{C2}R^{D2})_t$ $P(O)R^{A2}R^{B2}$, —$(CR^{C2}R^{D2})_tP(O)(OR^{A2})(OR^{B2})$, —$(CR^{C2}R^{D2})_tCO_2R^{B2}$, —$(CR^{C2}R^{D2})_tC(O)NR^{A2}R^{B2}$, —$(CR^{C2}R^{D2})_tNR^{A2}C(O)R^{B2}$, —$(CR^{C2}R^{D2})_tNR^{A2}CO_2R^{B2}$, —$(CR^{C2}R^{D2})_tOC(O)NR^{A2}R^{B2}$, —$(CR^{C2}R^{D2})_tNR^{A2}CONR^{A2}R^{B2}$, —$(CR^{C2}R^{D2})_tNR^{A2}SO_2NR^{A2}R^{B2}$, —$NR^{A2}(CR^{C2}R^{D2})_tNR^{A2}R^{B2}$, —$O(CR^{C2}R^{D2})_tNR^{A2}R^{B2}$, —$S(CR^{C2}R^{D2})_tNR^{A2}R^{B2}$, —$S(O)_r(CR^{C2}R^{D2})_tNR^{A2}R^{B2}$, —$C(O)R^{A2}$, —$C(O)(CR^{C2}R^{D2})_tNR^{A2}R^{B2}$, —$C(O)(CR^{C2}R^{D2})_tOR^{B2}$, —$C(O)(CR^{C2}R^{D2})_tSR^{B2}$, —$C(O)(CR^{C2}R^{D2})_tS(O)_rR^{B2}$, —$CO_2R^{B2}$, —$CO_2(CR^{C2}R^{D2})_tC(O)NR^{A2}R^{B2}$, —$OC(O)R^{A2}$, —$CN$, —$C(O)NR^{A2}R^{B2}$, —$NR^{A2}C(O)R^{B2}$, —$NR^{A2}CO_2R^{B2}$, —$OC(O)NR^{A2}R^{B2}$, —$NR^{A2}C(O)NR^{A2}R^{B2}$, —$NR^{A2}S(O)_rR^{B2}$, —$CR^{A2}(=N-OR^{B2})$, —$C(=NR^{E2})R^{A2}$, —$C(=NR^{E2})NR^{A2}R^{B2}$, —$NR^{A2}C(=NR^{E2})NR^{A2}R^{B2}$, —$CHF_2$, —$CF_3$, —$OCHF_2$, and —$OCF_3$, wherein alkyl, alkenyl, alkynyl, cycloalkyl, heterocyclyl, aryl and heteroaryl are each unsubstituted or substituted with at least one substituent, such as one, two, three, or four substituents, independently selected from $R^X$;

or two $R^3$ together with the carbon atoms to which they are attached form a cyclic ring of 3 to 7 members containing 0, 1, or 2 additional heteroatoms independently selected from oxygen, sulfur and nitrogen, and optionally substituted with 1, 2 or 3 $R^X$ groups;

$R^4$ is selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —$NO_2$, —$NR^{A3}R^{B3}$, —$OR^{A3}$, —$SR^{A3}$, —$S(O)_rR^{A3}$, —$S(O)_2OR^{A3}$, —$OS(O)_2R^{B3}$, —$S(O)_rNR^{A3}R^{B3}$, —$P(O)R^{A3}R^{B3}$, —$P(O)(OR^{A3})(OR^{B3})$, —$(CR^{C3}R^{D3})_tNR^{A3}R^{B3}$, —$(CR^{C3}R^{D3})_tOR^{B3}$, —$(CR^{C3}R^{D3})_tSR^{B3}$, —$(CR^{C3}R^{D3})_tS(O)_rR^{B3}$, —$(CR^{C3}R^{D3})_tP(O)R^{A3}R^{B3}$, —$(CR^{C3}R^{D3})_tP(O)(OR^{A3})(OR^{B3})$, —$(CR^{C3}R^{D3})_tCO_2R^{B3}$, —$(CR^{C3}R^{D3})_tC(O)NR^{A3}R^{B3}$, —$(CR^{C3}R^{D3})_tNR^{A3}C(O)R^{B3}$, —$(CR^{C3}R^{D3})_tNR^{A3}CO_2R^{B3}$, —$(CR^{C3}R^{D3})_tOC(O)NR^{A3}R^{B3}$, —$(CR^{C3}R^{D3})_tNR^{A3}CONR^{A3}R^{B3}$, —$(CR^{C3}R^{D3})_tNR^{A3}SO_2NR^{A3}R^{B3}$, —$NR^{A3}(CR^{C3}R^{D3})_tNR^{A3}R^{B3}$, —$O(CR^{C3}R^{D3})_tNR^{A3}R^{B3}$, —$S(CR^{C3}R^{D3})_tNR^{A3}R^{B3}$, —$S(O)_r(CR^{C3}R^{D3})_tNR^{A3}R^{B3}$, —$C(O)R^{A3}$, —$C(O)(CR^{C3}R^{D3})_tNR^{A3}R^{B3}$, —$C(O)(CR^{C3}R^{D3})_tOR^{B3}$, —$C(O)(CR^{C3}R^{D3})_tSR^{B3}$, —$C(O)(CR^{C3}R^{D3})_tS(O)_rR^{B3}$, —$CO_2R^{B3}$, —$CO_2(CR^{C3}R^{D3})_tC(O)NR^{A3}R^{B3}$, —$OC(O)R^{A3}$, —$CN$, —$C(O)NR^{A3}R^{B3}$, —$NR^{A3}C(O)R^{B3}$, —$NR^{A3}CO_2R^{B3}$, —$OC(O)NR^{A3}R^{B3}$, —$NR^{A3}C(O)NR^{A3}R^{B3}$, —$NR^{A3}S(O)_rR^{B3}$, —$CR^{A3}(=N-OR^{B3})$, —$C(=NR^{E3})R^{A3}$, —$C(=NR^{E3})NR^{A3}R^{B3}$, —$NR^{A3}C(=NR^{E3})NR^{A3}R^{B3}$, —$CHF_2$, —$CF_3$, —$OCHF_2$, and —$OCF_3$, wherein alkyl, alkenyl, alkynyl, cycloalkyl, heterocyclyl, aryl and heteroaryl are each unsubstituted or substituted with at least one substituent, such as one, two, three, or four substituents, independently selected from $R^X$;

each $R^5$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —$NO_2$, —$NR^{A4}R^{B4}$, —$OR^{A4}$, —$SR^{A4}$, —$S(O)_rR^{A4}$, —$S(O)_2OR^{A4}$, —$OS(O)_2R^{B4}$, —$S(O)_rNR^{A4}R^{B4}$, —$P(O)R^{A4}R^{B4}$, —$P(O)(OR^{A4})(OR^{B4})$, —$(CR^{C4}R^{D4})_tNR^{A4}R^{B4}$, —$(CR^{C4}R^{D4})_tOR^{B4}$, —$(CR^{C4}R^{D4})_tSR^{B4}$, —$(CR^{C4}R^{D4})_tS(O)_rR^{B4}$, —$(CR^{C4}R^{D4})_tP(O)R^{A4}R^{B4}$, —$(CR^{C4}R^{D4})_tP(O)(OR^{A4})(OR^{B4})$, —$(CR^{C4}R^{D4})_tCO_2R^{B4}$, —$(CR^{C4}R^{D4})_tC(O)NR^{A4}R^{B4}$, —$(CR^{C4}R^{D4})_tNR^{A4}C(O)R^{B4}$, —$(CR^{C4}R^{D4})_tNR^{A4}CO_2R^{B4}$, —$(CR^{C4}R^{D4})_tOC(O)NR^{A4}R^{B4}$, —$(CR^{C4}R^{D4})_tNR^{A4}CONR^{A4}R^{B4}$, —$(CR^{C4}R^{D4})_tNR^{A4}SO_2NR^{A4}R^{B4}$, —$NR^{A4}(CR^{C4}R^{D4})_tNR^{A4}R^{B4}$, —$O(CR^{C4}R^{D4})_tNR^{A4}R^{B4}$, —$S(CR^{C4}R^{D4})_tNR^{A4}R^{B4}$, —$S(O)_r(CR^{C4}R^{D4})_tNR^{A4}R^{B4}$, —$C(O)R^{A4}$, —$C(O)(CR^{C4}R^{D4})_tNR^{A4}R^{B4}$, —$C(O)(CR^{C4}R^{D4})_tOR^{B4}$, —$C(O)(CR^{C4}R^{D4})_tSR^{B4}$, —$C(O)(CR^{C4}R^{D4})_tS(O)_rR^{B4}$, —$CO_2R^{B4}$, —$CO_2(CR^{C4}R^{D4})_tC(O)NR^{A4}R^{B4}$, —$OC(O)R^{A4}$, —$CN$, —$C(O)NR^{A4}R^{B4}$, —$NR^{A4}C(O)R^{B4}$, —$NR^{A4}CO_2R^{B4}$, —$OC(O)NR^{A4}R^{B4}$, —$NR^{A4}C(O)NR^{A4}R^{B4}$, —$NR^{A4}S(O)_rR^{B4}$, —$CR^{A4}(=N-OR^{B4})$, —$C(=NR^{E4})R^{A4}$, —$C(=NR^{E4})NR^{A4}R^{B4}$, —$NR^{A4}C(=NR^{E4})NR^{A4}R^{B4}$, —$CHF_2$, —$CF_3$, —$OCHF_2$, and —$OCF_3$, wherein alkyl, alkenyl, alkynyl, cycloalkyl, heterocyclyl, aryl and heteroaryl are each unsubstituted or substituted with at least one substituent, such as one, two, three, or four substituents, independently selected from $R^X$;

each $R^6$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —$NO_2$, —$NR^{A5}R^{B5}$, —$OR^{A5}$, —$SR^{A5}$, —$S(O)_rR^{A5}$, —$S(O)_2OR^{A5}$, —$OS(O)_2R^{B5}$, —$S(O)_rNR^{A5}R^{B5}$, —$P(O)R^{A5}R^{B5}$, —$P(O)(OR^{A5})(OR^{B5})$, —$(CR^{C5}R^{D5})_tNR^{A5}R^{B5}$, —$(CR^{C5}R^{D5})_tOR^{B5}$, —$(CR^{C5}R^{D5})_tSR^{B5}$, —$(CR^{C5}R^{D5})_tS(O)_rR^{B5}$, —$(CR^{C5}R^{D5})_tP(O)R^{A5}R^{B5}$, —$(CR^{C5}R^{D5})_tP(O)(OR^{A5})(OR^{B5})$, —$(CR^{C5}R^{D5})_tCO_2R^{B5}$, —$(CR^{C5}R^{D5})_tC(O)NR^{A5}R^{B5}$, —$(CR^{C5}R^{D5})_tNR^{A5}C(O)R^{B5}$, —$(CR^{C5}R^{D5})_tNR^{A5}CO_2R^{B5}$, —$(CR^{C5}R^{D5})_tOC(O)NR^{A5}R^{B5}$, —$(CR^{C5}R^{D5})_tNR^{A5}CONR^{A5}R^{B5}$, —$(CR^{C5}R^{D5})_tNR^{A5}SO_2NR^{A5}R^{B5}$, —$NR^{A5}(CR^{C5}R^{D5})_tNR^{A5}R^{B5}$, —$O(CR^{C5}R^{D5})_tNR^{A5}R^{B5}$, —$S(CR^{C5}R^{D5})_tNR^{A5}R^{B5}$, —$S(O)_r(CR^{C5}R^{D5})_tNR^{A5}R^{B5}$, —$C(O)R^{A5}$, —$C(O)(CR^{C5}R^{D5})_tNR^{A5}R^{B5}$, —$C(O)(CR^{C5}R^{D5})_tOR^{B5}$, —$C(O)(CR^{C5}R^{D5})_tSR^{B5}$, —$C(O)(CR^{C5}R^{D5})_tS(O)_rR^{B5}$, —$CO_2R^{B5}$, —$CO_2(CR^{C5}R^{D5})_tC(O)NR^{A5}R^{B5}$, —$OC(O)R^{A5}$, —$CN$, —$C(O)NR^{A5}R^{B5}$, —$NR^{A5}C(O)R^{B5}$, —$NR^{A5}CO_2R^{B5}$, —$OC(O)NR^{A5}R^{B5}$, —$NR^{A5}C(O)NR^{A5}R^{B5}$, —$NR^{A5}S(O)_rR^{B5}$, —$CR^{A5}(=N-OR^{B5})$, —$C(=NR^{E5})R^{A5}$, —$C(=NR^{E5})NR^{A5}R^{B5}$, —$NR^{A5}C(=NR^{E5})NR^{A5}R^{B5}$, —$CHF_2$, —$CF_3$, —$OCHF_2$, and —$OCF_3$, wherein alkyl, alkenyl, alkynyl, cycloalkyl, heterocyclyl, aryl and heteroaryl are each unsubstituted or substituted with at least one substituent, such as one, two, three, or four substituents, independently selected from $R^X$;

each $R^{A1}$, $R^{A2}$, $R^{A3}$, $R^{A4}$, $R^{A5}$, $R^{B1}$, $R^{B2}$, $R^{B3}$, $R^{B4}$, and $R^{B5}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from $R^X$;

or each "$R^{A1}$ and $R^{B1}$", "$R^{A2}$ and $R^{B2}$", "$R^{A3}$ and $R^{B3}$", "$R^{A4}$ and $R^{B4}$", and "$R^{A5}$ and $R^{B5}$", together with the atom(s) to which they are attached form a heterocyclic ring of 4 to 12 members containing 0, 1, or 2 additional heteroatoms independently selected from oxygen, sulfur and nitrogen, and optionally substituted with 1 2, or 3 $R^X$ groups;

each $R^{C1}$, $R^{C2}$, $R^{C3}$, $R^{C4}$, $R^{C5}$, $R^{D1}$, $R^{D2}$, $R^{D3}$, $R^{D4}$, and $R^{D5}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from $R^X$;

or "$R^{C1}$ and $R^{D1}$", "$R^{C2}$ and $R^{D2}$", "$R^{C3}$ and $R^{D3}$", "$R^{C4}$ and $R^{D4}$", and "$R^{C5}$ and $R^{D5}$" together with the carbon atom(s) to which they are attached form a ring of 3 to 12 members containing 0, 1, or 2 heteroatoms independently selected from oxygen, sulfur and nitrogen, and optionally substituted with 12, or 3 $R^X$ groups;

each $R^{E1}$, $R^{E2}$, $R^{E3}$, $R^{E4}$, and $R^{E5}$ is independently selected from hydrogen, $C_{1-10}$ alkyl, CN, $NO_2$, $OR^{a2}$, $SR^{a2}$, $-S(O)_rR^{a2}$, $-C(O)R^{a2}$, $-S(O)_rNR^{A2}R^{b2}$, and $-C(O)NR^{a2}R^{b2}$;

each $R^X$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, $-NO_2$, $-NR^{a1}R^{b1}$, $-OR^{a1}$, $-SR^{a1}$, $-S(O)_rR^{a1}$, $-S(O)_2OR^{a1}$, $-OS(O)_2R^{b1}$, $-S(O)_rNR^{a1}R^{b1}$, $-P(O)R^{a1}R^{b1}$, $-P(O)(OR^{a1})(OR^{b1})$, $-(CR^{c1}R^{d1})_tNR^{a1}R^{b1}$, $-(CR^{c1}R^{d1})_tOR^{b1}$, $-(CR^{c1}R^{d1})_tSR^{b1}$, $-(CR^{c1}R^{d1})_tS(O)_rR^{b1}$, $-(CR^{c1}R^{d1})_tP(O)R^{a1}R^{b1}$, $-(CR^{c1}R^{d1})_tP(O)(OR^{a1})(OR^{b1})$, $-(CR^{c1}R^{d1})_tCO_2R^{b1}$, $-(CR^{c1}R^{d1})_tC(O)NR^{a1}R^{b1}$, $-(CR^{c1}R^{d1})_tNR^{a1}C(O)R^{b1}$, $-(CR^{c1}R^{d1})_tNR^{a1}CO_2R^{b1}$, $-(CR^{c1}R^{d1})_tOC(O)NR^{a1}R^{b1}$, $-(CR^{c1}R^{d1})_tNR^{a1}C(O)NR^{a1}R^{b1}$, $-(CR^{c1}R^{d1})_tNR^{a1}SO_2NR^{a1}R^{b1}$, $-NR^{a1}(CR^{c1}R^{d1})_tNR^{a1}R^{b1}$, $-O(CR^{c1}R^{d1})_tNR^{a1}R^{b1}$, $-S(CR^{c1}R^{d1})_tNR^{a1}R^{b1}$, $-S(O)_r(CR^{c1}R^{d1})_tNR^{a1}R^{b1}$, $-C(O)R^{a1}$, $-C(O)(CR^{c1}R^{d1})_tNR^{a1}R^{b1}$, $-C(O)(CR^{c1}R^{d1})_tOR^{b1}$, $-C(O)(CR^{c1}R^{d1})_tSR^{b1}$, $-C(O)(CR^{c1}R^{d1})_tS(O)_rR^{b1}$, $-CO_2R^{b1}$, $-CO_2(CR^{c1}R^{d1})_tC(O)NR^{a1}R^{b1}$, $-OC(O)R^{a1}$, $-CN$, $-C(O)NR^{a1}R^{b1}$, $-NR^{a1}C(O)R^{b1}$, $-OC(O)NR^{a1}R^{b1}$, $-NR^{a1}C(O)OR^{b1}$, $-NR^{a1}C(O)NR^{a1}R^{b1}$, $-NR^{a1}S(O)_rR^{b1}$, $-CR^{a1}(=N-OR^{b1})$, $-C(=NR^{e1})R^{a1}$, $-C(=NR^{e1})NR^{a1}R^{b1}$, $-NR^{a1}C(=NR^{e1})NR^{a1}R^{b1}$, $-CHF_2$, $-CF_3$, $-OCHF_2$, and $-OCF_3$, wherein alkyl, alkenyl, alkynyl, cycloalkyl, heterocyclyl, aryl and heteroaryl are each unsubstituted or substituted with at least one substituent, such as one, two, three, or four substituents, independently selected from $R^Y$;

each $R^{a1}$ and each $R^{b1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from $R^Y$;

or $R^{a1}$ and $R^{b1}$ together with the atom(s) to which they are attached form a heterocyclic ring of 4 to 12 members containing 0, 1, or 2 additional heteroatoms independently selected from oxygen, sulfur and nitrogen, and optionally substituted with 12, or 3 $R^Y$ groups;

each $R^{c1}$ and each $R^{d1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from $R^Y$;

or $R^{c1}$ and $R^{d1}$ together with the carbon atom(s) to which they are attached form a ring of 3 to 12 members containing 0, 1, or 2 heteroatoms independently selected from oxygen, sulfur and nitrogen, and optionally substituted with 1, 2, or 3 $R^Y$ groups;

each $R^{e1}$ is independently selected from hydrogen, $C_{1-10}$ alkyl, CN, $NO_2$, $OR^{a2}$, $SR^{a2}$, $-S(O)_rR^{a2}$, $-C(O)R^{a2}$, $-S(O)_rNR^{a2}R^{b2}$, and $-C(O)NR^{a2}R^{b2}$;

$R^Y$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, $-NO_2$, $-NR^{a2}R^{b2}$, $-OR^{a2}$, $-SR^{a2}$, $-S(O)_rR^{a2}$, $-S(O)_2OR^{a2}$, $-OS(O)_2R^{b2}$, $-S(O)_rNR^{a2}R^{b2}$, $-P(O)R^{a2}R^{b2}$, $-P(O)(OR^{a2})(OR^{b2})$, $-(CR^{c2}R^{d2})_tNR^{a2}R^{b2}$, $-(CR^{c2}R^{d2})_tOR^{b2}$, $-(CR^{c2}R^{d2})_tSR^{b2}$, $-(CR^{c2}R^{d2})_tS(O)_rR^{b2}$, $-(CR^{c2}R^{d2})_tP(O)R^{a2}R^{b2}$, $-(CR^{c2}R^{d2})_tP(O)(OR^{a2})(OR^{b2})$, $-(CR^{c2}R^{d2})_tCO_2R^{b2}$, $-(CR^{c2}R^{d2})_tC(O)NR^{a2}R^{b2}$, $-(CR^{c2}R^{d2})_tNR^{a2}C(O)R^{b2}$, $-(CR^{c2}R^{d2})_tNR^{a2}CO_2R^{b2}$, $-(CR^{c2}R^{d2})_tOC(O)NR^{a2}R^{b2}$, $-(CR^{c2}R^{d2})_tNR^{a2}C(O)NR^{a2}R^{b2}$, $-(CR^{c2}R^{d2})_tNR^{a2}SO_2NR^{a2}R^{b2}$, $-NR^{a2}(CR^{c2}R^{d2})_tNR^{a2}R^{b2}$, $-O(CR^{c2}R^{d2})_tNR^{a2}R^{b2}$, $-S(CR^{c2}R^{d2})_tNR^{a2}R^{b2}$, $-S(O)_r(CR^{c2}R^{d2})_tNR^{a2}R^{b2}$, $-C(O)R^{a2}$, $-C(O)(CR^{c2}R^{d2})_tOR^{b2}$, $-C(O)(CR^{c2}R^{d2})_tNR^{a2}R^{b2}$, $-C(O)(CR^{c2}R^{d2})_tSR^{b2}$, $-C(O)(CR^{c2}R^{d2})_tS(O)_rR^{b2}$, $-CO_2R^{b2}$, $-CO_2(CR^{c2}R^{d2})_tC(O)NR^{a2}R^{b2}$, $-OC(O)R^{a2}$, $-CN$, $-C(O)NR^{a2}R^{b2}$, $-NR^{a2}C(O)R^{b2}$, $-OC(O)NR^{a2}R^{b2}$, $-NR^{a2}C(O)OR^{b2}$, $-NR^{a2}C(O)NR^{a2}R^{b2}$, $-NR^{a2}S(O)_rR^{b2}$, $-CR^{a2}(=N-OR^{b2})$, $-C(=NR^{e2})R^{a2}$, $-C(=NR^{e2})NR^{a2}R^{b2}$, $-NR^{a2}C(=NR^{e2})NR^{a2}R^{b2}$, $-CHF_2$, $-CF_3$, $-OCHF_2$, and $-OCF_3$, wherein alkyl, alkenyl, alkynyl, cycloalkyl, heterocyclyl, aryl and heteroaryl are each unsubstituted or substituted with at least one substituent, such as one, two, three, or four substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkylamino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkylamino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$cycloalkylthio, $C_{1-10}$ alkylamino, $C_{3-10}$ cycloalkylamino, and di($C_{1-10}$ alkylamino;

or $R^{a2}$ and $R^{b2}$ together with the atom(s) to which they are attached form a heterocyclic ring of 4 to 12 members containing 0, 1, or 2 additional heteroatoms independently selected from oxygen, sulfur and nitrogen, and optionally substituted with 1 or 2 substituents, independently selected from OH, CN, amino, halogen, $C_{1-10}$ alkyl, $C_{2-10}$alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, and di($C_{1-10}$ alkylamino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkylamino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, and di($C_{1-10}$ alkylamino;

or $R^{e2}$ and $R^{d2}$ together with the carbon atom(s) to which they are attached form a ring of 3 to 12 members containing 0, 1, or 2 heteroatoms independently selected from oxygen, sulfur and nitrogen, and optionally substituted with 1 or 2 substituents, independently selected from OH, CN, amino, halogen, $C_{1-10}$ alkyl, $C_{2-10}$ alkenyl, $C_{2-10}$alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, and di($C_{1-10}$ alkylamino;

each $R^{e2}$ is independently selected from hydrogen, $C_{1-10}$ alkyl, CN and $NO_2$;

m is selected from 0, 1, 2, 3 and 4;

n is selected from 0, 1, and 2;

p is selected from 0, 1, 2 and 3;

q is selected from 1, 2, and 3;

each r is independently selected from 1 and 2;

each t is independently selected from 1, 2, 3 and 4.

In yet another aspect, the present disclosure provides pharmaceutical compositions comprising a compound of formula (I) or a pharmaceutically acceptable salt thereof and a pharmaceutically acceptable excipient.

In yet another aspect, the disclosure provides methods for modulating CDK4/6, comprising administering to a system or a subject in need thereof, a therapeutically effective amount of a compound of formula (I) or a pharmaceutically acceptable salt thereof or pharmaceutical compositions thereof, thereby modulating said CDK4/6.

In yet another aspect, disclosed is a method to treat, ameliorate or prevent a condition which responds to inhibition of CDK4/6 comprising administering to a system or subject in need of such treatment an effective amount of a compound of formula (I) or a pharmaceutically acceptable salt thereof or pharmaceutical compositions thereof, and optionally in combination with a second therapeutic agent, thereby treating said condition.

Alternatively, the present disclosure provides the use of a compound of formula (I) or a pharmaceutically acceptable salt thereof in the manufacture of a medicament for treating a condition mediated by CDK4/6. In particular embodiments, the compounds of the disclosure may be used alone or in combination with a second therapeutic agent to treat a condition mediated by CDK4/6.

Alternatively, disclosed is a compound of formula (I) for treating a condition mediated by CDK4/6.

Specifically, the condition herein includes but not limited to, an autoimmune disease, a transplantation disease, an infectious disease or a cell proliferative disorder.

Furthermore, the disclosure provides methods for treating a cell proliferative disorder, comprising administering to a system or subject in need of such treatment an effective amount of a compound of formula (I) or a pharmaceutically acceptable salt thereof or pharmaceutical compositions thereof, and optionally in combination with a second therapeutic agent, thereby treating said condition.

Alternatively, the present disclosure provides the use of a compound of formula (I) or a pharmaceutically acceptable salt thereof in the manufacture of a medicament for treating a cell-proliferative disorder. In particular examples, the compounds of the disclosure may be used alone or in combination with a chemotherapeutic agent to treat a cell proliferative disorder.

Specifically, the cell proliferative disorder disclosed herein includes but not limited to, lymphoma, osteosarcoma, melanoma, or a tumor of breast, renal, prostate, colorectal, thyroid, ovarian, pancreatic, neuronal, lung, uterine or gastrointestinal tumor.

In the above methods for using the compounds of the disclosure, a compound of formula (I) or a pharmaceutically acceptable salt thereof may be administered to a system comprising cells or tissues, or to a subject including a mammalian subject such as a human or animal subject.

Certain Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

The term "substituted" means that a hydrogen atom is removed and replaced by a substituent. It is to be understood that substitution at a given atom is limited by valency. Throughout the definitions, the term "$C_{i-j}$" indicates a range which includes the endpoints, wherein i and j are integers and indicate the number of carbons. Examples include $C_{1-4}$, $C_{1-10}$, $C_{3-10}$, and the like.

The term "alkyl", employed alone or in combination with other terms, refers to both branched and straight-chain saturated aliphatic hydrocarbon groups having the specified number of carbon atoms. Unless otherwise specified, "alkyl" refers to $C_1$-$C_6$ alkyl. For example, $C_1$-$C_6$, as in "$Q_{1-6}$ alkyl" is defined to include groups having 1, 2, 3, 4, 5, or 6 carbons in a linear or branched arrangement. For example, "$C_{1-8}$ alkyl" includes but is not limited to methyl, ethyl, n-propyl, i-propyl, n-butyl, t-butyl, i-butyl, pentyl, hexyl, heptyl, and octyl.

The term "cycloalkyl", employed alone or in combination with other terms, refers to a monocyclic or bridged hydrocarbon ring system. The monocyclic cycloalkyl is a carbocyclic ring system containing three to ten carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Representative examples of such bridged cycloalkyl ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.03,7]nonane, and tricyclo[3.3.1.13,7]decane (adamantane). The monocyclic and bridged cycloalkyl can be attached to the parent molecular moiety through any substitutable atom contained within the ring system.

The term "alkenyl", employed alone or in combination with other terms, refers to a non-aromatic hydrocarbon radical, straight, branched or cyclic, containing from 2 to 10 carbon atoms and at least one carbon to carbon double bond. In some embodiments, one carbon to carbon double bond is present, and up to four non-aromatic carbon-carbon double bonds may be present. Thus, "$C_{2-6}$ alkenyl" means an alkenyl radical having from 2 to 6 carbon atoms. Alkenyl groups include but are not limited to ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl", employed alone or in combination with other terms, refers to a hydrocarbon radical straight, branched or cyclic, containing from 2 to 10 carbon atoms and at least one carbon to carbon triple bond. In some embodiments, up to three carbon-carbon triple bonds may be present. Thus, "$C_{2-6}$ alkynyl" means an alkynyl radical having from 2 to 6 carbon atoms. Alkynyl groups include but are not limited to ethynyl, propynyl, butynyl, and 3-methylbutynyl. The straight, branched or cyclic portion of the alkynyl group may contain triple bonds and may be substituted if a substituted alkynyl group is indicated.

The term "halogen" (or "halo") refers to fluorine, chlorine, bromine and iodine.

The term "alkoxy", employed alone or in combination with other terms, refers to an alkyl radical that is single bonded to an oxygen atom. The attachment point of an alkoxy radical to a molecule is through the oxygen atom. An alkoxy radical may be depicted as —O-alkyl. The term "$C_{1-10}$ alkoxy" refers to an alkoxy radical containing from one to ten carbon atoms, having straight or branched moieties. Alkoxy groups, includes but is not limited to, methoxy, ethoxy, propoxy, isopropoxy, butoxy, pentyloxy, hexyloxy, and the like.

The term "cycloalkoxy", employed alone or in combination with other terms, refers to cycloalkyl radical that is single bonded to an oxygen atom. The attachment point of a cycloalkoxy radical to a molecule is through the oxygen atom. A cycloalkoxy radical may be depicted as —O-cycloalkyl. "$C_{3-10}$ cycloalkoxy" refers to a cycloalkoxy radical containing from three to ten carbon atoms. Cycloalkoxy groups, includes but is not limited to, cyclopropoxy, cyclobutoxy, cyclopentyloxy, cyclohexyloxy, and the like.

The term "alkylthio", employed alone or in combination with other terms, refers to an alkyl radical that is single bonded to a sulfur atom. The attachment point of an alkylthio radical to a molecule is through the sulfur atom. An alkylthio radical may be depicted as —S-alkyl. The term "$C_{1-10}$ alkylthio" refers to an alkylthio radical containing from one to ten carbon atoms, having straight or branched moieties. Alkylthio groups, includes but is not limited to, methylthio, ethylthio, propylthio, isopropylthio, butylthio, hexylthio, and the like.

The term "cycloalkylthio", employed alone or in combination with other terms, refers to cycloalkyl radical that is single bonded to a sulfur atom. The attachment point of a cycloalkylthio radical to a molecule is through the sulfur atom. A cycloalkylthio radical may be depicted as —S-cycloalkyl. "$C_{3-10}$ cycloalkylthio" refers to a cycloalkylthio radical containing from three to ten carbon atoms. Cycloalkylthio groups, includes but is not limited to, cyclopropylthio, cyclobutylthio, cyclohexylthio, and the like.

The term "alkylamino", employed alone or in combination with other terms, refers to an alkyl radical that is single bonded to a nitrogen atom. The attachment point of an alkylamino radical to a molecule is through the nitrogen atom. An alkylamino radical may be depicted as —NH(alkyl). The term "$C_{1-10}$ alkylamino" refers to an alkylamino radical containing from one to ten carbon atoms, having straight or branched moieties. Alkylamino groups, includes but is not limited to, methylamino, ethylamino, propylamino, isopropylamino, butylamino, hexylamoino, and the like.

The term "cycloalkylamino", employed alone or in combination with other terms, refers to cycloalkyl radical that is single bonded to a nitrogen atom. The attachment point of a cycloalkylamino radical to a molecule is through the nitrogen atom. A cycloalkylamino radical may be depicted as —NH(cycloalkyl). "$C_{3-10}$ cycloalkylamino" refers to a cycloalkylamino radical containing from three to ten carbon atoms. Cycloalkylamino groups, includes but is not limited to, cyclopropylamino, cyclobutylamino, cyclohexylamino, and the like.

The term "di(alkyl)amino", employed alone or in combination with other terms, refers to two alkyl radicals that are single bonded to a nitrogen atom. The attachment point of an di(alkyl)amino radical to a molecule is through the nitrogen atom. A dialkylamino radical may be depicted as —N(alkyl)$_2$. The term "di($C_{1-10}$ alkylamino" refers to a di($C_{1-10}$ alkylamino radical wherein the alkyl radicals each independently contains from one to ten carbon atoms, having straight or branched moieties.

The term "aryl", employed alone or in combination with other terms, encompasses: 5- and 6-membered carbocyclic aromatic rings, for example, benzene; bicyclic ring systems wherein at least one ring is carbocyclic and aromatic, for example, naphthalene, indane, and 1, 2, 3, 4-tetrahydroquinoline; and tricyclic ring systems wherein at least one ring is carbocyclic and aromatic, for example, fluorene. In cases where the aryl substituent is bicyclic or tricyclic and at least one ring is non-aromatic, it is understood that attachment is via the aromatic ring.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "heteroaryl", employed alone or in combination with other terms, refers to
- 5- to 8-membered aromatic, monocyclic rings containing one or more, for example, from 1 to 4, or, in some embodiments, from 1 to 3, heteroatoms selected from N, O, and S, with the remaining ring atoms being carbon;
- 8- to 12-membered bicyclic rings containing one or more, for example, from 1 to 4, or, in some embodiments, from 1 to 3, heteroatoms selected from N, O, and S, with the remaining ring atoms being carbon and wherein at least one heteroatom is present in an aromatic ring; and
- 11- to 14-membered tricyclic rings containing one or more, for example, from 1 to 4, or in some embodiments, from 1 to 3, heteroatoms selected from N, O, and S, with the remaining ring atoms being carbon and wherein at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl, and 5,6,7,8-tetrahydroisoquinoline.

Further heteroaryl groups include but are not limited to pyrrolyl, isothiazolyl, triazinyl, pyrazinyl, pyridazinyl, indolyl, benzotriazolyl, quinoxalinyl, and isoquinolinyl. As with the definition of heterocycle below, "heteroaryl" is also understood to include the N-oxide derivative of any nitrogen-containing heteroaryl.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In cases where the heteroaryl substituent is bicyclic or tricyclic and at least one ring is non-aromatic or contains no heteroatoms, it is understood that attachment is via the aromatic ring or via the heteroatom containing ring, respectively.

The term "heterocycle", employed alone or in combination with other terms, (and variations thereof such as "heterocyclic", or "heterocyclyl") broadly refers to a single aliphatic ring, usually with 3 to 12 ring atoms, containing at least 2 carbon atoms in addition to one or more, preferably one to three heteroatoms independently selected from oxygen, sulfur, and nitrogen, as well as combinations comprising at least one of the foregoing heteroatoms. Alternatively, a heterocycle as defined above may be multicyclic ring system (e.g. bicyclic) in which two or more rings may be fused or bridged or spiro together, wherein at least one such ring contains one or more heteroatoms independently selected from oxygen, sulfur, and nitrogen. "Heterocycle" also refers to 5- to 7-membered heterocyclic ring containing one or more heteroatoms selected from N, O, and S fused with 5- and 6-membered carbocyclic aromatic ring, provided that the point of attachment is at the heterocyclic ring. The rings may be saturated or have one or more double bonds (i.e. partially unsaturated). The heterocycle can be substituted by oxo. The point of the attachment may be carbon or heteroatom in the heterocyclic ring, provided that attachment results in the creation of a stable structure. When the heterocyclic ring has substituents, it is understood that the substituents may be attached to any atom in the ring, whether a heteroatom or a carbon atom, provided that a stable chemical structure results. Heterocycle does not overlap with heteroaryl.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl. 1,4-piperazinyl, and 2,3-pyridazinyl. Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl. Bicyclic heterocycles include, for example:

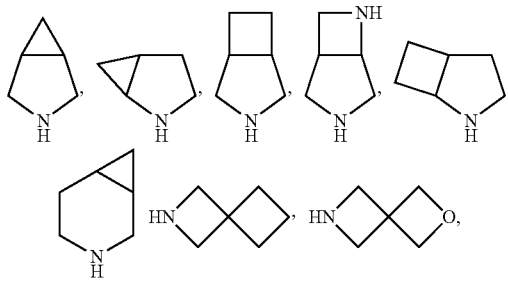

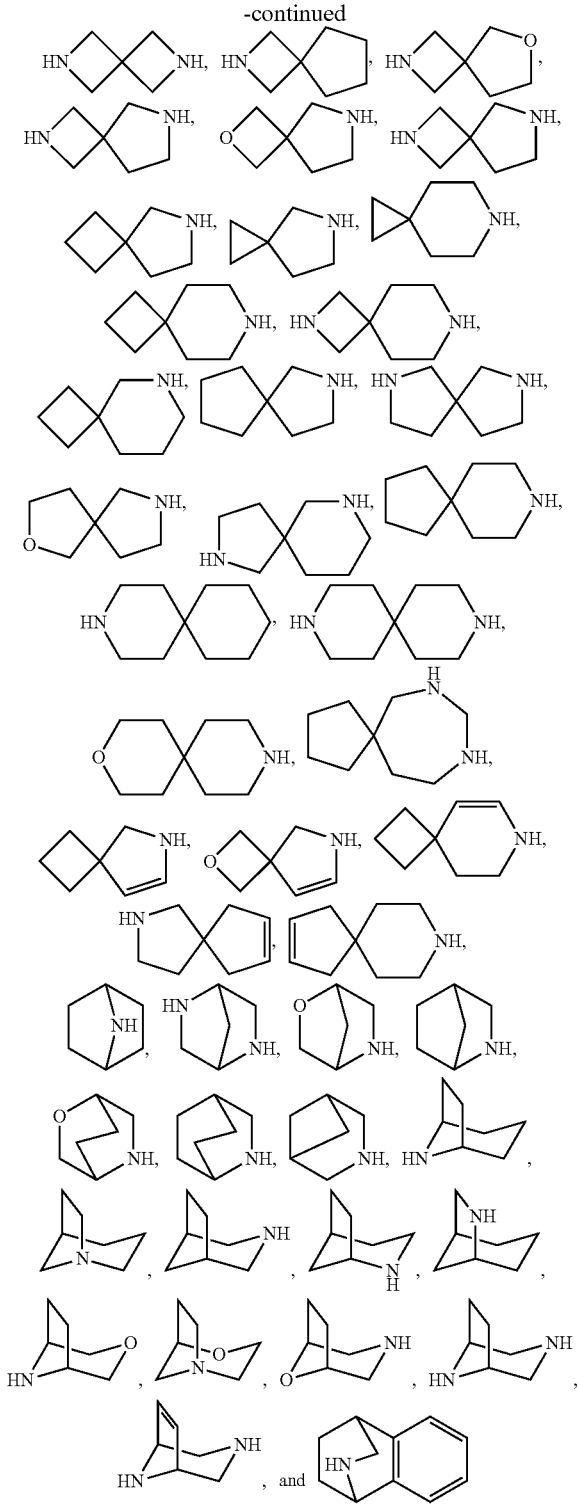

As used herein, "aryl-alkyl" refers to an alkyl moiety substituted by an aryl group. Example arylalkyl groups include benzyl, phenethyl, and naphthylmethyl groups. In some embodiments, arylalkyl groups have from 7 to 20 or 7 to 11 carbon atoms. When used in the phrase "aryl$C_{1-4}$ alkyl", the term "$C_{1-4}$" refers to the alkyl portion of the moiety and does not describe the number of atoms in the aryl portion of the moiety.

As used herein, "heterocyclyl-alkyl" refers to alkyl substituted by heterocyclyl. When used in the phrase "heterocyclyl-$C_{1-6}$ alkyl", the term "$C_{1-6}$" refers to the alkyl portion of the moiety and does not describe the number of atoms in the heterocyclyl portion of the moiety.

As used herein, "cycloalkyl-alkyl" refers to alkyl substituted by cycloalkyl. When used in the phrase "$C_{3-10}$ cycloalkyl-$C_{1-4}$ alkyl", the term "$C_{3-10}$" refers to the cycloalkyl portion of the moiety and does not describe the number of atoms in the alkyl portion of the moiety, and the term "$C_{1-4}$" refers to the alkyl portion of the moiety and does not describe the number of atoms in the cycloalkyl portion of the moiety.

As used herein, "heteroaryl-alkyl" refers to alkyl substituted by heteroaryl. When used in the phrase "heteroaryl-$C_{1-4}$ alkyl", the term "$C_{1-4}$" refers to the alkyl portion of the moiety and does not describe the number of atoms in the heteroaryl portion of the moiety.

For avoidance of doubt, reference, for example, to substitution of alkyl, cycloalkyl, heterocyclyl, aryl, and/or heteroaryl refers to substitution of each of those groups individually as well as to substitutions of combinations of those groups. That is, if $R^1$ is aryl-$C_{1-4}$ alkyl, the aryl portion may be unsubstituted or substituted with at least one substituent, such as one, two, three, or four substituents, independently selected from $R^X$ and the alkyl portion may also be unsubstituted or substituted with at least one substituent, such as one, two, three, or four substituents, independently selected from $R^X$.

The term "pharmaceutically acceptable salts" refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts in the solid form may exist in one or more crystal structures, and may also be in the form of hydrates. Salts derived from pharmaceutically acceptable organic non-toxic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, and tripropylamine, tromethamine.

When the compound disclosed herein is basic, salts may be prepared using at least one pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. In some embodiments, such acid may be selected, for example, from citric, hydrobromic, hydrochloric, maleic, phosphoric, sulfuric, fumaric, and tartaric acids.

The terms "administration of" and or "administering" at least one compound and/or at least one pharmaceutically acceptable salt should be understood to mean providing at least one compound and/or at least one pharmaceutically acceptable salt thereof to the individual in recognized need of treatment.

The term "effective amount" means the amount of the at least one compound and/or at least one pharmaceutically acceptable salt that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

The term "pharmaceutically acceptable" it is meant compatible with the other ingredients of the formulation and not unacceptably deleterious to the recipient thereof.

The term "subject" as used herein in reference to individuals suffering from a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The term "protecting group" or "Pg" refers to a substituent that can be commonly employed to block or protect a certain functionality while reacting other functional groups on the compound. For example, an "amino-protecting group" is a substituent attached to an amino group that blocks or protects the amino functionality in the compound. Suitable amino-protecting groups include but are not limited to acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include but are not limited to acetyl and silyl. A "carboxy-protecting group" refers to a substituent of the carboxy group that blocks or protects the carboxy functionality. Common carboxy-protecting groups include —CH2CH2SO2Ph, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The term "NH protecting group" as used herein includes, but not limited to, trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyloxycarbonyl, 4-(phenylazo)-benzyloxycarbonyl, 2-furfuryloxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthylmethylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclo-hexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group" as used herein includes, but not limited to, methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl, 2-tetrahydrofuranyl, 2,2,2-trichloro-ethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group" as used herein includes, but not limited to, benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl) ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, 4-ethoxy-1-naphthyloxycarbonyl, 8-quinolyloxy carbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxy ethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble J. Org. Chem. 1998, 63, 2758-2760.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85-90%, more preferably an excess of about 95-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, nitrogen, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuterated acid such as $D_2SO_4/D_2O$. In addition to the above, relevant procedures and intermediates are disclosed, for instance, in Lizondo, J et al, Drugs Fut, 21(11), 1116 (1996); Brickner, S J et al., J Med Chem, 39(3), 673 (1996); Mallesham, B et al, Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of CDK4/6 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al, J. Labelled Comp. Radiopharmaceut., 36(10):927-932 (1995); Kushner et al., Can. J. Physiol. Pharmacol, 77, 79-88 (1999)).

In addition, non-radio active isotope containing drugs, such as deuterated drugs called "heavy drugs" can be used for the treatment of diseases and conditions related to CDK4/6 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

1. A compound of formula (I)

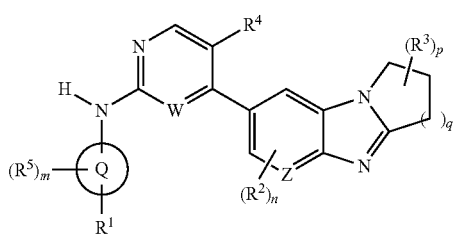

(I)

or a pharmaceutically acceptable salt thereof, wherein:
Q is selected from aryl and heteroaryl;
W is selected from N and $CR^6$;
Z is selected from N and $CR^6$;
$R^1$ is selected from hydrogen, halogen, hydroxyl, CN, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkylamino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from $R^X$;

each $R^2$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —$NO_2$, —$NR^{A1}R^{B1}$, —$OR^{A1}$, —$SR^{A1}$, —$S(O)_rR^{A1}$, —$S(O)_2OR^{A1}$, —$OS(O)_2R^{B1}$, —$S(O)_rNR^{A1}R^{B1}$, —$P(O)R^{A1}R^{B1}$, —$P(O)(OR^{A1})(OR^{B1})$, —$(CR^{C1}R^{D1})_tNR^{A1}R^{B1}$, —$(CR^{C1}R^{D1})_tOR^{B1}$, —$(CR^{C1}R^{D1})_tSR^{B1}$, —$(CR^{C1}R^{D1})_tS(O)_rR^{B1}$, —$(CR^{C1}R^{D1})_t$ $P(O)R^{A1}R^{B1}$, —$(CR^{C1}R^{D1})_tP(O)(OR^{A1})(OR^{B1})$, —$(CR^{C1}R^{D1})_tCO_2R^{B1}$, —$(CR^{C1}R^{D1})_tC(O)NR^{A1}R^{B1}$, —$(CR^{C1}R^{D1})_tNR^{A1}C(O)R^{B1}$, —$(CR^{C1}R^{D1})_tNR^{A1}CO_2R^{B1}$, —$(CR^{C1}R^{D1})_tOC(O)NR^{A1}R^{B1}$, —$(CR^{C1}R^{D1})_tNR^{A1}CONR^{A1}R^{B1}$, —$(CR^{C1}R^{D1})_tNR^{A1}SO_2NR^{A1}R^{B1}$, —$NR^{A1}(CR^{C1}R^{D1})_tNR^{A1}R^{B1}$, —$O(CR^{C1}R^{D1})_tNR^{A1}R^{B1}$, —$S(CR^{C1}R^{D1})_tNR^{A1}R^{B1}$, —$S(O)_r(CR^{C1}R^{D1})_tNR^{A1}R^{B1}$, —$C(O)R^{A1}$, —$C(O)(CR^{C1}R^{D1})_tNR^{A1}R^{B1}$, —$C(O)(CR^{C1}R^{D1})_tOR^{B1}$, —$C(O)(CR^{C1}R^{D1})_tSR^{B1}$, —$C(O)(CR^{C1}R^{D1})_tS(O)_rR^{B1}$, —$CO_2R^{B1}$, —$CO_2(CR^{C1}R^{D1})_tC(O)NR^{A1}R^{B1}$, —$OC(O)R^{A1}$, —CN, —$C(O)NR^{A1}R^{B1}$, —$NR^{A1}C(O)R^{B1}$, —$NR^{A1}CO_2R^{B1}$, —$OC(O)NR^{A1}R^{B1}$, —$NR^{A1}C(O)NR^{A1}R^{B1}$, —$NR^{A1}S(O)_rR^{B1}$, —$CR^{A1}(=N—OR^{B1})$, —$C(=NR^{E1})R^{A1}$, —$C(=NR^{E1})NR^{A1}R^{B1}$, —$NR^{A1}C(=NR^{E1})NR^{A1}R^{B1}$, —$CHF_2$, —$CF_3$, —$OCHF_2$, and —$OCF_3$, wherein alkyl, alkenyl, alkynyl, cycloalkyl, heterocyclyl, aryl and heteroaryl are each unsubstituted or substituted with at least one substituent, such as one, two, three, or four substituents, independently selected from $R^X$;

each $R^3$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —$NO_2$, —$NR^{A2}R^{B2}$, —$OR^{A2}$, —$SR^{A2}$, —$S(O)_rR^{A2}$, —$S(O)_2OR^{A2}$, —$OS(O)_2R^{B2}$, —$S(O)_rNR^{A2}R^{B2}$, —$P(O)R^{A2}R^{B2}$, —$P(O)(OR^{A2})(OR^{B2})$, —$(CR^{C2}R^{D2})_tNR^{A2}R^{B2}$, —$(CR^{C2}R^{D2})_tOR^{B2}$, —$(CR^{C2}R^{D2})_t$ $SR^{B2}$, —$(CR^{C2}R^{D2})_tS(O)_rR^{B2}$, —$(CR^{C2}R^{D2})_t$ $P(O)R^{A2}R^{B2}$, —$(CR^{C2}R^{D2})_tP(O)(OR^{A2})(OR^{B2})$, —$(CR^{C2}R^{D2})_tCO_2R^{B2}$, —$(CR^{C2}R^{D2})_tC(O)NR^{A2}R^{B2}$, —$(CR^{C2}R^{D2})_tNR^{A2}C(O)R^{B2}$, —$(CR^{C2}R^{D2})_tNR^{A2}CO_2R^{B2}$, —$(CR^{C2}R^{D2})_tOC(O)NR^{A2}R^{B2}$, —$(CR^{C2}R^{D2})_tNR^{A2}CONR^{A2}R^{B2}$, —$(CR^{C2}R^{D2})_tNR^{A2}SO_2NR^{A2}R^{B2}$, —$NR^{A2}(CR^{C2}R^{D2})_tNR^{A2}R^{B2}$, —$O(CR^{C2}R^{D2})_tNR^{A2}R^{B2}$, —$S(CR^{C2}R^{D2})_tNR^{A2}R^{B2}$, —$S(O)_r(CR^{C2}R^{D2})_tNR^{A2}R^{B2}$, —$C(O)R^{A2}$, —$C(O)(CR^{C2}R^{D2})_tNR^{A2}R^{B2}$, —$C(O)(CR^{C2}R^{D2})_tOR^{B2}$, —$C(O)(CR^{C2}R^{D2})_tSR^{B2}$, —$C(O)(CR^{C2}R^{D2})_tS(O)_rR^{B2}$, —$CO_2R^{B2}$, —$CO_2(CR^{C2}R^{D2})_tC(O)NR^{A2}R^{B2}$, —$OC(O)R^{A2}$, —CN, —$C(O)NR^{A2}R^{B2}$, —$NR^{A2}C(O)R^{B2}$, —$NR^{A2}CO_2R^{B2}$, —$OC(O)NR^{A2}R^{B2}$, —$NR^{A2}C(O)NR^{A2}R^{B2}$, —$NR^{A2}S(O)_rR^{B2}$, —$CR^{A2}(=N—OR^{B2})$, —$C(=NR^{E2})R^{A2}$, —$C(=NR^{E2})NR^{A2}R^{B2}$, —$NR^{A2}C(=NR^{E2})NR^{A2}R^{B2}$, —$CHF_2$, —$CF_3$, —$OCHF_2$, and —$OCF_3$, wherein alkyl, alkenyl, alkynyl, cycloalkyl, heterocyclyl, aryl and heteroaryl are each unsubstituted or substituted with at least one substituent, such as one, two, three, or four substituents, independently selected from $R^X$;

or two $R^3$ together with the carbon atoms to which they are attached form a cyclic ring of 3 to 7 members containing 0, 1, or 2 additional heteroatoms independently selected from oxygen, sulfur and nitrogen, and optionally substituted with 1, 2 or 3 $R^X$ groups;

$R^4$ is selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —$NO_2$, —$NR^{A3}R^{B3}$, —$OR^{A3}$, —$SR^{A3}$, —$S(O)_rR^{A3}$, —$S(O)_2OR^{A3}$, —$OS(O)_2R^{B3}$, —$S(O)_rNR^{A3}R^{B3}$, —$P(O)R^{A3}R^{B3}$, —$P(O)(OR^{A3})(OR^{B3})$, —$(CR^{C3}R^{D3})_tNR^{A3}R^{B3}$, —$(CR^{C3}R^{D3})_tOR^{B3}$, —$(CR^{C3}R^{D3})_tSR^{B3}$, —$(CR^{C3}R^{D3})_tS(O)_rR^{B3}$, —$(CR^{C3}R^{D3})_tP(O)R^{A3}R^{B3}$, —$(CR^{C3}R^{D3})_tP(O)(OR^{A3})(OR^{B3})$, —$(CR^{C3}R^{D3})_tCO_2R^{B3}$, —$(CR^{C3}R^{D3})_tC(O)NR^{A3}R^{B3}$, —$(CR^{C3}R^{D3})_tNR^{A3}C(O)R^{B3}$, —$(CR^{C3}R^{D3})_tNR^{A3}CO_2R^{B3}$, —$(CR^{C3}R^{D3})_tOC(O)NR^{A3}R^{B3}$, —$(CR^{C3}R^{D3})_tNR^{A3}CONR^{A3}R^{B3}$, —$(CR^{C3}R^{D3})_tNR^{A3}SO_2NR^{A3}R^{B3}$, —$NR^{A3}(CR^{C3}R^{D3})_tNR^{A3}R^{B3}$, —$O(CR^{C3}R^{D3})_tNR^{A3}R^{B3}$, —$S(CR^{C3}R^{D3})_tNR^{A3}R^{B3}$, —$S(O)_r(CR^{C3}R^{D3})_tNR^{A3}R^{B3}$, —$C(O)R^{A3}$, —$C(O)(CR^{C3}R^{D3})_tNR^{A3}R^{B3}$, —$C(O)(CR^{C3}R^{D3})_tOR^{B3}$, —$C(O)(CR^{C3}R^{D3})_tSR^{B3}$, —$C(O)(CR^{C3}R^{D3})_tS(O)_rR^{B3}$, —$CO_2R^{B3}$, —$CO_2(CR^{C3}R^{D3})_tC(O)NR^{A3}R^{B3}$, —$OC(O)R^{A3}$, —CN, —$C(O)NR^{A3}R^{B3}$, —$NR^{A3}C(O)R^{B3}$, —$NR^{A3}CO_2R^{B3}$, —$OC(O)NR^{A3}R^{B3}$, —$NR^{A3}C(O)NR^{A3}R^{B3}$, —$NR^{A3}S(O)_rR^{B3}$, —$CR^{A3}(=N—OR^{B3})$, —$C(=NR^{E3})R^{A3}$, —$C(=NR^{E3})NR^{A3}R^{B3}$, —$NR^{A3}C(=NR^{E3})NR^{A3}R^{B3}$, —$CHF_2$, —$CF_3$, —$OCHF_2$, and —$OCF_3$, wherein alkyl, alkenyl, alkynyl, cycloalkyl, heterocyclyl, aryl and heteroaryl are each unsubstituted or substituted with at least one substituent, such as one, two, three, or four substituents, independently selected from $R^X$;

each $R^5$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$alkyl, aryl, aryl-$C_{1-4}$ alkyl, heteroaryl, heteroaryl-$C_{1-4}$ alkyl, —$NO_2$, —$NR^{A4}R^{B4}$, —$OR^{A4}$, —$SR^{A4}$, —S(O)$_r$R$^{A4}$, —S(O)$_2$OR$^{A4}$, —OS(O)$_2$R$^{B4}$, —S(O)$_r$NR$^{A4}$R$^{B4}$, —P(O)R$^{A4}$R$^{B4}$, —P(O)(OR$^{A4}$)(OR$^{B4}$), —(CR$^{C4}$R$^{D4}$)$_t$NR$^{A4}$R$^{B4}$, —(CR$^{C4}$R$^{D4}$)$_t$OR$^{B4}$, —(CR$^{C4}$R$^{D4}$)$_t$SR$^{B4}$, —(CR$^{C4}$R$^{D4}$)$_t$S(O)$_r$R$^{B4}$, —(CR$^{C4}$R$^{D4}$)$_t$P(O)R$^{A4}$R$^{B4}$, —(CR$^{C4}$R$^{D4}$)$_t$P(O)(OR$^{A4}$)(OR$^{B4}$), —(CR$^{C4}$R$^{D4}$)$_t$CO$_2$R$^{B4}$, —(CR$^{C4}$R$^{D4}$)$_t$C(O)NR$^{A4}$R$^{B4}$, —(CR$^{C4}$R$^{D4}$)$_t$NR$^{A4}$C(O)R$^{B4}$, —(CR$^{C4}$R$^{D4}$)$_t$NR$^{A4}$CO$_2$R$^{B4}$, —(CR$^{C4}$R$^{D4}$)$_t$OC(O)NR$^{A4}$R$^{B4}$, —(CR$^{C4}$R$^{D4}$)$_t$NR$^{A4}$CONR$^{A4}$R$^{B4}$, —(CR$^{C4}$R$^{D4}$)$_t$NR$^{A4}$SO$_2$NR$^{A4}$R$^{B4}$, —NR$^{A4}$(CR$^{C4}$R$^{D4}$)$_t$NR$^{A4}$R$^{B4}$, —O(CR$^{C4}$R$^{D4}$)$_t$NR$^{A4}$R$^{B4}$, —S(CR$^{C4}$R$^{D4}$)$_t$NR$^{A4}$R$^{B4}$, —S(O)$_r$(CR$^{C4}$R$^{D4}$)$_t$NR$^{A4}$R$^{B4}$, —C(O)R$^{A4}$, —C(O)(CR$^{C4}$R$^{D4}$)$_t$NR$^{A4}$R$^{B4}$, —C(O)(CR$^{C4}$R$^{D4}$)$_t$OR$^{B4}$, —C(O)(CR$^{C4}$R$^{D4}$)$_t$SR$^{B4}$, —C(O)(CR$^{C4}$R$^{D4}$)$_t$S(O)$_r$R$^{B4}$, —CO$_2$R$^{B4}$, —CO$_2$(CR$^{C4}$R$^{D4}$)$_t$C(O)NR$^{A4}$R$^{B4}$, —OC(O)R$^{A4}$, —CN, —C(O)NR$^{A4}$R$^{B4}$, —NR$^{A4}$C(O)R$^{B4}$, —NR$^{A4}$CO$_2$R$^{B4}$, —OC(O)NR$^{A4}$R$^{B4}$, —NR$^{A4}$C(O)NR$^{A4}$R$^{B4}$, —NR$^{A4}$S(O)$_r$R$^{B4}$, —CR$^{A4}$(=N—OR$^{B4}$), —C(=NR$^{E4}$)R$^{A4}$, —C(=NR$^{E4}$)NR$^{A4}$R$^{B4}$, —NR$^{A4}$C(=NR$^{E4}$)NR$^{A4}$R$^{B4}$, —CHF$_2$, —CF$_3$, —OCHF$_2$, and —OCF$_3$, wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

each R$^6$ is independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, —NO$_2$, —NR$^{A5}$R$^{B5}$, —OR$^{A5}$, —SR$^{A5}$, —S(O)$_r$R$^{A5}$, —S(O)$_2$OR$^{A5}$, —OS(O)$_2$R$^{B5}$, —S(O)$_r$NR$^{A5}$R$^{B5}$, —P(O)R$^{A5}$R$^{B5}$, —P(O)(OR$^{A5}$)(OR$^{B5}$), —(CR$^{C5}$R$^{D5}$)$_t$NR$^{A5}$R$^{B5}$, —(CR$^{C5}$R$^{D5}$)$_t$OR$^{B5}$, —(CR$^{C5}$R$^{D5}$)$_t$SR$^{B5}$, —(CR$^{C5}$R$^{D5}$)$_t$S(O)$_r$R$^{B5}$, —(CR$^{C5}$R$^{D5}$)$_t$P(O)R$^{A5}$R$^{B5}$, —(CR$^{C5}$R$^{D5}$)$_t$P(O)(OR$^{A5}$)(OR$^{B5}$), —(CR$^{C5}$R$^{D5}$)$_t$CO$_2$R$^{B5}$, —(CR$^{C5}$R$^{D5}$)$_t$C(O)NR$^{A5}$R$^{B5}$, —(CR$^{C5}$R$^{D5}$)$_t$NR$^{A5}$C(O)R$^{B5}$, —(CR$^{C5}$R$^{D5}$)$_t$NR$^{A5}$CO$_2$R$^{B5}$, —(CR$^{C5}$R$^{D5}$)$_t$OC(O)NR$^{A5}$R$^{B5}$, —(CR$^{C5}$R$^{D5}$)$_t$NR$^{A5}$CONR$^{A5}$R$^{B5}$, —(CR$^{C5}$R$^{D5}$)$_t$NR$^{A5}$SO$_2$NR$^{A5}$R$^{B5}$, —NR$^{A5}$(CR$^{C5}$R$^{D5}$)$_t$NR$^{A5}$R$^{B5}$, —O(CR$^{C5}$R$^{D5}$)$_t$NR$^{A5}$R$^{B5}$, —S(CR$^{C5}$R$^{D5}$)$_t$NR$^{A5}$R$^{B5}$, —S(O)$_r$(CR$^{C5}$R$^{D5}$)$_t$NR$^{A5}$R$^{B5}$, —C(O)R$^{A5}$, —C(O)(CR$^{C5}$R$^{D5}$)$_t$NR$^{A5}$R$^{B5}$, —C(O)(CR$^{C5}$R$^{D5}$)$_t$OR$^{B5}$, —C(O)(CR$^{C5}$R$^{D5}$)$_t$SR$^{B5}$, —C(O)(CR$^{C5}$R$^{D5}$)$_t$S(O)$_r$R$^{B5}$, —CO$_2$R$^{B5}$, —CO$_2$(CR$^{C5}$R$^{D5}$)$_t$C(O)NR$^{A5}$R$^{B5}$, —OC(O)R$^{A5}$, —CN, —C(O)NR$^{A5}$R$^{B5}$, —NR$^{A5}$C(O)R$^{B5}$, —NR$^{A5}$CO$_2$R$^{B5}$, —OC(O)NR$^{A5}$R$^{B5}$, —NR$^{A5}$C(O)NR$^{A5}$R$^{B5}$, —NR$^{A5}$S(O)$_r$R$^{B5}$, —CR$^{A5}$(=N—OR$^{B5}$), —C(=NR$^{E5}$)R$^{A5}$, —C(=NR$^{E5}$)NR$^{A5}$R$^{B5}$, —NR$^{A5}$C(=NR$^{E5}$)NR$^{A5}$R$^{B5}$, —CHF$_2$, —CF$_3$, —OCHF$_2$, and —OCF$_3$, wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

each R$^{A1}$, R$^{A2}$, R$^{A3}$, R$^{A4}$, R$^{A5}$, R$^{B1}$, R$^{B2}$, R$^{B3}$, R$^{B4}$, and R$^{B5}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

or each "R$^{A1}$ and R$^{B1}$", "R$^{A2}$ and R$^{B2}$", "R$^{A3}$ and R$^{B3}$", "R$^{A4}$ and R$^{B4}$", and "R$^{A5}$ and R$^{B5}$", together with the atom(s) to which they are attached form a heterocyclic ring of 4 to 12 members containing 0, 1, or 2 additional heteroatoms independently selected from oxygen, sulfur and nitrogen, and optionally substituted with 12, or 3 R$^X$ groups;

each R$^{C1}$, R$^{C2}$, R$^{C3}$, R$^{C4}$, R$^{C5}$, R$^{D1}$, R$^{D2}$, R$^{D3}$, R$^{D4}$, and R$^{D5}$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

or "R$^{C1}$ and R$^{D1}$", "R$^{C2}$ and R$^{D2}$", "R$^{C3}$ and R$^{D3}$", "R$^{C4}$ and R$^{D4}$", and "R$^{C5}$ and R$^{D5}$" together with the carbon atom(s) to which they are attached form a ring of 3 to 12 members containing 0, 1, or 2 heteroatoms independently selected from oxygen, sulfur and nitrogen, and optionally substituted with 12, or 3 R$^X$ groups;

each R$^{E1}$, R$^{E2}$, R$^{E3}$, R$^{E4}$, and R$^{E5}$ is independently selected from hydrogen, C$_{1-10}$ alkyl, CN, NO$_2$, OR$^{a2}$, SR$^{a2}$, —S(O)$_r$R$^{a2}$, —C(O)R$^{a2}$, —S(O)$_r$NR$^{a2}$R$^{b2}$, and —C(O)NR$^{a2}$R$^{b2}$;

each R$^X$ is independently selected from C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, halogen, —NO$_2$, —NR$^{a1}$R$^{b1}$, —OR$^{a1}$, —SR$^{a1}$, —S(O)$_r$R$^{a1}$, —S(O)$_2$OR$^{a1}$, —OS(O)$_2$R$^{b1}$, —S(O)$_r$NR$^{a1}$R$^{b1}$, —P(O)R$^{a1}$R$^{b1}$, —P(O)(OR$^{a1}$)(OR$^{b1}$), —(CR$^{c1}$R$^{d1}$)$_t$NR$^{a1}$R$^{b1}$, —(CR$^{c1}$R$^{d1}$)$_t$OR$^{b1}$, —(CR$^{c1}$R$^{d1}$)$_t$SR$^{b1}$, —(CR$^{c1}$R$^{d1}$)$_t$S(O)$_r$R$^{b1}$, —(CR$^{c1}$R$^{d1}$)$_t$P(O)R$^{a1}$R$^{b1}$, —(CR$^{c1}$R$^{d1}$)$_t$P(O)(OR$^{a1}$)(OR$^{b1}$), —(CR$^{c1}$R$^{d1}$)$_t$CO$_2$R$^{b1}$, —(CR$^{c1}$R$^{d1}$)$_t$C(O)NR$^{a1}$R$^{b1}$, —(CR$^{c1}$R$^{d1}$)$_t$NR$^{a1}$C(O)R$^{b1}$, —(CR$^{c1}$R$^{d1}$)$_t$NR$^{a1}$CO$_2$R$^{b1}$, —(CR$^{c1}$R$^{d1}$)$_t$OC(O)NR$^{a1}$R$^{b1}$, —(CR$^{c1}$R$^{d1}$)$_t$NR$^{a1}$C(O)NR$^{a1}$R$^{b1}$, —(CR$^{c1}$R$^{d1}$)$_t$NR$^{a1}$SO$_2$NR$^{a1}$R$^{b1}$, —NR$^{a1}$(CR$^{c1}$R$^{d1}$)$_t$NR$^{a1}$R$^{b1}$, —O(CR$^{c1}$R$^{d1}$)$_t$NR$^{a1}$R$^{b1}$, —S(CR$^{c1}$R$^{d1}$)$_t$NR$^{a1}$R$^{b1}$, —S(O)$_r$(CR$^{c1}$R$^{d1}$)$_t$NR$^{a1}$R$^{b1}$, —C(O)R$^{a1}$, —C(O)(CR$^{c1}$R$^{d1}$)$_t$NR$^{a1}$R$^{b1}$, —C(O)(CR$^{c1}$R$^{d1}$)$_t$OR$^{b1}$, —C(O)(CR$^{c1}$R$^{d1}$)$_t$SR$^{b1}$, —C(O)(CR$^{c1}$R$^{d1}$)$_t$S(O)$_r$R$^{b1}$, —CO$_2$R$^{b1}$, —CO$_2$(CR$^{c1}$R$^{d1}$)$_t$C(O)NR$^{a1}$R$^{b1}$, —OC(O)R$^{a1}$, —CN, —C(O)NR$^{a1}$R$^{b1}$, —NR$^{a1}$C(O)R$^{b1}$, —OC(O)NR$^{a1}$R$^{b1}$, —NR$^{a1}$C(O)OR$^{b1}$, —NR$^{a1}$C(O)NR$^{a1}$R$^{b1}$, —NR$^{a1}$S(O)$_r$R$^{b1}$, —CR$^{a1}$(=N—OR$^{b1}$), —C(=NR$^{e1}$)R$^{a1}$, —C(=NR$^{e1}$)NR$^{a1}$R$^{b1}$, —NR$^{a1}$C(=NR$^{e1}$)NR$^{a1}$R$^{b1}$, —CHF$_2$, —CF$_3$, —OCHF$_2$, and —OCF$_3$, wherein alkyl, alkenyl, alkynyl, cycloalkyl, heterocyclyl, aryl and heteroaryl are each unsubstituted or substituted with at least one substituent, such as one, two, three, or four substituents, independently selected from R$^Y$;

each R$^{a1}$ and each R$^{b1}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from R$^Y$;

or R$^{a1}$ and R$^{b1}$ together with the atom(s) to which they are attached form a heterocyclic ring of 4 to 12 members containing 0, 1, or 2 additional heteroatoms independently selected from oxygen, sulfur and nitrogen, and optionally substituted with 12, or 3 R$^Y$ groups;

each R$^{c1}$ and each R$^{d1}$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from $R^Y$;

or $R^{c1}$ and $R^{d1}$ together with the carbon atom(s) to which they are attached form a ring of 3 to 12 members containing 0, 1, or 2 heteroatoms independently selected from oxygen, sulfur and nitrogen, and optionally substituted with 1, 2, or 3 $R^Y$ groups;

each $R^{e1}$ is independently selected from hydrogen, $C_{1-10}$ alkyl, CN, $NO_2$, $OR^{a2}$, $SR^{a2}$, —$S(O)_rR^{a2}$, —$C(O)R^{a2}$, —$S(O)_rNR^{a2}R^{b2}$, and —$C(O)NR^{a2}R^{b2}$;

$R^Y$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, —$NO_2$, —$NR^{a2}R^{b2}$, —$OR^{a2}$, —$SR^{a2}$, —$S(O)_rR^{a2}$, —$S(O)_2OR^{a2}$, —$OS(O)_2R^{b2}$, —$S(O)_rNR^{a2}R^{b2}$, —$P(O)R^{a2}R^{b2}$, —$P(O)(OR^{a2})(OR^{b2})$, —$(CR^{c2}R^{d2})_rNR^{a2}R^{b2}$, —$(CR^{c2}R^{d2})_rOR^{b2}$, —$(CR^{c2}R^{d2})_rSR^{b2}$, —$(CR^{c2}R^{d2})_rS(O)_rR^{b2}$, —$(CR^{c2}R^{d2})_rP(O)R^{a2}R^{b2}$, —$(CR^{c2}R^{d2})_rP(O)(OR^{a2})(OR^{b2})$, —$(CR^{c2}R^{d2})_tCO_2R^{b2}$, —$(CR^{c2}R^{d2})_rC(O)NR^{a2}R^{b2}$, —$(CR^{c2}R^{d2})_rNR^{a2}C(O)R^{b2}$, —$(CR^{c2}R^{d2})_rNR^{a2}CO_2R^{b2}$, —$(CR^{c2}R^{d2})_rOC(O)NR^{a2}R^{b2}$, —$(CR^{c2}R^{d2})_rNR^{a2}C(O)NR^{a2}R^{b2}$, —$(CR^{c2}R^{d2})_rNR^{a2}SO_2NR^{a2}R^{b2}$, —$NR^{a2}(CR^{c2}R^{d2})_rNR^{a2}R^{b2}$, —$O(CR^{c2}R^{d2})_rNR^{a2}R^{b2}$, —$S(CR^{c2}R^{d2})_rNR^{a2}R^{b2}$, —$S(O)_r(CR^{c2}R^{d2})_rNR^{a2}R^{b2}$, —$C(O)R^{a2}$, —$C(O)(CR^{c2}R^{d2})_rOR^{b2}$, —$C(O)(CR^{c2}R^{d2})_rNR^{a2}R^{b2}$, —$C(O)(CR^{c2}R^{d2})_rSR^{b2}$, —$C(O)(CR^{c2}R^{d2})_rS(O)_rR^{b2}$, —$CO_2R^{b2}$, —$CO_2(CR^{c2}R^{d2})_tC(O)NR^{a2}R^{b2}$, —$OC(O)R^{a2}$, —CN, —$C(O)NR^{a2}R^{b2}$, —$NR^{a2}C(O)R^{b2}$, —$OC(O)NR^{a2}R^{b2}$, —$NR^{a2}C(O)OR^{b2}$, —$NR^{a2}C(O)NR^{a2}R^{b2}$, —$NR^{a2}S(O)_rR^{b2}$, —$CR^{a2}(=N—OR^{b2})$, —$C(=NR^{e2})R^{a2}$, —$C(=NR^{e2})NR^{a2}R^{b2}$, —$NR^{a2}C(=NR^{e2})NR^{a2}R^{b2}$, —$CHF_2$, —$CF_3$, —$OCHF_2$, and —$OCF_3$, wherein alkyl, alkenyl, alkynyl, cycloalkyl, heterocyclyl, aryl and heteroaryl are each unsubstituted or substituted with at least one substituent, such as one, two, three, or four substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkylamino);

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkylamino), heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, and di($C_{1-10}$ alkylamino);

or $R^{a2}$ and $R^{b2}$ together with the atom(s) to which they are attached form a heterocyclic ring of 4 to 12 members containing 0, 1, or 2 additional heteroatoms independently selected from oxygen, sulfur and nitrogen, and optionally substituted with 1 or 2 substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, and di($C_{1-10}$ alkylamino);

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkylamino), heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, and di($C_{1-10}$ alkylamino);

or $R^{c2}$ and $R^{d2}$ together with the carbon atom(s) to which they are attached form a ring of 3 to 12 members containing 0, 1, or 2 heteroatoms independently selected from oxygen, sulfur and nitrogen, and optionally substituted with 1 or 2 substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, and di($C_{1-10}$ alkylamino);

each $R^{e2}$ is independently selected from hydrogen, $C_{1-10}$ alkyl, CN and $NO_2$;

m is selected from 0, 1, 2, 3 and 4;

n is selected from 0, 1, and 2;

p is selected from 0, 1, 2 and 3;

q is selected from 1, 2, and 3;

each r is independently selected from 1 and 2;

each t is independently selected from 1, 2, 3 and 4.

2. A compound of 1 or a pharmaceutically acceptable salt thereof, wherein Q is heteroaryl.

3. A compound of 2 or a pharmaceutically acceptable salt thereof, wherein Q is selected from pyridinyl, pyrimidinyl, pyrazinyl, and pyridazinyl.

4. A compound of 3 or a pharmaceutically acceptable salt thereof, wherein Q is selected from pyridinyl and pyrimidinyl.

5. A compound of any one of 1 to 4 or a pharmaceutically acceptable salt thereof, wherein W is N.

6. A compound of any one of 1 to 4 or a pharmaceutically acceptable salt thereof, wherein W is $CR^6$.

7. A compound of 6 or a pharmaceutically acceptable salt thereof, wherein W is CH.

8. A compound of any one of 1 to 7 or a pharmaceutically acceptable salt thereof, wherein Z is selected from N and $CR^6$, wherein $R^6$ is selected from hydrogen and halogen.

9. A compound of 8 or a pharmaceutically acceptable salt thereof, wherein Z is selected from N, CH and CF.

10. A compound of any one of 1 to 9 or a pharmaceutically acceptable salt thereof, wherein $R^1$ is selected from heterocyclyl and heterocyclyl-$C_{1-4}$ alkyl, wherein alkyl and heterocyclyl are each unsubstituted or substituted with at least one substituent, such as one, two, three, or four substituents, independently selected from $R^X$.

11. A compound of 10 or a pharmaceutically acceptable salt thereof, wherein $R^1$ is selected from heterocyclyl and heterocyclyl-$C_{1-4}$ alkyl, wherein alkyl and heterocyclyl are each unsubstituted or substituted with at least one substituent independently selected from $C_{1-4}$ alkyl, $C_{3-10}$ cycloalkyl, $C_{3-10}$ cycloalkyl-$C_{1-4}$ alkyl, halogen, —$NR^{a1}R^{b1}$, —$OR^{a1}$, —$S(O)_rR^{a1}$, —$S(O)_rNR^{a1}R^{b1}$, —$(CR^{c1}R^{d1})_rNR^{a1}R^{b1}$, and —$(CR^{c1}R^{d1})_rOR^{b1}$, wherein alkyl and cycloalkyl are each unsubstituted or substituted with at least one substituent independently selected from $R^Y$.

12. A compound of 11 or a pharmaceutically acceptable salt thereof, wherein $R^1$ is selected from

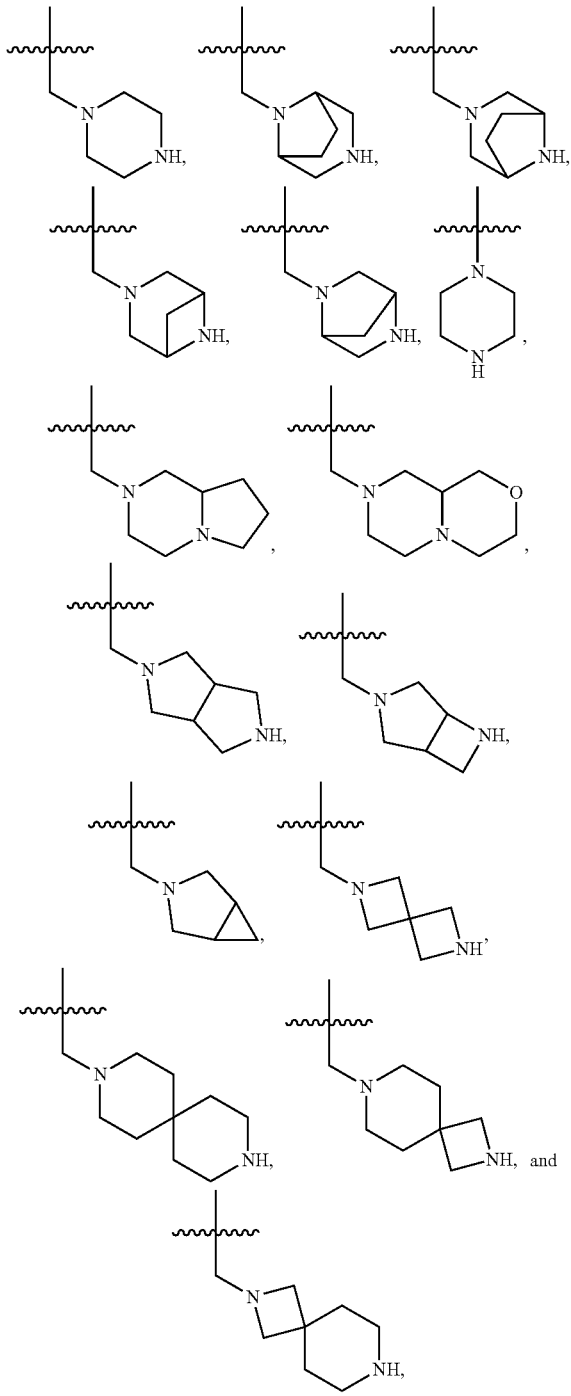

which are each unsubstituted or substituted with at least one substituent independently selected from methyl, ethyl, —NH$_2$ and —OH.

13. A compound of any one of 1 to 12 or a pharmaceutically acceptable salt thereof, wherein $R^2$ is hydrogen.

14. A compound of any one of 1 to 13 or a pharmaceutically acceptable salt thereof, wherein $R^3$ is selected from $C_{1-10}$ alkyl and $C_{3-10}$ cycloalkyl, or two $R^3$ together with the carbon atoms to which they are attached form a cyclic ring of 3 to 7 members, wherein alkyl and cycloalkyl are each unsubstituted or substituted with at least one substituent independently selected from $R^X$.

15. A compound of 14 or a pharmaceutically acceptable salt thereof, wherein $R^3$ is $C_{1-10}$ alkyl or two $R^3$ together with the carbon atoms to which they are attached form a 3-membered cyclic ring, wherein $C_{1-10}$ alkyl is unsubstituted or substituted with at least one substituent independently selected from $R^X$.

16. A compound of 15 or a pharmaceutically acceptable salt thereof, wherein $R^3$ is selected from methyl, hydroxymethyl, methoxymethyl, fluoromethyl, difluoromethyl and trifluoromethyl, or two $R^3$ together with the carbon atoms to which they are attached form a 3-membered cyclic ring.

17. A compound of any one of 1 to 16 or a pharmaceutically acceptable salt thereof, wherein $R^4$ is selected from halogen and CN.

18. A compound of any one of 1 to 17 or a pharmaceutically acceptable salt thereof, wherein $R^4$ is fluoro.

19. A compound of any one of 1 to 18 or a pharmaceutically acceptable salt thereof, wherein $R^5$ is hydrogen.

20. A compound of any one of 1 to 19 or a pharmaceutically acceptable salt thereof, wherein q is 1.

21. A compound, selected from
(S)-(5-fluoro-7-(5-fluoro-2-((5-(piperazin-1-ylmethyl)pyridin-2-yl)amino)pyrimidin-4-yl)-2,3-dihydro-1H-benzo[d]pyrrolo[1,2-a]imidazol-1-yl)methanol,
(S)-(5-fluoro-7-(5-fluoro-2-((5-((4-methylpiperazin-1-yl)methyl)pyridin-2-yl)amino)pyrimidin-4-yl)-2,3-dihydro-1H-benzo[d]pyrrolo[1,2-a]imidazol-1-yl)methanol,
(S)-(7-(2-((5-((4-ethylpiperazin-1-yl)methyl)pyridin-2-yl)amino)-5-fluoropyrimidin-4-yl)-5-fluoro-2,3-dihydro-1H-benzo[d]pyrrolo[1,2-a]imidazol-1-yl)methanol,
(S)-5-fluoro-4-(5-fluoro-1-(fluoromethyl)-2,3-dihydro-1H-benzo[d]pyrrolo[1,2-a]imidazo-7-yl)-N-(5-(piperazin-1-ylmethyl)pyridin-2-yl)pyrimidin-2-amine,
(S)-5-fluoro-4-(5-fluoro-1-(fluoromethyl)-2,3-dihydro-1H-benzo[d]pyrrolo[1,2-a]imidazo-7-yl)-N-(5-((4-methylpiperazin-1-yl)methyl)pyridin-2-yl)pyrimidin-2-amine,
(S)—N-(5-((4-ethylpiperazin-1-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine,
(S)-5-fluoro-4-(5-fluoro-1-(methoxymethyl)-2,3-dihydro-1H-benzo[d]pyrrolo[1,2-a]imidazol-7-yl)-N-(5-(piperazin-1-ylmethyl)pyridin-2-yl)pyrimidin-2-amine,
(S)-5-fluoro-4-(5-fluoro-1-(methoxymethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine,
(S)—N-(5-((4-ethylpiperazin-1-yl)methyl)pyridin-2-yl)-5-fluoro-4-(5-fluoro-1-(methoxymethyl)-2,3-dihydro-1H-benzo[d]pyrrolo[1,2-a]imidazol-7-yl)pyrimidin-2-amine,
(S)-4-(1-(difluoromethyl)-5-fluoro-2,3-dihydro-1H-benzo[d]pyrrolo[1,2-a]imidazol-7-yl)-5-fluoro-N-(5-(piperazin-1-ylmethyl)pyridin-2-yl)pyrimidin-2-amine,
(S)-4-(1-(difluoromethyl)-5-fluoro-2,3-dihydro-1H-benzo[d]pyrrolo[1,2-a]imidazol-7-yl)-5-fluoro-N-(5-((4-methylpiperazin-1-yl)methyl)pyridin-2-yl)pyrimidin-2-amine,
(S)-4-(1-(difluoromethyl)-5-fluoro-2,3-dihydro-1H-benzo[d]pyrrolo[1,2-a]imidazol-7-yl)-N-(5-((4-ethylpiperazin-1-yl)methyl)pyridin-2-yl)-5-fluoropyrimidin-2-amine,
5-fluoro-4-(5-fluoro-2,3-dihydrospiro[benzo[d]pyrrolo[1,2-a]imidazole-1,1'-cyclopropan]-7-yl)-N-(5-(piperazin-1-ylmethyl)pyridin-2-yl)pyrimidin-2-amine, 5-fluoro-4-(5-fluoro-2,3-dihydrospiro[benzo[d]pyrrolo[1,2-a]imidazole-1,1'-cyclopropan]-7-yl)-N-(5-((4-methylpiperazin-1-yl)methyl)pyridin-2-yl)pyrimidin-2-amine, N-(5-((4-ethylpiperazin-1-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, (S)-5-fluoro-4-(5-fluoro-1-(trifluoromethyl)-2,3-dihydro-1H-benzo[d]pyrrolo[1,2-a]imidazol-7-yl)-N-(5-(piperazin-1-ylmethyl)pyridin-2-yl)pyrimidin-2-amine, (S)-5-fluoro-4-(5-fluoro-1-(trifluoromethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine, (S)—N-(5-((4-ethylpiperazin-1-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, 5-fluoro-4-((S)-5-fluoro-1-(fluoromethyl)-2,3-dihydro-1H-benzo[d]pyrrolo[1,2-a]imidazo-7-yl)-N-(5-(((R)-hexahydropyrrolo[1,2-a]pyrazin-2(1H)-yl)methyl)pyridin-2-yl)pyrimidin-2-amine, (S)—N-(5-((2,7-diazaspiro[3.5]nonan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine, (S)-5-fluoro-4-(5-fluoro-1-(fluoromethyl)-2,3-dihydro-1H-benzo[d]pyrrolo[1,2-a]imidazo-7-yl)-N-(5-((7-methyl-2,7-diazaspiro[3.5]nonan-2-yl)methyl)pyridin-2-yl)pyrimidin-2-amine, (S)—N-(5-((7-ethyl-2,7-diazaspiro[3.5]nonan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine, (S)—N-(5-((2,6-diazaspiro[3.3]heptan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine, (S)-5-fluoro-4-(5-fluoro-1-(fluoromethyl)-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine, (S)—N-(5-((6-ethyl-2,6-diazaspiro[3.3]heptan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine, 5-fluoro-4-((S)-5-fluoro-1-(fluoromethyl)-2,3-dihydro-1H-benzo[d]pyrrolo[1,2-a]imidazo-7-yl)-N-(5-((hexahydropyrrolo[3,4-c]pyrrol-2(1H)-yl)methyl)pyridin-2-yl)pyrimidin-2-amine, 5-fluoro-4-((S)-5-fluoro-1-(fluoromethyl)-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine, N-(5-((5-ethylhexahydropyrrolo[3,4-c]pyrrol-2(1H)-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine, (S)—N-(5-((3,9-diazaspiro[5.5]undecan-3-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine, (S)-5-fluoro-4-(5-fluoro-1-(fluoromethyl)-2,3-dihydro-1H-benzo[d]pyrrolo[1,2-a]imidazo-7-yl)-N-(5-((9-methyl-3,9-diazaspiro[5.5]undecan-3-yl)methyl)pyridin-2-yl)pyrimidin-2-amine, (S)—N-(5-((9-ethyl-3,9-diazaspiro[5.5]undecan-3-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine, N-(5-((3,8-diazabicyclo[3.2.1]octan-8-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine, 5-fluoro-4-((S)-5-fluoro-1-(fluoromethyl)-2,3-dihydro-1H-benzo[d]pyrrolo[1,2-a]imidazo-7-yl)-N-(5-((3-methyl-3,8-diazabicyclo[3.2.1]octan-8-yl)methyl)pyridin-2-yl)pyrimidin-2-amine, N-(5-((3-ethyl-3,8-diazabicyclo[3.2.1]octan-8-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine, N-(5-((3,8-diazabicyclo[3.2.1]octan-3-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine, 5-fluoro-4-((S)-5-fluoro-1-(fluoromethyl)-2,3-dihydro-1H-benzo[d]pyrrolo[1,2-a]imidazo-7-yl)-N-(5-((8-methyl-3,8-diazabicyclo[3.2.1]octan-3-yl)methyl)pyridin-2-yl)pyrimidin-2-amine, N-(5-((8-ethyl-3,8-diazabicyclo[3.2.1]octan-3-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine, (S)-4-(1-(difluoromethyl)-5-fluoro-2,3-dihydro-1H-benzo[d]pyrrolo[1,2-a]imidazol-7-yl)-5-fluoro-N-(5-(piperazin-1-yl)pyridin-2-yl)pyrimidin-2-amine, (S)-4-(1-(difluoromethyl)-5-fluoro-2,3-dihydro-1H-benzo[d]pyrrolo[1,2-a]imidazol-7-yl)-5-fluoro-N-(5-(4-methylpiperazin-1-yl)pyridin-2-yl)pyrimidin-2-amine, (S)-4-(1-(difluoromethyl)-5-fluoro-2,3-dihydro-1H-benzo[d]pyrrolo[1,2-a]imidazol-7-yl)-N-(5-(4-ethylpiperazin-1-yl)pyridin-2-yl)-5-fluoropyrimidin-2-amine, 4-((S)-1-(difluoromethyl)-5-fluoro-2,3-dihydro-1H-benzo[d]pyrrolo[1,2-a]imidazol-7-yl)-5-fluoro-N-(5-(((R)-hexahydropyrrolo[1,2-a]pyrazin-2(1H)-yl)methyl)pyridin-2-yl)pyrimidin-2-amine, (S)—N-(5-((2,7-diazaspiro[3.5]nonan-2-yl)methyl)pyridin-2-yl)-4-(1-(difluoromethyl)-5-fluoro-2,3-dihydro-1H-benzo[d]pyrrolo[1,2-a]imidazol-7-yl)-5-fluoropyrimidin-2-amine, (S)-4-(1-(difluoromethyl)-5-fluoro-2,3-dihydro-1H-benzo[d]pyrrolo[1,2-a]imidazol-7-yl)-5-fluoro-N-(5-((7-methyl-2,7-diazaspiro[3.5]nonan-2-yl)methyl)pyridin-2-yl)pyrimidin-2-amine, (S)-4-(1-(difluoromethyl)-5-fluoro-2,3-dihydro-1H-benzo[d]pyrrolo[1,2-a]imidazol-7-yl)-N-(5-((7-ethyl-2,7-diazaspiro[3.5]nonan-2-yl)methyl)pyridin-2-yl)-5-fluoropyrimidin-2-amine, (S)—N-(5-((2,6-diazaspiro[3.3]heptan-2-yl)methyl)pyridin-2-yl)-4-(1-(difluoromethyl)-5-fluoro-2,3-dihydro-1H-benzo[d]pyrrolo[1,2-a]imidazol-7-yl)-5-fluoropyrimidin-2-amine, (S)-4-(1-(difluoromethyl)-5-fluoro-2,3-dihydro-1H-benzo[d]pyrrolo[1,2-a]imidazol-7-yl)-5-fluoro-N-(5-((6-methyl-2,6-diazaspiro[3.3]heptan-2-yl)methyl)pyridin-2-yl)pyrimidin-2-amine, (S)-4-(1-(difluoromethyl)-5-fluoro-2,3-dihydro-1H-benzo[d]pyrrolo[1,2-a]imidazol-7-yl)-N-(5-((6-ethyl-2,6-diazaspiro[3.3]heptan-2-yl)methyl)pyridin-2-yl)-5-fluoropyrimidin-2-amine, 4-((S)-1-(difluoromethyl)-5-fluoro-2,3-dihydro-1H-benzo[d]pyrrolo[1,2-a]imidazol-7-yl)-5-fluoro-N-(5-((hexahydropyrrolo[3,4-c]pyrrol-2(1H)-yl)methyl)pyridin-2-yl)pyrimidin-2-amine, 4-((S)-1-(difluoromethyl)-5-fluoro-2,3-dihydro-1H-benzo[d]pyrrolo[1,2-a]imidazol-7-yl)-5-fluoro-N-(5-((5-methylhexahydropyrrolo[3,4-c]pyrrol-2(1H)-yl)methyl)pyridin-2-yl)pyrimidin-2-amine, 4-((S)-1-(difluoromethyl)-5-fluoro-2,3-dihydro-1H-benzo[d]pyrrolo[1,2-a]imidazol-7-yl)-N-(5-((5-ethylhexahydropyrrolo[3,4-c]pyrrol-2(1H)-yl)methyl)pyridin-2-yl)-5-fluoropyrimidin-2-amine, (S)—N-(5-((3,9-diazaspiro[5.5]undecan-3-yl)methyl)pyridin-2-yl)-4-(1-(difluoromethyl)-5-fluoro-2,3-dihydro-1H-benzo[d]pyrrolo[1,2-a]imidazol-7-yl)-5-fluoropyrimidin-2-amine, (S)-4-(1-(difluoromethyl)-5-fluoro-2,3-dihydro-1H-benzo[d]pyrrolo[1,2-a]imidazol-7-yl)-5-fluoro-N-(5-((9-methyl-3,9-diazaspiro[5.5]undecan-3-yl)methyl)pyridin-2-yl)pyrimidin-2-amine, (S)-4-(1-(difluoromethyl)-5-fluoro-2,3-dihydro-1H-benzo[d]pyrrolo[1,2-a]imidazol-7-yl)-N-(5-((9-ethyl-3,9-diazaspiro[5.5]undecan-3-yl)methyl)pyridin-2-yl)-5-fluoropyrimidin-2-amine, N-(5-((3,8-diazabicyclo[3.2.1]octan-8-yl)methyl)pyridin-2-yl)-4-((S)-1-(difluoromethyl)-5-fluoro-2,3-dihydro-1H-benzo[d]pyrrolo[1,2-a]imidazol-7-yl)-5-fluoropyrimidin-2-amine, 4-((S)-1-(difluoromethyl)-5-fluoro-2,3-dihydro-1H-benzo[d]pyrrolo[1,2-a]imidazol-7-yl)-5-fluoro-N-(5-((3-methyl-3,8-diazabicyclo[3.2.1]octan-8-yl)methyl)pyridin-2-yl)pyrimidin-2-amine, 4-((S)-1-(difluoromethyl)-5-fluoro-2,3-dihydro-1H-benzo[d]pyrrolo[1,2-a]imidazol-7-yl)-N-(5-((3-ethyl-3,8-diazabicyclo[3.2.1]octan-8-yl)methyl)pyridin-2-yl)-5-fluoropyrimidin-2-amine, N-(5-((3,8-diazabicyclo[3.2.1]octan-3-yl)methyl)pyridin-2-yl)-4-((S)-1-(difluoromethyl)-5-fluoro-2,3-dihydro-1H-benzo[d]pyrrolo[1,2-a]imidazol-7-yl)-5-fluoropyrimidin-2-amine, 4-((S)-1-(difluoromethyl)-5-fluoro-2,3-dihydro-1H-benzo[d]pyrrolo[1,2-a]imidazol-7-yl)-5-fluoro-N-(5-((8-methyl-3,8-diazabicyclo[3.2.1]octan-3-yl)methyl)pyridin-2-yl)pyrimidin-2-amine, 4-((S)-1-(difluoromethyl)-5-fluoro-2,3-dihydro-1H-benzo[d]pyrrolo[1,2-a]imidazol-7-yl)-N-(5-((8-ethyl-3,8-diazabicyclo[3.2.1]octan-3-yl)methyl)pyridin-2-yl)-5-fluoropyrimidin-2-amine, 5-fluoro-4-((S)-5-fluoro-1-(trifluoromethyl)-2,3-dihydro-1H-benzo[d]pyrrolo[1,2-a]imidazol-7-yl)-N-(5-(((R)-hexahydropyrrolo[1,2-a]pyrazin-2(1H)-yl)methyl)pyridin-2-yl)pyrimidin-2-amine, (S)—N-(5-((2,7-diazaspiro[3.5]nonan-2-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, (S)-5-fluoro-4-(5-fluoro-1-(trifluoromethyl)-2,3-dihydro-1H-benzo[d]pyrrolo[1,2-a]imidazol-7-yl)-N-(5-((7-methyl-2,7-diazaspiro[3.5]nonan-2-yl)methyl)pyridin-2-yl)pyrimidin-2-amine, (S)—N-(5-((7-ethyl-2,7-diazaspiro[3.5]nonan-2-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, (S)—N-(5-((2,7-diazaspiro[3.5]nonan-7-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, (S)-5-fluoro-4-(5-fluoro-1-(trifluoromethyl)-2,3-dihydro-1H-benzo[d]pyrrolo[1,2-a]imidazol-7-yl)-N-(5-((2-methyl-2,7-diazaspiro[3.5]nonan-7-yl)methyl)pyridin-2-yl)pyrimidin-2-amine, (S)—N-(5-((2-ethyl-2,7-diazaspiro[3.5]nonan-7-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, (S)—N-(5-((2,6-diazaspiro[3.3]heptan-2-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, (S)-5-fluoro-4-(5-fluoro-1-(trifluoromethyl)-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine, (S)—N-(5-((6-ethyl-2,6-diazaspiro[3.3]heptan-2-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, (S)—N-(5-((3,9-diazaspiro[5.5]undecan-3-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, (S)-5-fluoro-4-(5-fluoro-1-(trifluoromethyl)-2,3-dihydro-1H-benzo[d]pyrrolo[1,2-a]imidazol-7-yl)-N-(5-((9-methyl-3,9-diazaspiro[5.5]undecan-3-yl)methyl)pyridin-2-yl)pyrimidin-2-amine, (S)—N-(5-((9-ethyl-3,9-diazaspiro[5.5]undecan-3-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, 5-fluoro-4-((S)-5-fluoro-1-(trifluoromethyl)-2,3-dihydro-1H-benzo[d]pyrrolo[1,2-a]imidazol-7-yl)-N-(5-((hexahydropyrrolo[3,4-c]pyrrol-2(1H)-yl)methyl)pyridin-2-yl)pyrimidin-2-amine, 5-fluoro-4-((S)-5-fluoro-1-(trifluoromethyl)-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine, N-(5-((5-ethylhexahydropyrrolo[3,4-c]pyrrol-2(1H)-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine, N-(5-((3,8-diazabicyclo[3.2.1]octan-8-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine, 5-fluoro-4-((S)-5-fluoro-1-(trifluoromethyl)-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine, N-(5-((3-ethyl-3,8-diazabicyclo[3.2.1]octan-8-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine, N-(5-((3,8-diazabicyclo[3.2.1]octan-3-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine, 5-fluoro-4-((S)-5-fluoro-1-(trifluoromethyl)-2,3-dihydro-1H-benzo[d]pyrrolo[1,2-a]imidazol-7-yl)-N-(5-((8-methyl-3,8-diazabicyclo[3.2.1]octan-3-yl)methyl)pyridin-2-yl)pyrimidin-2-amine, N-(5-((8-ethyl-3,8-diazabicyclo[3.2.1]octan-3-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine, (R)-5-fluoro-4-(5-fluoro-1-methyl-2,3-dihydro-1H-benzo[d]pyrrolo[1,2-a]imidazol-7-yl)-N-(5-(piperazin-1-ylmethyl)pyridin-2-yl)pyrimidin-2-amine, (R)-5-fluoro-4-(5-fluoro-1-methyl-2,3-dihydro-1H-benzo[d]pyrrolo[1,2-a]imidazol-7-yl)-N-(5-((4-methylpiperazin-1-yl)methyl)pyridin-2-yl)pyrimidin-2-amine, (R)—N-(5-((4-ethylpiperazin-1-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, 5-fluoro-4-((R)-5-fluoro-1-methyl-2,3-dihydro-1H-benzo[d]pyrrolo[1,2-a]imidazol-7-yl)-N-(5-(((R)-hexahydropyrrolo[1,2-a]pyrazin-2(1H)-yl)methyl)pyridin-2-yl)pyrimidin-2-amine, (R)—N-(5-((2,7-diazaspiro[3.5]nonan-7-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, (R)-5-fluoro-4-(5-fluoro-1-methyl-2,3-dihydro-1H-benzo[d]pyrrolo[1,2-a]imidazol-7-yl)-N-(5-((2-methyl-2,7-diazaspiro[3.5]nonan-7-yl)methyl)pyridin-2-yl)pyrimidin-2-amine, (R)—N-(5-((2-ethyl-2,7-diazaspiro[3.5]nonan-7-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, (R)—N-(5-((2,7-diazaspiro[3.5]nonan-2-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, (R)-5-fluoro-4-(5-fluoro-1-methyl-2,3-dihydro-1H-benzo[d]pyrrolo[1,2-a]imidazol-7-yl)-N-(5-((7-methyl-2,7-diazaspiro[3.5]nonan-2-yl)methyl)pyridin-2-yl)pyrimidin-2-amine, (R)—N-(5-((7-ethyl-2,7-diazaspiro[3.5]nonan-2-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, (R)—N-(5-((3,9-diazaspiro[5.5]undecan-3-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, (R)-5-fluoro-4-(5-fluoro-1-methyl-2,3-dihydro-1H-benzo[d]pyrrolo[1,2-a]imidazol-7-yl)-N-(5-((9-methyl-3,9-diazaspiro[5.5]undecan-3-yl)methyl)pyridin-2-yl)pyrimidin-2-amine, (R)—N-(5-((9-ethyl-3,9-diazaspiro[5.5]undecan-3-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, (R)—N-(5-((2,6-diazaspiro[3.3]heptan-2-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, (R)-5-fluoro-4-(5-fluoro-1-methyl-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine, (R)—N-(5-((6-ethyl-2,6-diazaspiro[3.3]heptan-2-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, 5-fluoro-4-((R)-5-fluoro-1-methyl-2,3-dihydro-1H-benzo[d]pyrrolo[1,2-a]imidazol-7-yl)-N-(5-((hexahydropyrrolo[3,4-c]pyrrol-2(1H)-yl)methyl)pyridin-2-yl)pyrimidin-2-amine, 5-fluoro-4-((R)-5-fluoro-1-methyl-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine, N-(5-((5-ethylhexahydropyrrolo[3,4-c]pyrrol-2(1H)-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine, N-(5-((3,8-diazabicyclo[3.2.1]octan-8-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine, 5-fluoro-4-((R)-5-fluoro-1-methyl-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine, N-(5-((3-ethyl-3,8-diazabicyclo[3.2.1]octan-8-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine, N-(5-((3,8-diazabicyclo[3.2.1]octan-3-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine, 5-fluoro-4-((R)-5-fluoro-1-methyl-2,3-dihydro-1H-benzo[d]pyrrolo[1,2-a]imidazol-7-yl)-N-(5-((8-methyl-3,8-diazabicyclo[3.2.1]octan-3-yl)methyl)pyridin-2-yl)pyrimidin-2-amine, N-(5-((8-ethyl-3,8-diazabicyclo[3.2.1]octan-3-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-(piperazin-1-ylmethyl)pyridin-2-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((4-methylpiperazin-1-yl)methyl)pyridin-2-yl)pyrimidin-2-amine, N-(5-((4-ethylpiperazin-1-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, (R)-5-fluoro-4-(5-fluoro-1,1-dimethyl-2,3-dihydro-1H-benzo[d]pyrrolo[1,2-a]imidazol-7-yl)-N-(5-((hexahydropyrrolo[1,2-a]pyrazin-2(1H)-yl)methyl)pyridin-2-yl)pyrimidin-2-amine, N-(5-((2,7-diazaspiro[3.5]nonan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((7-methyl-2,7-diazaspiro[3.5]nonan-2-yl)methyl)pyridin-2-yl)pyrimidin-2-amine, N-(5-((7-ethyl-2,7-diazaspiro[3.5]nonan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, N-(5-((2,7-diazaspiro[3.5]nonan-7-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((2-methyl-2,7-diazaspiro[3.5]nonan-7-yl)methyl)pyridin-2-yl)pyrimidin-2-amine, N-(5-((2-ethyl-2,7-diazaspiro[3.5]nonan-7-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, N-(5-((2,6-diazaspiro[3.3]heptan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine, N-(5-((6-ethyl-2,6-diazaspiro[3.3]heptan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, N-(5-((3,9-diazaspiro[5.5]undecan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((9-methyl-3,9-diazaspiro[5.5]undecan-3-yl)methyl)pyridin-2-yl)pyrimidin-2-amine, N-(5-((9-ethyl-3,9-diazaspiro[5.5]undecan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((hexahydropyrrolo[3,4-c]pyrrol-2(1H)-yl)methyl)pyridin-2-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine, N-(5-((5-ethylhexahydropyrrolo[3,4-c]pyrrol-2(1H)-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine N-(5-((3,8-diazabicyclo[3.2.1]octan-8-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine, N-(5-((3-ethyl-3,8-diazabicyclo[3.2.1]octan-8-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, N-(5-((3,8-diazabicyclo[3.2.1]octan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((8-methyl-3,8-diazabicyclo[3.2.1]octan-3-yl)methyl)pyridin-2-yl)pyrimidin-2-amine, N-(5-((8-ethyl-3,8-diazabicyclo[3.2.1]octan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, N-(5-((3,6-diazabicyclo[3.1.1]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, 5-fluoro-4-(5-fluoro-2,3-dihydrospiro[benzo[d]pyrrolo[1,2-a]imidazole-1,1'-cyclopropan]-7-yl)-N-(5-((6-methyl-3,6-diazabicyclo[3.1.1]heptan-3-yl)methyl)pyridin-2-yl)pyrimidin-2-amine, N-(5-((6-ethyl-3,6-diazabicyclo[3.1.1]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, N-(5-(((1S,4S)-2,5-diazabicyclo[2.2.1]heptan-2-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, 5-fluoro-4-(5-fluoro-2,3-dihydrospiro[benzo[d]pyrrolo[1,2-a]imidazole-1,1'-cyclopropan]-7-yl)-N-(5-(((1S,4S)-5-methyl-2,5-diazabicyclo[2.2.1]heptan-2-yl)methyl)pyridin-2-yl)pyrimidin-2-amine, N-(5-(((1S,4S)-5-ethyl-2,5-diazabicyclo[2.2.1]heptan-2-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, N-(5-(((3aR,6aS)-3a,6a-dimethylhexahydropyrrolo[3,4-c]pyrrol-2(1H)-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, 5-fluoro-4-(5-fluoro-2,3-dihydrospiro[benzo[d]pyrrolo[1,2-a]imidazole-1,1'-cyclopropan]-7-yl)-N-(5-(((3aR,6aS)-3a,5,6a-trimethylhexahydropyrrolo[3,4-c]pyrrol-2(1H)-yl)methyl)pyridin-2-yl)pyrimidin-2-amine, N-(5-(((3aR,6aS)-5-ethyl-3a,6a-dimethylhexahydropyrrolo[3,4-c]pyrrol-2(1H)-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, N-(5-((3,6-diazabicyclo[3.2.0]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, 5-fluoro-4-(5-fluoro-2,3-dihydrospiro[benzo[d]pyrrolo[1,2-a]imidazole-1,1'-cyclopropan]-7-yl)-N-(5-((6-methyl-3,6-diazabicyclo[3.2.0]heptan-3-yl)methyl)pyridin-2-yl)pyrimidin-2-amine, N-(5-((6-ethyl-3,6-diazabicyclo[3.2.0]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, (S)-5-fluoro-4-(5-fluoro-2,3-dihydrospiro[benzo[d]pyrrolo[1,2-a]imidazole-1,1'-cyclopropan]-7-yl)-N-(5-((hexahydropyrrolo[1,2-a]pyrazin-2(1H)-yl)methyl)pyridin-2-yl)pyrimidin-2-amine, (R)-5-fluoro-4-(5-fluoro-2,3-dihydrospiro[benzo[d]pyrrolo[1,2-a]imidazole-1,1'-cyclopropan]-7-yl)-N-(5-((hexahydropyrrolo[1,2-a]pyrazin-2(1H)-yl)methyl)pyridin-2-yl)pyrimidin-2-amine, (7R,8aS)-2-((6-((5-fluoro-4-(5-fluoro-2,3-dihydrospiro[benzo[d]pyrrolo[1,2-a]imidazole-1,1'-cyclopropan]-7-yl)pyrimidin-2-yl)amino)pyridin-3-yl)methyl)octahydropyrrolo[1,2-a]pyrazin-7-ol, 3-((6-((5-fluoro-4-(5-fluoro-2,3-dihydrospiro[benzo[d]pyrrolo[1,2-a]imidazole-1,1'-cyclopropan]-7-yl)pyrimidin-2-yl)amino)pyridin-3-yl)methyl)-3-azabicyclo[3.1.0]hexan-6-amine, (R)-5-fluoro-4-(5-fluoro-2,3-dihydrospiro[benzo[d]pyrrolo[1,2-a]imidazole-1,1'-cyclopropan]-7-yl)-N-(5-((hexahydropyrazino[2,1-c][1,4]oxazin-8(1H)-yl)methyl)pyridin-2-yl)pyrimidin-2-amine, 5-fluoro-4-(5-fluoro-2,3-dihydro-1H-benzo[d]pyrrolo[1,2-a]imidazol-7-yl)-N-(5-(piperazin-1-ylmethyl)pyridin-2-yl)pyrimidin-2-amine, 5-fluoro-4-(5-fluoro-2,3-dihydro-1H-benzo[d]pyrrolo[1,2-a]imidazol-7-yl)-N-(5-((4-methylpiperazin-1-yl)methyl)pyridin-2-yl)pyrimidin-2-amine, N-(5-((4-ethylpiperazin-1-yl)methyl)pyridin-2-yl)-5-fluoro-4-(5-fluoro-2,3-dihydro-1H-benzo[d]pyrrolo[1,2-a]imidazol-7-yl)pyrimidin-2-amine,
(R)-4-(1-(difluoromethyl)-5-fluoro-2,3-dihydro-1H-benzo[d]pyrrolo[1,2-a]imidazol-7-yl)-5-fluoro-N-(5-(piperazin-1-ylmethyl)pyridin-2-yl)pyrimidin-2-amine,
(R)-4-(1-(difluoromethyl)-5-fluoro-2,3-dihydro-1H-benzo[d]pyrrolo[1,2-a]imidazol-7-yl)-5-fluoro-N-(5-((4-methylpiperazin-1-yl)methyl)pyridin-2-yl)pyrimidin-2-amine,
(R)-4-(1-(difluoromethyl)-5-fluoro-2,3-dihydro-1H-benzo[d]pyrrolo[1,2-a]imidazol-7-yl)-N-(5-((4-ethylpiperazin-1-yl)methyl)pyridin-2-yl)-5-fluoropyrimidin-2-amine,
(S)-5-fluoro-4-(5-fluoro-1-methyl-2,3-dihydro-1H-benzo[d]pyrrolo[1,2-a]imidazol-7-yl)-N-(5-(piperazin-1-ylmethyl)pyridin-2-yl)pyrimidin-2-amine,
(S)-5-fluoro-4-(5-fluoro-1-methyl-2,3-dihydro-1H-benzo[d]pyrrolo[1,2-a]imidazol-7-yl)-N-(5-((4-methylpiperazin-1-yl)methyl)pyridin-2-yl)pyrimidin-2-amine,
(S)—N-(5-((4-ethylpiperazin-1-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine,
(R)-5-fluoro-4-(5-fluoro-1-(methoxymethyl)-2,3-dihydro-1H-benzo[d]pyrrolo[1,2-a]imidazol-7-yl)-N-(5-(piperazin-1-ylmethyl)pyridin-2-yl)pyrimidin-2-amine,
(R)-5-fluoro-4-(5-fluoro-1-(methoxymethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine,
(R)—N-(5-((4-ethylpiperazin-1-yl)methyl)pyridin-2-yl)-5-fluoro-4-(5-fluoro-1-(methoxymethyl)-2,3-dihydro-1H-benzo[d]pyrrolo[1,2-a]imidazol-7-yl)pyrimidin-2-amine,
N-(5-((3,8-diazabicyclo[3.2.1]octan-8-yl)methyl)pyridin-2-yl)-5-fluoro-4-(5-fluoro-1,1-dimethyl-2,3-dihydro-1H-benzo[d]pyrrolo[1,2-a]imidazol-7-yl)pyridin-2-amine,
5-fluoro-4-(5-fluoro-1,1-dimethyl-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyridin-2-amine,
N-(5-((3-ethyl-3,8-diazabicyclo[3.2.1]octan-8-yl)methyl)pyridin-2-yl)-5-fluoro-4-(5-fluoro-1,1-dimethyl-2,3-dihydro-1H-benzo[d]pyrrolo[1,2-a]imidazol-7-yl)pyridin-2-amine,
N-(5-fluoro-4-(5-fluoro-1,1-dimethyl-2,3-dihydro-1H-benzo[d]Pyrrolo[1,2-a]imidazol-7-yl)pyridin-2-yl)-5-(piperazin-1-ylmethyl)pyrimidin-2-amine,
N-(5-fluoro-4-(5-fluoro-1,1-dimethyl-2,3-dihydro-1H-benzo[d]pyrrolo[1,2-a]imidazol-7-yl)pyridin-2-yl)-5-((4-methylpiperazin-1-yl)methyl)pyrimidin-2-amine,
5-((4-ethylpiperazin-1-yl)methyl)-N-(5-fluoro-4-(5-fluoro-1,1-dimethyl-2,3-dihydro-1H-benzo[d]pyrrolo[1,2-a]imidazol-7-yl)pyridin-2-yl)pyrimidin-2-amine,
N-(5-((3,8-diazabicyclo[3.2.1]octan-8-yl)methyl)pyridin-2-yl)-4-(6,6-dimethyl-7,8-dihydro-6H-pyrrolo[1',2':1,2]imidazo[4,5-b]pyridin-3-yl)-5-fluoropyridin-2-amine,
4-(6,6-dimethyl-7,8-dihydro-6H-pyrrolo[1',2':1,2]imidazo[4,5-b]pyridin-3-yl)-5-fluoro-N-(5-((3-methyl-3,8-diazabicyclo[3.2.1]octan-8-yl)methyl)pyridin-2-yl)pyridin-2-amine,
4-(6,6-dimethyl-7,8-dihydro-6H-pyrrolo[1',2':1,2]imidazo[4,5-b]pyridin-3-yl)-N-(5-((3-ethyl-3,8-diazabicyclo[3.2.1]octan-8-yl)methyl)pyridin-2-yl)-5-fluoropyridin-2-amine,
or pharmaceutically acceptable salt thereof.

In another of its aspects, provided is a pharmaceutical composition comprising a compound according to any one of 1-21, and/or a pharmaceutically acceptable salts thereof.

In yet another of its aspects, there is provided a kit comprising a compound of any one of 1-21, or a pharmaceutically acceptable salts thereof; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound of any one of 1-21, or a pharmaceutically acceptable salts thereof; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound of 1-21, or a pharmaceutically acceptable salts thereof.

In another of its aspects, there is provided a method of inhibiting a CDK4/6 kinase comprising contacting the CDK4/6 with a compound of 1-21, or a pharmaceutically acceptable salts thereof.

In yet another of its aspects, there is provided a method of inhibiting a CDK4/6 comprising causing a compound of any one of 1-21, or a pharmaceutically acceptable salts thereof, to be present in a subject in order to inhibit the CDK4/6 in vivo.

In a further of its aspects, there is provided a method of inhibiting CDK4/6 comprising administering a first compound to a subject that is converted in vivo to a second compound wherein the second compound inhibits the CDK4/6 in vivo, the second compound being a compound according to any one of 1-21.

In another of its aspects, there is provided a method of treating a disease state for which a CDK4/6 possesses activity that contributes to the pathology and/or symptomology of the disease state, the method comprising causing a compound of 1-21, or a pharmaceutically acceptable salts thereof, to be present in a subject in a therapeutically effective amount for the disease state.

In a further of its aspects, there is provided a method of treating a disease state for which a CDK4/6 possesses activity that contributes to the pathology and/or symptomology of the disease state, the method comprising administering a first compound to a subject that is converted in vivo to a second compound wherein the second compound inhibits the CDK4/6 in vivo. It is noted that the compounds of the present invention may be the first or second compounds.

In one variation of each of the above methods the disease state is selected from the group consisting of cancerous hyperproliferative disorders (e.g., brain, lung, squamous cell, bladder, gastric, pancreatic, breast, head, neck, renal, kidney, ovarian, prostate, colorectal, epidermoid, esophageal, testicular, gynecological or thyroid cancer); non-cancerous hyperproliferative disorders (e.g., benign hyperplasia of the skin (e.g., psoriasis), restenosis, and benign prostatic hypertrophy (BPH)); pancreatitis; kidney disease; pain; preventing blastocyte implantation; treating diseases related to vasculogenesis or angiogenesis (e.g., tumor angiogenesis, acute and chronic inflammatory disease such as rheumatoid arthritis, atherosclerosis, inflammatory bowel disease, skin diseases such as psoriasis, exzema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer); asthma; neutrophil chemotaxis (e.g., reperfusion injury in myocardial infarction and stroke and inflammatory arthritis); septic shock; T-cell mediated diseases where immune suppression would be of value (e.g., the prevention of organ transplant rejection, graft versus host disease, lupus erythematosus, multiple sclerosis, and rheumatoid arthritis); atherosclerosis; inhibition of keratinocyte responses to growth factor cocktails; chronic obstructive pulmonary disease (COPD) and other diseases.

In another of its aspects, there is provided a method of treating a disease state for which a mutation in the CDK4/6 gene contributes to the pathology and/or symptomology of the disease state including, for example, breast cancer, melanomas, lung cancer, colon cancer and other tumor types.

In still another of its aspects, the present invention relates to the use of a compound of any of 1-21, or a pharmaceutically acceptable salts thereof. In yet another of its aspects, the present invention relates to the use of a compound according to any one of the above embodiments and variations in the manufacture of a medicament for inhibiting a CDK4/6.

In a further of its aspects, the present invention relates to the use of a compound according to any one of 1-21, or a pharmaceutically acceptable salts thereof, in the manufacture of a medicament for treating a disease state for which a CDK4/6 possesses activity that contributes to the pathology and/or symptomology of the disease state.

Administration and Pharmaceutical Compositions

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.001 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 1000 mg, conveniently administered, for example, in divided doses up to four times a day or in retard form. Suitable unit dosage forms for oral administration comprise from ca. 1 to 50 mg active ingredient.

Compounds of the disclosure may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present disclosure in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the disclosure in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length C8 to C12 from Hüls AG, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arable, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The disclosure also provides for a pharmaceutical combinations, e.g. a kit, comprising a) a first agent which is a compound of the disclosure as disclosed herein, in free form or in pharmaceutically acceptable salt form, and b) at least one co-agent. The kit can comprise instructions for its administration.

Combination Therapies

The compounds or pharmaceutical acceptable salts of the disclosure may be administered as the sole therapy, or together with other therapeutic agent or agents.

For example, the therapeutic effectiveness of one of the compounds described herein may be enhanced by administration of an adjuvant (i.e. by itself the adjuvant may only have minimal therapeutic benefit, but in combination with another therapeutic agent, the overall therapeutic benefit to the individual is enhanced). Or, by way of example only, the benefit experienced by an individual may be increased by administering one of the compounds described herein with another therapeutic agent that also has therapeutic benefit. By way of example only, in a treatment for gout involving administration of one of the compounds described herein, increased therapeutic benefit may result by also providing the individual with another therapeutic agent for gout. Or, by way of example only, if one of the side effects experienced by an individual upon receiving one of the compounds described herein is nausea, then it may be appropriate to administer an anti-nausea agent in combination with the compound. Or, the additional therapy or therapies include, but are not limited to physiotherapy, psychotherapy, radiation therapy, application of compresses to a diseased area, rest, altered diet, and the like. Regardless of the disease, disorder or condition being treated, the overall benefit experienced by the individual may be additive of the two therapies or the individual may experience a synergistic benefit.

In the instances where the compounds described herein are administered in combination with other therapeutic agents, the compounds described herein may be administered in the same pharmaceutical composition as other therapeutic agents, or because of different physical and chemical characteristics, be administered by a different route. For example, the compounds described herein may be administered orally to generate and maintain good blood levels thereof, while the other therapeutic agent may be administered intravenously. Thus the compounds described herein may be administered concurrently, sequentially or dosed separately to other therapeutic agents.

Compounds having Formula (I) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and I. A. Trapani, J. of Immunology 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)-propyl)amino)-3-((trifluoromethyl)sulfonyl)benzenesulfonamide) or ABT-737 (i.e., N-(4-(4-((4'-chloro(1,r-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al, Cancer Research 2008, 68(9), 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDKs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-P-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)-sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXI A® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immuno liposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145 (lexatumumab), HGS-1029, LBY-135, PRO-1762 and trastuzumab.

Kinesin inhibitors include Eg5 inhibitors such as AZD4877, ARRY-520; CENPE inhibitors such as GSK923295 A and the like.

JAK-2 inhibitors include CEP-701 (lesaurtinib), XL019 and INCBO 18424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like. Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGFIR-specific antibodies, lintuzumab, PANOREX® (edrecolomab), RENCAREX® (WX G250), RITUXAN® (rituximab), ticilimumab, trastuzumab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DBSOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TREE STAR® (luteinizing hormone releasing hormone (LHRH)), VANT AS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, Vindesine, vinorelbine and the like. Proteasome inhibitors include VELCADE® (bortezomib), MG132, NPI-0052, PR-171 and the like.

Examples of immunological include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-nl, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOT ARG™ (gemtuzumab ozogamicin), NEUPOGEN® (filgrastim), OncoVAC-CL, OVAREX® (oregovomab), pemtumomab (Y-muHMFGl), PROVENGE® (sipuleucel-T), sargaramostim, sizofilan, teceleukin, THERACYS® (*Bacillus* Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PRO- LEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like. Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly Lpoly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combretastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxy doxorubicin); O: Vincristine (ONCOVIN®); P: prednisone), CYPAT™ (cyproterone acetate), combretastatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-*pseudomonas* exotoxin, interferon-α, interferon-γ, JUNO VAN™ or MEPACT™ (mifamurtide), lonafarnib, 5, 10-methylenetetrahydro folate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces* staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-a), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

EXAMPLES

Various methods may be developed for synthesizing the at least one compound of formula (I) and/or at least one pharmaceutically acceptable salt thereof. Representative methods for synthesizing the at least one compound of formula (I) and/or at least one pharmaceutically acceptable salt thereof are provided in the Examples. It is noted, however, that the at least one compound of formula (I) and/or at least one pharmaceutically acceptable salt thereof may also be synthesized by other synthetic routes that others may devise.

It will be readily recognized that certain compounds of formula (I) have atoms with linkages to other atoms that confer a particular stereochemistry to the compound (e.g., chiral centers). It is recognized that synthesis of the at least one compound of formula (I) and/or at least one pharmaceutically acceptable salt thereof may result in the creation of mixtures of different stereoisomers (enantiomers, diastereomers). Unless a particular stereochemistry is specified, recitation of a compound is intended to encompass all of the different possible stereoisomers.

The at least one compound of formula (I) can also be prepared as a pharmaceutically acceptable acid addition salt by, for example, reacting the free base form of the at least one compound with a pharmaceutically acceptable inorganic or organic acid. Alternatively, a pharmaceutically acceptable base addition salt of the at least one compound of formula (I) can be prepared by, for example, reacting the free acid form of the at least one compound with a pharmaceutically acceptable inorganic or organic base. Inorganic and organic acids and bases suitable for the preparation of the pharmaceutically acceptable salts of compounds of formula (I) are set forth in the definitions section of this Application. Alternatively, the salt forms of the compounds of formula (I) can be prepared using salts of the starting materials or intermediates.

The free acid or free base forms of the compounds of formula (I) can be prepared from the corresponding base addition salt or acid addition salt form. For example, a compound of formula (I) in an acid addition salt form can be converted to the corresponding free base thereof by treating with a suitable base (e.g., ammonium hydroxide solution, sodium hydroxide, and the like). A compound of formula (I) in a base addition salt form can be converted to the corresponding free acid thereof by, for example, treating with a suitable acid (e.g., hydrochloric acid, etc).

The N-oxides of the at least one compound of formula (I) and/or at least one pharmaceutically acceptable salt thereof can be prepared by methods known to those of ordinary skill in the art. For example, N-oxides can be prepared by treating an unoxidized form of the compound of formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0 to 80° C. Alternatively, the N-oxides of the compounds of formula (I) can be prepared from the N-oxide of an appropriate starting material.

Compounds of formula (I) in an unoxidized form can be prepared from N-oxides of compounds of formula (I) by, for example, treating with a reducing agent (e.g., sulfur, sulfur dioxide, triphenyl phosphine, lithium borohydride, sodium borohydride, phosphorus trichloride, tribromide, and the like) in a suitable inert organic solvent (e.g., acetonitrile, ethanol, aqueous dioxane, and the like) at 0 to 80° C.

Protected derivatives of the compounds of formula (I) can be made by methods known to those of ordinary skill in the art. A detailed description of the techniques applicable to the creation of protecting groups and their removal can be found in T. W. Greene, Protecting Groups in Organic Synthesis, 3rd edition, John Wiley & Sons, Inc. 1999.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. For example, the following abbreviations may be used in the examples and throughout the specification: g (grams); mg (milligrams); L (liters); mL (milliliters); μL (microliters); psi (pounds per square inch); M (molar); mM (millimolar); i.v. (intravenous); Hz (Hertz); MHz (megahertz); mol (moles); mmol (millimoles); r.t. (room temperature); min (minutes); h (hours); mp (melting point); TLC (thin layer chromatography); Rt (retention time); RP (reverse phase); MeOH (methanol); EtOH (ethanol); i-PrOH (isopropanol); TEA (triethylamine); TFA (trifluoroacetic acid); TFA A (trifluoroacetic anhydride); THF (tetrahydrofuran); DMSO (dimethyl sulfoxide); EtOAc (ethyl acetate); PE (petroleum ether) DME (1,2-dimethoxyethane); DCM (dichloromethane); DCE (dichloroethane); DMF (N,N-dimethylformamide); DMPU (N,N'-dimethylpropyleneurea); CDI (1,1-carbonyldiimidazole); IBCF (isobutyl chloroformate); HOAc (acetic acid); HOSu (N-hydroxysuccinimide); HOBT (1-hydroxybenzotriazole); Et$_2$O (diethyl ether); EDCl (1-(3-dimethylaminopropyl)-3-ethylcarbodiimide hydrochloride); BOC (tert-butyloxycarbonyl); FMOC (9-fluorenylmethoxycarbonyl); DCC (dicyclohexylcarbodiimide); CBZ (benzyloxycarbonyl); Ac (acetyl); atm (atmosphere); TMSE (2-(trimethylsilylethyl); TMS (trimethylsilyl); TIPS (triisopropylsilyl); TBS (t-butyldimethylsilyl); TBSCl (tert-Butylchlorodimethylsilane); TsOH (4-methylbenzenesulfonic acid); DMAP (4-dimethylaminopyridine); DHP (3,4-Dihydro-2H-pyran); Me (methyl); OMe (methoxy); Et (ethyl); tBu (tert-butyl); HPLC (high pressure liquid chromatography); BOP (bis(2-oxo-3-oxazolidinyl)phosphinic chloride); TBAF (tetra-n-butylammonium fluoride); m-CPBA (meta-chloroperbenzoic acid); IBX (2-idoxybenzoic acid) DAST (Diethylaminosulfur trifluoride).

References to ether or Et$_2$O are to diethyl ether; brine refers to a saturated aqueous solution of NaCl. Unless otherwise indicated, all temperatures are expressed in ° C. (degrees Centigrade). All reactions were conducted under an inert atmosphere at r.t. unless otherwise noted.

$^1$H NMR spectra were recorded on a Varian Mercury Plus 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet), and br (broad).

Low-resolution mass spectra (MS) and compound purity data were acquired on a Shimadzu LC/MS single quadrapole system equipped with electrospray ionization (ESI) source, UV detector (220 and 254 nm), and evaporative light scattering detector (ELSD). Thin-layer chromatography was performed on 0.25 mm Superchemgroup silica gel plates (60F-254), visualized with UV light, 5% ethanolic phosphomolybdic acid, ninhydrin, or p-anisaldehyde solution. Flash column chromatography was performed on silica gel (200-300 mesh, Branch of Qingdao Haiyang Chemical Co., Ltd).

Synthetic Schemes

At least one compound of formula I or II and/or at least one pharmaceutically acceptable salt thereof may be synthesized according to a variety of reaction schemes. Some illustrative schemes are provided below and in the examples. Other reaction schemes could be readily devised by those skilled in the art in view of the present disclosure.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Synthetic methods for preparing the compounds of the present disclosure are illustrated in the following Schemes and Examples. Starting materials are commercially available or may be made according to procedures known in the art or as illustrated herein.

The intermediates shown in the following schemes are either known in the literature or may be prepared by a variety of methods familiar to those skilled in the art.

As an illustration, one of the synthetic approach the compound of formula I of the present disclosure is outlined in Scheme 1. As shown in the Scheme, the compound of formula I can be assembled from intermediates II and arylamine III, the coupling of which will readily give compound of formula I under coupling conditions such as Buchwald reactions or other conditions known in the art.

Scheme 1

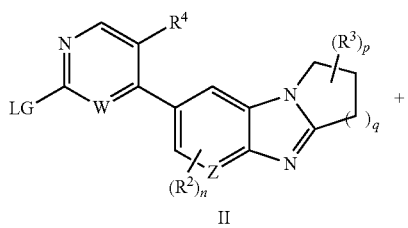

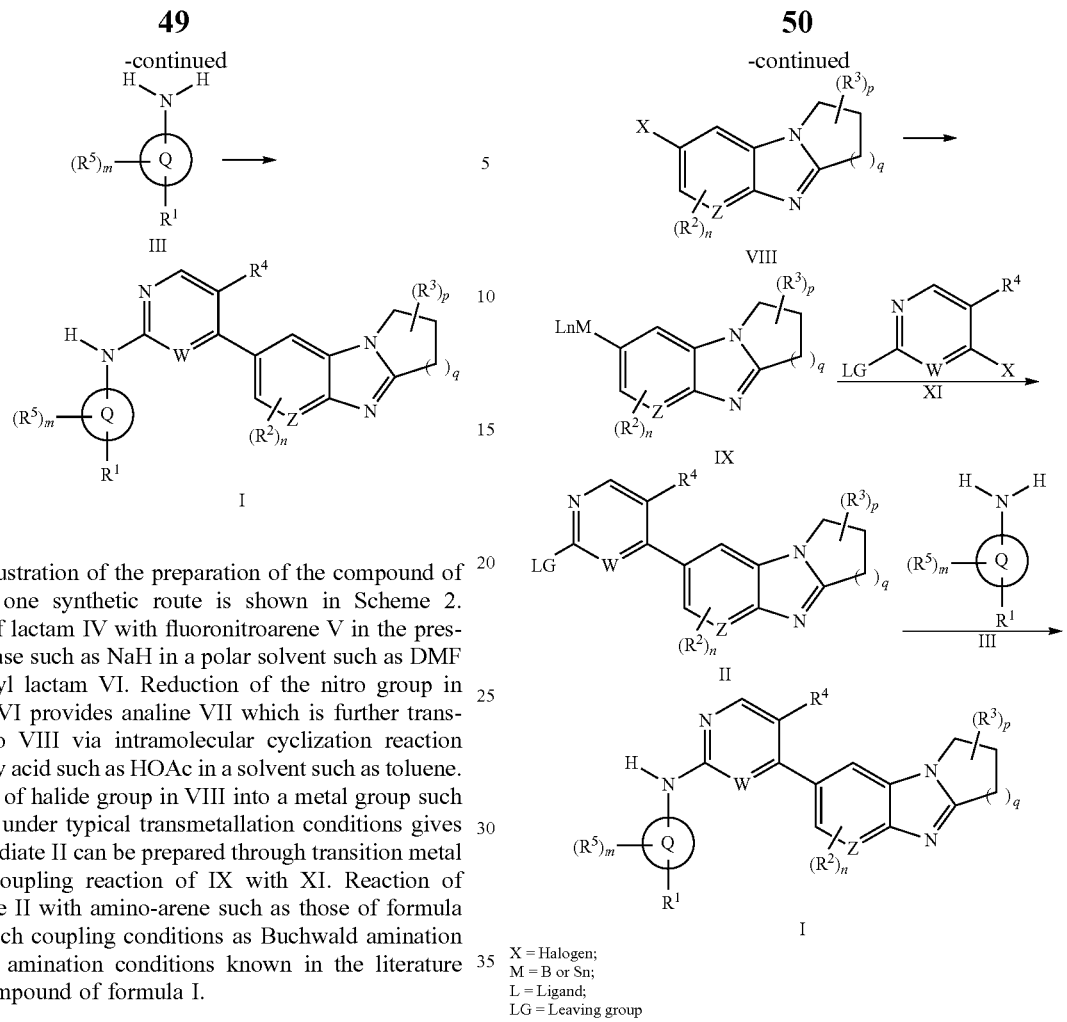

As an illustration of the preparation of the compound of formula I, one synthetic route is shown in Scheme 2. Coupling of lactam IV with fluoronitroarene V in the presence of a base such as NaH in a polar solvent such as DMF leads to aryl lactam VI. Reduction of the nitro group in aryllactam VI provides analine VII which is further transformed into VIII via intramolecular cyclization reaction catalyzed by acid such as HOAc in a solvent such as toluene. Conversion of halide group in VIII into a metal group such as B or Sn under typical transmetallation conditions gives IX. Intermediate II can be prepared through transition metal catalyzed coupling reaction of IX with XI. Reaction of intermediate II with amino-arene such as those of formula III using such coupling conditions as Buchwald amination reaction or amination conditions known in the literature leads to compound of formula I.

X = Halogen;
M = B or Sn;
L = Ligand;
LG = Leaving group

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Preparation of Intermediates

Intermediate A (1S)-7-(2-chloro-5-fluoropyrimidin-4-yl)-5-fluoro-1-(((tetrahydro-2H-pyran-2-yl) oxy)methyl)-2,3-dihydro-1H-benzo[d]pyrrolo[1,2-a]imidazole (Intermediate A)

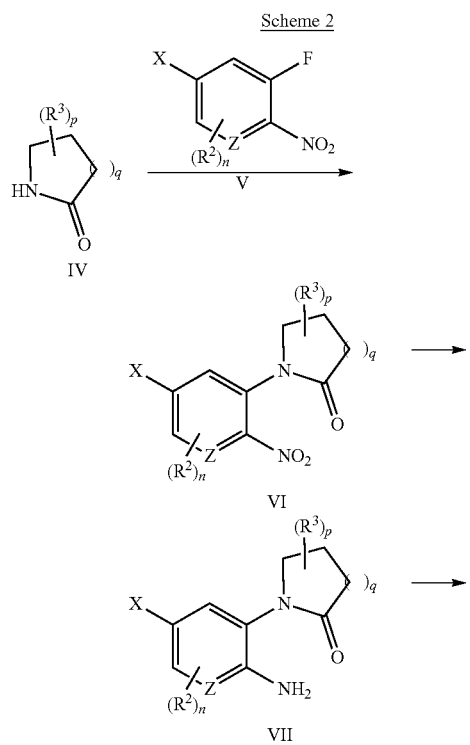

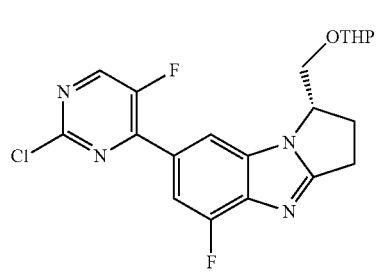

Intermediate A

(S)-5-(hydroxymethyl)pyrrolidin-2-one (A-1)

To a solution of commercial available ethyl L-pyroglutamate (5.2 g, 33.1 mmol) in EtOH (100 mL) was added NaBH$_4$ (2.5 g, 65.8 mmol) portionwise at 0° C. for 0.5 h, then the mixture was stirred at r.t. overnight. To the mixture was added acetic acid (4.5 mL) slowly at 0° C. The mixture was stirred at r.t. for 0.5 h, filtrated through celite and washed with EtOH (60 mL). The filtrate was concentrated and purified by silica gel column chromatography (eluent: DCM/MeOH=20:1) to give the title compound (S)-5-(hydroxymethyl)pyrrolidin-2-one (A-1). MS-ESI (m/z): 116 [M+1]$^+$.

(S)-5-(((tert-butyldimethylsilyl)oxy)methyl)pyrrolidin-2-one (A-2)

To a solution of (S)-5-(hydroxymethyl)pyrrolidin-2-one (A-1)(500 mg, 4.35 mmol), imidazole (650 mg, 9.57 mmol) and DMAP (16 mg, 0.13) in DCM (15 mL) was added a solution of TBSCl in DCM (2 mL) dropwise at 0° C. The mixture was stirred at r.t. overnight and purified by column chromatography on silica gel eluting with DCM/MeOH (20:1) to give the title compound (S)-5-(((tert-butyldimethylsilyl)oxy)methyl)pyrrolidin-2-one (A-2). MS-ESI (m/z): 230[M+1]$^+$.

(S)-1-(5-bromo-3-fluoro-2-nitrophenyl)-5-(((tert-butyldimethylsilyl)oxy)methyl)pyrrolidin-2-one (A-3)

To a solution of (S)-5-(((tert-butyldimethylsilyl)oxy)methyl)pyrrolidin-2-one (A-2)(860 mg, 3.74 mmol) in DMF (10 mL) was added NaH (180 mg, 4.49 mmol, 60% in oil) at r.t. The mixture was stirred at r.t. for 30 min. A solution of commercial available 5-bromo-1,3-difluoro-2-nitrobenzene (890 mg, 3.74 mmol) was added at r.t., and the resulting solution was stirred at r.t. for another 1 h. Water (30 mL) was added to quench the reaction, and the mixture was extracted with EtOAc (3×30 mL). The extracts were washed sequentially with water (3×30 mL) and brine (30 mL), dried over Na$_2$SO$_4$ and concentrated. The residue was purified by flash column chromatography on silica gel eluting with EtOAc/PE (1:5) to give the title compound (S)-1-(5-bromo-3-fluoro-2-nitrophenyl)-5-(((tert-butyldimethylsilyl)oxy)methyl)pyrrolidin-2-one (A-3). MS-ESI (m/z): 447[M+1]$^+$.

(S)-1-(2-amino-5-bromo-3-fluorophenyl)-5-(((tert-butyldimethylsilyl)oxy)methyl) pyrrolidin-2-one (A-4)

A suspension of (S)-1-(5-bromo-3-fluoro-2-nitrophenyl)-5-(((tert-butyldimethylsilyl)oxy)methyl)pyrrolidin-2-one (A-3)(200 mg, 0.45 mmol), iron powder (124 mg, 2.21 mmol), NH$_4$Cl (72 mg, 1.36 mmol) and water (1.2 mL) in EtOH (4 mL) was stirred at 80° C. for 2 h. The mixture was filtrated through celite and washed with MeOH (30 mL). The filtrate was concentrated, dissolved in EtOAc (50 mL), washed sequentially with water (2×30 mL) and brine (30 mL), dried over Na$_2$SO$_4$ and concentrated to give the title compound (S)-1-(2-amino-5-bromo-3-fluorophenyl)-5-(((tert-butyldimethylsilyl)oxy)-methyl)pyrrolidin-2-one (A-4). MS-ESI (m/z): 417[M+1]$^+$.

(S)-7-bromo-1-(((tert-butyldimethylsilyl)oxy)methyl)-5-fluoro-2,3-dihydro-1H-benzo[d]pyrrolo[1,2-a]imidazole (A-5)

A solution of (S)-1-(2-amino-5-bromo-3-fluorophenyl)-5-(((tert-butyldimethylsilyl)oxy)methyl)pyrrolidin-2-one (A-4)(200 mg) in acetic acid (2.4 mL) was stirred at 110° C. for 16 h. The solvent was removed by evaporation. The residue was purified by flash column chromatography on silica gel eluting with EtOAc/DCM (1:30) to give the title compound (S)-7-bromo-1-(((tert-butyldimethylsilyl)oxy)methyl)-5-fluoro-2,3-dihydro-1H-benzo[d]pyrrolo[1,2-a]imidazole (A-5). MS-ESI (m/z): 399[M+1]$^+$.

(S)-(7-bromo-5-fluoro-2,3-dihydro-1H-benzo[d]pyrrolo[1,2-a]imidazol-1-yl) methano (A-6)

To a solution of (S)-7-bromo-1-(((tert-butyldimethylsilyl)oxy)methyl)-5-fluoro-2,3-dihydro-1H-benzo[d]pyrrolo[1,2-a]imidazole (A-5) (178 mg, 0.45 mmol) in MeOH (3 mL) was added con. HCl (0.3 mL), and the mixture was stirred at r.t. for 2 h. The reaction was quenched by addition of sat. NaHCO$_3$ (50 mL) and extracted with EtOAc (3×20 mL), the combined organic layer was washed with brine (20 mL), dried over Na$_2$SO$_4$ and concentrated to give the title compound (S)-(7-bromo-5-fluoro-2,3-dihydro-1H-benzo[d]pyrrolo[1,2-a]imidazol-1-yl)methanol (A-6). MS-ESI (m/z): 285[M+1]$^+$.

(1S)-7-bromo-5-fluoro-1-(((tetrahydro-2H-pyran-2-yl)oxy)methyl)-2,3-dihydro-1H-benzo[d]pyrrolo[1,2-a]imidazole (A-7)

A mixture of (S)-(7-bromo-5-fluoro-2,3-dihydro-1H-benzo[d]pyrrolo[1,2-a]imidazol-1-yl)methanol (A-6)(130 mg, 0.45 mmol), DHP (445 mg, 5.3 mmol) and TsOH (8.7 mg, 0.046 mmol) in DCM (13 mL) was stirred at r.t. for 72 h. The reaction was quenched by addition of sat. NaHCO$_3$ (100 mL) and extracted with DCM (2×50 mL), the combined organic layer was washed with brine (20 mL), dried over Na$_2$SO$_4$ and concentrated. The residue was purified by column chromatography on silica gel eluting with EtOAc/PE (3:2) to give the title compound (1S)-7-bromo-5-fluoro-1-(((tetrahydro-2H-pyran-2-yl)oxy)methyl)-2,3-dihydro-1H-benzo[d]pyrrolo[1,2-a]imidazole (A-7). MS-ESI (m/z): 369[M+1]$^+$.

(1S)-5-fluoro-1-(((tetrahydro-2H-pyran-2-yl)oxy)methyl)-7-(4,4,5,5-tetramethyl-1,3,2-dioxaborolan-2-yl)-2,3-dihydro-1H-benzo[d]pyrrolo[1,2-a]imidazole (A-8)

A mixture of (1S)-7-bromo-5-fluoro-1-(((tetrahydro-2H-pyran-2-yl)oxy)methyl)-2,3-dihydro-1H-benzo[d]pyrrolo[1,2-a]imidazole (A-7)(140 mg, 0.378 mmol), bis(pinacolato)diboron (144 mg, 0.568 mmol), palladium diacetate (8.5 mg, 0.038 mmol), tricyclohexyl phosphine (21 mg, 0.076 mmol), and potassium acetate (111 mg, 1.135 mmol) in DMSO (2.1 mL) was stirred at 100° C. for 2 h under nitrogen atmosphere. Water (30 mL) was added, and the mixture was extracted with EtOAc (3×30 mL). The extracts were washed sequentially with water (3×30 mL) and brine (30 mL), dried over Na$_2$SO$_4$ and concentrated. The residue was purified by column chromatography on silica gel eluting with EtOAc/PE (1:99~1:50) to give the title compound (1S)-5-fluoro-1-(((tetrahydro-2H-pyran-2-yl)oxy)methyl)-7-(4,4,5,5-tetramethyl-1,3,2-dioxaborolan-2-yl)-2,3-dihydro-1H-benzo[d]pyrrolo[1,2-a]imidazole (A-8). MS-ESI (m/z): 417[M+1]$^+$.

(1S)-7-(2-chloro-5-fluoropyrimidin-4-yl)-5-fluoro-1-(((tetrahydro-2H-pyran-2-yl) oxy)methyl)-2,3-dihydro-1H-benzo[d]pyrrolo[1,2-a]imidazole (Intermediate A1)

A mixture of 2,4-dichloro-5-fluoropyrimidine (126 mg, 0.756 mmol), (1S)-5-fluoro-1-(((tetrahydro-2H-pyran-2-yl)

oxy)methyl)-7-(4,4,5,5-tetramethyl-1,3,2-dioxaborolan-2-yl)-2,3-dihydro-1H-benzo[d]pyrrolo[1,2-a]imidazole (A-8) (270 mg, 0.378 mmol), sodium carbonate (120 mg, 1.134 mmol), bis(triphenylphosphine)palladium (II) chloride (27 mg, 0.038 mmol), water (1 mL) and 1,2-dimethoxyethane (2.5 mL) was stirred at 80° C. for 3.5 h. The reaction was quenched by addition of water (30 mL) and extracted with DCM (3×30 mL). The extracts were washed with water (3×30 mL), brine (20 mL), dried over $Na_2SO_4$ and concentrated. The residue was purified by flash column chromatography on silica gel eluting with EtOAc/DCM (1:30) to give the title compound (1S)-7-(2-chloro-5-fluoropyrimidin-4-yl)-5-fluoro-1-(((tetrahydro-2H-pyran-2-yl)oxy)methyl)-2,3-dihydro-1H-benzo[d]pyrrolo[1,2-a]imidazole (Intermediate A). MS-ESI (m/z): 421 [M+1]$^+$.

Intermediate B (S)-7-(2-chloro-5-fluoropyrimidin-4-yl)-5-fluoro-1-(methoxymethyl)-2,3-dihydro-1H-benzo[d]pyrrolo[1,2-a]imidazole (Intermediate B)

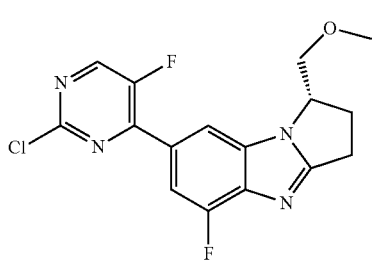

Intermediate B (S)-1-(5-bromo-3-fluoro-2-nitrophenyl)-5-(hydroxymethyl)pyrrolidin-2-one (B-1)

The title compound (S)-1-(5-bromo-3-fluoro-2-nitrophenyl)-5-(hydroxylmethyl)pyrrolidin-2-one (B-1) was prepared according to the synthetic method of A-6 by replacing (S)-7-bromo-1-(((tert-butyldimethylsilyl)oxy)methyl)-5-fluoro-2,3-dihydro-1H-benzo[d]pyrrolo[1,2-a]imidazole (A-5) with (S)-1-(5-bromo-3-fluoro-2-nitrophenyl)-5-(((tert-butyldimethylsilyl)oxy)methyl)pyrrolidin-2-one (A-3). MS-ESI (m/z): 333[M+1]$^+$.

(S)-1-(2-amino-5-bromo-3-fluorophenyl)-5-(hydroxymethyl)pyrrolidin-2-one (B2)

The title compound (S)-1-(2-amino-5-bromo-3-fluorophenyl)-5-(hydroxylmethyl)pyrrolidin-2-one (B-2) was prepared according to the synthetic method of A-4 by replacing (S)-1-(5-bromo-3-fluoro-2-nitrophenyl)-5-(((tert-butyldimethylsilyl)-oxy)-methyl)pyrrolidin-2-one (A-3) with (S)-1-(5-bromo-3-fluoro-2-nitrophenyl)-5-(hydroxymethyl)pyrrolidin-2-one (B-1). MS-ESI (m/z): 303 [M+1]$^+$.

(S)-(7-bromo-5-fluoro-2,3-dihydro-1H-benzo[d]pyrrolo[1,2-a]imidazol-1-yl)methanol (B-3)

The title compound (S)-(7-bromo-5-fluoro-2,3-dihydro-1H-benzo[d]pyrrolo-[1,2-a]imidazol-1-yl)methanol (B-3) (400 mg, 92%) was prepared according to the synthetic method of A-5 by replacing (S)-1-(2-amino-5-bromo-3-fluorophenyl)-5-(((tert-butyldimethylsilyl)oxy)methyl)pyr-rolidin-2-one (A-4) with (S)-1-(2-amino-5-bromo-3-fluorophenyl)-5-(hydroxymethyl)pyrrolidin-2-one (B-2). MS-ESI (m/z): 285 [M+1]$^+$.

(S)-7-bromo-5-fluoro-1-(methoxymethyl)-2,3-dihydro-1H-benzo[d]pyrrolo[1,2-a]imidazole (B-4)

To a suspension of (S)-(7-bromo-5-fluoro-2,3-dihydro-1H-benzo[d]pyrrolo-[1,2-a]imidazol-1-yl)methanol (B-3) (400 mg, 1.40 mmol) in THF (5 mL) was added NaH (112 mg, 2.80 mmol) slowly at 0° C. The mixture was stirred at r.t. for 1 h. MeI (400 mg, 2.80 mmol) was added thereto and the mixture was stirred at r.t. for 2 h. The mixture was poured into ice-water (80 ml) and extracted with EtOAc (3×40 mL). The extracts were washed with water (2×40 mL), brine (20 mL), dried over $Na_2SO_4$ and concentrated. The residue was purified by flash column chromatography on silica gel eluting with EtOAc/PE (1:2) to give the title compound (S)-7-bromo-5-fluoro-1-(methoxymethyl)-2,3-dihydro-1H-benzo[d]pyrrolo[1,2-a]imidazole (B-4). MS-ESI (m/z): 299[M+1]$^+$.

(S)-7-(2-chloro-5-fluoropyrimidin-4-yl)-5-fluoro-1-(methoxymethyl)-2,3-dihydro-1H-benzo[d]pyrrolo[1,2-a]imidazole (Intermediate B)

The title compound (S)-7-(2-chloro-5-fluoropyrimidin-4-yl)-5-fluoro-1-(methoxymethyl)-2,3-dihydro-1H-benzo[d]pyrrolo[1,2-a]imidazole (Intermediate B) was prepared according to the synthetic method of Intermediate Aby replacing (1S)-7-bromo-5-fluoro-1-(((tetrahydro-2H-pyran-2-yl)oxy)methyl)-2,3-dihydro-1H-benzo[d]pyrrolo[1,2-a]imidazole (A-7) with (S)-7-bromo-5-fluoro-1-(methoxymethyl)-2,3-dihydro-1H-benzo[d]-pyrrolo[1,2-a]imidazole (B-4). MS-ESI (m/z): 351 [M+1]$^+$.

Intermediate C (S)-7-(2-chloro-5-fluoropyrimidin-4-yl)-1-(difluoromethyl)-5-fluoro-2,3-dihydro-1H-benzo[d]pyrrolo[1,2-a]imidazole (Intermediate C)

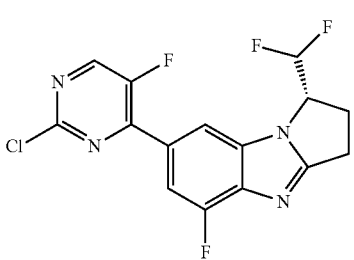

Intermediate C (S)-1-(5-bromo-3-fluoro-2-nitrophenyl)-5-oxopyrrolidine-2-carbaldehyde (C-1)

To a solution of IBX (560 mg, 2.0 mmol) in DMSO (10 mL) was added a solution of (S)-1-(5-bromo-3-fluoro-2-nitrophenyl)-5-(hydroxymethyl)pyrrolidin-2-one (B-1)(372 mg, 1.12 mmol) in DMSO (15 mL) slowly, and the mixture was stirred at r.t. overnight. The mixture was poured into ice-water (100 ml) and extracted with EtOAc (3×50 mL). The extracts were washed sequentially with sat. $NaHCO_3$ (3×50 mL), water (2×50 mL) and brine (50 mL), dried over Na₂SO₄ and concentrated to give the title compound (S)-1-(5-bromo-3-fluoro-2-nitrophenyl)-5-oxopyrrolidine-2-carbaldehyde (C-1). MS-ESI (m/z): 331[M+1]⁺.

(S)-1-(5-bromo-3-fluoro-2-nitrophenyl)-5-(difluoromethyl)pyrrolidin-2-one (Q-2)

To a solution of (S)-1-(5-bromo-3-fluoro-2-nitrophenyl)-5-oxopyrrolidine-2-carbaldehyde (C-1)(325 mg, 0.98 mmol) in DCM (16 mL) was added DAST (90 mg, 4.9 mmol) dropwise at 0° C., and the mixture was stirred at r.t. overnight. MeOH (1 mL) was added thereto at 0° C. to quench the reaction followed by water (100 mL), and the mixture was extracted with DCM (3×50 mL). The extracts were washed with brine (50 mL), dried over Na₂SO₄ and concentrated to give the title compound (S)-1-(5-bromo-3-fluoro-2-nitrophenyl)-5-(difluoromethyl)pyrrolidin-2-one (C-2). MS-ESI (m/z): 353[M+1]⁺.

(S)-7-bromo-1-(difluoromethyl)-5-fluoro-2,3-dihydro-1H-benzo[d]pyrrolo[1,2-a]imidazole (C-3)

The title compound (S)-7-bromo-1-(difluoromethyl)-5-fluoro-2,3-dihydro-1H-benzo[d]pyrrolo[1,2-a]imidazole (C-3) was prepared according to the synthetic method of A-5 by replacing (S)-1-(5-bromo-3-fluoro-2-nitrophenyl)-5-(((tert-butyldimethylsilyl)-oxy)-methyl)pyrrolidin-2-one (A-3) with (S)-1-(5-bromo-3-fluoro-2-nitrophenyl)-5-(difluoromethyl)pyrrolidin-2-one (C-2). MS-ESI (m/z): 305 [M+1]⁺.

(S)-7-(2-chloro-5-fluoropyrimidin-4-yl)-1-(difluoromethyl)-5-fluoro-2,3-dihydro-1H-benzo[d]pyrrolo[1,2-a]imidazole (Intermediate C)

The title compound (S)-7-(2-chloro-5-fluoropyrimidin-4-yl)-1-(difluoromethyl)-5-fluoro-2,3-dihydro-1H-benzo[d]pyrrolo[1,2-a]imidazole (Intermediate C) was prepared according to the synthetic method of Intermediate A by replacing (1S)-7-bromo-5-fluoro-1-(((tetrahydro-2H-pyran-2-yl)oxy)methyl)-2,3-dihydro-1H-benzo[d]pyrrolo[1,2-a]imidazole (A-7) with (S)-7-bromo-1-(difluoromethyl)-5-fluoro-2,3-dihydro-1H-benzo[d]pyrrolo[1,2-a]imidazole (C-3). MS-ESI (m/z): 351 [M+1]⁺.

Intermediate D 7-(2-chloro-5-fluoropyrimidin-4-yl)-5-fluoro-2,3-dihydrospiro[benzo[d]pyrrolo[1,2-a]imidazole-1,1'-cyclopropane] (Intermediate D)

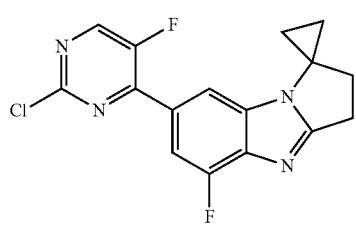

Intermediate D 4-azaspiro[2.4]heptan-5-one (D-1)

To a solution of commercial available methyl 3-cyanopropanoate (2.0 g, 17.7 mmol) and titanium tetraisopropanolate (1.0 g, 3.5 mmol) in diethyl ether (80 mL) was added ethylmagnesium bromide (3 M in diethyl ether, 13 mL) dropwise at r.t. under nitrogen atmosphere for 1 h. The mixture was stirred at r.t. for 2 h, and water (1.0 mL) was added to quench the reaction. The solids were filtered out, and the filter cake was washed with diethyl ether (40 mL). Filtrate was concentrated. The residue was purified by column chromatography on silica gel eluting with ethyl acetate to give the title compound 4-azaspiro[2.4]heptan-5-one (D-1). MS-ESI (m/z): 112 [M+1]⁺.

4-(5-bromo-3-fluoro-2-nitrophenyl)-4-azaspiro[2.4]heptan-5-one (D-2)

To a solution of 4-azaspiro[2.4]heptan-5-one (D-1)(200 mg, 1.79 mmol) in dimethyl formamide (5 mL) was added NaH (107 mg, 2.68 mmol, 60% in oil) at r.t. The mixture was stirred at r.t. for 30 min. A solution of commercial available 5-bromo-1,3-difluoro-2-nitrobenzene (423 mg, 1.79 mmol) was added at r.t., and the resulting solution was stirred at r.t. for another 1 h. Water (30 mL) was added to quench the reaction, and the mixture was extracted with ethyl acetate (3×30 mL). The extracts was washed sequentially with water (3×30 mL) and brine (30 mL), dried over sodium sulfate and concentrated. The residue was purified by flash column chromatography on silica gel eluting with ethyl acetate/petroleum ether (1:5) to give the title compound 4-(5-bromo-3-fluoro-2-nitrophenyl)-4-azaspiro[2.4]heptan-5-one (D-2). MS-ESI (m/z): 329, 331 [M+1]⁺.

4-(2-amino-5-bromo-3-fluorophenyl)-4-azaspiro[2.4]heptan-5-one (D-3)

A suspension of 4-(5-bromo-3-fluoro-2-nitrophenyl)-4-azaspiro[2.4]heptan-5-one (D-2)(300 mg, 1.00 mmol), iron powder (337 mg, 6.00 mmol), ammonium chloride (106 mg, 2.00 mmol) and water (2.5 mL) in ethanol (10 mL) was stirred at 80° C. for 2 h. The solids were filtered out by celite, and filter cake was washed with methanol (30 mL). Filtrate was concentrated in vacuum. The residue was dissolved in ethyl acetate (50 mL), washed sequentially with water (2×30 mL) and brine (30 mL), dried over sodium sulfate and concentrated. The residue was purified by flash column chromatography on silica gel eluting with ethyl acetate/petroleum ether (1:2) to give the title compound 4-(2-amino-5-bromo-3-fluorophenyl)-4-azaspiro[2.4]heptan-5-one (D-3). MS-ESI (m/z): 299, 301 [M+1]⁺.

7-bromo-5-fluoro-2,3-dihydrospiro[benzo[d]pyrrolo[1,2-a]imidazole-1,1'-cyclopropane] (D-4)

A solution of 4-(2-amino-5-bromo-3-fluorophenyl)-4-azaspiro[2.4]heptan-5-one (D-3)(260 mg, 0.93 mmol), acetic acid (1 mL) in toluene (10 mL) was stirred at 110° C. for 16 h. The solvent was removed by evaporation. The residue was purified by flash column chromatography on silica gel eluting with ethyl acetate/dichloromethane (1:30) to give the title compound 7-bromo-5-fluoro-2,3-dihydrospiro[benzo[d]pyrrolo[1,2-a]-imidazole-1,1'-cyclopropane] (D-4). MS-ESI (m/z): 281, 283 [M+1]⁺.

5-fluoro-7-(4,4,5,5-tetramethyl-1,3,2-dioxaborolan-2-yl)-2,3-dihydrospiro[benzo[d]pyrrolo[1,2-a]imidazole-1,1'-cyclopropane] (D-5)

A mixture of 7-bromo-5-fluoro-2,3-dihydrospiro[benzo[d]pyrrolo[1,2-a]-imidazole-1,1'-cyclopropane] (D-4) (240 mg, 0.85 mmol), bis(pinacolato)diboron (325 mg, 1.28 mmol), palladium diacetate (19 mg, 0.085 mmol), tricyclohexyl phosphine (48 mg, 0.171 mmol), and potassium acetate (251 mg, 2.56 mmol) in dimethyl sulfoxide (3 mL) was stirred at 100° C. for 2 h under nitrogen atmosphere. Water (30 mL) was added, and the mixture was extracted with ethyl acetate (3×30 mL). The extracts was washed sequentially with water (3×30 mL) and brine (30 mL), dried over sodium sulfate and concentrated. The residue was purified by column chromatography on silica gel eluting with ethyl acetate/petroleum ether (1:99~1:50) to give the title compound 5-fluoro-7-(4,4,5,5-tetramethyl-1,3,2-dioxaborolan-2-yl)-2,3-dihydrospiro[benzo[d]pyrrolo-[1,2-a]imidazole-1,1'-cyclo-propane] (D-5). MS-ESI (m/z): 329 $[M+1]^+$.

7-(2-chloro-5-fluoropyrimidin-4-yl)-5-fluoro-2,3-dihydrospiro[benzo[d]pyrrolo[1,2-a]imidazole-1,1'-cyclopropane](Intermediate D)

Nitrogen was bubbled into a mixture of 2, 4-dichloro-5-fluoropyrimidine (183 mg, 1.10 mmol), sodium carbonate (155 mg, 1.47 mmol) in water (2 mL) and 1,2-dimethoxyethane (5 mL), bis(triphenylphosphine)palladium(II) chloride (51 mg, 0.073 mmol) was added. The mixture was heated at 80° C. and a solution of 5-fluoro-7-(4,4,5,5-tetramethyl-1,3,2-dioxaborolan-2-yl)-2,3-dihydrospiro[benzo[d]pyrrolo-[1,2-a]imidazole-1,1'-cyclopropane] (D-5) (241 mg, 0.73 mmol) in 1,2-dimethoxy ethane (2 mL) was added dropwise. The mixture was stirred at 80° C. for 3 h, and cooled to r.t. Then water (30 mL) was added, and the mixture was extracted with dichloromethane (3×30 mL). The extracts were washed sequentially with water (3×30 mL) and brine (20 mL), dried over sodium sulfate and concentrated. The residue was purified by flash column chromatography on silica gel eluting with ethyl acetate/dichloromethane (1:30) to give the title compound 7-(2-chloro-5-fluoropyrimidin-4-yl)-5-fluoro-2,3-dihydrospiro[benzo[d]pyrrolo[1,2-a]-imidazole-1,1'-cyclopropane] (Intermediate D). MS-ESI (m/z): 333 $[M+1]^+$.

Intermediate E (S)-7-(2-chloro-5-fluoropyrimidin-4-yl)-5-fluoro-1-(trifluoromethyl)-2,3-dihydro-1H-benzo[d]pyrrolo[1,2-a]imidazole (Intermediate E)

Intermediate E

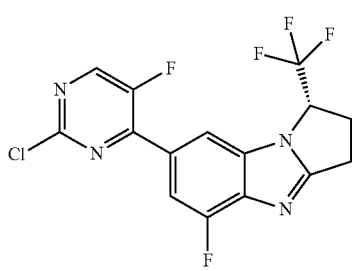

(S)-1-(5-bromo-3-fluoro-2-nitrophenyl)-5-(trifluoromethyl)pyrrolidin-2-one (E-1)

To a solution of (S)-5-(trifluoromethyl)pyrrolidin-2-one (145 mg, 0.95 mmol) in dimethyl formamide (3 mL) was added NaH (57 mg, 1.42 mmol, 60% in oil) at r.t. The mixture was stirred at r.t. for 30 min. A solution of commercial available 5-bromo-1,3-difluoro-2-nitrobenzene (225 mg, 0.95 mmol) was added at r.t., and the resulting solution was stirred at r.t. for another 1 h. Water (30 mL) was added to quench the reaction, and the mixture was extracted with ethyl acetate (3×30 mL). The extracts was washed sequentially with water (3×30 mL) and brine (30 mL), dried over sodium sulfate and concentrated. The residue was purified by flash column chromatography on silica gel eluting with ethyl acetate/petroleum ether (1:5) to give the title compound (S)-1-(5-bromo-3-fluoro-2-nitrophenyl)-5-(trifluoromethyl)pyrrolidin-2-one (E-1). MS-ESI (m/z): 371, 373 $[M+1]^+$.

(S)-1-(2-amino-5-bromo-3-fluorophenyl)-5-(trifluoromethyl) pyrrolidin-2-one (E-2)

A suspension of (S)-1-(5-bromo-3-fluoro-2-nitrophenyl)-5-(trifluoromethyl)-pyrrolidin-2-one (E-1)(200 mg, 0.54 mmol), iron powder (181 mg, 3.23 mmol), ammonium chloride (58 mg, 1.08 mmol) and water (2.0 mL) in ethanol (10 mL) was stirred at 80° C. for 2 h. The solids were filtered out by celite, and filter cake was washed with methanol (30 mL). Filtrate was concentrated in vacuum. The residue was dissolved in ethyl acetate (50 mL), washed sequentially with water (2×30 mL) and brine (30 mL), dried over sodium sulfate and concentrated. The residue was purified by flash column chromatography on silica gel eluting with ethyl acetate/petroleum ether (1:2) to give the title compound (S)-1-(2-amino-5-bromo-3-fluorophenyl)-5-(trifluoromethyl)pyrrolidin-2-one (E-2). MS-ESI (m/z): 341, 343$[M+1]^+$.

(S)-7-bromo-5-fluoro-1-(trifluoromethyl)-2,3-dihydro-1H-benzo[d]pyrrolo[1,2-a]imidazole (E-3)

A solution of (S)-1-(2-amino-5-bromo-3-fluorophenyl)-5-(trifluoromethyl)-pyrrolidin-2-one (E-2)(180 mg, 0.53 mmol), acetic acid (1 mL) in toluene (10 mL) was stirred at 110° C. for 16 h. The solvent was removed by evaporation. The residue was purified by flash column chromatography on silica gel eluting with ethyl acetate/dichloromethane (1:30) to give the title compound (S)-7-bromo-5-fluoro-1-(trifluoromethyl)-2,3-dihydro-1H-benzo[d]pyrrolo[1,2-a]imidazole (E-3) MS-ESI (m/z): 323, 325$[M+1]^+$.

(S)-5-fluoro-7-(4,4,5,5-tetramethyl-1,3,2-dioxaborolan-2-yl)-1-(trifluoromethyl)-2,3-dihydro-1H-benzo[d]pyrrolo[1,2-a]imidazole (E-4)

A mixture of (S)-7-bromo-5-fluoro-1-(trifluoromethyl)-2,3-dihydro-1H-benzo[d]pyrrolo[1,2-a]imidazole (E-3)(150 mg, 0.46 mmol), bis(pinacolato)diboron (175 mg, 1.28 mmol), palladium diacetate (10 mg, 0.046 mmol), tricyclohexyl phosphine (26 mg, 0.092 mmol), and potassium acetate (135 mg, 1.38 mmol) in dimethyl sulfoxide (3 mL) was stirred at 100° C. for 2 h under nitrogen atmosphere. Water (30 mL) was added, and the mixture was extracted with ethyl acetate (3×30 mL). The extracts was washed with water (3×30 mL), brine (30 mL), dried over sodium sulfate and concentrated. The residue was purified by column chromatography on silica gel eluting with ethyl acetate/petroleum ether (1:99~1:50) to give the title compound (S)-5-fluoro-7-(4,4,5,5-tetramethyl-1,3,2-dioxaborolan-2- yl)-1-(trifluoromethyl)-2,3-dihydro-1H-benzo[d]pyrrolo[1,2-a]imidazole (E-4). MS-ESI (m/z): 371 [M+1]⁺.

(S)-7-(2-chloro-5-fluoropyrimidin-4-yl)-5-fluoro-1-(trifluoromethyl)-2,3-dihydro-1H-benzo[d]pyrrolo[1,2-a]imidazole (Intermediate E)

Nitrogen was bubbled into a mixture of 2,4-dichloro-5-fluoropyrimidine (82 mg, 0.49 mmol), sodium carbonate (155 mg, 1.47 mmol) in water (2 mL) and 1,2-dimethoxyethane (5 mL), bis(triphenylphosphine)palladium(II) chloride (34 mg, 0.049 mmol) was added. The mixture was heated at 80° C. and a solution of (S)-5-fluoro-7-(4,4,5,5-tetramethyl-1,3,2-dioxaborolan-2-yl)-1-(trifluoromethyl)-2,3-dihydro-1H-benzo[d]pyrrolo-[1,2-a]imidazole (E-4)(180 mg, 0.49 mmol) in 1,2-dimethoxy ethane (2 mL) was added dropwise. The mixture was stirred at 80° C. for 3 h, and cooled to r.t. Then water (30 mL) was added, and the mixture was extracted with dichloromethane (3×30 mL). The extracts were washed sequentially with water (3×30 mL) and brine (20 mL), dried over sodium sulfate and concentrated. The residue was purified by flash column chromatography on silica gel eluting with ethyl acetate/dichloromethane (1:30) to give the title compound (S)-7-(2-chloro-5-fluoropyrimidin-4-yl)-5-fluoro-1-(trifluoromethyl)-2,3-dihydro-1H-benzo[d]pyrrolo[1,2-a]imidazole (Intermediate E). MS-ESI (m/z): 375 [M+1]⁺.

Intermediate F (S)-7-(2-chloro-5-fluoropyrimidin-4-yl)-5-fluoro-1-(fluoromethyl)-2,3-dihydro-1H-benzo[d]pyrrolo[1,2-a]imidazole (Intermediate F)

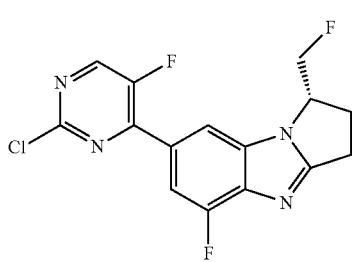

Intermediate F (S)-1-(5-bromo-3-fluoro-2-nitrophenyl)-5-(fluoromethyl)pyrrolidin-2-one (F-1)

The title compound (S)-1-(5-bromo-3-fluoro-2-nitrophenyl)-5-(fluoromethyl)-pyrrolidin-2-one (F-1) was prepared according to the synthetic method of C-2 by replacing (S)-1-(5-bromo-3-fluoro-2-nitrophenyl)-5-oxopyrrolidine-2-carbaldehyde (C-1) with (S)-1-(5-bromo-3-fluoro-2-nitrophenyl)-5-(hydroxymethyl)pyrrolidin-2-one (B-1). MS-ESI (m/z): 335[M+1]⁺.

(S)-1-(2-amino-5-bromo-3-fluorophenyl)-5-(fluoromethyl)pyrrolidin-2-one (F-2)

The title compound (S)-1-(2-amino-5-bromo-3-fluorophenyl)-5-(fluoromethyl)pyrrolidin-2-one (F-2) was prepared according to the synthetic method of A-4 by replacing (S)-1-(5-bromo-3-fluoro-2-nitrophenyl)-5-(((tert-butyldimethylsilyl)oxy)methyl)pyrrolidin-2-one (A-3) with (S)-1-(5-bromo-3-fluoro-2-nitrophenyl)-5-(fluoromethyl)pyrrolidin-2-one (F-1) MS-ESI (m/z): 305 [M+1]⁺.

(S)-7-bromo-1-(difluoromethyl)-5-fluoro-2,3-dihydro-1H-benzo[d]pyrrolo[1,2-a]imidazole (F-3)

The title compound (S)-7-bromo-1-(difluoromethyl)-5-fluoro-2,3-dihydro-1H-benzo[d]pyrrolo[1,2-a]imidazole (F-3) was prepared according to the synthetic method of A-5 by replacing (S)-1-(2-amino-5-bromo-3-fluorophenyl)-5-(((tert-butyldimethylsilyl)oxy)methyl)pyrrolidin-2-one (A-4) with (S)-1-(2-amino-5-bromo-3-fluorophenyl)-5-(fluoromethyl)pyrrolidin-2-one (F-2). MS-ESI (m/z): 287 [M+1]⁺

(S)-7-(2-chloro-5-fluoropyrimidin-4-yl)-5-fluoro-1-(fluoromethyl)-2,3-dihydro-1H-benzo[d]pyrrolo[1,2-a]imidazolyl (Intermediate F)

The title compound (S)-7-(2-chloro-5-fluoropyrimidin-4-yl)-5-fluoro-1-(fluoromethyl)-2,3-dihydro-1H-benzo[d]pyrrolo[1,2-a]imidazole (Intermediate F) was prepared according to the synthetic method of Intermediate A by replacing (1S)-7-bromo-5-fluoro-1-(((tetrahydro-2H-pyran-2-yl)oxy)methyl)-2,3-dihydro-1H-benzo[d]pyrrolo[1,2-a]imidazole (A-7) with (S)-7-bromo-1-(difluoromethyl)-5-fluoro-2,3-dihydro-1H-benzo[d]pyrrolo[1,2-a]imidazole (F-3). MS-ESI (m/z): 339 [M+1]⁺.

Intermediate G (R)-7-(2-chloro-5-fluoropyrimidin-4-yl)-5-fluoro-1-methyl-2,3-dihydro-1H-benzo[d]pyrrolo[1,2-a]imidazole (Intermediate G)

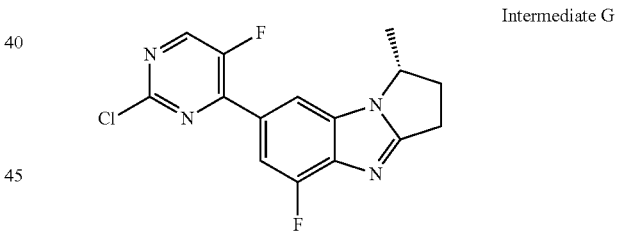

Intermediate G (R)-1-(5-bromo-3-fluoro-2-nitrophenyl)-5-methylpyrrolidin-2-one (G-1)

The title compound (R)-1-(5-bromo-3-fluoro-2-nitrophenyl)-5-methylpyrrolidin-2-one (G-1) was prepared according to the synthetic method of A-3 by replacing (S)-5-(((tert-butyldimethylsilyl)oxy)methyl)pyrrolidin-2-one (A-2) with (R)-5-methylpyrrolidin-2-one (EP2565182A1). MS-ESI (m/z): 317 [M+1]⁺.

(R)-1-(2-amino-5-bromo-3-fluorophenyl)-5-methylpyrrolidin-2-one (G-D)

The title compound (R)-1-(2-amino-5-bromo-3-fluorophenyl)-5-methylpyrrolidin-2-one (G-2) was prepared according to the synthetic method of A-4 by replacing (S)-1-(5-bromo-3-fluoro-2-nitrophenyl)-5-(((tert-butyldimethylsilyl)oxy)methyl)pyrrolidin-2-one (A-3) with (R)-1-(5- bromo-3-fluoro-2-nitrophenyl)-5-methylpyrrolidin-2-one (G-1). MS-ESI (m/z): 287 [M+1]⁺.

(R)-7-bromo-5-fluoro-1-methyl-2,3-dihydro-1H-benzo[d]pyrrolo[1,2-a]imidazole (G-3)

The title compound (R)-7-bromo-5-fluoro-1-methyl-2,3-dihydro-1H-benzo[d]pyrrolo[1,2-a]imidazole (G-3) was prepared according to the synthetic method of A-5 by replacing (S)-1-(2-amino-5-bromo-3-fluorophenyl)-5-(((tert-butyldimethylsilyl)oxy)methyl)pyrrolidin-2-one (A-4) with (R)-1-(2-amino-5-bromo-3-fluorophenyl)-5-methylpyrrolidin-2-one (G-2). MS-ESI (m/z):269 [M+1]⁺.

(R)-7-(2-chloro-5-fluoropyrimidin-4-yl)-5-fluoro-1-methyl-2,3-dihydro-1H-benzo[d]pyrrolo[1,2-a]imidazole (Intermediate G)

The title compound (R)-7-(2-chloro-5-fluoropyrimidin-4-yl)-5-fluoro-1-methyl-2,3-dihydro-1H-benzo[d]pyrrolo[1,2-a]imidazole (Intermediate G) was prepared according to the synthetic method of Intermediate A by replacing (1S)-7-bromo-5-fluoro-1-(((tetrahydro-2H-pyran-2-yl)oxy)methyl)-2,3-dihydro-1H-benzo[d]pyrrolo[1,2-a]imidazole (A-7) with (R)-7-bromo-5-fluoro-1-methyl-2,3-dihydro-1H-benzo[d]pyrrolo[1,2-a]imidazole (G-3). MS-ESI (m/z): 321 [M+1]⁺.

Intermediate H 7-(2-chloro-5-fluoropyrimidin-4-yl)-5-fluoro-1,1-dimethyl-2,3-dihydro-1H-benzo[d]pyrrolo[1,2-a]imidazole (Intermediate H)

Intermediate H

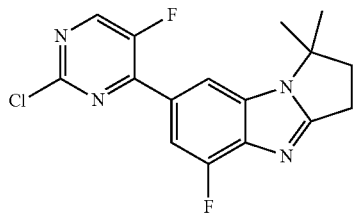

Methyl 4-methyl-4-nitropentanoate (H-1)

A mixture of 2-nitropropane (8.9 g, 0.1 mol), methyl acrylate (8.6 g, 0.1 mol) and potassium fluoride (0.58 g, 10 mmol) in ethanol was refluxed for 4 h. The mixture was cooled and concentrated under vacuum. The residue was diluted with EA and water. The organic layer was washed sequentially with water and brine, dried over Na₂SO₄, and concentrated to give the title compound methyl 4-methyl-4-nitropentanoate (H-1).

5,5-Dimethylpyrrolidin-2-one (H-2)

To a solution of NiCl₂.6H₂O (9.85 g, 41.4 mmol) in methanol (500 ml) was added NaBH₄ (4.7 g, 0.12 mol) in portions at 0-5° C. After stirring for 0.5 h, a solution of methyl 4-methyl-4-nitropentanoate (H-1)(14.5 g, 0.83 mol) in methanol (20 ml) was added thereto followed by the addition of NaBH₄ (11 g, 0.29 mol) in portions. Then the mixture was stirred at 30-35° C. overnight and filtrated. The filtrate was concentrated and purified by column chromatography on silica gel eluting with ethyl acetate/petroleum ether (1:1~9:1) to give the title compound 5,5-dimethylpyrrolidin-2-one (H-2). MS-ESI (m/z): 114 [M+1]⁺.

1-(5-bromo-3-fluoro-2-nitrophenyl)-5,5-dimethylpyrrolidin-2-one (H-3)

The title compound 1-(5-bromo-3-fluoro-2-nitrophenyl)-5,5-dimethylpyrrolidin-2-one (H-3) was prepared according to the synthetic method of A-3 by replacing (S)-5-(((tert-butyldimethylsilyl)oxy)methyl)pyrrolidin-2-one (A-2) with 5,5-dimethylpyrrolidin-2-one (H-2). MS-ESI (m/z): 331 [M+1]⁺.

1-(2-Amino-5-bromo-3-fluorophenyl)-5,5-dimethylpyrrolidin-2-one (H-4)

The title compound 1-(2-amino-5-bromo-3-fluorophenyl)-5,5-dimethylpyrrolidin-2-one (H-4) was prepared according to the synthetic method of A-4 by replacing (S)-1-(5-bromo-3-fluoro-2-nitrophenyl)-5-(((tert-butyldimethylsilyl)oxy)methyl)-pyrrolidin-2-one (A-3) with 1-(5-bromo-3-fluoro-2-nitrophenyl)-5,5-dimethylpyrrolidin-2-one (H-3). MS-ESI (m/z): 301 [M+1]⁺.

7-bromo-5-fluoro-1,1-dimethyl-2,3-dihydro-1H-benzo[d]pyrrolo[1,2-a]imidazole (H-5)

The title compound 7-bromo-5-fluoro-1,1-dimethyl-2,3-dihydro-1H-benzo[d]-pyrrolo[1,2-a]imidazole (H-5) was prepared according to the synthetic method of A-5 by replacing (S)-1-(2-amino-5-bromo-3-fluorophenyl)-5-(((tert-butyldimethylsilyl)oxy)methyl)-pyrrolidin-2-one (A-4) with 1-(2-amino-5-bromo-3-fluorophenyl)-5,5-dimethylpyrrolidin-2-one (H-4). MS-ESI (m/z):283 [M+1]⁺.

5-Fluoro-1,1-dimethyl-7-(4,4,5,5-tetramethyl-1,3,2-dioxaborolan-2-yl)-2,3-dihydro-1H-benzo[d]pyrrolo[1,2-a]imidazole (H-6)

The title compound 5-fluoro-1,1-dimethyl-7-(4,4,5,5-tetramethyl-1,3,2-dioxaborolan-2-yl)-2,3-dihydro-1H-benzo[d]pyrrolo[1,2-d]imidazole (H-6) was prepared according to the synthetic method of A-8 by replacing (1S)-7-bromo-5-fluoro-1-(((tetrahydro-2H-pyran-2-yl)oxy)methyl)-2,3-dihydro-1H-benzo[d]pyrrolo[1,2-a]imidazole (A-7) with 7-bromo-5-fluoro-1,1-dimethyl-2,3-dihydro-1H-benzo[d]pyrrolo[1,2-a]imidazole (H-5). MS-ESI (m/z): 331 [M+1]⁺.

7-(2-chloro-5-fluoropyrimidin-4-yl)-5-fluoro-1,1-dimethyl-2,3-dihydro-1H-benzo[d]pyrrolo[1,2-a]imidazole (Intermediate H)

A mixture of 2, 4-dichloro-5-fluoropyrimidine (1.46 g, 8.7 mmol), 5-fluoro-1,1-dimethyl-7-(4,4,5,5-tetramethyl-1,3,2-dioxaborolan-2-yl)-2,3-dihydro-1H-benzo[d]-pyrrolo[1,2-a]imidazole (H-6)(1.8 g, 4.36 mmol), sodium carbonate (1.48 g, 13.1 mmol), bis(triphenylphosphine)palladium (II) chloride (306 mg, 0.44 mmol), water (12 mL) and 1,2-dimethoxyethane (30 mL) was stirred at 80° C. for 3.5 h. The reaction was quenched by addition of water (100 mL) and the mixture was extracted with EtOAc (3×50 mL). The extracts were washed sequentially with water (3×50 mL) and brine (50 mL), dried over Na₂SO₄ and concentrated. The residue was purified by column chromatography on silica gel eluting with EtOAc/PE (1:2~1:1) to give the title compound 7-(2-chloro-5-fluoropyrimidin-4-yl)-5-fluoro-1,1-dimethyl-2,3-dihydro-1H-benzo[d]pyrrolo[1,2-a]imidazole (Intermediate H). MS-ESI (m/z): 335[M+1]⁺.

Intermediate I 7-(2-chloro-5-fluoropyrimidin-4-yl)-5-fluoro-2,3-dihydro-1H-benzo[d]pyrrolo[1,2-a]imidazole (Intermediate I)

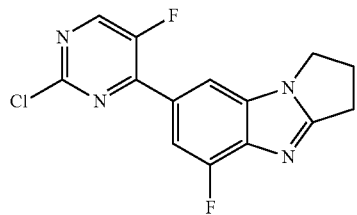

Intermediate I 1-(5-bromo-3-fluoro-2-nitrophenyl)pyrrolidin-2-one (I-1)

The title compound 1-(5-bromo-3-fluoro-2-nitrophenyl)pyrrolidin-2-one (I-1) was prepared according to the synthetic method of A-3 by replacing (S)-5-(((tert-butyldimethylsilyl)oxy)methyl)pyrrolidin-2-one (A-2) with pyrrolidin-2-one. MS-ESI (m/z): 303 [M+1]⁺.

1-(2-amino-5-bromo-3-fluorophenyl)pyrrolidin-2-one (I-2)

The title compound 1-(2-amino-5-bromo-3-fluorophenyl)pyrrolidin-2-one (I-2) was prepared according to the synthetic method of A-4 by replacing (S)-1-(5-bromo-3-fluoro-2-nitrophenyl)-5-(((tert-butyldimethylsilyl)oxy)methyl)pyrrolidin-2-one (A-3) with 1-(5-bromo-3-fluoro-2-nitrophenyl)pyrrolidin-2-one (I-1). MS-ESI (m/z): 273 [M+1]⁺.

7-bromo-5-fluoro-2,3-dihydro-1H-benzo[d]pyrrolo[1,2-a]imidazole (I-3)

The title compound 7-bromo-5-fluoro-2,3-dihydro-1H-benzo[d]pyrrolo[1,2-a]imidazole (I-3) was prepared according to the synthetic method of A-5 by replacing (S)-1-(2-amino-5-bromo-3-fluorophenyl)-5-(((tert-butyldimethylsilyl)oxy)methyl)pyrrolidin-2-one (A-4) with 1-(2-amino-5-bromo-3-fluorophenyl)pyrrolidin-2-one (I-2). MS-ESI (m/z):255 [M+1]⁺.

7-(2-chloro-5-fluoropyrimidin-4-yl)-5-fluoro-2,3-dihydro-1H-benzo[d]pyrrolo[1, 2-a]imidazole (Intermediate I)

The title compound 7-(2-chloro-5-fluoropyrimidin-4-yl)-5-fluoro-2,3-dihydro-1H-benzo[d]pyrrolo[1,2-a]imidazole (Intermediate I) was prepared according to the synthetic method of Intermediate A by replacing (1S)-7-bromo-5-fluoro-1-(((tetrahydro-2H-pyran-2-yl)oxy)methyl)-2,3-dihydro-1H-benzo[d]pyrrolo[1,2-a]imidazole (A-7) with 7-bromo-5-fluoro-2,3-dihydro-1H-benzo[d]pyrrolo[1,2-a]imidazole (I-3). MS-ESI (m/z): 307 [M+1]⁺.

Intermediate J (R)-7-(2-chloro-5-fluoropyrimidin-4-yl)-1-(difluoromethyl)-5-fluoro-2,3-dihydro-1H-benzo[d]pyrrolo[1,2-a]imidazole (Intermediate J)

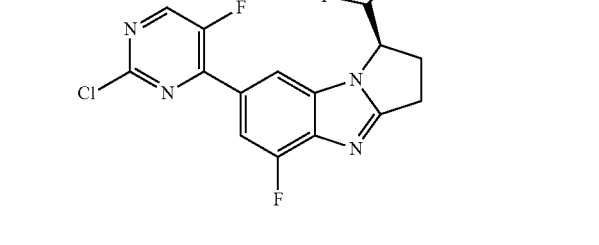

Intermediate J

The title compound (R)-7-(2-chloro-5-fluoropyrimidin-4-yl)-1-(difluoromethyl)-5-fluoro-2,3-dihydro-1H-benzo[d]pyrrolo[1,2-a]imidazole (Intermediate J) was prepared according to the synthetic method of Intermediate C by replacing ethyl L-pyroglutamate with ethyl D-pyroglutamate. MS-ESI (m/z): 357 [M+1]⁺.

Intermediate K (S)-7-(2-chloro-5-fluoropyrimidin-4-yl)-5-fluoro-1-methyl-2,3-dihydro-1H-benzo[d]dipyrrolo[1,2-a]imidazole (Intermediate K)

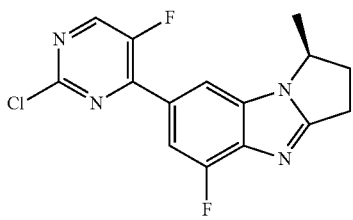

Intermediate K

The title compound (S)-7-(2-chloro-5-fluoropyrimidin-4-yl)-5-fluoro-1-methyl-2,3-dihydro-1H-benzo[d]pyrrolo[1,2-a]imidazole (Intermediate K) was prepared according to the synthetic method of Intermediate G by replacing (R)-5-methylpyrrolidin-2-one with (S)-5-methylpyrrolidin-2-one. MS-ESI (m/z): 321 [M+1]⁺.

Intermediate L (R)-7-(2-chloro-5-fluoropyrimidin-4-yl)-5-fluoro-1-(methoxymethyl)-2,3-dihydro-1H-benzo[d]pyrrolo[1,2-a]imidazole (Intermediate L)

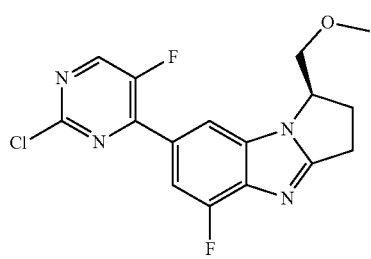

Intermediate L

The title compound (R)-7-(2-chloro-5-fluoropyrimidin-4-yl)-5-fluoro-1-(methoxymethyl)-2,3-dihydro-1H-benzo[d]pyrrolo[1,2-a]imidazole (Intermediate L) was prepared according to the synthetic method of Intermediate B by replacing ethyl L-pyroglutamate with ethyl D-pyroglutamate. MS-ESI (m/z): 351 [M+1]$^+$.

Intermediate M 7-(2-bromo-5-fluoropyridin-4-yl)-5-fluoro-1,1-dimethyl-2,3-dihydro-1H-benzo[d]pyrrolo[1,2-a]imidazole (Intermediate M)

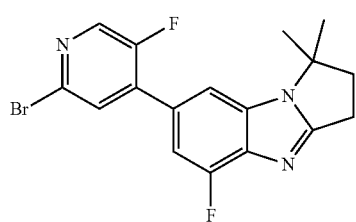

Intermediate M

The title compound 7-(2-bromo-5-fluoropyridin-4-yl)-5-fluoro-1,1-dimethyl-2,3-dihydro-1H-benzo[d]pyrrolo[1,2-a]imidazole (Intermediate M) was prepared according to the synthetic method of Intermediate H by replacing 2,4-dichloro-5-fluoropyrimidine with 2-bromo-5-fluoro-4-iodopyridine (WO2015/2915 A1). MS-ESI (m/z): 378 [M+1]$^+$.

Intermediate N tert-butyl 4-((6-aminopyridin-3-yl)methyl)piperazine-1-carboxylate (Intermediate N)

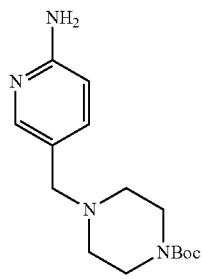

Intermediate N

Tert-butyl 4-((6-bromopyridin-3-yl)methyl)piperazine-1-carboxylate (N-1)

To a solution of 2-bromo-5-formylpyridine (11.0 g, 59.1 mmol) and tert-butyl piperazine-1-carboxylate (10.0 g, 53.7 mmol) in DCM (100 mL) was added sodium triacetoxyborohydride (13.6 g, 64.1 mmol) portionwise at 0° C. The mixture was warmed to r.t. and stirred at r.t. overnight. DCM (100 mL) was added, followed by sodium hydroxide aqueous solution (2N, 100 mL) at 0° C. The aqueous layer was extracted with DCM (100 mL). The combined organic layer was washed with brine (100 mL), dried over Na$_2$SO$_4$ and concentrated to give the crude product of the title compound tert-butyl 4-((6-bromopyridin-3-yl)methyl)piperazine-1-carboxylate (N-1), which was used for the next step without further purification. MS-ESI (m/z): 356[M+1]$^+$.

tert-butyl 4-((6-aminopyridin-3-yl)methyl)piperazine-1-carboxylate (Intermediate N)

Nitrogen was bubbled into a mixture of tert-butyl 4-((6-bromopyridin-3-yl)methyl)piperazine-1-carboxylate (N-1) (3.56 g, 10.0 mmol), cuprous oxide (0.50 g, 0.3 mmol) in ammonium hydroxide (20 mL) and MeOH (20 mL), and the mixture was heated at 70° C. in sealed tube overnight. The reaction mixture was cooled to r.t., and filtered. The filtrate was concentrated under vacuum. The residue was diluted with sodium hydroxide aqueous solution (2N, 50 mL), and the mixture was extracted with DCM (2×100 mL). The extracts were washed with brine (100 mL), dried over Na$_2$SO$_4$ and concentrated to give crude product as yellow oil. The crude product was recrystallized with tert-Butyl methyl ether to give the title compound tert-butyl 4-((6-aminopyridin-3-yl)methyl)piperazine-1-carboxylate (Intermediate N). MS-ESI (m/z): 293 [M+1]$^+$.

Following essentially the same procedures described for Intermediate N, Intermediate O-DD were prepared by replacing tert-butyl piperazine-1-carboxylate with proper amines which were commercially available or readily prepared using the method known in the art. The structures and names of Intermediate O-DD are given in Table 1.

TABLE 1

| Intermediate | Structure | NAME | DATA |
|---|---|---|---|
| O | 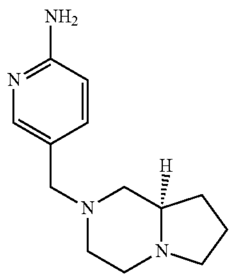 [SMILES: Nc1ccc(CN2CCN3CCC[C@@H]3C2)cn1] | (R)-5-((hexahydropyrrolo[1,2-a]pyrazin-2(1H)-yl)methyl)pyridin-2-amine | MS-ESI (m/z): 233 [M + 1]⁺ |
| P | 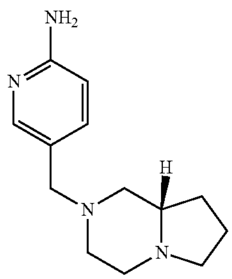 [SMILES: Nc1ccc(CN2CCN3CCC[C@H]3C2)cn1] | (S)-5-((hexahydropyrrolo[1,2-a]pyrazin-2(1H)-yl)methyl)pyridin-2-amine | MS-ESI (m/z): 233 [M + 1]⁺ |
| Q | 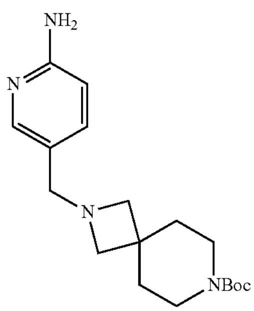 [SMILES: CC(C)(C)OC(=O)N1CCC2(CC1)CN(Cc1ccc(N)nc1)C2] | tert-butyl 2-((6-aminopyridin-3-yl)methyl)-2,7-diazaspiro[3.5]nonane-7-carboxylate | MS-ESI (m/z): 333 [M + 1]⁺ |
| R | 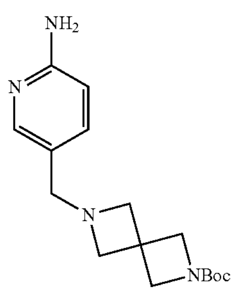 | tert-butyl 6-((6-aminopyridin-3-yl)methyl)-2,6-diazaspiro[3.3]heptane-2-carboxylate | MS-ESI (m/z): 305 [M + 1]⁺ |
| S | 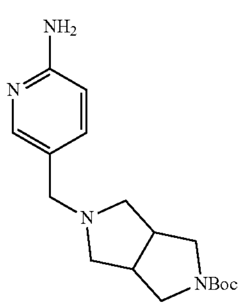 [SMILES: CC(C)(C)OC(=O)N1CC2CN(Cc3ccc(N)nc3)CC2C1] | tert-butyl 5-((6-aminopyridin-3-yl)methyl)hexahydropyrrolo[3,4-c]pyrrole-2(1H)-carboxylate | MS-ESI (m/z): 319 [M + 1]⁺ |

TABLE 1-continued

| Intermediate | Structure | NAME | DATA |
| --- | --- | --- | --- |
| T | 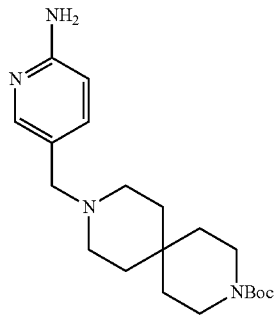 [SMILES: CC(C)(C)OC(=O)N1CCC2(CCN(Cc3ccc(N)nc3)CC2)CC1] | tert-butyl 9-((6-aminopyridin-3-yl)methyl)-3,9-diazaspiro[5.5]undecane-3-carboxylate | MS-ESI (m/z): 361 [M + 1]+ |
| U | 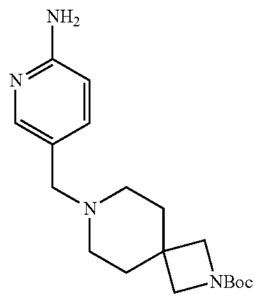 [SMILES: CC(C)(C)OC(=O)N1CC2(CCN(Cc3ccc(N)nc3)CC2)C1] | tert-butyl 7-((6-aminopyridin-3-yl)methyl)-2,7-diazaspiro[3.5]nonane-2-carboxylate | MS-ESI (m/z): 333 [M + 1]+ |
| V | 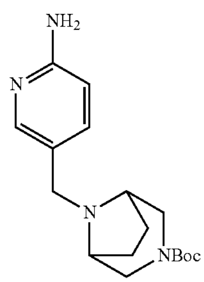 [SMILES: CC(C)(C)OC(=O)N1CC2CCC(C1)N2Cc1ccc(N)nc1] | tert-butyl 8-((6-aminopyridin-3-yl)methyl)-3,8-diazabicyclo[3.2.1]octane-3-carboxylate | MS-ESI (m/z): 319 [M + 1]+ |
| W | 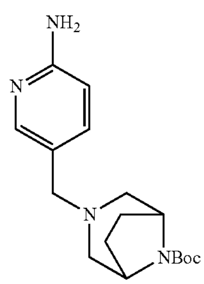 [SMILES: CC(C)(C)OC(=O)N1C2CCC1CN(Cc1ccc(N)nc1)C2] | tert-butyl 3-((6-aminopyridin-3-yl)methyl)-3,8-diazabicyclo[3.2.1]octane-8-carboxylate | MS-ESI (m/z): 319 [M + 1]+ |
| X | 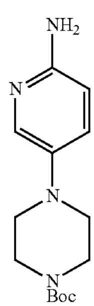 | tert-butyl 4-(6-aminopyridin-3-yl)piperazine-1-carboxylate | MS-ESI (m/z): 279 [M + 1]+ |

TABLE 1-continued

| Intermediate | Structure | NAME | DATA |
|---|---|---|---|
| Y | 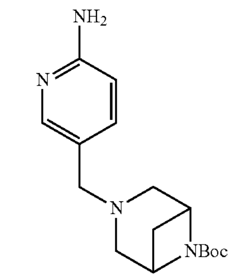 [SMILES: CC(C)(C)OC(=O)N1C2CC1CN(Cc1ccc(N)nc1)C2] | tert-butyl 3-((6-aminopyridin-3-yl)methyl)-3,6-diazabicyclo[3.1.1]heptane-6-carboxylate | MS-ESI (m/z): 305 [M + 1]+ |
| Z | 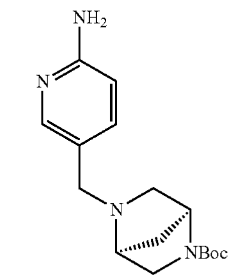 | tert-butyl (1S,4S)-5-((6-aminopyridin-3-yl)methyl)-2,5-diazabicyclo[2.2.1]heptane-2-carboxylate | MS-ESI (m/z): 305 [M + 1]+ |
| AA | 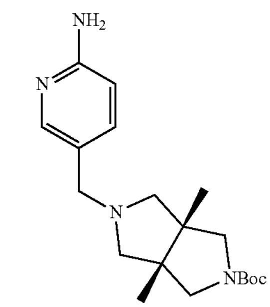 [SMILES: CC(C)(C)OC(=O)N1C[C@]2(C)CN(Cc3ccc(N)nc3)C[C@]2(C)C1] | tert-butyl (3aR,6aS)-5-((6-aminopyridin-3-yl)methyl)-3a,6a-dimethyl-hexahydropyrrolo[3,4-c]pyrrole-2(1H)-carboxylate | MS-ESI (m/z): 347 [M + 1]+ |
| BB | 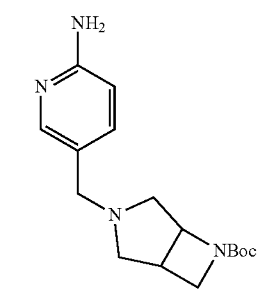 [SMILES: CC(C)(C)OC(=O)N1CC2CN(Cc3ccc(N)nc3)CC21] | tert-butyl 3-((6-aminopyridin-3-yl)methyl)-3,6-diazabicyclo[3.2.0]heptane-6-carboxylate | MS-ESI (m/z): 305 [M + 1]+ |
| CC | 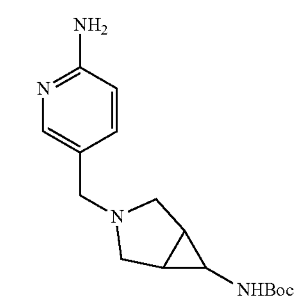 [SMILES: CC(C)(C)OC(=O)NC1C2CN(Cc3ccc(N)nc3)CC21] | tert-butyl (3-((6-aminopyridin-3-yl)methyl)-3-azabicyclo[3.1.0]hexan-6-yl)carbamate | MS-ESI (m/z): 305 [M + 1]+ |

TABLE 1-continued

| Intermediate | Structure | NAME | DATA |
| --- | --- | --- | --- |
| DD | 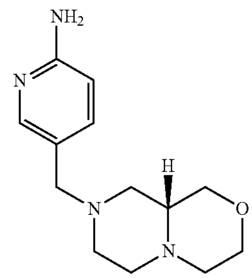 [SMILES: Nc1ccc(CN2CCN3CCOC[C@H]3C2)cn1] | (R)-5-((hexahydropyrazino[2,1-c][1,4]oxazin-8(1H)-yl)methyl)pyridin-2-amine | MS-ESI (m/z): 249 [M + 1]+ |

Intermediate EE tert-butyl 4-((2-aminopyrimidin-5-yl)methyl)piperazine-1-carboxylate (Intermediate EE)

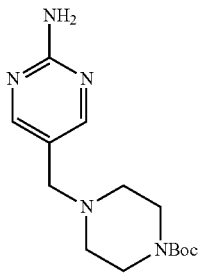

Intermediate EE

The title compound tert-butyl 4-((2-aminopyrimidin-5-yl)methyl)piperazine-1-carboxylate (Intermediate EE) was prepared according to the synthetic method of Intermediate N by replacing 2-bromo-5-formylpyridine with 2-bromopyrimidine-5-carbaldehyde. MS-ESI (m/z): 294 [M+1]+.

Example 1

(S)-(5-fluoro-7-(5-fluoro-2-((5-(piperazin-1-ylmethyl)pyridin-2-yl)amino)pyrimidin-4-yl)-2,3-dihydro-1H-benzo[d]pyrrolo[1,2-a]imidazol-1-yl)methanol (1)

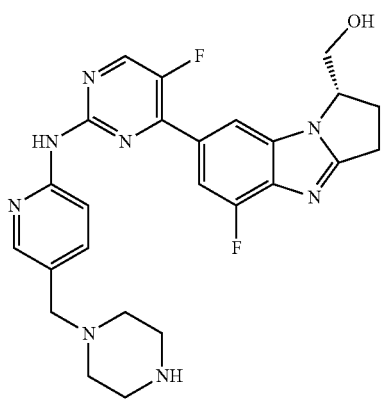

tert-butyl 4-((6-((5-fluoro-4-(1S)-5-fluoro-1-(((tetrahydro-2H-pyran-2-yl)oxy)methyl)-2,3-dihydro-1H-benzo[d]pyrrolo[1,2-a]imidazol-7-yl)pyrimidin-2-yl)amino)pyridin-3-yl)methyl)piperazine-1-carboxylate (1a)

A mixture of (1S)-7-(2-chloro-5-fluoropyrimidin-4-yl)-5-fluoro-1-(((tetrahydro-2H-pyran-2-yl)oxy)methyl)-2,3-dihydro-1H-benzo[d]pyrrolo[1,2-a]imidazole (Intermediate A) (150 mg, 0.356 mmol), Intermediate N (125 mg, 0.427 mmol), bis(dibenzylideneacetone) palladium (16 mg, 0.018 mmol), 4,5-bis(diphenylphosphino)-9,9-dimethyl-xanthene (21 mg, 0.036 mmol) and potassium carbonate (98 mg, 0.712 mmol) in tert-amyl alcohol (5 mL) was stirred at 100° C. under nitrogen atmosphere for 3 h. The mixture was cooled to r.t. and diluted with DCM (10 mL). The solid was removed by filtration, and the filtrate was concentrated. The residue was purified by column chromatography on silica gel eluting with EtOAc/DCM (1:30) to give the title compound tert-butyl 4-((6-((5-fluoro-4-((1S)-5-fluoro-1-(((tetrahydro-2H-pyran-2-yl)oxy) methyl)-2,3-dihydro-1H-benzo[d]pyrrolo[1,2-a]imidazol-7-yl)pyrimidin-2-yl)amino) pyridin-3-yl)methyl)-piperazine-1-carboxylate (1a). MS-ESI (m/z): 677[M+1]+.

tert-butyl (S)-4-(#6-((5-fluoro-4-(5-fluoro-1-(hydroxymethyl)-2,3-dihydro-1H-benzo[d]pyrrolo[1,2-a]imidazol-7-yl)pyrimidin-2-yl)amino)pyridin-3-yl) methyl)piperazine-1-carboxylate (1b)

To a solution of tert-butyl 4-((6-((5-fluoro-4-((1S)-5-fluoro-1-(((tetrahydro-2H-pyran-2-yl)oxy)methyl)-2,3-dihydro-1H-benzo[d]pyrrolo[1,2-a]imidazol-7-yl)-pyrimidin-2-yl)amino)pyridin-3-yl)methyl)-piperazine-1-carboxylate (1a) (140 mg, 0.24 mmol) in MeOH (5 mL) was added hydrochloric acid (1 N, 0.5 mL), and the mixture was stirred at r.t. overnight. The mixture was poured into sat. NaHCO$_3$ (100 ml) and extracted with DCM (5×50 mL). The extracts were dried over Na$_2$SO$_4$ and concentrated. The residue was purified by column chromatography on silica gel eluting with MeOH/DCM (1:10) to give the title compound tert-butyl (S)-4-((6-((5-fluoro-4-(5-fluoro-1-(hydroxymethyl)-2,3-dihydro-1H-benzo[d]pyrrolo[1,2-a]imidazol-7-yl)pyrimidin-2-yl)amino)pyridin-3-yl)methyl)-piperazine-1-carboxylate (1b). MS-ESI (m/z): 593 [M+1]+.

(S)-(5-fluoro-7-(5-fluoro-2-((5-(piperazin-1-ylmethyl)pyridin-2-yl)amino)pyrimidin-4-yl)-2,3-dihydro-1H-benzo[d]pyrrolo[1,2-a]imidazol-1-yl) methanol (1)

A solution of tert-butyl (S)-4-((6-((5-fluoro-4-(5-fluoro-1-(hydroxymethyl)-2,3-dihydro-1H-benzo[d]pyrrolo[1,2-a]

imidazol-7-yl)pyrimidin-2-yl)amino)pyridin-3-yl)-methyl) piperazine-1-carboxylate (1b) (28 mg, 0.047 mmol) and trifluoroacetic acid (0.5 mL) in DCM (1 mL) was stirred at r.t. for 2 h. The solvent was removed by evaporation, and the residue was diluted by water (20 mL). The mixture was adjusted top H9-10 using potassium carbonate, and extracted with DCM (3×20 mL). The extracts were washed with brine (30 mL), dried over $Na_2SO_4$ and concentrated. The residue was purified by column chromatography on silica gel eluting with DCM/MeOH (10:1) to give the title compound (S)-(5-fluoro-7-(5-fluoro-2-((5-(piperazin-1-yl) methyl)pyridin-2-yl)amino)pyrimidin-4-yl)-2, 3-dihydro-1H-benzo[d]pyrrolo[1,2-a]imidazol-1-yl)methanol (1). MS-ESI (m/z): 493[M+1]$^+$.

Example 2

(S)-(5-fluoro-7-(5-fluoro-2-((5-((4-methylpiperazin-1-yl)methyl)pyridin-2-yl)amino)pyrimidin-4-yl)-2,3-dihydro-1H-benzo[d]pyrrolo[1,2-a]imidazol-1-yl) methanol (2)

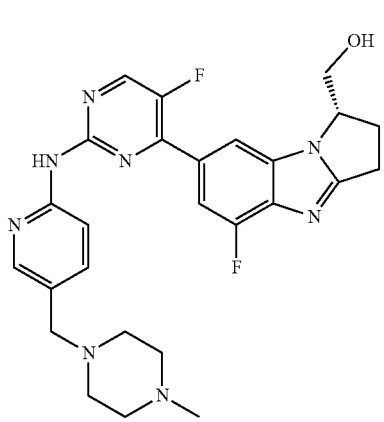

To a solution of (S)-(5-fluoro-7-(5-fluoro-2-((5-(piperazin-1-ylmethyl)-pyridin-2-yl)amino)pyrimidin-4-yl)-2,3-dihydro-1H-benzo[d]pyrrolo[1,2-a]imidazol-1-yl-methanol (1)(13 mg, 0.026 mmol) and sodium triacetoxyborohydride (11 mg, 0.053 mmol) in 1,2-dichloroethane (0.5 mL) was added formaldehyde (36.5%, 10 mg) at r.t. The resulting solution was stirred at r.t. for 1 h. The reaction was quenched by water (20 mL), and the mixture was extracted with DCM (3×20 mL). The extracts were washed sequentially with water (2×20 mL) and brine (20 mL), dried over $Na_2SO_4$ and concentrated. The residue was purified by column chromatography on silica gel eluting with DCM/MeOH (10:1) to give the title compound (S)-(5-fluoro-7-(5-fluoro-2-((5-((4-methylpiperazin-1-yl)methyl)pyridin-2-yl)amino)pyrimidin-4-yl)-2,3-dihydro-1H-benzo[d]pyrrolo[1,2-a]imidazol-1-yl)methanol (2). MS-ESI (m/z): 507[M+1]$^+$.

Example 3

(S)-(7-(2-((5-((4-ethylpiperazin-1-yl)methyl)pyridin-2-yl)amino)-5-fluoropyrimidin-4-yl)-5-fluoro-2,3-dihydro-1H-benzo[d]pyrrolo[1,2-a]imidazol-1-yl) methanolic)

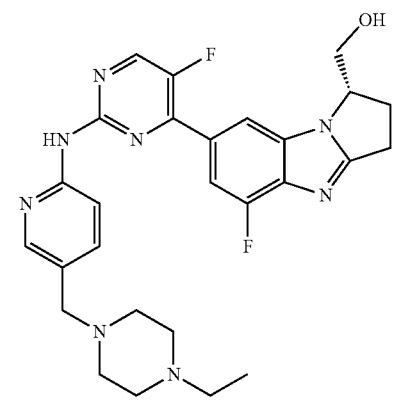

To a solution of (S)-(5-fluoro-7-(5-fluoro-2-((5-(piperazin-1-ylmethyl)-pyridin-2-yl)amino)pyrimidin-4-yl)-2,3-dihydro-1H-benzo[d]pyrrolo[1,2-a]imidazol-1-yl-methanol (1)(12 mg, 0.025 mmol) and sodium triacetoxyborohydride (10 mg, 0.05 mmol) in 1,2-dichloroethane (0.5 mL) was added acetaldehyde (40% in isopropanol, 10 mg) at r.t. The resulting solution was stirred at r.t. for 1 h. The reaction was quenched by water (20 mL), and the mixture was extracted with DCM (3*20 mL). The extracts were washed sequentially with water (2*20 mL) and brine (20 mL), dried over $Na_2SO_4$ and concentrated. The residue was purified by column chromatography on silica gel eluting with DCM/MeOH (10:1) to give the title compound (S)-(7-(2-((5-((4-ethylpiperazin-1-yl)methyl)pyridin-2-yl)amino)-5-fluoro-pyrimidin-4-yl)-5-fluoro-2,3-dihydro-1H-benzo[d]pyrrolo[1,2-a]imidazol-1-yl) methanol (3). MS-ESI (m/z): 521[M+1]$^+$.

Example 4

(S)-5-fluoro-4-(5-fluoro-1-(fluoromethyl)-2,3-di-hydro-1H-benzo[d]pyrrolo[1,2-a]imidazol-7-yl)-N-(5-(piperazin-1-ylmethyl)pyridin-2-yl)pyrimidin-2-amine (4)

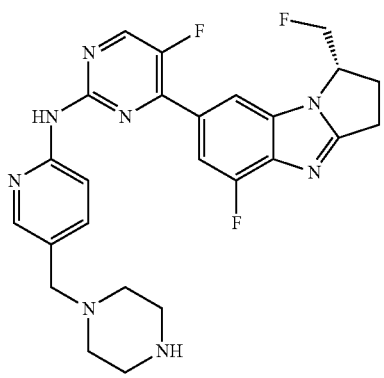

tert-butyl (S)-4-((6-((5-fluoro-4-(5-fluoro-1-(fluoromethyl)-2,3-dihydro-1H-benzo[d]pyrrolo[1,2-a]imidazol-7-yl)pyrimidin-2-yl)amino)pyridin-3-yl)methyl)piperazine-1-carboxylate (4a)

To a solution of tert-butyl (S)-4-((6-((5-fluoro-4-(5-fluoro-1-(hydroxymethyl)-2,3-dihydro-1H-benzo[d]pyrrolo[1,2-a]imidazol-7-yl)pyrimidin-2-yl)-amino)pyridin-3-yl)methyl)piperazine-1-carboxylate (1b)(60 mg, 0.101 mmol) in DCM (10 mL) was added DAST (50 mg, 0.304 mmol) dropwise at 0° C., and the mixture was stirred at r.t. for 0.5 h. MeOH (1 mL) was added thereto at 0° C. to quench the reaction followed by the addition of water (100 mL), and the mixture was extracted with DCM (3×50 mL). The extracts were washed with brine (50 mL), dried over $Na_2SO_4$ and concentrated to give the title compound tert-butyl (S)-4-((6-((5-fluoro-4-(5-fluoro-1-(fluoromethyl)-2,3-dihydro-1H-benzo[d]-pyrrolo[1,2-a]imidazol-7-yl)pyrimidin-2-yl)amino)pyridin-3-yl)methyl)piperazine-1-carboxylate (4a). MS-ESI (m/z): 595[M+1]$^+$.

(S)-5-fluoro-4-(5-fluoro-1-(fluoromethyl)-2,3-di-hydro-1H-benzo[d]pyrrolo[1,2-a]imidazol-7-yl)-N-(5-(piperazin-1-ylmethyl)pyridin-2-yl)pyrimidin-2-amine (4)

The title compound (S)-5-fluoro-4-(5-fluoro-1-(fluoromethyl)-2,3-dihydro-1H-benzo[d]pyrrolo[1,2-a]imidazol-7-yl)-N-(5-(piperazin-1-ylmethyl)pyridin-2-yl)pyrimidin-2-amine (4) was prepared according to the synthetic method of 1 by replacing tert-butyl (S)-4-((6-((5-fluoro-4-(5-fluoro-1-(hydroxymethyl)-2,3-dihydro-1H-benzo[d]-pyrrolo[1,2-a]imidazol-7-yl)pyrimidin-2-yl)amino)pyridin-3-yl)-methyl)piperazine-1-carboxylate (1b) with tert-butyl (S)-4-((6-((5-fluoro-4-(5-fluoro-1-(fluoromethyl)-2,3-dihydro-1H-benzo[d]-pyrrolo[1,2-a]imidazol-7-yl)pyrimidin-2-yl)amino)pyridin-3-yl)-methyl)piperazine-1-carboxylate (4a). MS-ESI (m/z): 495[M+1]$^+$.

Example 5

(S)-5-fluoro-4-(5-fluoro-1-(fluoromethyl)-2,3-dihydro-1H-benzo[d]pyrrolo[1,2-a]imidazol-7-yl)-N-(5-((4-methyl-piperazin-1-yl)methyl)pyridin-2-yl)pyrimidin-2-amine (5)

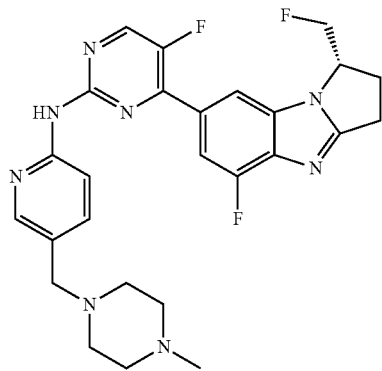

The title compound (S)-5-fluoro-4-(5-fluoro-1-(fluoromethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine (5) was prepared according to the synthetic method of 2 by replacing (S)-(5-fluoro-7-(5-fluoro-2-((5-(piperazin-1-ylmethyl)pyridin-2-yl)amino)-pyrimidin-4-yl)-2,3-dihydro-1H-benzo[d]pyrrolo[1,2-a]imidazol-1-yl)methanol (1) with (S)-5-fluoro-4-(5-fluoro-1-(fluoromethyl)-2,3-dihydro-1H-benzo[d]pyrrolo[1,2-a]imidazol-7-yl)-N-(5-(piperazin-1-ylmethyl)pyridin-2-yl)pyrimidin-2-amine (4). MS-ESI (m/z): 509[M+1]$^+$.

Example 6

(S)—N-(5-((4-ethylpiperazin-1-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine (6)

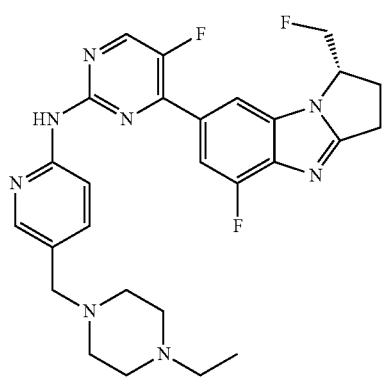

The title compound (S)—N-(5-((4-ethylpiperazin-1-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine (6) was prepared according to the synthetic method of 3 by replacing (S)-(5-fluoro-7-(5-fluoro-2-((5-(piperazin-1-ylmethyl)pyridin-2-yl)amino)-pyrimidin-4-yl)-2,3-dihydro-1H-benzo[d]pyrrolo[1,2-a]imidazol-1-yl)methanol (1) with (S)-5-fluoro-4-(5-fluoro-1-(fluoromethyl)-2,3-dihydro-1H-benzo[d]pyrrolo[1,2-a]imidazol-7-yl)-N-(5-(piperazin-1-ylmethyl)pyridin-2-yl)pyrimidin-2-amine (4). MS-ESI (m/z): 523 [M+1]$^+$.

Example 7

(S)-5-fluoro-4-(5-fluoro-1-(methoxymethyl)-2,3-dihydro-1H-benzo[d]pyrrolo[1,2-a]imidazol-7-yl)-N-(5-(piperazin-1-ylmethyl)pyridin-2-yl)pyrimidin-2-amine (7)

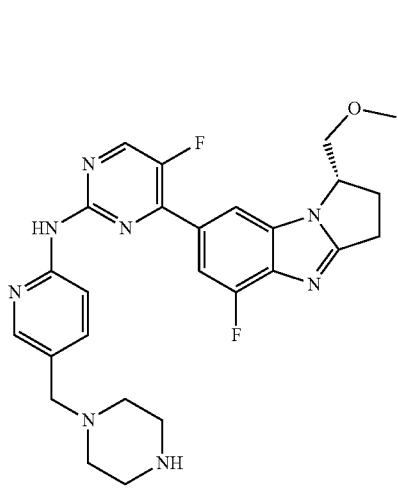

tert-butyl (S)-4-(((6-((5-fluoro-4-(5-fluoro-1-(methoxymethyl)-2,3-dihydro-1H-benzo[d]pyrrolo[1,2-a]imidazol-7-yl)pyrimidin-2-yl)amino)pyridin-3-yl)methyl)piperazine-1-carboxylated (7a)

The title compound tert-butyl (S)-4-(((6-((5-fluoro-4-(5-fluoro-1-(methoxymethyl)-2,3-dihydro-1H-benzo[d]pyrrolo[1,2-a]imidazol-7-yl)pyrimidin-2-yl)-amino)pyridin-3-yl)methyl)piperazine-1-carboxylate (7a) was prepared according to the synthetic method of 1a by replacing (1S)-7-(2-chloro-5-fluoropyrimidin-4-yl)-5-fluoro-1-(((tetrahydro-2H-pyran-2-yl)oxy)methyl)-2,3-dihydro-1H-benzo[d]pyrrolo[1,2-a]imidazole (Intermediate A) with (S)-7-(2-chloro-5-fluoropyrimidin-4-yl)-5-fluoro-1-(methoxymethyl)-2,3-dihydro-1H-benzo[d]pyrrolo[1,2-a]imidazole (Intermediate B). MS-ESI (m/z): 607[M+1]⁺.

(S)-5-fluoro-4-(5-fluoro-1-(methoxymethyl)-2,3-dihydro-1H-benzo[d]pyrrolo[1,2-a]imidazol-7-yl)-N-(5-(piperazin-1-ylmethyl)pyridin-2-yl)pyrimidin-2-amine (7)

The title compound (S)-5-fluoro-4-(5-fluoro-1-(methoxymethyl)-2,3-dihydro-1H-benzo[d]pyrrolo[1,2-a]imidazol-7-yl)-N-(5-(piperazin-1-ylmethyl)pyridin-2-yl)pyrimidin-2-amine (7) was prepared according to the synthetic method of 1 by replacing tert-butyl (S)-4-(((6-((5-fluoro-4-(5-fluoro-1-(hydroxymethyl)-2,3-dihydro-1H-benzo[d]pyrrolo[1,2-a]imidazol-7-yl)pyrimidin-2-yl)amino)pyridin-3-yl)methyl)piperazine-1-carboxylate (1b) with tert-butyl (S)-4-(((6-((5-fluoro-4-(5-fluoro-1-(methoxymethyl)-2,3-dihydro-1H-benzo[d]pyrrolo[1,2-a]imidazol-7-yl)pyrimidin-2-yl)-amino)pyridin-3-yl)methyl)piperazine-1-carboxylate (7a). MS-ESI (m/z): 507[M+1]⁺.

Example 8

(S)-5-fluoro-4-(5-fluoro-1-(methoxymethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine (8)

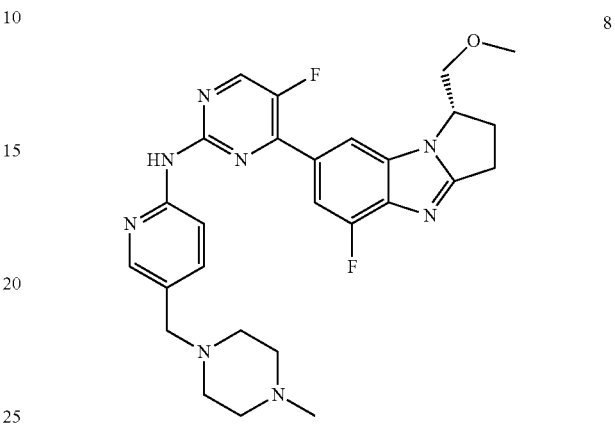

The title compound (S)-5-fluoro-4-(5-fluoro-1-(methoxymethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine (8) was prepared according to the synthetic method of 2 by replacing (S)-(5-fluoro-7-(5-fluoro-2-((5-(piperazin-1-ylmethyl)pyridin-2-yl)amino)-pyrimidin-4-yl)-2,3-dihydro-1H-benzo[d]pyrrolo[1,2-a]imidazol-1-yl)methanol (1) with (S)-5-fluoro-4-(5-fluoro-1-(methoxymethyl)-2,3-dihydro-1H-benzo[d]pyrrolo[1,2-a]imidazol-7-yl)-N-(5-(piperazin-1-ylmethyl)pyridin-2-yl)pyrimidin-2-amine (7). MS-ESI (m/z): 521 [M+1]⁺.

Example 9

(S)—N-(5-((4-ethylpiperazin-1-yl)methyl)pyridin-2-yl)-5-fluoro-4-(5-fluoro-1-(methoxymethyl)-2,3-dihydro-1H-benzo[d]pyrrolo[1,2-a]imidazol-7-yl)pyrimidin-2-amine (9)

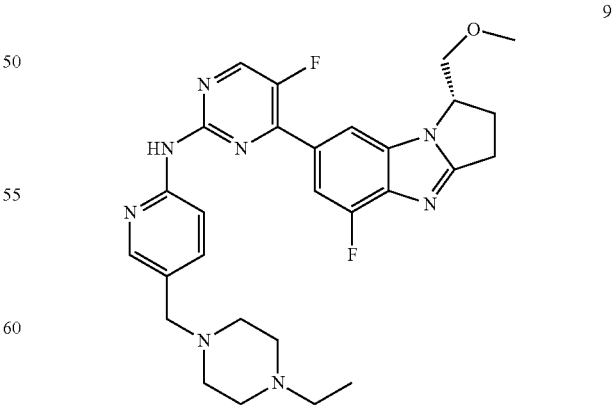

The title compound (S)—N-(5-((4-ethylpiperazin-1-yl)methyl)pyridin-2-yl)-5-fluoro-4-(5-fluoro-1-(methoxymethyl)-2,3-dihydro-1H-benzo[d]pyrrolo[1,2-a]imidazol-7- yl)pyrimidin-2-amine (9) was prepared according to the synthetic method of 3 by replacing (S)-(5-fluoro-7-(5-fluoro-2-((5-(piperazin-1-ylmethyl)pyridin-2-yl)amino)-pyrimidin-4-yl)-2,3-dihydro-1H-benzo[d]pyrrolo[1,2-a]imidazol-1-yl)methanol (1) with (S)-5-fluoro-4-(5-fluoro-1-(methoxymethyl)-2,3-dihydro-1H-benzo[d]pyrrolo[1,2-a]imidazol-7-yl)-N-(5-(piperazin-1-ylmethyl)pyridin-2-yl)pyrimidin-2-amine (7). MS-ESI (m/z): 535[M+1]+

Example 10

(S)-4-(1-(difluoromethyl)-5-fluoro-2,3-dihydro-1H-benzo[d]pyrrolo[1,2-a]imidazol-7-yl)-5-fluoro-N-(5-(piperazin-1-ylmethyl)pyridin-2-yl)pyrimidin-2-amine (10)

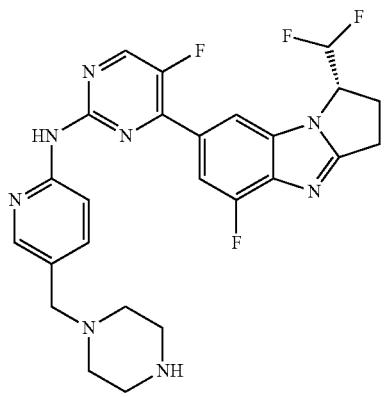

tert-butyl (S)-4-((6-((4-(1-(difluoromethyl)-5-fluoro-2,3-dihydro-1H-benzo[d]pyrrolo[1,2-a]imidazol-7-yl)-5-fluoropyrimidin-2-yl)amino)pyridin-3-yl)methyl)piperazine-1-carboxylate (10a)

The title compound tert-butyl (S)-4-((6-((4-(1-(difluoromethyl)-5-fluoro-2,3-dihydro-1H-benzo[d]pyrrolo[1,2-a]imidazol-7-yl)-5-fluoropyrimidin-2-yl)amino)pyridin-3-yl)methyl)piperazine-1-carboxylate (10a) was prepared according to the synthetic method of 1a by replacing (1S)-7-(2-chloro-5-fluoropyrimidin-4-yl)-5-fluoro-1-(((tetrahydro-2H-pyran-2-yl)oxy)methyl)-2,3-dihydro-1H-benzo[d]pyrrolo[1,2-a]imidazole (Intermediate A) with (S)-7-(2-chloro-5-fluoropyrimidin-4-yl)-1-(difluoromethyl)-5-fluoro-2,3-dihydro-1H-benzo[d]pyrrolo[1,2-a]imidazole (Intermediate C). MS-ESI (m/z): 613[M+1]+.

(S)-4-(1-(difluoromethyl)-5-fluoro-2,3-dihydro-1H-benzo[d]pyrrolo[1,2-a]imidazol-7-yl)-5-fluoro-N-(5-(piperazin-1-ylmethyl)pyridin-2-yl)pyrimidin-2-amine (10)

The title compound (S)-4-(1-(difluoromethyl)-5-fluoro-2,3-dihydro-1H-benzo[d]pyrrolo[1,2-a]imidazol-7-yl)-5-fluoro-N-(5-(piperazin-1-ylmethyl)pyridin-2-yl)-pyrimidin-2-amine (10) was prepared according to the synthetic method of 1 by replacing tert-butyl (S)-4-((6-((5-fluoro-4-(5-fluoro-1-(hydroxymethyl)-2,3-dihydro-1H-benzo[d]-pyrrolo[1,2-a]imidazol-7-yl)pyrimidin-2-yl)amino)pyridin-3-yl)methyl)piperazine-1-carboxylate (1b) with tert-butyl (S)-4-((6-((4-(1-(difluoromethyl)-5-fluoro-2,3-dihydro-1H-benzo[d]pyrrolo[1,2-a]imidazol-7-yl)-5-fluoropyrimidin-2-yl)amino)pyridin-3-yl)methyl)-piperazine-1-carboxylate (10a). MS-ESI (m/z): 513[M+1]+.

Example 11

(S)-4-(1-(difluoromethyl)-5-fluoro-2,3-dihydro-1H-benzo[d]pyrrolo[1,2-a]imidazol-7-yl)-5-fluoro-N-(5-((4-methylpiperazin-1-yl)methyl)pyridin-2-yl)pyrimidin-2-amine (11)

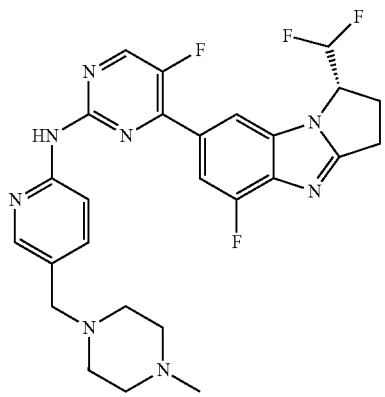

The title compound (S)-4-(1-(difluoromethyl)-5-fluoro-2,3-dihydro-1H-benzo[d]pyrrolo[1,2-a]imidazol-7-yl)-5-fluoro-N-(5-((4-methylpiperazin-1-yl)methyl)-pyridin-2-yl)pyrimidin-2-amine (11) was prepared according to the synthetic method of 2 by replacing (S)-(5-fluoro-7-(5-fluoro-2-((5-(piperazin-1-ylmethyl)pyridin-2-yl)amino)-pyrimidin-4-yl)-2,3-dihydro-1H-benzo[d]pyrrolo[1,2-a]imidazol-1-yl)methanol (1) with (S)-4-(1-(difluoromethyl)-5-fluoro-2,3-dihydro-1H-benzo[d]pyrrolo[1,2-a]imidazol-7-yl)-5-fluoro-N-(5-(piperazin-1-ylmethyl)pyridin-2-yl)-pyrimidin-2-amine (10). MS-ESI (m/z): 527[M+1]+.

Example 12

(S)-4-(1-(difluoromethyl)-5-fluoro-2,3-dihydro-1H-benzo[d]pyrrolo[1,2-a]imidazol-7-yl)-N-(5-((4-ethylpiperazin-1-yl)methyl)pyridin-2-yl)-5-fluoropyrimidin-2-amine (12)

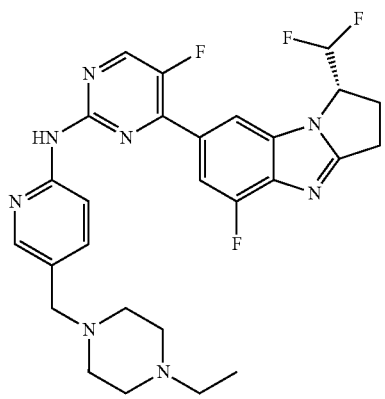

The title compound (S)-4-(1-(difluoromethyl)-5-fluoro-2,3-dihydro-1H-benzo[d]pyrrolo[1,2-a]imidazol-7-yl)-N-(5-((4-ethylpiperazin-1-yl)methyl)pyridin-2-yl)-5-fluoropyrimidin-2-amine (12) was prepared according to the synthetic method of 3 by replacing (S)-(5-fluoro-7-(5-fluoro-2-((5-(piperazin-1-ylmethyl)pyridin-2-yl)amino)-pyrimidin-4-yl)-2,3-dihydro-1H-benzo[d]pyrrolo[1,2-a]imidazol-1-yl)methanol (1) with (S)-4-(1-(difluoromethyl)-5-fluoro-2,3-dihydro-1H-benzo[d]pyrrolo[1,2-a]imidazol-7-yl)-5-fluoro-N-(5-(piperazin-1-ylmethyl)pyridin-2-yl)-pyrimidin-2-amine (10). MS-ESI (m/z): 541 [M+1]$^+$.

Example 13

5-fluoro-4-(5-fluoro-2,3-dihydrospiro[benzo[d]pyrrolo[1,2-a]imidazole-1,1'-cyclopropan]-7-yl)-N-(5-(piperazin-1-ylmethyl)pyridin-2-yl)pyrimidin-2-amine (13)

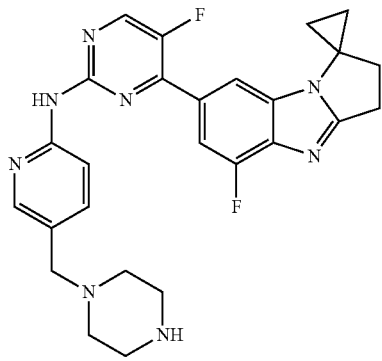

13 tert-butyl 4-((6-((5-fluoro-4-(5-fluoro-2,3-dihydrospiro[benzo[d]pyrrolo[1,2-a]imidazole-1,1'-cyclopropan]-7-yl)pyrimidin-2-yl)amino)pyridin-3-yl)methyl)piperazine-1-carboxylate (13a)

The title compound tert-butyl 4-((6-((5-fluoro-4-(5-fluoro-2,3-dihydrospiro-[benzo[d]pyrrolo[1,2-a]imidazole-1,1'-cyclopropan]-7-yl)pyrimidin-2-yl)amino)pyridin-3-yl)methyl)piperazine-1-carboxylate (13a) was prepared by using the same procedure as described for 1a by replacing (1S)-7-(2-chloro-5-fluoropyrimidin-4-yl)-5-fluoro-1-(((tetrahydro-2H-pyran-2-yl)oxy)methyl)-2,3-dihydro-1H-benzo[d]pyrrolo[1,2-a]imidazole (Intermediate A) with 7-(2-chloro-5-fluoropyrimidin-4-yl)-5-fluoro-2,3-dihydrospiro-[benzo[d]pyrrolo[1,2-a]-imidazole-1,1'-cyclopropane] (Intermediate D). MS-ESI (m/z): 589 [M+1]$^+$.

5-fluoro-4-(5-fluoro-2,3-dihydrospiro[benzo[d]pyrrolo[1,2-a]imidazole-1,1'-cyclopropan]-7-yl)-N-(5-(piperazin-1-ylmethyl)pyridin-2-yl)pyrimidin-2-amine (13)

The title compound 5-fluoro-4-(5-fluoro-2,3-dihydrospiro[benzo[d]-pyrrolo[1,2-a]imidazole-1,1'-cyclopropan]-7-yl)-N-(5-(piperazin-1-ylmethyl)pyridin-2-yl)-pyrimidin-2-amine (13) was prepared according to the synthetic method of 1 by replacing tertbutyl (S)-4-((6-((5-fluoro-4-(5-fluoro-1-(hydroxymethyl)-2,3-dihydro-1H-benzo[d]-pyrrolo[1,2-a]imidazol-7-yl)pyrimidin-2-yl)amino)pyridin-3-yl)methyl)piperazine-1-carboxylate (1 b) with tert-butyl 4-((6-((5-fluoro-4-(5-fluoro-2,3-dihydrospiro[benzo[d]-pyrrolo[1,2-a]imidazole-1,1'-cyclopropan]-7-yl)pyrimidin-2-yl)amino)pyridin-3-yl)methyl)-piperazine-1-carboxylate (13a). MS-ESI (m/z): 489[M+1]$^+$.

Example 14

5-fluoro-4-(5-fluoro-2,3-dihydrospiro[benzo[d]pyrrolo[1,2-a]imidazole-1,1'-cyclopropan]-7-yl)-N-(5-((4-methylpiperazin-1-yl)methyl)pyridin-2-yl)pyrimidin-2-amine (4)

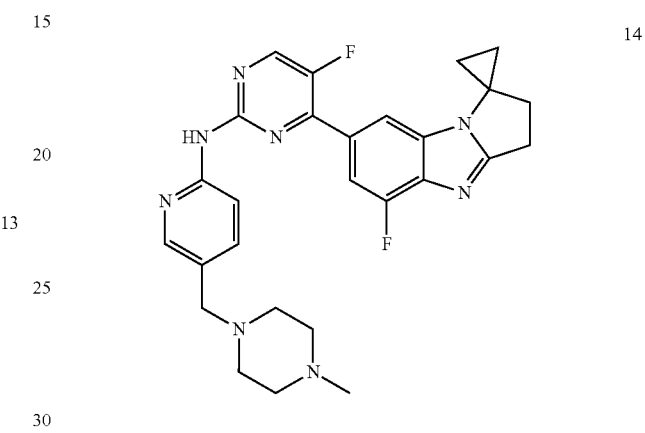

14

The title compound 5-fluoro-4-(5-fluoro-2,3-dihydrospiro[benzo[d]-pyrrolo[1,2-a]imidazole-1,1'-cyclopropan]-7-yl)-N-(5-((4-methylpiperazin-1-yl)methyl)-pyridin-2-yl)pyrimidin-2-amine (14) was prepared according to the synthetic method of 2 by replacing (S)-(5-fluoro-7-(5-fluoro-2-((5-(piperazin-1-ylmethyl)pyridin-2-yl)amino)-pyrimidin-4-yl)-2,3-dihydro-1H-benzo[d]pyrrolo[1,2-a]imidazol-1-yl)methanol (1) with 5-fluoro-4-(5-fluoro-2,3-dihydrospiro[benzo[d]pyrrolo[1,2-a]imidazole-1,1'-cyclopropan]-7-yl)-N-(5-(piperazin-1-ylmethyl)pyridin-2-yl)pyrimidin-2-amine (13). MS-ESI (m/z): 503 [M+1]$^+$.

Example 15

N-(5-((4-ethylpiperazin-1-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine (15)

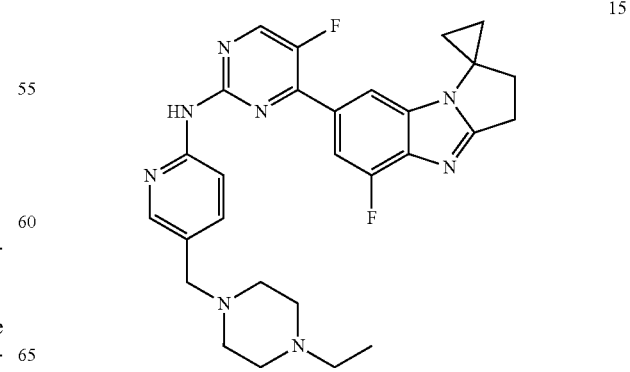

15

The title compound N-(5-((4-ethylpiperazin-1-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine (15) was prepared according to the synthetic method of 3 by replacing (S)-(5-fluoro-7-(5-fluoro-2-((5-(piperazin-1-ylmethyl)pyridin-2-yl)amino)-pyrimidin-4-yl)-2,3-dihydro-1H-benzo[d]pyrrolo[1,2-a]imidazol-1-yl)methanol (1) with 5-fluoro-4-(5-fluoro-2,3-dihydrospiro[benzo[d]pyrrolo[1,2-a]imidazole-1,1'-cyclopropan]-7-yl)-N-(5-(piperazin-1-ylmethyl)pyridin-2-yl)pyrimidin-2-amine (13). MS-ESI (m/z): 517[M+1]+.

Example 16

(S)-5-fluoro-4-(5-fluoro-1-(trifluoromethyl)-2,3-dihydro-1H-benzo[d]pyrrolo[1,2-a]imidazol-7-yl)-N-(5-(piperazin-1-ylmethyl)pyridin-2-yl)pyrimidin-2-amine (16)

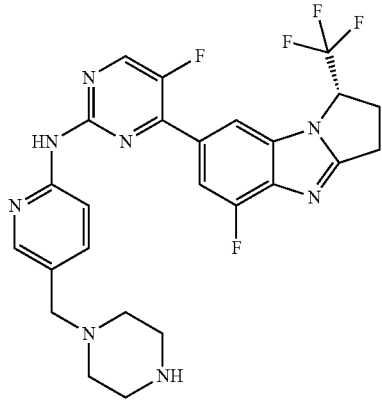

16 tert-butyl (S)-4-((6-((5-fluoro-4-(5-fluoro-1-(trifluoromethyl)-2,3-dihydro-1H-benzo[d]pyrrolo[1,2-a]imidazol-7-yl)pyrimidin-2-yl)amino)pyridin-3-yl)methyl)piperazine-1-carboxylate (16a)

The title compound tert-butyl (S)-4-((6-((5-fluoro-4-(5-fluoro-1-(trifluoromethyl)-2,3-dihydro-1H-benzo[d]pyrrolo[1,2-a]imidazol-7-yl)pyrimidin-2-yl)amino)pyridin-3-yl)methyl)piperazine-1-carboxylate (16a) was prepared according to the synthetic method of 1a by replacing (1S)-7-(2-chloro-5-fluoropyrimidin-4-yl)-5-fluoro-1-(((tetrahydro-2H-pyran-2-yl)oxy)methyl)-2,3-dihydro-1H-benzo[d]pyrrolo[1,2-a]imidazole (Intermediate A) with (S)-7-(2-chloro-5-fluoropyrimidin-4-yl)-5-fluoro-1-(trifluoromethyl)-2,3-dihydro-1H-benzo[d]pyrrolo[1,2-a]imidazole (Intermediate E). MS-ESI (m/z): 631[M+1]+.

(S)-5-fluoro-4-(5-fluoro-1-(trifluoromethyl)-2,3-dihydro-1H-benzo[d]pyrrolo[1,2-a]imidazol-7-yl)-N-(5-(piperazin-1-ylmethyl)pyridin-2-yl)pyrimidin-2-amine (16)

The title compound (S)-5-fluoro-4-(5-fluoro-1-(trifluoromethyl)-2,3-dihydro-1H-benzo[d]pyrrolo[1,2-a]imidazol-7-yl)-N-(5-(piperazin-1-ylmethyl)pyridin-2-yl)pyrimidin-2-amine (16) was prepared according to the synthetic method of a by replacing tert-butyl (S)-4-((6-((5-fluoro-4-(5-fluoro-1-(hydroxymethyl)-2,3-dihydro-1H-benzo[d]pyrrolo[1,2-a]imidazol-7-yl)pyrimidin-2-yl)amino)pyridin-3-yl)methyl)piperazine-1-carboxylate (1b) with tert-butyl (S)-4-((6-((5-fluoro-4-(5-fluoro-1-(trifluoromethyl)-2,3-dihydro-1H-benzo[d]-pyrrolo[1,2-a]imidazol-7-yl)pyrimidin-2-yl)amino)pyridin-3-yl)methyl)piperazine-1-carboxylate (16a). MS-ESI (m/z): 531[M+1]+.

Example 17

(S)-5-fluoro-4-(5-fluoro-1-(trifluoromethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine (17)

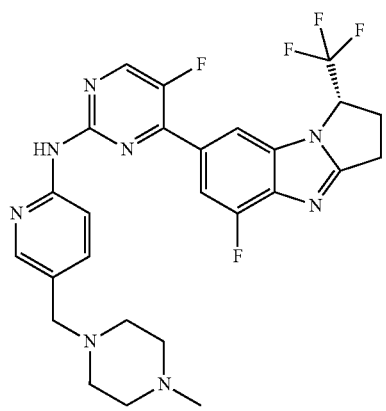

17

The title compound 17 (12 mg) was prepared according to the synthetic method of 2 by replacing (S)-(5-fluoro-7-(5-fluoro-2-((5-(piperazin-1-ylmethyl)pyridin-2-yl)amino)-pyrimidin-4-yl)-2,3-dihydro-1H-benzo[d]pyrrolo[1,2-a]imidazol-1-yl)methanol (1) with (S)-5-fluoro-4-(5-fluoro-1-(trifluoromethyl)-2,3-dihydro-1H-benzo[d]pyrrolo[1,2-a]imidazol-7-yl)-N-(5-(piperazin-1-ylmethyl)pyridin-2-yl)pyrimidin-2-amine (16). MS-ESI (m/z): 545 [M+1]+.

Example 18

(S)—N-(5-((4-ethylpiperazin-1-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine (18)

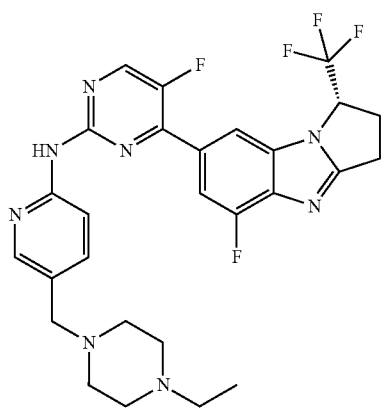

18

The title compound 18 (13 mg) was prepared according to the synthetic method of 3 by replacing (S)-(5-fluoro-7-(5-fluoro-2-((5-(piperazin-1-ylmethyl)pyridin-2-yl)amino)-pyrimidin-4-yl)-2,3-dihydro-1H-benzo[d]pyrrolo[1,2-a]imidazol-1-yl)methanol (1) with (S)-5-fluoro-4-(5-fluoro-1-(trifluoromethyl)-2,3-dihydro-1H-benzo[d]pyrrolo[1,2-a]imidazol-7-yl)-N-(5-(piperazin-1-ylmethyl)pyridin-2-yl)pyrimidin-2-amine (16). MS-ESI (m/z): 559[M+1]+.

Following essentially the same procedures described for Examples 1-6, Examples 19-166 listed in Table 2 were prepared from the appropriate intermediates (Intermediate A-EE). The structures and names of Examples 19-166 are given in Table 2.

TABLE 2

| EXAMPLE | STRUCTURE | NAME | DATA |
|---|---|---|---|
| 19 | 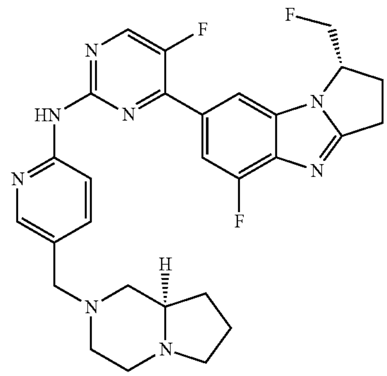 [SMILES: FC[C@@H]1CCc2nc3c(F)cc(-c4nc(Nc5ccc(CN6CCN7CCC[C@@H]7C6)cn5)ncc4F)cc3n21] | 5-fluoro-4-((S)-5-fluoro-1-(fluoromethyl)-2,3-dihydro-1H-benzo[d]pyrrolo[1,2-a]imidazol-7-yl)-N-(5-(((R)-hexahydropyrrolo[1,2-a]pyrazin-2(1H)-yl)methyl)pyridin-2-yl)pyrimidin-2-amine | MS-ESI (m/z): 535 [M + 1]+ |
| 20 | 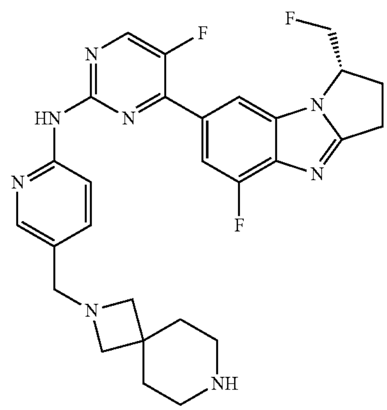 [SMILES: FC[C@@H]1CCc2nc3c(F)cc(-c4nc(Nc5ccc(CN6CC7(CCNCC7)C6)cn5)ncc4F)cc3n21] | (S)-N-(5-((2,7-diazaspiro[3.5]nonan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine | MS-ESI (m/z): 535 [M + 1]+ |
| 21 | 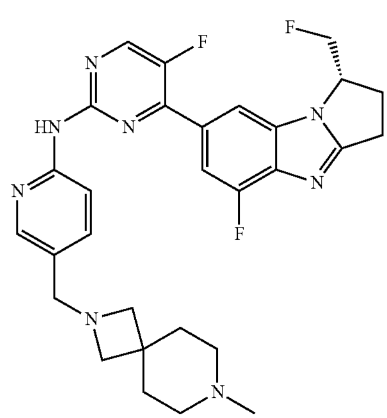 [SMILES: CN1CCC2(CC1)CN(Cc1ccc(Nc3ncc(F)c(-c4cc(F)c5nc6n(c5c4)[C@H](CF)CC6)n3)nc1)C2] | (S)-5-fluoro-4-(5-fluoro-1-(fluoromethyl)-2,3-dihydro-1H-benzo[d]pyrrolo[1,2-a]imidazol-7-yl)-N-(5-((7-methyl-2,7-diazaspiro[3.5]nonan-2-yl)methyl)pyridin-2-yl)pyrimidin-2-amine | MS-ESI (m/z): 549 [M + 1]+ |

TABLE 2-continued

| EXAMPLE | STRUCTURE | NAME | DATA |
|---|---|---|---|
| 22 | 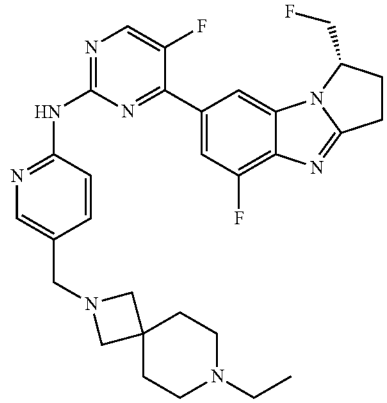 [SMILES: CCN1CCC2(CC1)CN(Cc1ccc(Nc3ncc(F)c(-c4cc(F)c5nc6n(c5c4)[C@H](CF)CC6)n3)nc1)C2] | (S)-N-(5-((7-ethyl-2,7-diazaspiro[3.5]nonan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine | MS-ESI (m/z): 563 [M + 1]+ |
| 23 | 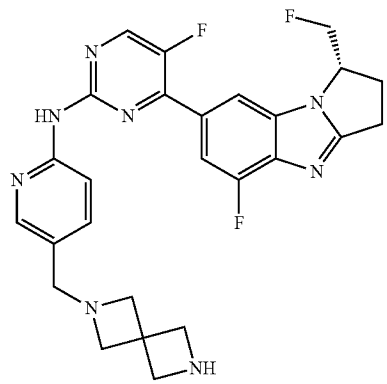 [SMILES: FC[C@@H]1CCc2nc3c(F)cc(-c4nc(Nc5ccc(CN6CC7(CNC7)C6)cn5)ncc4F)cc3n21] | (S)-N-(5-((2,6-diazaspiro[3.3]heptan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine | MS-ESI (m/z): 507 [M + 1]+ |
| 24 | 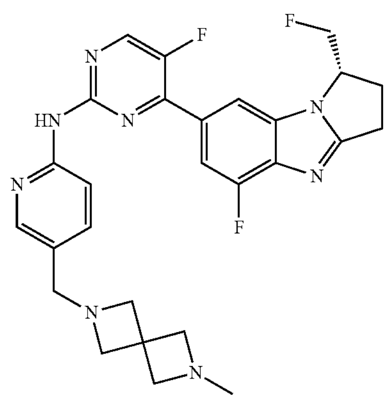 [SMILES: CN1CC2(C1)CN(Cc1ccc(Nc3ncc(F)c(-c4cc(F)c5nc6n(c5c4)[C@H](CF)CC6)n3)nc1)C2] | (S)-5-fluoro-4-(5-fluoro-1-(fluoromethyl)-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine | MS-ESI (m/z): 521 [M + 1]+ |
| 25 | 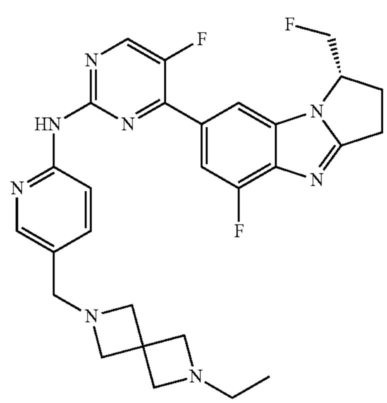 [SMILES: CCN1CC2(C1)CN(Cc1ccc(Nc3ncc(F)c(-c4cc(F)c5nc6n(c5c4)[C@H](CF)CC6)n3)nc1)C2] | (S)-N-(5-((6-ethyl-2,6-diazaspiro[3.3]heptan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine | MS-ESI (m/z): 535 [M + 1]+ |

TABLE 2-continued

| EXAMPLE | STRUCTURE | NAME | DATA |
|---|---|---|---|
| 26 | 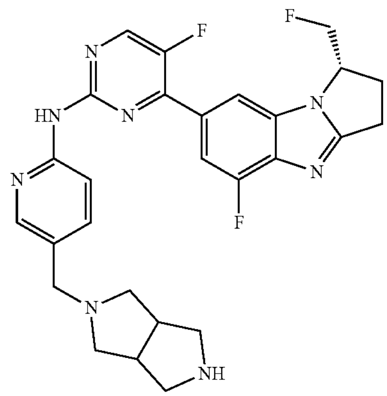 [SMILES: FC[C@@H]1CCc2nc3c(F)cc(-c4nc(Nc5ccc(CN6CC7CNCC7C6)cn5)ncc4F)cc3n21] | 5-fluoro-4-((S)-5-fluoro-1-(fluoromethyl)-2,3-dihydro-1H-benzo[d]pyrrolo[1,2-a]imidazol-7-yl)-N-(5-((hexahydropyrrolo[3,4-c]pyrrol-2(1H)-yl)m ethyl)pyridin-2-yl)pyrimidin-2-amine | MS-ESI (m/z): 521 [M + 1]+ |
| 27 | 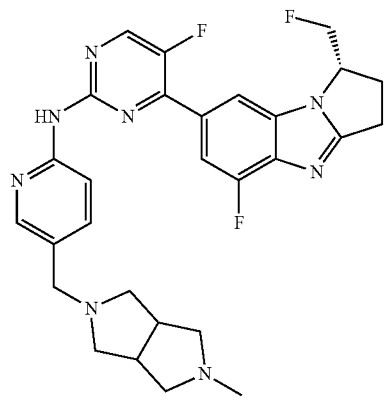 [SMILES: CN1CC2CN(Cc3ccc(Nc4ncc(F)c(-c5cc(F)c6nc7n(c6c5)[C@H](CF)CC7)n4)nc3)CC2C1] | 5-fluoro-4-((S)-5-fluoro-1-(fluoromethyl)-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine | MS-ESI (m/z): 535 [M + 1]+ |
| 28 | 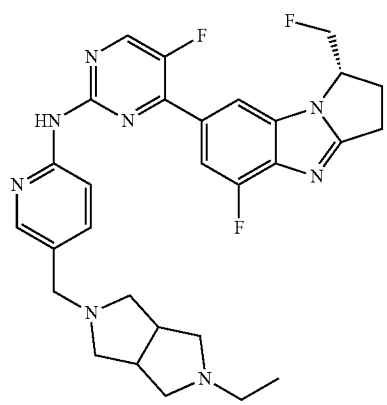 [SMILES: CCN1CC2CN(Cc3ccc(Nc4ncc(F)c(-c5cc(F)c6nc7n(c6c5)[C@H](CF)CC7)n4)nc3)CC2C1] | N-(5-((5-ethylhexahydropyrrolo[3,4-c]pyrrol-2(1H)-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine | MS-ESI (m/z): 549 [M + 1]+ |
| 29 | 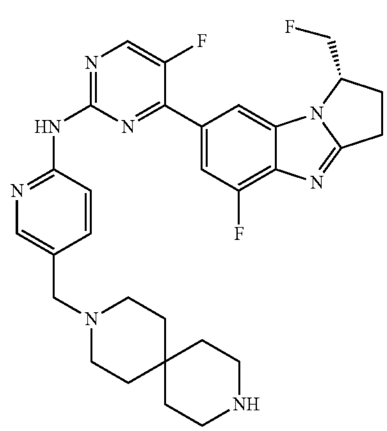 [SMILES: FC[C@@H]1CCc2nc3c(F)cc(-c4nc(Nc5ccc(CN6CCC7(CCNCC7)CC6)cn5)ncc4F)cc3n21] | (S)-N-(5-((3,9-diazaspiro[5.5]undecan-3-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine | MS-ESI (m/z): 563 [M + 1]+ |

TABLE 2-continued

| EXAMPLE | STRUCTURE | NAME | DATA |
|---|---|---|---|
| 30 | 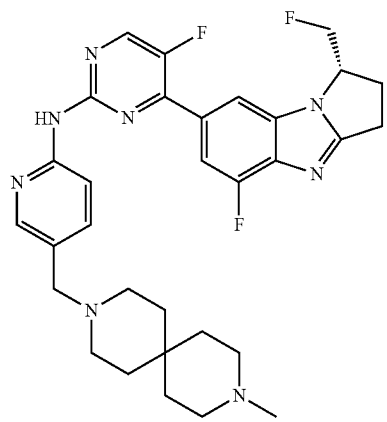 [SMILES: CN1CCC2(CC1)CCN(Cc1ccc(Nc3ncc(F)c(-c4cc(F)c5nc6n(c5c4)[C@H](CF)CC6)n3)nc1)CC2] | (S)-5-fluoro-4-(5-fluoro-1-(fluoromethyl)-2,3-dihydro-1H-benzo[d]pyrrolo[1,2-a]imidazol-7-yl)-N-(5-((9-methyl-3,9-diazaspiro[5.5]undecan-3-yl)methyl)pyridin-2-yl)pyrimidin-2-amine | MS-ESI (m/z): 577 [M + 1]⁺ |
| 31 | 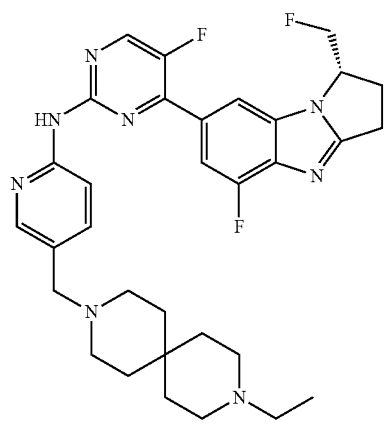 [SMILES: CCN1CCC2(CC1)CCN(Cc1ccc(Nc3ncc(F)c(-c4cc(F)c5nc6n(c5c4)[C@H](CF)CC6)n3)nc1)CC2] | (S)-N-(5-((9-ethyl-3,9-diazaspiro[5.5]undecan-3-yl)methyl)pyridin-2-yl)-5-fluoro-4-(5-fluoro-1-(fluoromethyl)-2,3-dihydro-1H-benzo[d]pyrrolo[1, 2-a]imidazol-7-yl)pyrimidin-2-amine | MS-ESI (m/z): 591 [M + 1]⁺ |
| 32 | 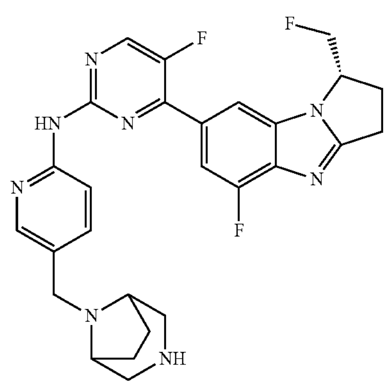 [SMILES: FC[C@@H]1CCc2nc3c(F)cc(-c4nc(Nc5ccc(CN6C7CCC6CNC7)cn5)ncc4F)cc3n21] | N-(5-((3,8-diazabicyclo[3.2.1]octan-8-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine | MS-ESI (m/z): 521 [M + 1]⁺ |
| 33 | 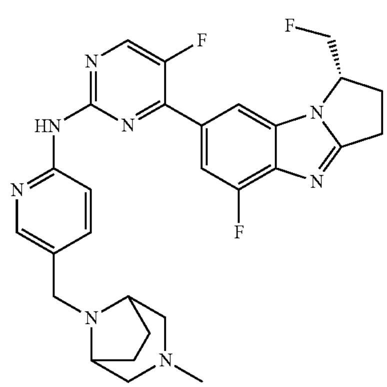 [SMILES: CN1CC2CCC(C1)N2Cc1ccc(Nc2ncc(F)c(-c3cc(F)c4nc5n(c4c3)[C@H](CF)CC5)n2)nc1] | 5-fluoro-4-((S)-5-fluoro-1-(fluoromethyl)-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine | MS-ESI (m/z): 535 [M + 1]⁺ |

TABLE 2-continued

| EXAMPLE | STRUCTURE | NAME | DATA |
| --- | --- | --- | --- |
| 34 | 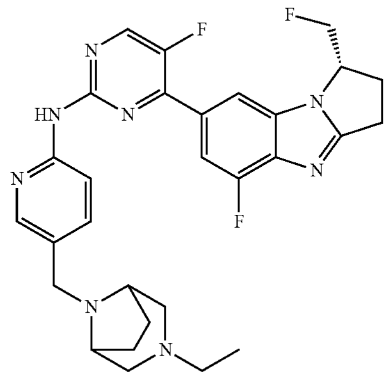 [SMILES: CCN1CC2CCC(C1)N2Cc1ccc(Nc2ncc(F)c(-c3cc(F)c4nc5n(c4c3)[C@H](CF)CC5)n2)nc1] | N-(5-((3-ethyl-3,8-diazabicyclo[3.2.1]octan-8-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine | MS-ESI (m/z): 549 [M + 1]+ |
| 35 | 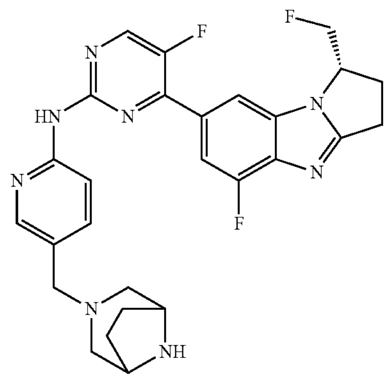 [SMILES: FC[C@@H]1CCc2nc3c(F)cc(-c4nc(Nc5ccc(CN6CC7CCC(C6)N7)cn5)ncc4F)cc3n21] | N-(5-((3,8-diazabicyclo[3.2.1]octan-3-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine | MS-ESI (m/z): 521 [M + 1]+ |
| 36 | 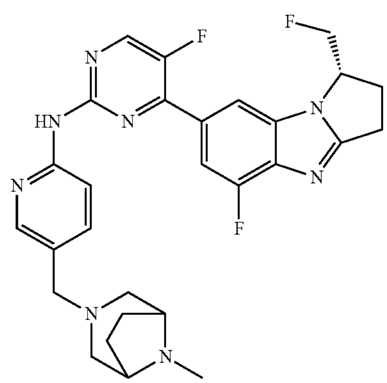 [SMILES: CN1C2CCC1CN(Cc1ccc(Nc3ncc(F)c(-c4cc(F)c5nc6n(c5c4)[C@H](CF)CC6)n3)nc1)C2] | 5-fluoro-4-((S)-5-fluoro-1-(fluoromethyl)-2,3-dihydro-1H-benzo[d]pyrrolo[1,2-a]imidazol-7-yl)-N-(5-((8-methyl-3,8-diazabicyclo[3.2.1]octan-3-yl)methyl)pyridin-2-yl)pyrimidin-2-amine | MS-ESI (m/z): 535 [M + 1]+ |
| 37 | 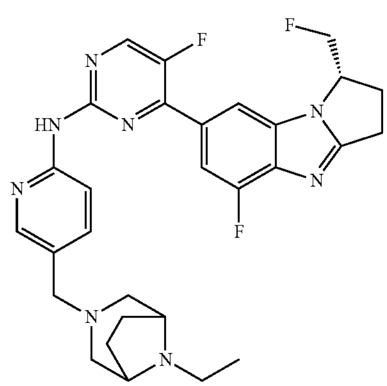 [SMILES: CCN1C2CCC1CN(Cc1ccc(Nc3ncc(F)c(-c4cc(F)c5nc6n(c5c4)[C@H](CF)CC6)n3)nc1)C2] | N-(5-((8-ethyl-3,8-diazabicyclo[3.2.1]octan-3-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine | MS-ESI (m/z): 549 [M + 1]+ |

| EXAMPLE | STRUCTURE | NAME | DATA |
|---|---|---|---|
| 38 | 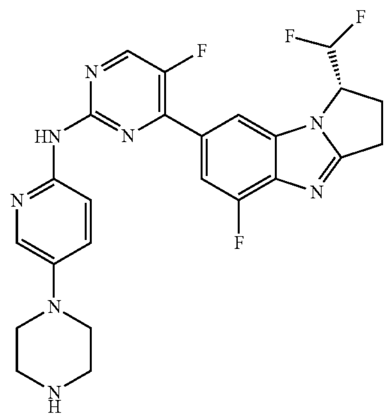 [SMILES: Fc1cnc(Nc2ccc(N3CCNCC3)cn2)nc1-c1cc(F)c2nc3n(c2c1)[C@H](C(F)F)CC3] | (S)-4-(1-(difluoromethyl)-5-fluoro-2,3-dihydro-1H-benzo[d]pyrrolo[1,2-a]imidazol-7-yl)-5-fluoro-N-(5-(piperazin-1-yl)pyridin-2-yl)pyrimidin-2-amine | MS-ESI (m/z): 499 [M + 1]+ |
| 39 | 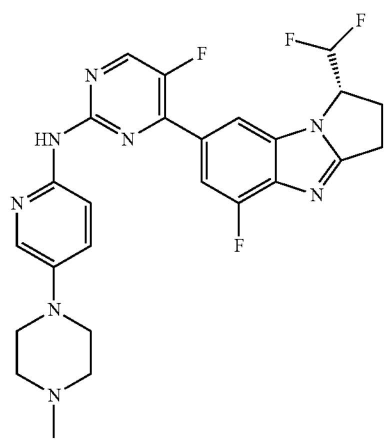 [SMILES: CN1CCN(c2ccc(Nc3ncc(F)c(-c4cc(F)c5nc6n(c5c4)[C@H](C(F)F)CC6)n3)nc2)CC1] | (S)-4-(1-(difluoromethyl)-5-fluoro-2,3-dihydro-1H-benzo[d]pyrrolo[1,2-a]imidazol-7-yl)-5-fluoro-N-(5-(4-methylpiperazin-1-yl)pyridin-2-yl)pyrimidin-2-amine | MS-ESI (m/z): 513 [M + 1]+ |
| 40 | 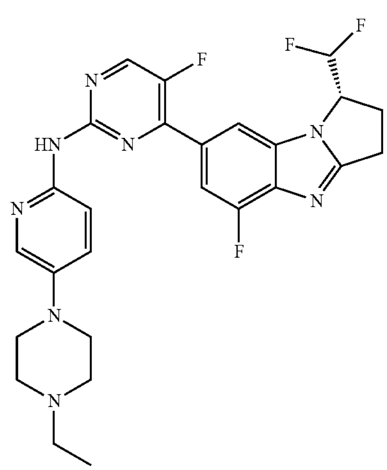 [SMILES: CCN1CCN(c2ccc(Nc3ncc(F)c(-c4cc(F)c5nc6n(c5c4)[C@H](C(F)F)CC6)n3)nc2)CC1] | (S)-4-(1-(difluoromethyl)-5-fluoro-2,3-dihydro-1H-benzo[d]pyrrolo[1,2-a]imidazol-7-yl)-N-(5-(4-ethylpiperazin-1-yl)pyridin-2-yl)-5-fluoropyrimidin-2-amine | MS-ESI (m/z): 527 [M + 1]+ |

TABLE 2-continued

| EXAMPLE | STRUCTURE | NAME | DATA |
|---|---|---|---|
| 41 | 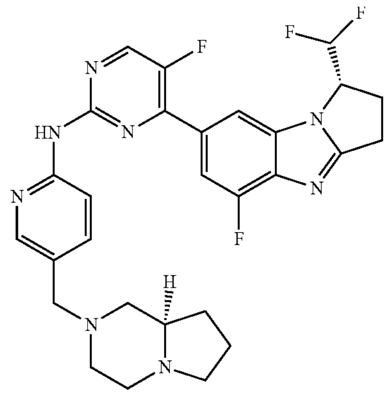 [SMILES: Fc1cnc(Nc2ccc(CN3CCN4CCC[C@@H]4C3)cn2)nc1-c1cc(F)c2nc3n(c2c1)[C@H](C(F)F)CC3] | 4-((S)-1-(difluoromethyl)-5-fluoro-2,3-dihydro-1H-benzo[d]pyrrolo[1,2-a]imidazol-7-yl)-5-fluoro-N-(5-(((R)-hexahydropyrrolo[1,2-a]pyrazin-2(1H)-yl)methyl)pyridin-2-yl)pyrimidin-2-amine | MS-ESI (m/z): 553 [M + 1]$^+$ |
| 42 | 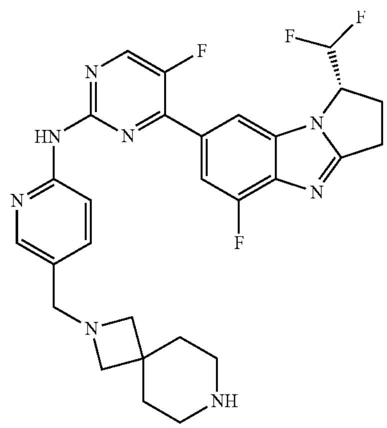 [SMILES: Fc1cnc(Nc2ccc(CN3CC4(CCNCC4)C3)cn2)nc1-c1cc(F)c2nc3n(c2c1)[C@H](C(F)F)CC3] | (S)-N-(5-((2,7-diazaspiro[3.5]nonan-2-yl)methyl)pyridin-2-yl)-4-(1-(difluoromethyl)-5-fluoro-2,3-dihydro-1H-benzo[d]pyrrolo[1,2-a]imidazol-7-yl)-5-fluoropyrimidin-2-amine | MS-ESI (m/z): 553 [M + 1]$^+$ |
| 43 | 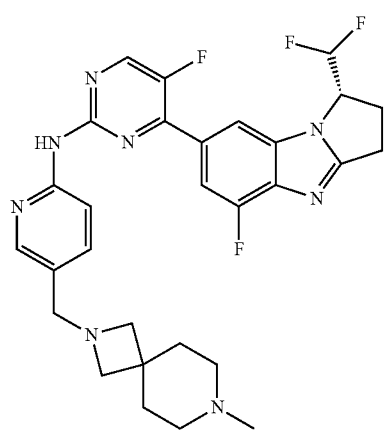 [SMILES: CN1CCC2(CC1)CN(Cc1ccc(Nc3ncc(F)c(-c4cc(F)c5nc6n(c5c4)[C@H](C(F)F)CC6)n3)nc1)C2] | (S)-4-(1-(difluoromethyl)-5-fluoro-2,3-dihydro-1H-benzo[d]pyrrolo[1,2-a]imidazol-7-yl)-5-fluoro-N-(5-((7-methyl-2,7-diazaspiro[3.5]nonan-2-yl)methyl)pyridin-2-yl)pyrimidin-2-amine | MS-ESI (m/z): 567 [M + 1]$^+$ |

TABLE 2-continued

| EXAMPLE | STRUCTURE | NAME | DATA |
|---|---|---|---|
| 44 | 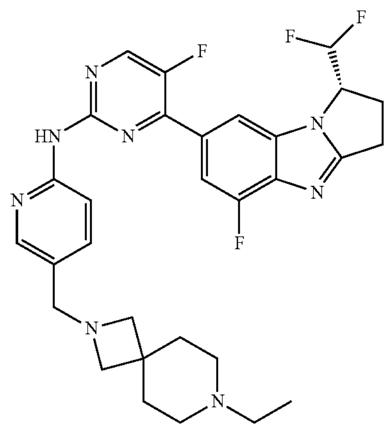 [SMILES: CCN1CCC2(CC1)CN(Cc1ccc(Nc3ncc(F)c(-c4cc(F)c5nc6n(c5c4)[C@H](C(F)F)CC6)n3)nc1)C2] | (S)-4-(1-(difluoromethyl)-5-fluoro-2,3-dihydro-1H-benzo[d]pyrrolo[1,2-a]imidazol-7-yl)-N-(5-((7-ethyl-2,7-diazaspiro[3.5]nonan-2-yl)methyl)pyridin-2-yl)-5-fluoropyrimidin-2-amine | MS-ESI (m/z): 581 [M + 1]+ |
| 45 | 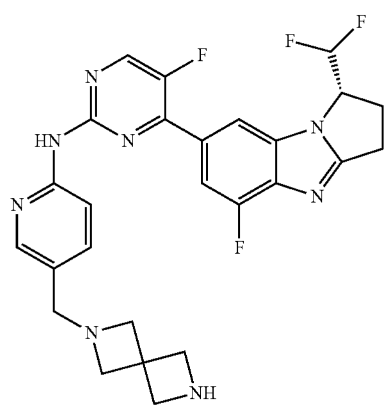 [SMILES: Fc1cnc(Nc2ccc(CN3CC4(CNC4)C3)cn2)nc1-c1cc(F)c2nc3n(c2c1)[C@H](C(F)F)CC3] | (S)-N-(5-((2,6-diazaspiro[3.3]heptan-2-yl)methyl)pyridin-2-yl)-4-(1-(difluoromethyl)-5-fluoro-2,3-dihydro-1H-benzo[d]pyrrolo[1,2-a]imidazol-7-yl)-5-fluoropyrimidin-2-amine | MS-ESI (m/z): 525 [M + 1]+ |
| 46 | 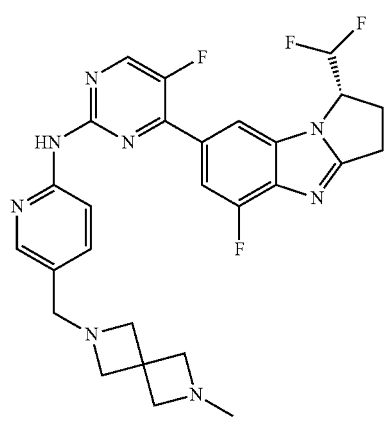 [SMILES: CN1CC2(C1)CN(Cc1ccc(Nc3ncc(F)c(-c4cc(F)c5nc6n(c5c4)[C@H](C(F)F)CC6)n3)nc1)C2] | (S)-4-(1-(difluoromethyl)-5-fluoro-2,3-dihydro-1H-benzo[d]pyrrolo[1,2-a]imidazol-7-yl)-5-fluoro-N-(5-((6-methyl-2,6-diazaspiro[3.3]heptan-2-yl)methyl)pyridin-2-yl)pyrimidin-2-amine | MS-ESI (m/z): 539 [M + 1]+ |

TABLE 2-continued

| EXAMPLE | STRUCTURE | NAME | DATA |
|---|---|---|---|
| 47 | 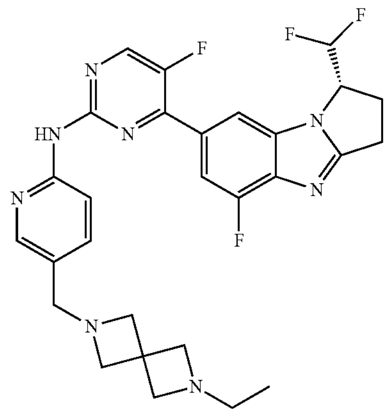 [SMILES: CCN1CC2(C1)CN(Cc1ccc(Nc3ncc(F)c(-c4cc(F)c5nc6n(c5c4)[C@H](C(F)F)CC6)n3)nc1)C2] | (S)-4-(1-(difluoromethyl)-5-fluoro-2,3-dihydro-1H-benzo[d]pyrrolo[1,2-a]imidazol-7-yl)-N-(5-((6-ethyl-2,6-diazaspiro[3.3]heptan-2-yl)methyl)pyridin-2-yl)-5-fluoropyrimidin-2-amine | MS-ESI (m/z): 553 [M + 1]+ |
| 48 | 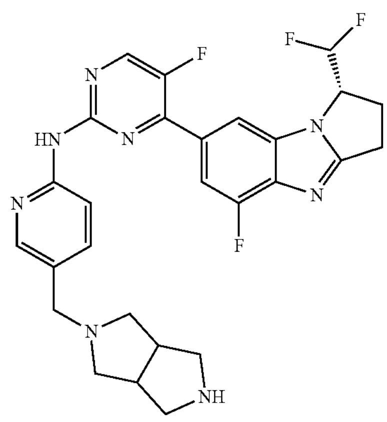 [SMILES: Fc1cnc(Nc2ccc(CN3CC4CNCC4C3)cn2)nc1-c1cc(F)c2nc3n(c2c1)[C@H](C(F)F)CC3] | 4-((S)-1-(difluoromethyl)-5-fluoro-2,3-dihydro-1H-benzo[d]pyrrolo[1,2-a]imidazol-7-yl)-5-fluoro-N-(5-((hexahydropyrrolo[3,4-c]pyrrol-2(1H)-yl)methyl)pyridin-2-yl)pyrimidin-2-amine | MS-ESI (m/z): 539 [M + 1]+ |
| 49 | 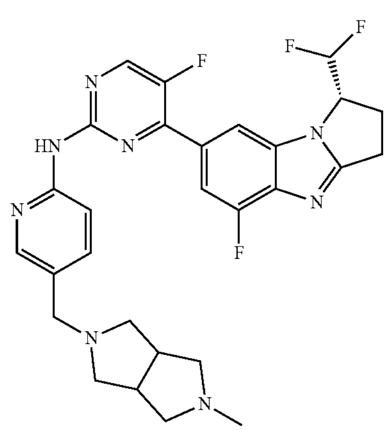 [SMILES: CN1CC2CN(Cc3ccc(Nc4ncc(F)c(-c5cc(F)c6nc7n(c6c5)[C@H](C(F)F)CC7)n4)nc3)CC2C1] | 4-((S)-1-(difluoromethyl)-5-fluoro-2,3-dihydro-1H-benzo[d]pyrrolo[1,2-a]imidazol-7-yl)-5-fluoro-N-(5-((5-methylhexahydropyrrolo[3,4-c]pyrrol-2(1H)-yl)methyl)pyridin-2-yl)pyrimidin-2-amine | MS-ESI (m/z): 553 [M + 1]+ |

TABLE 2-continued

| EXAMPLE | STRUCTURE | NAME | DATA |
|---|---|---|---|
| 50 | 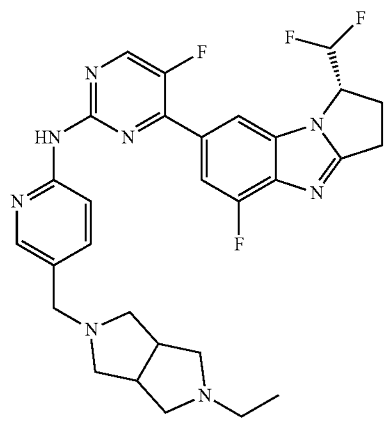 [SMILES: CCN1CC2CN(Cc3ccc(Nc4ncc(F)c(-c5cc(F)c6nc7n(c6c5)[C@H](C(F)F)CC7)n4)nc3)CC2C1] | 4-((S)-1-(difluoromethyl)-5-fluoro-2,3-dihydro-1H-benzo[d]pyrrolo[1,2-a]imidazol-7-yl)-N-(5-((5-ethylhexahydropyrrolo[3,4-c]pyrrol-2(1H)-yl)methyl)pyridin-2-yl)-5-fluoropyrimidin-2-amine | MS-ESI (m/z): 567 [M + 1]+ |
| 51 | 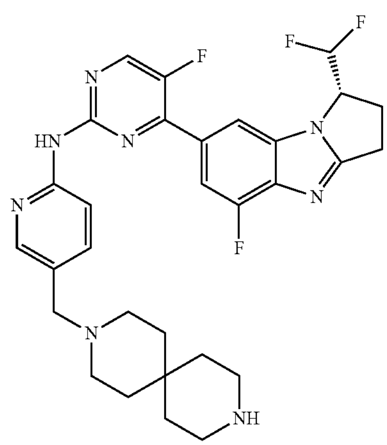 [SMILES: Fc1cnc(Nc2ccc(CN3CCC4(CCNCC4)CC3)cn2)nc1-c1cc(F)c2nc3n(c2c1)[C@H](C(F)F)CC3] | (S)-N-(5-((3,9-diazaspiro[5.5]undecan-3-yl)methyl)pyridin-2-yl)-4-(1-(difluoromethyl)-5-fluoro-2,3-dihydro-1H-benzo[d]pyrrolo[1,2-a]imidazol-7-yl)-5-fluoropyrimidin-2-amine | MS-ESI (m/z): 581 [M + 1]+ |
| 52 | 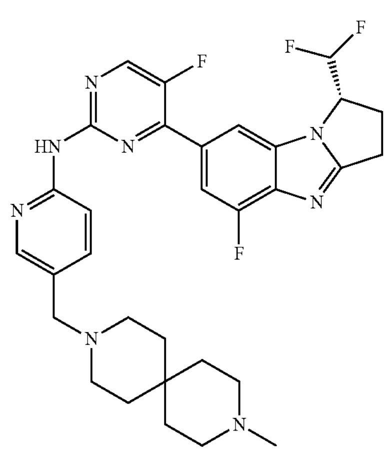 [SMILES: CN1CCC2(CC1)CCN(Cc1ccc(Nc3ncc(F)c(-c4cc(F)c5nc6n(c5c4)[C@H](C(F)F)CC6)n3)nc1)CC2] | (S)-4-(1-(difluoromethyl)-5-fluoro-2,3-dihydro-1H-benzo[d]pyrrolo[1,2-a]imidazol-7-yl)-5-fluoro-N-(5-((9-methyl-3,9-diazaspiro[5.5]undecan-3-yl)methyl)pyridin-2-yl)pyrimidin-2-amine | MS-ESI (m/z): 595 [M + 1]+ |

TABLE 2-continued

| EXAMPLE | STRUCTURE | NAME | DATA |
|---|---|---|---|
| 53 | 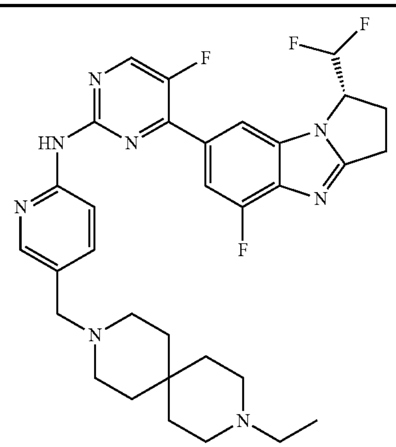 | (S)-4-(1-(difluoromethyl)-5-fluoro-2,3-dihydro-1H-benzo[d]pyrrolo[1,2-a]imidazol-7-yl)-N-(5-((9-ethyl-3,9-diazaspiro[5.5]undecan-3-yl)methyl)pyridin-2-yl)-5-fluoropyrimidin-2-amine | MS-ESI (m/z): 609 [M + 1]+ |
| 54 | 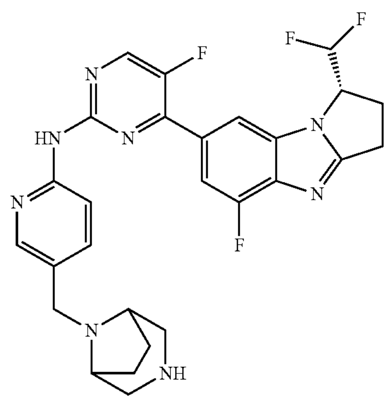 [SMILES: Fc1cnc(Nc2ccc(CN3C4CCC3CNC4)cn2)nc1-c1cc(F)c2nc3n(c2c1)[C@H](C(F)F)CC3] | N-(5-((3,8-diazabicyclo[3.2.1]octan-8-yl)methyl)pyridin-2-yl)-4-((S)-1-(difluoromethyl)-5-fluoro-2,3-dihydro-1H-benzo[d]pyrrolo[1,2-a]imidazol-7-yl)-5-fluoropyrimidin-2-amine | MS-ESI (m/z): 539 [M + 1]+ |
| 55 | 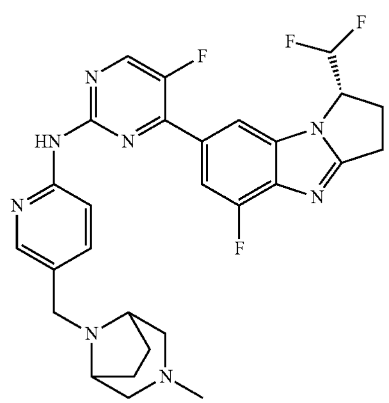 [SMILES: CN1CC2CCC(C1)N2Cc1ccc(Nc2ncc(F)c(-c3cc(F)c4nc5n(c4c3)[C@H](C(F)F)CC5)n2)nc1] | 4-((S)-1-(difluoromethyl)-5-fluoro-2,3-dihydro-1H-benzo[d]pyrrolo[1,2-a]imidazol-7-yl)-5-fluoro-N-(5-((3-methyl-3,8-diazabicyclo[3.2.1]octan-8-yl)methyl)pyridin-2-yl)pyrimidin-2-amine | MS-ESI (m/z): 553 [M + 1]+ |
| 56 | 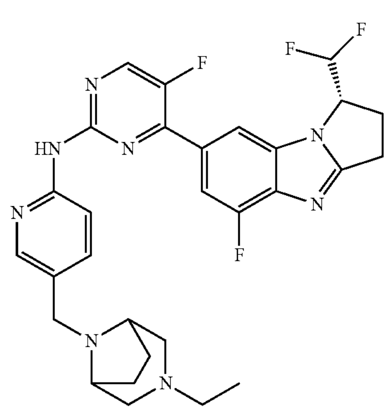 [SMILES: CCN1CC2CCC(C1)N2Cc1ccc(Nc2ncc(F)c(-c3cc(F)c4nc5n(c4c3)[C@H](C(F)F)CC5)n2)nc1] | 4-((S)-1-(difluoromethyl)-5-fluoro-2,3-dihydro-1H-benzo[d]pyrrolo[1,2-a]imidazol-7-yl)-N-(5-((3-ethyl-3,8-diazabicyclo[3.2.1]octan-8-yl)methyl)pyridin-2-yl)-5-fluoropyrimidin-2-amine | MS-ESI (m/z): 567 [M + 1]+ |

TABLE 2-continued

| EXAMPLE | STRUCTURE | NAME | DATA |
|---|---|---|---|
| 57 | 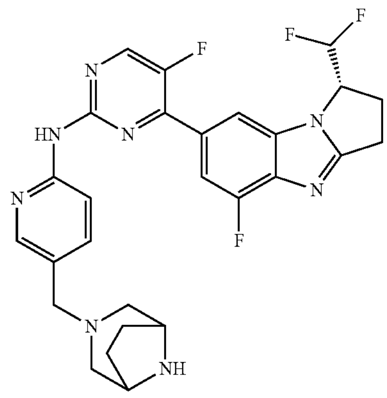 [SMILES: Fc1cnc(Nc2ccc(CN3CC4CCC(C3)N4)cn2)nc1-c1cc(F)c2nc3n(c2c1)[C@H](C(F)F)CC3] | N-(5-((3,8-diazabicyclo[3.2.1]octan-3-yl)methyl)pyridin-2-yl)-4-((S)-1-(difluoromethyl)-5-fluoro-2,3-dihydro-1H-benzo[d]pyrrolo[1,2-a]imidazol-7-yl)-5-fluoropyrimidin-2-amine | MS-ESI (m/z): 539 [M + 1]+ |
| 58 | 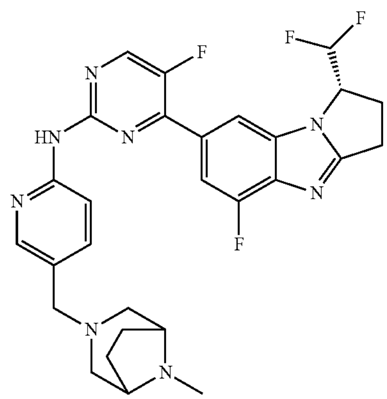 [SMILES: CN1C2CCC1CN(Cc1ccc(Nc3ncc(F)c(-c4cc(F)c5nc6n(c5c4)[C@H](C(F)F)CC6)n3)nc1)C2] | 4-((S)-1-(difluoromethyl)-5-fluoro-2,3-dihydro-1H-benzo[d]pyrrolo[1,2-a]imidazol-7-yl)-5-fluoro-N-(5-((8-methyl-3,8-diazabicyclo[3.2.1]octan-3-yl)methyl)pyridin-2-yl)pyrimidin-2-amine | MS-ESI (m/z): 553 [M + 1]+ |
| 59 | 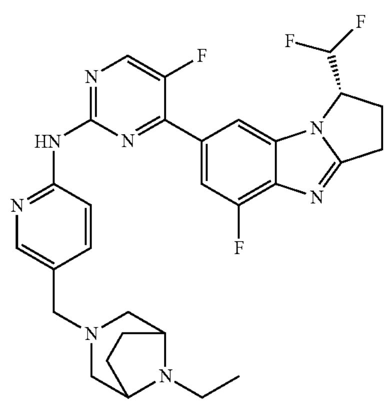 [SMILES: CCN1C2CCC1CN(Cc1ccc(Nc3ncc(F)c(-c4cc(F)c5nc6n(c5c4)[C@H](C(F)F)CC6)n3)nc1)C2] | 4-((S)-1-(difluoromethyl)-5-fluoro-2,3-dihydro-1H-benzo[d]pyrrolo[1,2-a]imidazol-7-yl)-N-(5-((8-ethyl-3,8-diazabicyclo[3.2.1]octan-3-yl)methyl)pyridin-2-yl)-5-fluoropyrimidin-2-amine | MS-ESI (m/z): 567 [M + 1]+ |
| 60 | 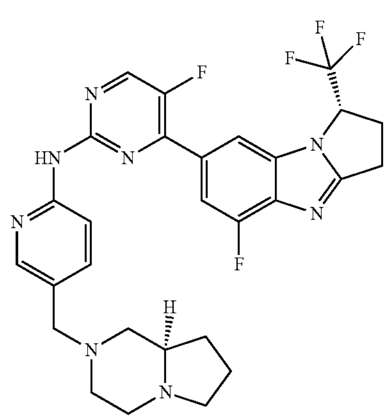 [SMILES: Fc1cnc(Nc2ccc(CN3CCN4CCC[C@@H]4C3)cn2)nc1-c1cc(F)c2nc3n(c2c1)[C@H](C(F)(F)F)CC3] | 5-fluoro-4-((S)-5-fluoro-1-(trifluoromethyl)-2,3-dihydro-1H-benzo[d]pyrrolo[1,2-a]imidazol-7-yl)-N-(5-(((R)-hexahydropyrrolo[1,2-a]pyrazin-2(1H)-yl)methyl)pyridin-2-yl)pyrimidin-2-amine | MS-ESI (m/z): 571 [M + 1]+ |

TABLE 2-continued

| EXAMPLE | STRUCTURE | NAME | DATA |
|---|---|---|---|
| 61 | 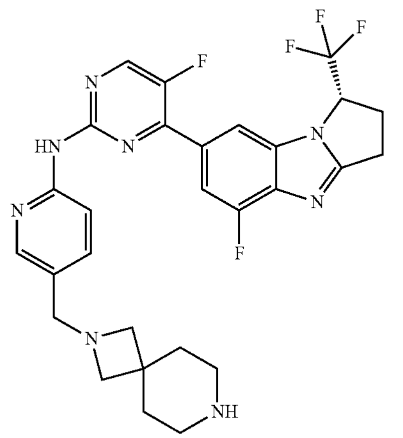 [SMILES: Fc1cnc(Nc2ccc(CN3CC4(CCNCC4)C3)cn2)nc1-c1cc(F)c2nc3n(c2c1)[C@H](C(F)(F)F)CC3] | (S)-N-(5-((2,7-diazaspiro[3.5]nonan-2-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine | MS-ESI (m/z): 571 [M + 1]+ |
| 62 | 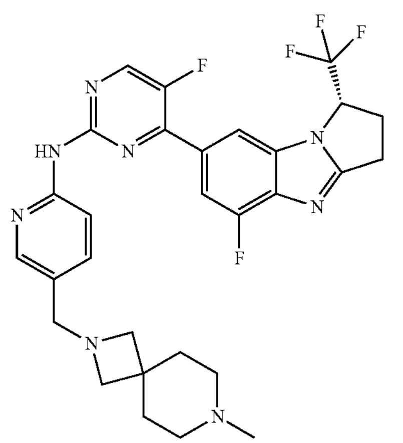 [SMILES: CN1CCC2(CC1)CN(Cc1ccc(Nc3ncc(F)c(-c4cc(F)c5nc6n(c5c4)[C@H](C(F)(F)F)CC6)n3)nc1)C2] | (S)-5-fluoro-4-(5-fluoro-1-(trifluoromethyl)-2,3-dihydro-1H-benzo[d]pyrrolo[1,2-a]imidazol-7-yl)-N-(5-((7-methyl-2,7-diazaspiro[3.5]nonan-2-yl)methyl)pyridin-2-yl)pyrimidin-2-amine | MS-ESI (m/z): 585 [M + 1]+ |
| 63 | 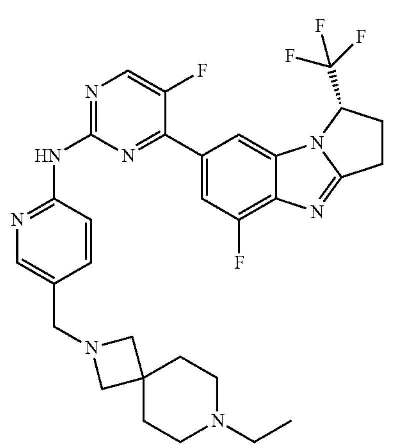 [SMILES: CCN1CCC2(CC1)CN(Cc1ccc(Nc3ncc(F)c(-c4cc(F)c5nc6n(c5c4)[C@H](C(F)(F)F)CC6)n3)nc1)C2] | (S)-N-(5-((7-ethyl-2,7-diazaspiro[3.5]nonan-2-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine | MS-ESI (m/z): 599 [M + 1]+ |

TABLE 2-continued

| EXAMPLE | STRUCTURE | NAME | DATA |
|---|---|---|---|
| 64 | 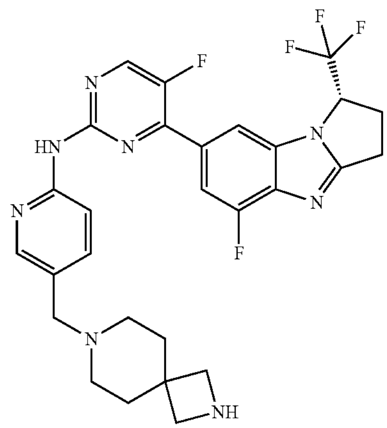 [SMILES: Fc1cnc(Nc2ccc(CN3CCC4(CC3)CNC4)cn2)nc1-c1cc(F)c2nc3n(c2c1)[C@H](C(F)(F)F)CC3] | (S)-N-(5-((2,7-diazaspiro[3.5]nonan-7-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine | MS-ESI (m/z): 571 [M + 1]+ |
| 65 | 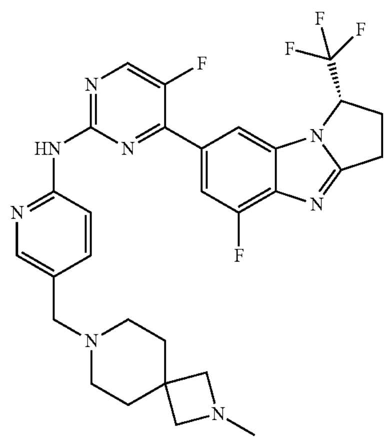 [SMILES: CN1CC2(CCN(Cc3ccc(Nc4ncc(F)c(-c5cc(F)c6nc7n(c6c5)[C@H](C(F)(F)F)CC7)n4)nc3)CC2)C1] | (S)-5-fluoro-4-(5-fluoro-1-(trifluoromethyl)-2,3-dihydro-1H-benzo[d]pyrrolo[1,2-a]imidazol-7-yl)-N-(5-((2-methyl-2,7-diazaspiro[3.5]nonan-7-yl)methyl)pyridin-2-yl)pyrimidin-2-amine | MS-ESI (m/z): 585 [M + 1]+ |
| 66 | 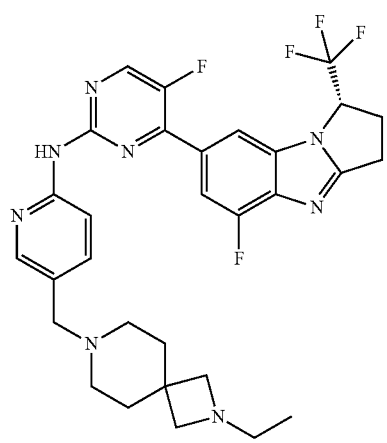 [SMILES: CCN1CC2(CCN(Cc3ccc(Nc4ncc(F)c(-c5cc(F)c6nc7n(c6c5)[C@H](C(F)(F)F)CC7)n4)nc3)CC2)C1] | (S)-N-5-((2-ethyl-2,7-diazaspiro[3.5]nonan-7-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine | MS-ESI (m/z): 599 [M + 1]+ |

TABLE 2-continued

| EXAMPLE | STRUCTURE | NAME | DATA |
|---|---|---|---|
| 67 | 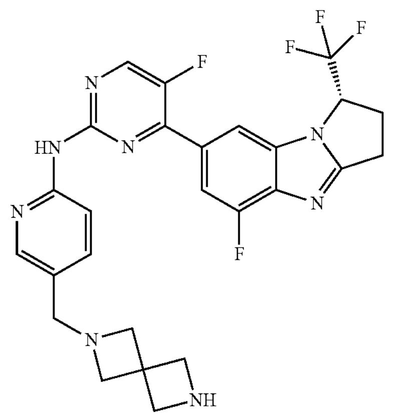 [SMILES: Fc1cnc(Nc2ccc(CN3CC4(CNC4)C3)cn2)nc1-c1cc(F)c2nc3n(c2c1)[C@H](C(F)(F)F)CC3] | (S)-N-(5-((2,6-diazaspiro[3.3]heptan-2-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine | MS-ESI (m/z): 543 [M + 1]$^+$ |
| 68 | 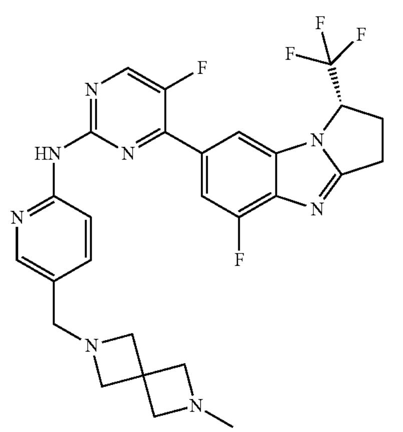 [SMILES: CN1CC2(C1)CN(Cc1ccc(Nc3ncc(F)c(-c4cc(F)c5nc6n(c5c4)[C@H](C(F)(F)F)CC6)n3)nc1)C2] | (S)-5-fluoro-4-(5-fluoro-1-(trifluoromethyl)-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine | MS-ESI (m/z): 557 [M + 1]$^+$ |
| 69 | 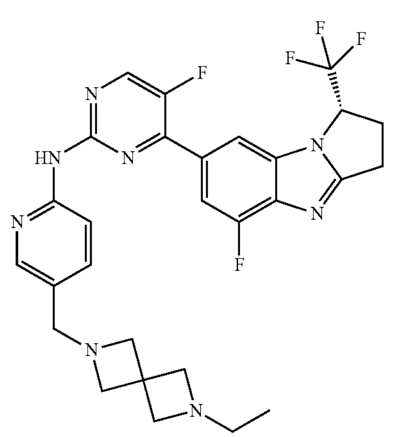 [SMILES: CCN1CC2(C1)CN(Cc1ccc(Nc3ncc(F)c(-c4cc(F)c5nc6n(c5c4)[C@H](C(F)(F)F)CC6)n3)nc1)C2] | (S)-N-(5-(((6-ethyl-2,6-diazaspiro[3.3]heptan-2-yl)methyl)pyridin-2-yl)-5-fluoro-4-(5-fluoro-1-(trifluoromethyl)-2,3-dihydro-1H-benzo[d]pyrrolo[1, 2-a]imidazol-7-yl)pyrimidin-2-amine | MS-ESI (m/z): 571 [M + 1]$^+$ |

TABLE 2-continued

| EXAMPLE | STRUCTURE | NAME | DATA |
|---|---|---|---|
| 70 | 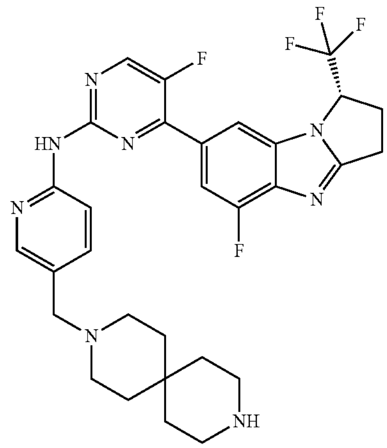 [SMILES: Fc1cnc(Nc2ccc(CN3CCC4(CCNCC4)CC3)cn2)nc1-c1cc(F)c2nc3n(c2c1)[C@H](C(F)(F)F)CC3] | (S)-N-(5-((3,9-diazaspiro[5.5]undecan-3-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine | MS-ESI (m/z): 599 [M + 1]+ |
| 71 | 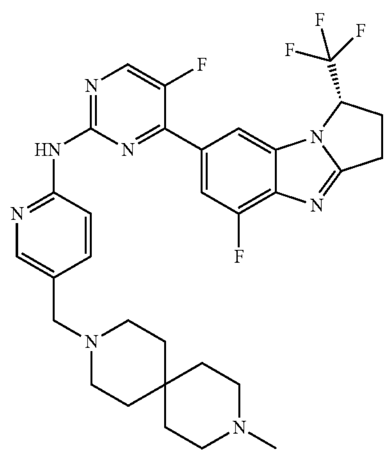 [SMILES: CN1CCC2(CC1)CCN(Cc1ccc(Nc3ncc(F)c(-c4cc(F)c5nc6n(c5c4)[C@H](C(F)(F)F)CC6)n3)nc1)CC2] | (S)-5-fluoro-4-(5-fluoro-1-(trifluoromethyl)-2,3-dihydro-1H-benzo[d]pyrrolo[1,2-a]imidazol-7-yl)-N-(5-((9-methyl-3,9-diazaspiro[5.5]undecan-3-yl)methyl)pyridin-2-yl)pyrimidin-2-amine | MS-ESI (m/z): 613 [M + 1]+ |
| 72 | 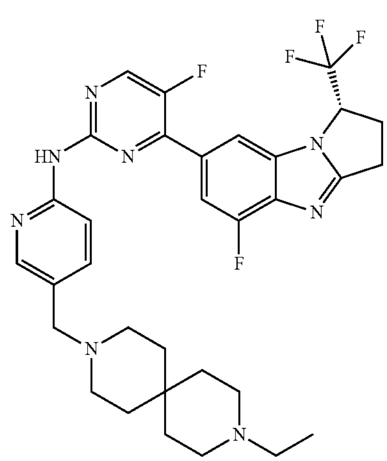 [SMILES: CCN1CCC2(CC1)CCN(Cc1ccc(Nc3ncc(F)c(-c4cc(F)c5nc6n(c5c4)[C@H](C(F)(F)F)CC6)n3)nc1)CC2] | (S)-N-(5-((9-ethyl-3,9-diazaspiro[5.5]undecan-3-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine | MS-ESI (m/z): 627 [M + 1]+ |

TABLE 2-continued

| EXAMPLE | STRUCTURE | NAME | DATA |
|---|---|---|---|
| 73 | 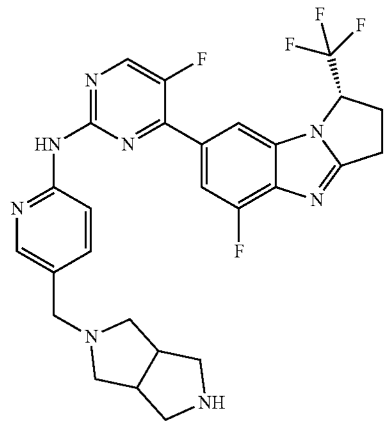 [SMILES: Fc1cnc(Nc2ccc(CN3CC4CNCC4C3)cn2)nc1-c1cc(F)c2nc3n(c2c1)[C@H](C(F)(F)F)CC3] | 5-fluoro-4-((S)-5-fluoro-1-(trifluoromethyl)-2,3-dihydro-1H-benzo[d]pyrrolo[1,2-a]imidazol-7-yl)-N-(5-((hexahydropyrrolo[3,4-c]pyrrol-2(1H)-yl)methyl)pyridin-2-yl)pyrimidin-2-amine | MS-ESI (m/z): 557 [M + 1]⁺ |
| 74 | 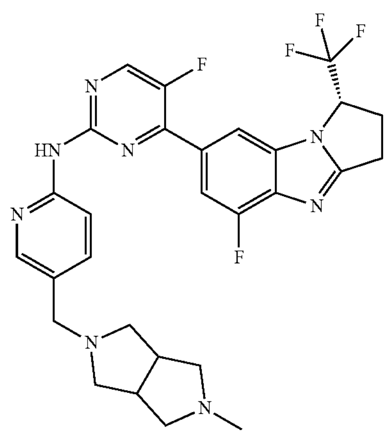 [SMILES: CN1CC2CN(Cc3ccc(Nc4ncc(F)c(-c5cc(F)c6nc7n(c6c5)[C@H](C(F)(F)F)CC7)n4)nc3)CC2C1] | 5-fluoro-4-((S)-5-fluoro-1-(trifluoromethyl)-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine | MS-ESI (m/z): 571 [M + 1]⁺ |
| 75 | 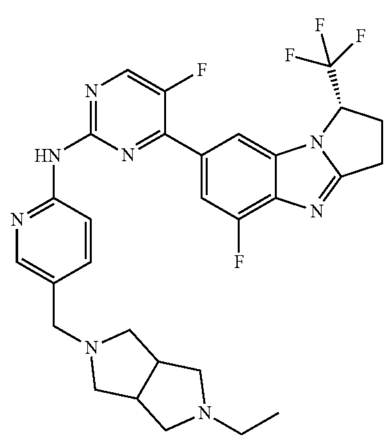 [SMILES: CCN1CC2CN(Cc3ccc(Nc4ncc(F)c(-c5cc(F)c6nc7n(c6c5)[C@H](C(F)(F)F)CC7)n4)nc3)CC2C1] | N-(5-((5-ethylhexahydropyrrolo[3,4-c]pyrrol-2(1H)-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine | MS-ESI (m/z): 585 [M + 1]⁺ |

TABLE 2-continued

| EXAMPLE | STRUCTURE | NAME | DATA |
|---|---|---|---|
| 76 | 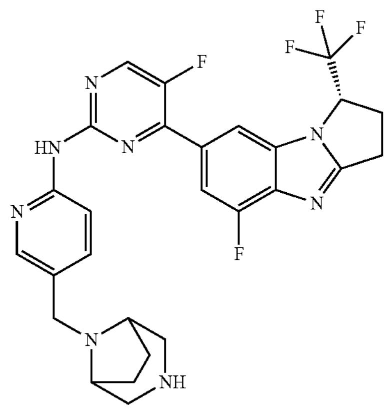 [SMILES: Fc1cnc(Nc2ccc(CN3C4CCC3CNC4)cn2)nc1-c1cc(F)c2nc3n(c2c1)[C@H](C(F)(F)F)CC3] | N-(5-((3,8-diazabicyclo[3.2.1]octan-8-yl)methyl) pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine | MS-ESI (m/z): 557 [M + 1]$^+$ |
| 77 | 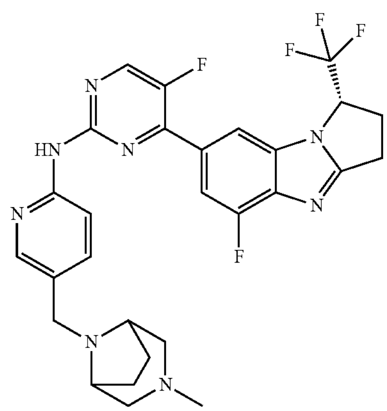 [SMILES: CN1CC2CCC(C1)N2Cc1ccc(Nc2ncc(F)c(-c3cc(F)c4nc5n(c4c3)[C@H](C(F)(F)F)CC5)n2)nc1] | 5-fluoro-4-((S)-5-fluoro-1-(trifluoromethyl)-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine | MS-ESI (m/z): 571 [M + 1]$^+$ |
| 78 | 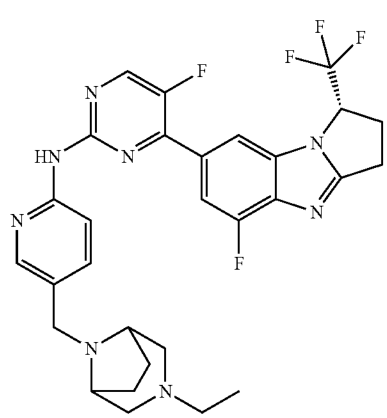 [SMILES: CCN1CC2CCC(C1)N2Cc1ccc(Nc2ncc(F)c(-c3cc(F)c4nc5n(c4c3)[C@H](C(F)(F)F)CC5)n2)nc1] | N-(5-((3-ethyl-3,8-diazabicyclo[3.2.1]octan-8-yl) methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine | MS-ESI (m/z): 585 [M + 1]$^+$ |

TABLE 2-continued

| EXAMPLE | STRUCTURE | NAME | DATA |
|---|---|---|---|
| 79 | 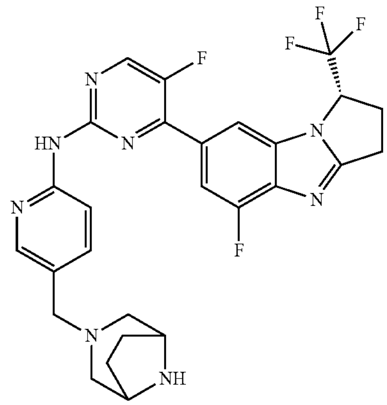 [SMILES: Fc1cnc(Nc2ccc(CN3CC4CCC(C3)N4)cn2)nc1-c1cc(F)c2nc3n(c2c1)[C@H](C(F)(F)F)CC3] | N-(5-((3,8-diazabicyclo[3.2.1]octan-3-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine | MS-ESI (m/z): 557 [M + 1]+ |
| 80 | 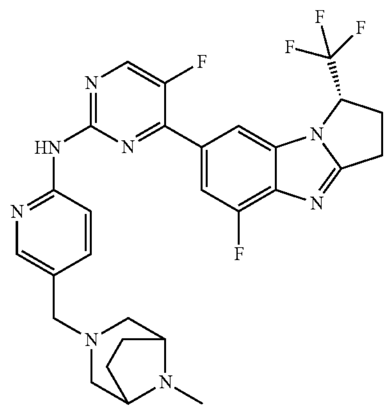 [SMILES: CN1C2CCC1CN(Cc1ccc(Nc3ncc(F)c(-c4cc(F)c5nc6n(c5c4)[C@H](C(F)(F)F)CC6)n3)nc1)C2] | 5-fluoro-4-((S)-5-fluoro-1-(trifluoromethyl)-2,3-dihydro-1H-benzo[d]pyrrolo[1,2-a]imidazol-7-yl)-N-(5-((8-methyl-3,8-diazabicyclo[3.2.1]octan-3-yl)methyl)pyridin-2-yl)pyrimidin-2-amine | MS-ESI (m/z): 571 [M + 1]+ |
| 81 | 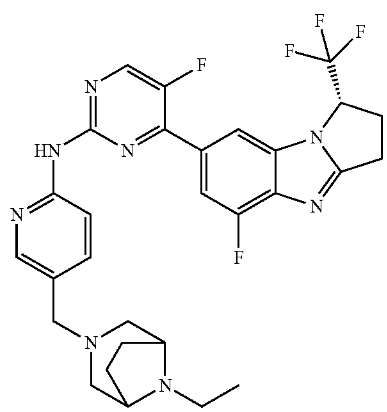 [SMILES: CCN1C2CCC1CN(Cc1ccc(Nc3ncc(F)c(-c4cc(F)c5nc6n(c5c4)[C@H](C(F)(F)F)CC6)n3)nc1)C2] | N-(5-((8-ethyl-3,8-diazabicyclo[3.2.1]octan-3-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine | MS-ESI (m/z): 585 [M + 1]+ |
| 82 | 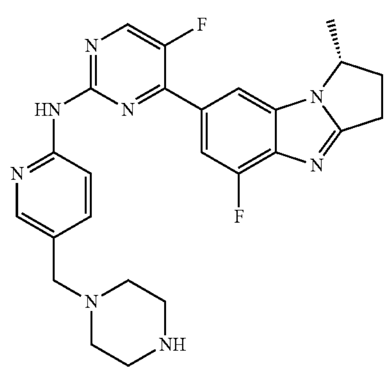 [SMILES: C[C@@H]1CCc2nc3c(F)cc(-c4nc(Nc5ccc(CN6CCNCC6)cn5)ncc4F)cc3n21] | (R)-5-fluoro-4-(5-fluoro-1-methyl-2,3-dihydro-1H-benzo[d]pyrrolo[1,2-a]imidazol-7-yl)-N-(5-(piperazin-1-ylmethyl)pyridin-2-yl)pyrimidin-2-amine | MS-ESI (m/z): 477 [M + 1]+ |

TABLE 2-continued

| EXAMPLE | STRUCTURE | NAME | DATA |
|---|---|---|---|
| 83 | 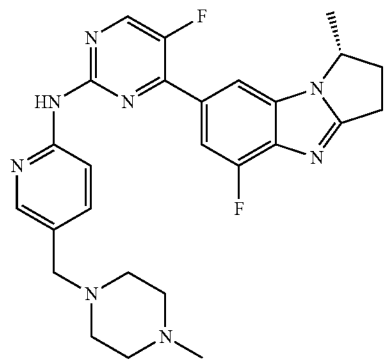 [SMILES: C[C@@H]1CCc2nc3c(F)cc(-c4nc(Nc5ccc(CN6CCN(C)CC6)cn5)ncc4F)cc3n21] | (R)-5-fluoro-4-(5-fluoro-1-methyl-2,3-dihydro-1H-benzo[d]pyrrolo[1,2-a]imidazol-7-yl)-N-(5-((4-methylpiperazin-1-yl)methyl)pyridin-2-yl)pyrimidin-2-amine | MS-ESI (m/z): 491 [M + 1]$^+$ |
| 84 | 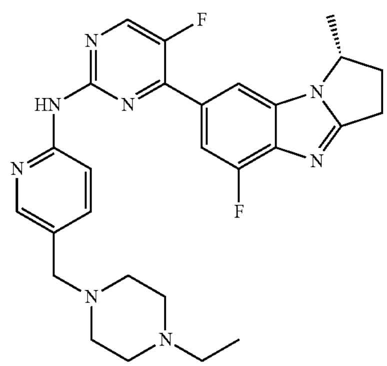 [SMILES: CCN1CCN(Cc2ccc(Nc3ncc(F)c(-c4cc(F)c5nc6n(c5c4)[C@H](C)CC6)n3)nc2)CC1] | (R)-N-(5-((4-ethylpiperazin-1-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine | MS-ESI (m/z): 505 [M + 1]$^+$ |
| 85 | 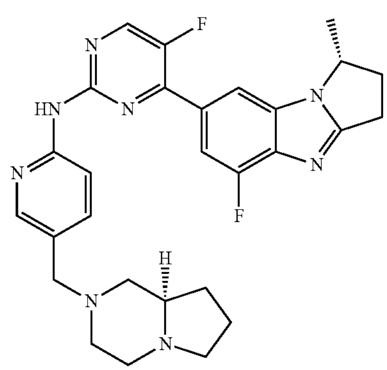 [SMILES: C[C@@H]1CCc2nc3c(F)cc(-c4nc(Nc5ccc(CN6CCN7CCC[C@@H]7C6)cn5)ncc4F)cc3n21] | 5-fluoro-4-((R)-5-fluoro-1-methyl-2,3-dihydro-1H-benzo[d]pyrrolo[1,2-a]imidazol-7-yl)-N-(5-(((R)-hexahydropyrrolo[1,2-a]pyrazin-2(1H)-yl)me thyl)pyridin-2-yl)pyrimidin-2-amine | MS-ESI (m/z): 517 [M + 1]$^+$ |
| 86 | 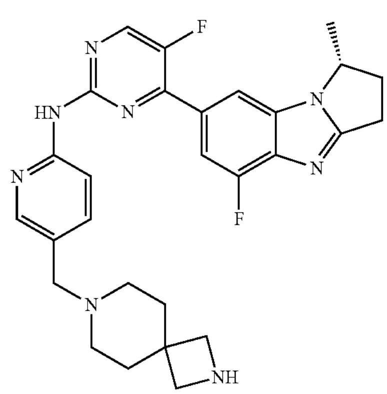 [SMILES: C[C@@H]1CCc2nc3c(F)cc(-c4nc(Nc5ccc(CN6CCC7(CC6)CNC7)cn5)ncc4F)cc3n21] | (R)-N-(5-((2,7-diazaspiro[3.5]nonan-7-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine | MS-ESI (m/z): 517 [M + 1]$^+$ |

TABLE 2-continued

| EXAMPLE | STRUCTURE | NAME | DATA |
|---|---|---|---|
| 87 | 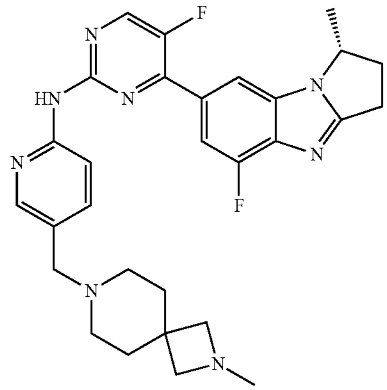 [SMILES: C[C@@H]1CCc2nc3c(F)cc(-c4nc(Nc5ccc(CN6CCC7(CC6)CN(C)C7)cn5)ncc4F)cc3n21] | (R)-5-fluoro-4-(5-fluoro-1-methyl-2,3-dihydro-1H-benzo[d]pyrrolo[1,2-a]imidazol-7-yl)-N-(5-((2-methyl-2,7-diazaspiro[3.5]nonan-7-yl)methyl)pyridin-2-yl)pyrimidin-2-amine | MS-ESI (m/z): 531 [M + 1]+ |
| 88 | 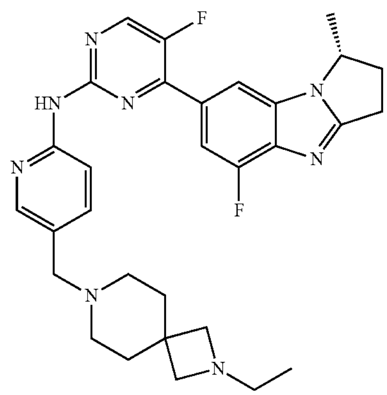 [SMILES: CCN1CC2(CCN(Cc3ccc(Nc4ncc(F)c(-c5cc(F)c6nc7n(c6c5)[C@H](C)CC7)n4)nc3)CC2)C1] | (R)-N-(5-((2-ethyl-2,7-diazaspiro[3.5]nonan-7-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine | MS-ESI (m/z): 545 [M + 1]+ |
| 89 | 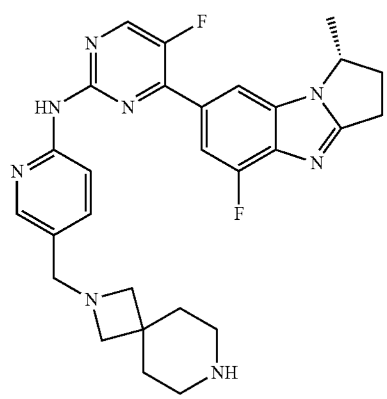 [SMILES: C[C@@H]1CCc2nc3c(F)cc(-c4nc(Nc5ccc(CN6CC7(CCNCC7)C6)cn5)ncc4F)cc3n21] | (R)-N-(5-((2,7-diazaspiro[3.5]nonan-2-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine | MS-ESI (m/z): 517 [M + 1]+ |
| 90 | 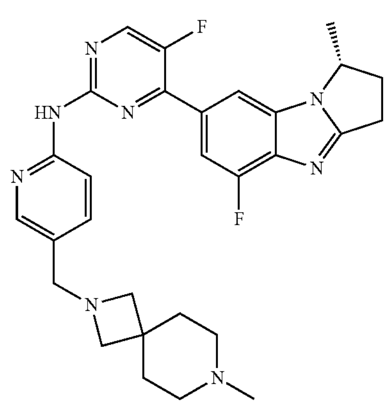 [SMILES: C[C@@H]1CCc2nc3c(F)cc(-c4nc(Nc5ccc(CN6CC7(CCN(C)CC7)C6)cn5)ncc4F)cc3n21] | (R)-5-fluoro-4-(5-fluoro-1-methyl-2,3-dihydro-1H-benzo[d]pyrrolo[1,2-a]imidazol-7-yl)-N-(5-((7-methyl-2,7-diazaspiro[3.5]nonan-2-yl)methyl)pyridin-2-yl)pyrimidin-2-amine | MS-ESI (m/z): 531 [M + 1]+ |

TABLE 2-continued

| EXAMPLE | STRUCTURE | NAME | DATA |
|---|---|---|---|
| 91 | 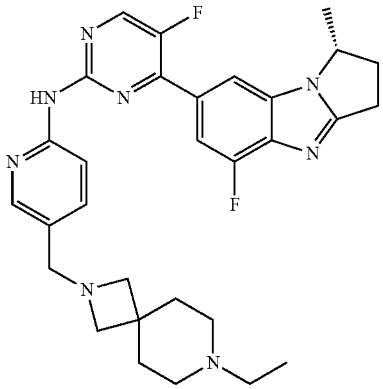 [SMILES: CCN1CCC2(CC1)CN(Cc1ccc(Nc3ncc(F)c(-c4cc(F)c5nc6n(c5c4)[C@H](C)CC6)n3)nc1)C2] | (R)-N-(5-((7-ethyl-2,7-diazaspiro[3.5]nonan-2-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine | MS-ESI (m/z): 545 [M + 1]$^+$ |
| 92 | 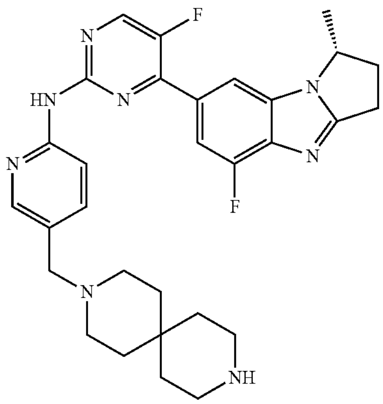 [SMILES: C[C@@H]1CCc2nc3c(F)cc(-c4nc(Nc5ccc(CN6CCC7(CCNCC7)CC6)cn5)ncc4F)cc3n21] | (R)-N-(5-((3,9-diazaspiro[5.5]undecan-3-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine | MS-ESI (m/z): 545 [M + 1]$^+$ |
| 93 | 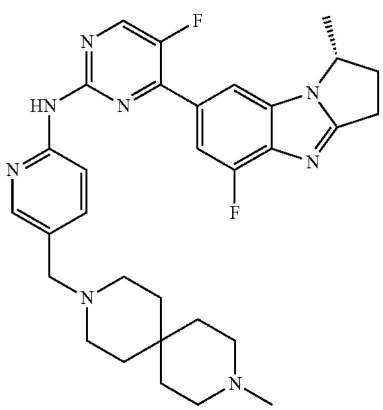 [SMILES: C[C@@H]1CCc2nc3c(F)cc(-c4nc(Nc5ccc(CN6CCC7(CCN(C)CC7)CC6)cn5)ncc4F)cc3n21] | (R)-5-fluoro-4-(5-fluoro-1-methyl-2,3-dihydro-1H-benzo[d]pyrrolo[1,2-a]imidazol-7-yl)-N-(5-((9-methyl-3,9-diazaspiro[5.5]undecan-3-yl)methyl)pyridin-2-yl)pyrimidin-2-amine | MS-ESI (m/z): 559 [M + 1]$^+$ |
| 94 | 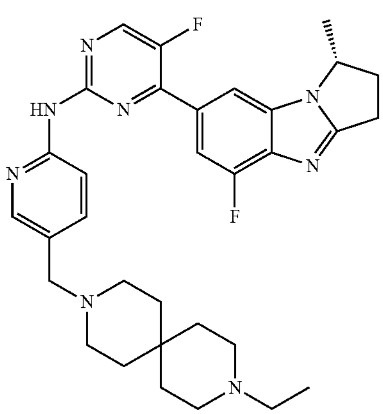 [SMILES: CCN1CCC2(CC1)CCN(Cc1ccc(Nc3ncc(F)c(-c4cc(F)c5nc6n(c5c4)[C@H](C)CC6)n3)nc1)CC2] | (R)-N-(5-((9-ethyl-3,9-diazaspiro[5.5]undecan-3-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine | MS-ESI (m/z): 573 [M + 1]$^+$ |

TABLE 2-continued

| EXAMPLE | STRUCTURE | NAME | DATA |
|---|---|---|---|
| 95 | 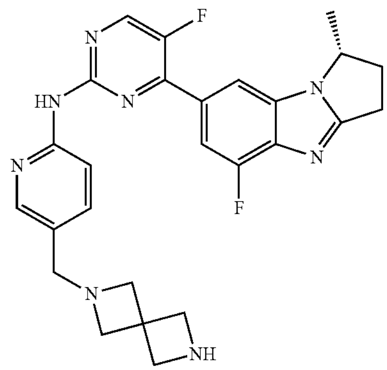 [SMILES: C[C@@H]1CCc2nc3c(F)cc(-c4nc(Nc5ccc(CN6CC7(CNC7)C6)cn5)ncc4F)cc3n21] | (R)-N-(5-((2,6-diazaspiro[3.3]heptan-2-yl)methyl) pyridin-2-yl)-5-fluoro-4-(5-fluoro-1-methyl-2,3-dihydro-1H-benzo[d]pyrrolo[1,2-a]imidazol-7-yl)pyrimidin-2-amine | MS-ESI (m/z): 489 [M + 1]$^+$ |
| 96 | 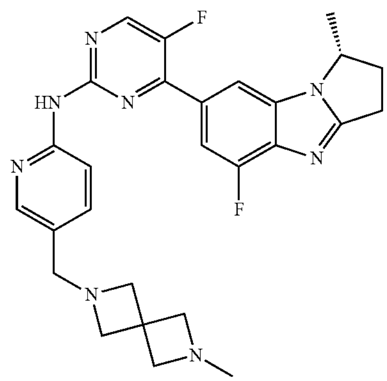 [SMILES: C[C@@H]1CCc2nc3c(F)cc(-c4nc(Nc5ccc(CN6CC7(CN(C)C7)C6)cn5)ncc4F)cc3n21] | (R)-5-fluoro-4-(5-fluoro-1-methyl-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine | MS-ESI (m/z): 503 [M + 1]$^+$ |
| 97 | 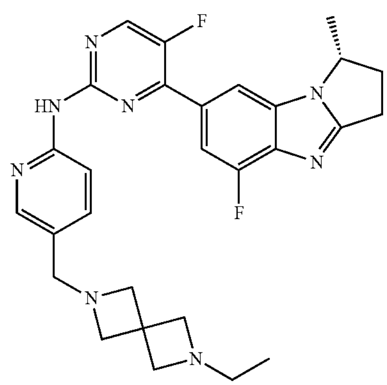 [SMILES: CCN1CC2(C1)CN(Cc1ccc(Nc3ncc(F)c(-c4cc(F)c5nc6n(c5c4)[C@H](C)CC6)n3)nc1)C2] | (R)-N-(5-((6-ethyl-2,6-diazaspiro[3.3]heptan-2-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine | MS-ESI (m/z): 517 [M + 1]$^+$ |
| 98 | 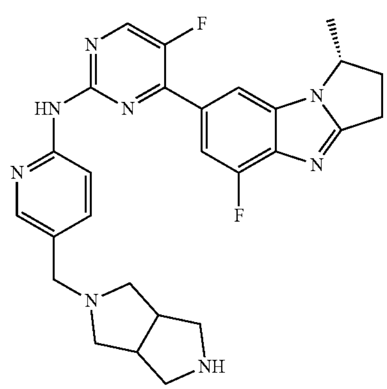 [SMILES: C[C@@H]1CCc2nc3c(F)cc(-c4nc(Nc5ccc(CN6CC7CNCC7C6)cn5)ncc4F)cc3n21] | 5-fluoro-4-((R)-5-fluoro-1-methyl-2,3-dihydro-1H-benzo[d]pyrrolo[1,2-a]imidazol-7-yl)-N-(5-((hexahydropyrrolo[3,4-c]pyrrol-2(1H)-yl)methyl)pyridin-2-yl)pyrimidin-2-amine | MS-ESI (m/z): 503 [M + 1]$^+$ |

TABLE 2-continued

| EXAMPLE | STRUCTURE | NAME | DATA |
|---|---|---|---|
| 99 | 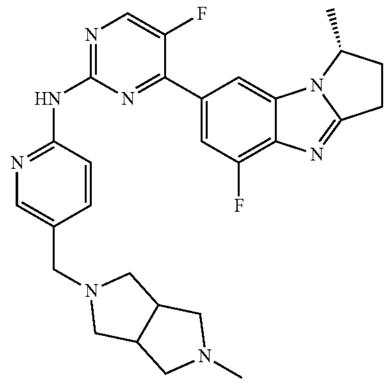 [SMILES: C[C@@H]1CCc2nc3c(F)cc(-c4nc(Nc5ccc(CN6CC7CN(C)CC7C6)cn5)ncc4F)cc3n21] | 5-fluoro-4-((R)-5-fluoro-1-methyl-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine | MS-ESI (m/z): 517 [M + 1]$^+$ |
| 100 | 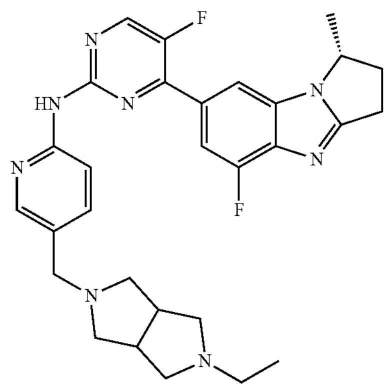 [SMILES: CCN1CC2CN(Cc3ccc(Nc4ncc(F)c(-c5cc(F)c6nc7n(c6c5)[C@H](C)CC7)n4)nc3)CC2C1] | N-(5-((5-ethylhexahydropyrrolo[3,4-c]pyrrol-2(1H)-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine | MS-ESI (m/z): 531 [M + 1]$^+$ |
| 101 | 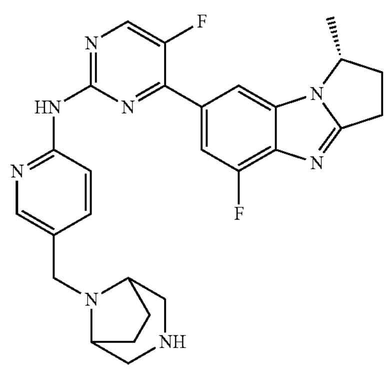 [SMILES: C[C@@H]1CCc2nc3c(F)cc(-c4nc(Nc5ccc(CN6C7CCC6CNC7)cn5)ncc4F)cc3n21] | N-(5-((3,8-diazabicyclo[3.2.1]octan-8-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine | MS-ESI (m/z): 503 [M + 1]$^+$ |
| 102 | 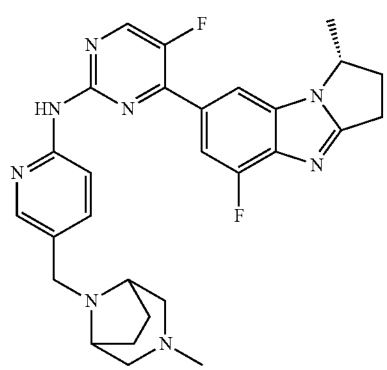 [SMILES: C[C@@H]1CCc2nc3c(F)cc(-c4nc(Nc5ccc(CN6C7CCC6CN(C)C7)cn5)ncc4F)cc3n21] | 5-fluoro-4-((R)-5-fluoro-1-methyl-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine | MS-ESI (m/z): 517 [M + 1]$^+$ |

TABLE 2-continued

| EXAMPLE | STRUCTURE | NAME | DATA |
|---|---|---|---|
| 103 | 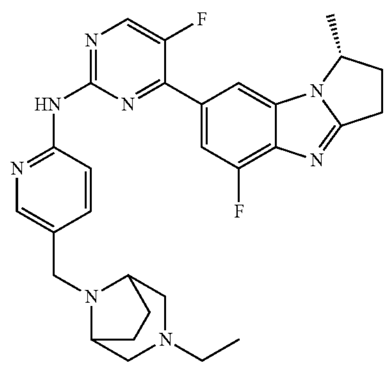 [SMILES: CCN1CC2CCC(C1)N2Cc1ccc(Nc2ncc(F)c(-c3cc(F)c4nc5n(c4c3)[C@H](C)CC5)n2)nc1] | N-(5-((3-ethyl-3,8-diazabicyclo[3.2.1]octan-8-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine | MS-ESI (m/z): 531 [M + 1]+ |
| 104 | 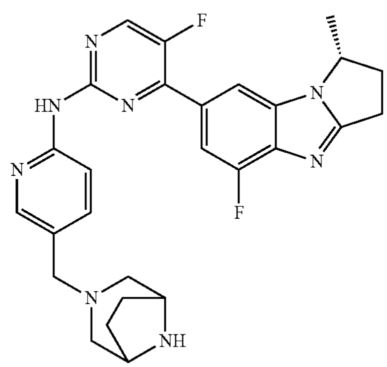 [SMILES: C[C@@H]1CCc2nc3c(F)cc(-c4nc(Nc5ccc(CN6CC7CCC(C6)N7)cn5)ncc4F)cc3n21] | N-(5-((3,8-diazabicyclo[3.2.1]octan-3-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine | MS-ESI (m/z): 503 [M + 1]+ |
| 105 | 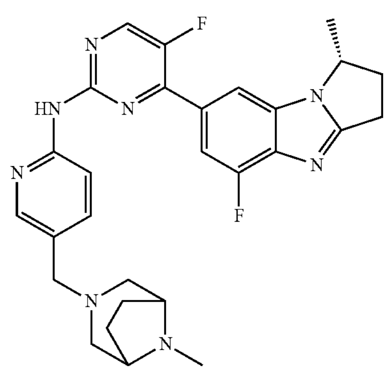 [SMILES: C[C@@H]1CCc2nc3c(F)cc(-c4nc(Nc5ccc(CN6CC7CCC(C6)N7C)cn5)ncc4F)cc3n21] | 5-fluoro-4-((R)-5-fluoro-1-methyl-2,3-dihydro-1H-benzo[d]pyrrolo[1,2-a]imidazol-7-yl)-N-(5-((8-methyl-3,8-diazabicyclo[3.2.1]octan-3-yl)methyl)pyridin-2-yl)pyrimidin-2-amine | MS-ESI (m/z): 517 [M + 1]+ |
| 106 | 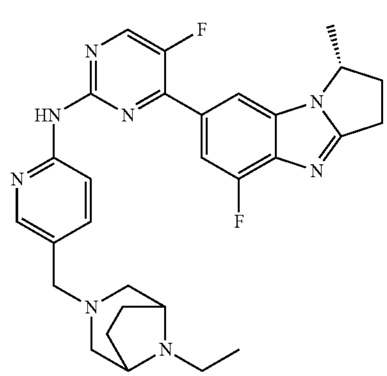 [SMILES: CCN1C2CCC1CN(Cc1ccc(Nc3ncc(F)c(-c4cc(F)c5nc6n(c5c4)[C@H](C)CC6)n3)nc1)C2] | N-(5-((8-ethyl-3,8-diazabicyclo[3.2.1]octan-3-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine | MS-ESI (m/z): 531 [M + 1]+ |

TABLE 2-continued

| EXAMPLE | STRUCTURE | NAME | DATA |
|---|---|---|---|
| 107 | 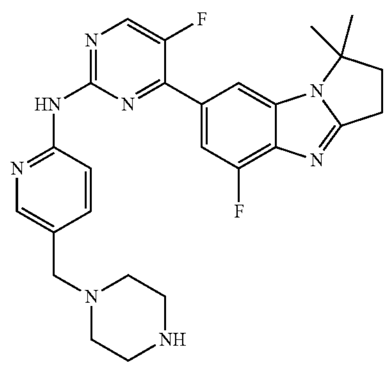 [SMILES: CC1(C)CCc2nc3c(F)cc(-c4nc(Nc5ccc(CN6CCNCC6)cn5)ncc4F)cc3n21] | 5-fluoro-4-(5-fluoro-1,1-dimethyl-2,3-dihydro-1H-benzo[d]pyrrolo[1,2-a]imidazol-7-yl)-N-(5-(piperazin-1-ylmethyl)pyridin-2-yl)pyrimidin-2-amine | MS-ESI (m/z): 491 [M + 1]$^+$ |
| 108 | 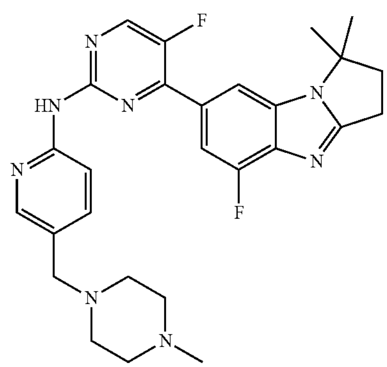 [SMILES: CN1CCN(Cc2ccc(Nc3ncc(F)c(-c4cc(F)c5nc6n(c5c4)C(C)(C)CC6)n3)nc2)CC1] | 5-fluoro-4-(5-fluoro-1,1-dimethyl-2,3-dihydro-1H-benzo[d]pyrrolo[1,2-a]imidazol-7-yl)-N-(5-((4-methylpiperazin-1-yl)methyl)pyridin-2-yl)pyrimidin-2-amine | MS-ESI (m/z): 505 [M + 1]$^+$ |
| 109 | 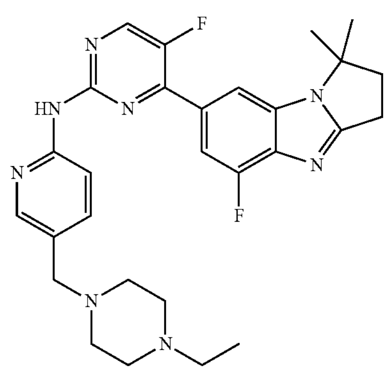 [SMILES: CCN1CCN(Cc2ccc(Nc3ncc(F)c(-c4cc(F)c5nc6n(c5c4)C(C)(C)CC6)n3)nc2)CC1] | N-(5-((4-ethylpiperazin-1-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine | MS-ESI (m/z): 519 [M + 1]$^+$ |
| 110 | 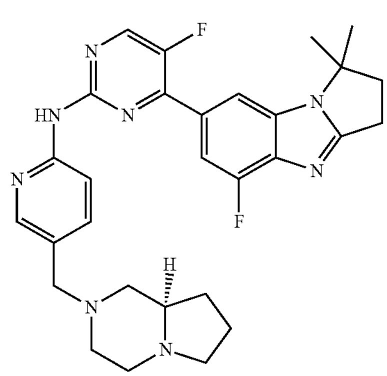 [SMILES: CC1(C)CCc2nc3c(F)cc(-c4nc(Nc5ccc(CN6CCN7CCC[C@@H]7C6)cn5)ncc4F)cc3n21] | (R)-5-fluoro-4-(5-fluoro-1,1-dimethyl-2,3-dihydro-1H-benzo[d]pyrrolo[1,2-a]imidazol-7-yl)-N-(5-((hexahydropyrrolo[1,2-a]pyrazin-2(1H)-yl)met hyl)pyridin-2-yl)pyrimidin-2-amine | MS-ESI (m/z): 531 [M + 1]$^+$ |

TABLE 2-continued

| EXAMPLE | STRUCTURE | NAME | DATA |
|---|---|---|---|
| 111 | 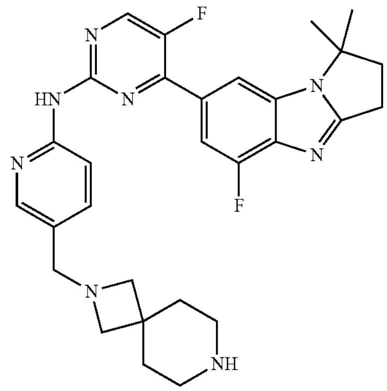 [SMILES: CC1(C)CCc2nc3c(F)cc(-c4nc(Nc5ccc(CN6CC7(CCNCC7)C6)cn5)ncc4F)cc3n21] | N-(5-((2,7-diazaspiro[3.5]nonan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine | MS-ESI (m/z): 531 [M + 1]⁺ |
| 112 | 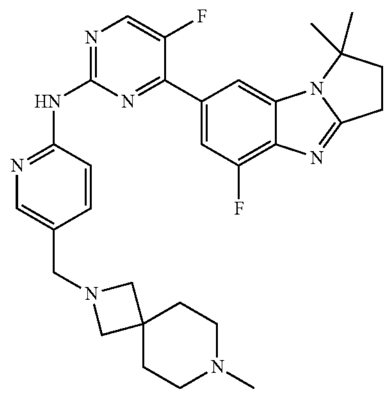 [SMILES: CN1CCC2(CC1)CN(Cc1ccc(Nc3ncc(F)c(-c4cc(F)c5nc6n(c5c4)C(C)(C)CC6)n3)nc1)C2] | 5-fluoro-4-(5-fluoro-1,1-dimethyl-2,3-dihydro-1H-benzo[d]pyrrolo[1,2-a]imidazol-7-yl)-N-(5-((7-methyl-2,7-diazaspiro[3.5]nonan-2-yl)methyl)pyridin-2-yl)pyrimidin-2-amine | MS-ESI (m/z): 545 [M + 1]⁺ |
| 113 | 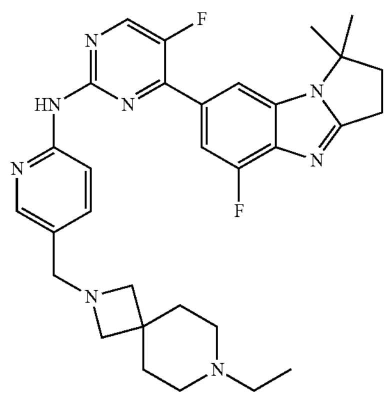 [SMILES: CCN1CCC2(CC1)CN(Cc1ccc(Nc3ncc(F)c(-c4cc(F)c5nc6n(c5c4)C(C)(C)CC6)n3)nc1)C2] | N-(5-((7-ethyl-2,7-diazaspiro[3.5]nonan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine | MS-ESI (m/z): 559 [M + 1]⁺ |
| 114 | 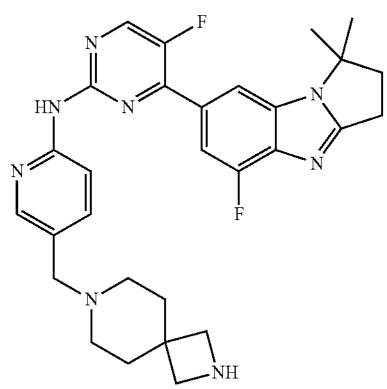 [SMILES: CC1(C)CCc2nc3c(F)cc(-c4nc(Nc5ccc(CN6CCC7(CC6)CNC7)cn5)ncc4F)cc3n21] | N-(5-((2,7-diazaspiro[3.5]nonan-7-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine | MS-ESI (m/z): 531 [M + 1]⁺ |

TABLE 2-continued

| EXAMPLE | STRUCTURE | NAME | DATA |
|---|---|---|---|
| 115 | 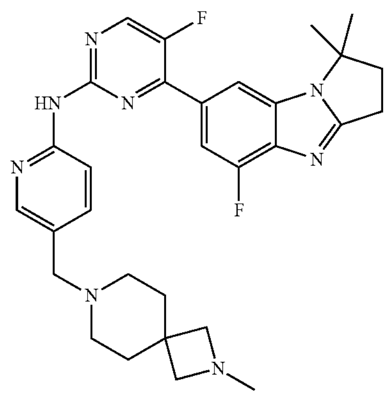 [SMILES: CN1CC2(CCN(Cc3ccc(Nc4ncc(F)c(-c5cc(F)c6nc7n(c6c5)C(C)(C)CC7)n4)nc3)CC2)C1] | 5-fluoro-4-(5-fluoro-1,1-dimethyl-2,3-dihydro-1H-benzo[d]pyrrolo[1,2-a]imidazol-7-yl)-N-(5-((2-methyl-2,7-diazaspiro[3.5]nonan-7-yl)methyl)pyridin-2-yl)pyrimidin-2-amine | MS-ESI (m/z): 545 [M + 1]$^+$ |
| 116 | 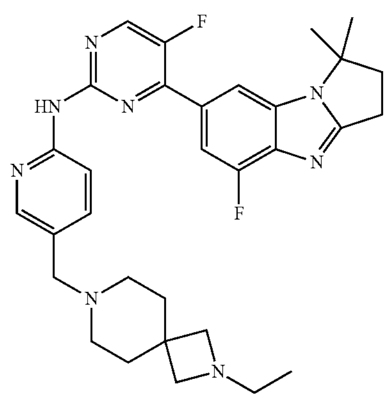 [SMILES: CCN1CC2(CCN(Cc3ccc(Nc4ncc(F)c(-c5cc(F)c6nc7n(c6c5)C(C)(C)CC7)n4)nc3)CC2)C1] | N-(5-((2-ethyl-2,7-diazaspiro[3.5]nonan-7-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine | MS-ESI (m/z): 559 [M + 1]$^+$ |
| 117 | 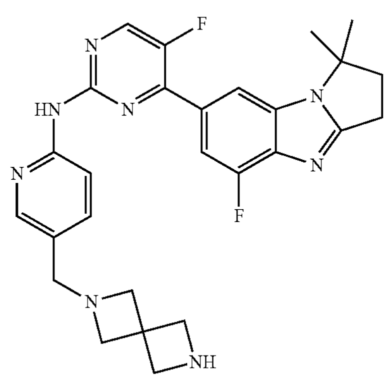 [SMILES: CC1(C)CCc2nc3c(F)cc(-c4nc(Nc5ccc(CN6CC7(CNC7)C6)cn5)ncc4F)cc3n21] | N-(5-((2,6-diazaspiro[3.3]heptan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine | MS-ESI (m/z): 503 [M + 1]$^+$ |
| 118 | 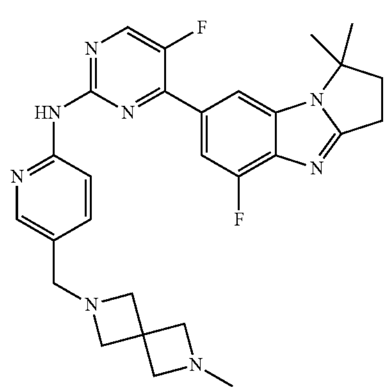 [SMILES: CN1CC2(C1)CN(Cc1ccc(Nc3ncc(F)c(-c4cc(F)c5nc6n(c5c4)C(C)(C)CC6)n3)nc1)C2] | 5-fluoro-4-(5-fluoro-1,1-dimethyl-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine | MS-ESI (m/z): 517 [M + 1]$^+$ |

TABLE 2-continued

| EXAMPLE | STRUCTURE | NAME | DATA |
|---|---|---|---|
| 119 | 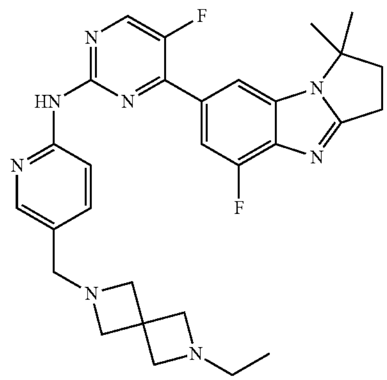 [SMILES: CCN1CC2(C1)CN(Cc1ccc(Nc3ncc(F)c(-c4cc(F)c5nc6n(c5c4)C(C)(C)CC6)n3)nc1)C2] | N-(5-((6-ethyl-2,6-diazaspiro[3.3]heptan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine | MS-ESI (m/z): 531 [M + 1]$^+$ |
| 120 | 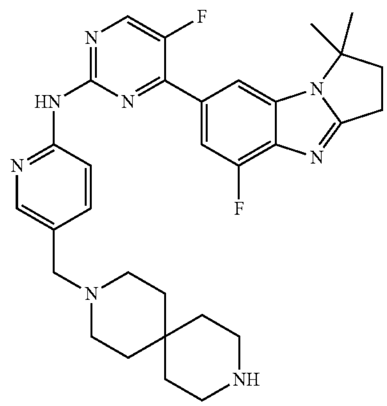 [SMILES: CC1(C)CCc2nc3c(F)cc(-c4nc(Nc5ccc(CN6CCC7(CCNCC7)CC6)cn5)ncc4F)cc3n21] | N-(5-((3,9-diazaspiro[5.5]undecan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine | MS-ESI (m/z): 559 [M + 1]$^+$ |
| 121 | 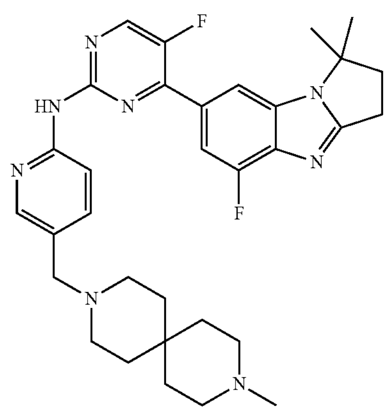 [SMILES: CN1CCC2(CC1)CCN(Cc1ccc(Nc3ncc(F)c(-c4cc(F)c5nc6n(c5c4)C(C)(C)CC6)n3)nc1)CC2] | 5-fluoro-4-(5-fluoro-1,1-dimethyl-2,3-dihydro-1H-benzo[d]pyrrolo[1,2-a]imidazol-7-yl)-N-(5-((9-methyl-3,9-diazaspiro[5.5]undecan-3-yl)methyl)pyridin-2-yl)pyrimidin-2-amine | MS-ESI (m/z): 573 [M + 1]$^+$ |
| 122 | 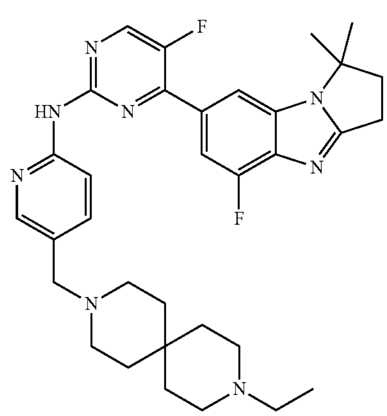 [SMILES: CCN1CCC2(CC1)CCN(Cc1ccc(Nc3ncc(F)c(-c4cc(F)c5nc6n(c5c4)C(C)(C)CC6)n3)nc1)CC2] | N-(5-((9-ethyl-3,9-diazaspiro[5.5]undecan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine | MS-ESI (m/z): 587 [M + 1]$^+$ |

TABLE 2-continued

| EXAMPLE | STRUCTURE | NAME | DATA |
|---------|-----------|------|------|
| 123 | 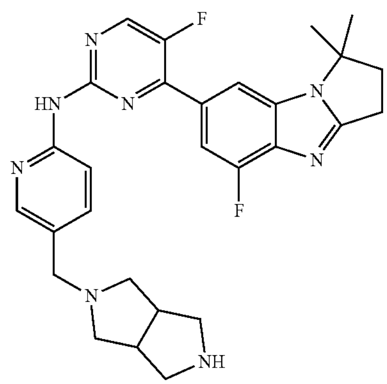 [SMILES: CC1(C)CCc2nc3c(F)cc(-c4nc(Nc5ccc(CN6CC7CNCC7C6)cn5)ncc4F)cc3n21] | 5-fluoro-4-(5-fluoro-1,1-dimethyl-2,3-dihydro-1H-benzo[d]pyrrolo[1,2-a]imidazol-7-yl)-N-(5-((hexahydropyrrolo[3,4-c]pyrrol-2(1H)-yl)methyl)pyridin-2-yl)pyrimidin-2-amine | MS-ESI (m/z): 517 [M + 1]+ |
| 124 | 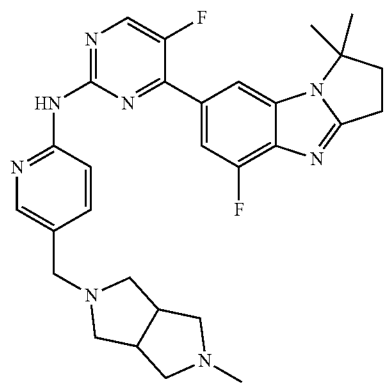 [SMILES: CN1CC2CN(Cc3ccc(Nc4ncc(F)c(-c5cc(F)c6nc7n(c6c5)C(C)(C)CC7)n4)nc3)CC2C1] | 5-fluoro-4-(5-fluoro-1,1-dimethyl-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine | MS-ESI (m/z): 531 [M + 1]+ |
| 125 | 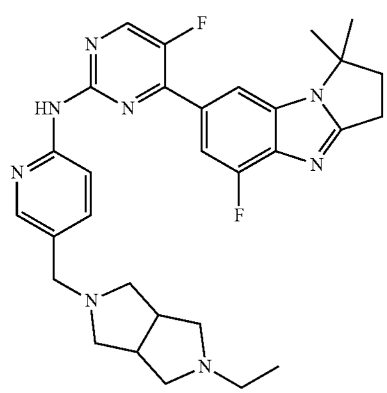 [SMILES: CCN1CC2CN(Cc3ccc(Nc4ncc(F)c(-c5cc(F)c6nc7n(c6c5)C(C)(C)CC7)n4)nc3)CC2C1] | N-(5-((5-ethylhexahydropyrrolo[3,4-c]pyrrol-2(1H)-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine | MS-ESI (m/z): 545 [M + 1]+ |
| 126 | 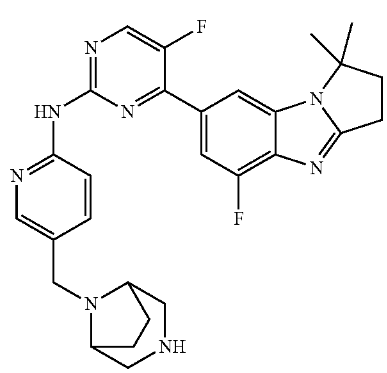 [SMILES: CC1(C)CCc2nc3c(F)cc(-c4nc(Nc5ccc(CN6C7CCC6CNC7)cn5)ncc4F)cc3n21] | N-(5-((3,8-diazabicyclo[3.2.1]octan-8-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine | MS-ESI (m/z): 517 [M + 1]+ |

| EXAMPLE | STRUCTURE | NAME | DATA |
|---|---|---|---|
| 127 | 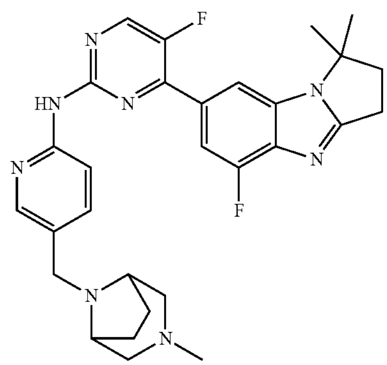 [SMILES: CN1CC2CCC(C1)N2Cc1ccc(Nc2ncc(F)c(-c3cc(F)c4nc5n(c4c3)C(C)(C)CC5)n2)nc1] | 5-fluoro-4-(5-fluoro-1,1-dimethyl-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine | MS-ESI (m/z): 531 [M + 1]+ |
| 128 | 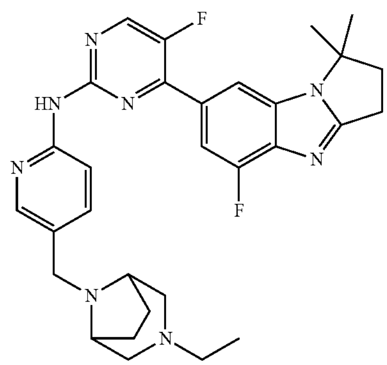 [SMILES: CCN1CC2CCC(C1)N2Cc1ccc(Nc2ncc(F)c(-c3cc(F)c4nc5n(c4c3)C(C)(C)CC5)n2)nc1] | N-(5-((3-ethyl-3,8-diazabicyclo[3.2.1]octan-8-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine | MS-ESI (m/z): 545 [M + 1]+ |
| 129 | 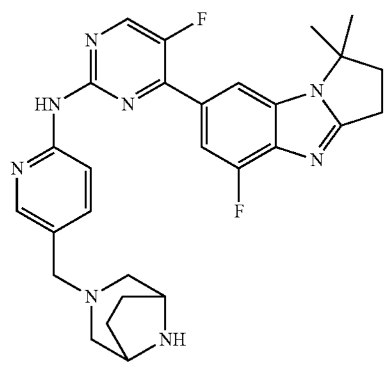 [SMILES: CC1(C)CCc2nc3c(F)cc(-c4nc(Nc5ccc(CN6CC7CCC(C6)N7)cn5)ncc4F)cc3n21] | N-(5-((3,8-diazabicyclo[3.2.1]octan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine | MS-ESI (m/z): 517 [M + 1]+ |
| 130 | 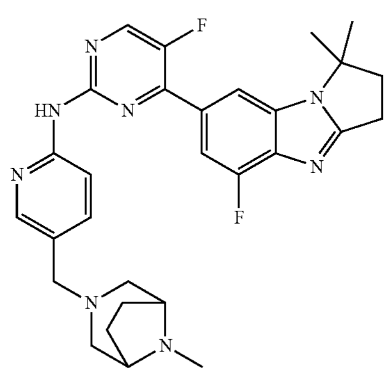 [SMILES: CN1C2CCC1CN(Cc1ccc(Nc3ncc(F)c(-c4cc(F)c5nc6n(c5c4)C(C)(C)CC6)n3)nc1)C2] | 5-fluoro-4-(5-fluoro-1,1-dimethyl-2,3-dihydro-1H-benzo[d]pyrrolo[1,2-a]imidazol-7-yl)-N-(5-((8-methyl-3,8-diazabicyclo[3.2.1]octan-3-yl)methyl)pyridin-2-yl)pyrimidin-2-amine | MS-ESI (m/z): 531 [M + 1]+ |

TABLE 2-continued

| EXAMPLE | STRUCTURE | NAME | DATA |
|---|---|---|---|
| 131 | 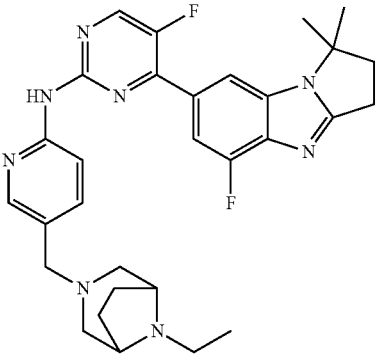 [SMILES: CCN1C2CCC1CN(Cc1ccc(Nc3ncc(F)c(-c4cc(F)c5nc6n(c5c4)C(C)(C)CC6)n3)nc1)C2] | N-(5-((8-ethyl-3,8-diazabicyclo[3.2.1]octan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine | MS-ESI (m/z): 545 [M + 1]+ |
| 132 | 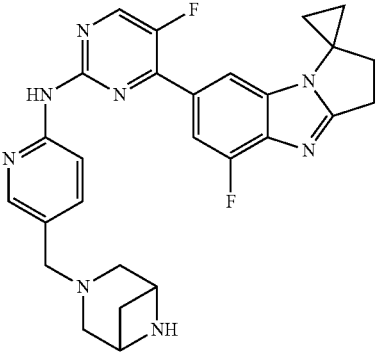 [SMILES: Fc1cnc(Nc2ccc(CN3CC4CC(C3)N4)cn2)nc1-c1cc(F)c2nc3n(c2c1)C1(CC3)CC1] | N-(5-((3,6-diazabicyclo[3.1.1]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine | MS-ESI (m/z): 501 [M + 1]+ |
| 133 | 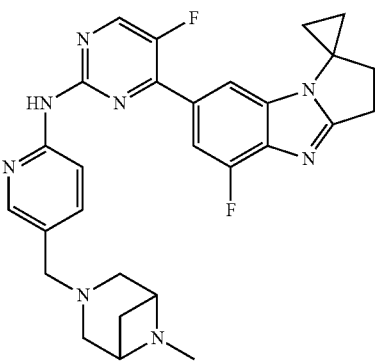 [SMILES: CN1C2CC1CN(Cc1ccc(Nc3ncc(F)c(-c4cc(F)c5nc6n(c5c4)C4(CC6)CC4)n3)nc1)C2] | 5-fluoro-4-(5-fluoro-2,3-dihydrospiro[benzo[d]pyrrolo[1,2-a]imidazole-1,1'-cyclopropan]-7-yl)-N-(5-((6-methyl-3,6-diazabicyclo[3.1.1]heptan-3-yl)methyl)pyridin-2-yl)pyrimidin-2-amine | MS-ESI (m/z): 515 [M + 1]+ |
| 134 | 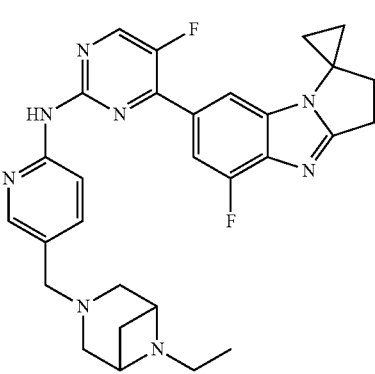 [SMILES: CCN1C2CC1CN(Cc1ccc(Nc3ncc(F)c(-c4cc(F)c5nc6n(c5c4)C4(CC6)CC4)n3)nc1)C2] | N-(5-((6-ethyl-3,6-diazabicyclo[3.1.1]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine | MS-ESI (m/z): 529 [M + 1]+ |

TABLE 2-continued

| EXAMPLE | STRUCTURE | NAME | DATA |
|---------|-----------|------|------|
| 135 | 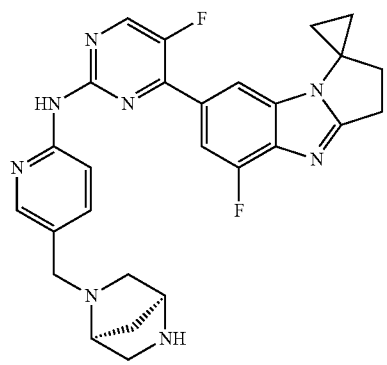 | N-(5-(((1S,4S)-2,5-diazabicyclo[2.2.1]heptan-2-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine | MS-ESI (m/z): 501 [M + 1]⁺ |
| 136 | 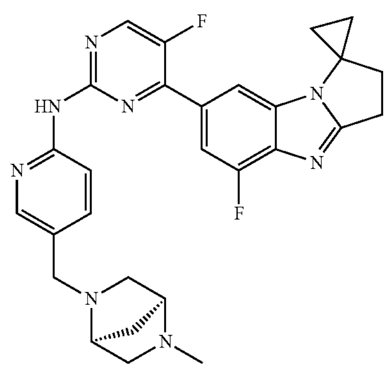 | 5-fluoro-4-(5-fluoro-2,3-dihydrospiro[benzo[d]pyrrolo[1,2-a]imidazole-1,1'-cyclopropan]-7-yl)-N-(5-(((1S,4S)-5-methyl-2,5-diazabicyclo[2.2.1]heptan-2-yl)methyl)pyridin-2-yl)pyrimidin-2-amine | MS-ESI (m/z): 515 [M + 1]⁺ |
| 137 | 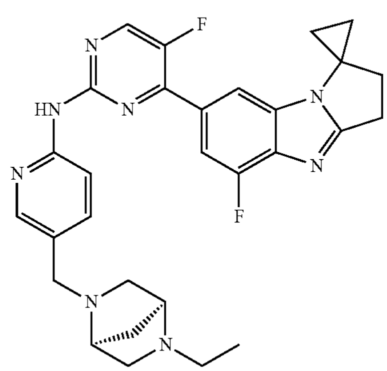 | N-(5-(((1S,4S)-5-ethyl-2,5-diazabicyclo[2.2.1]heptan-2-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine | MS-ESI (m/z): 529 [M + 1]⁺ |
| 138 | 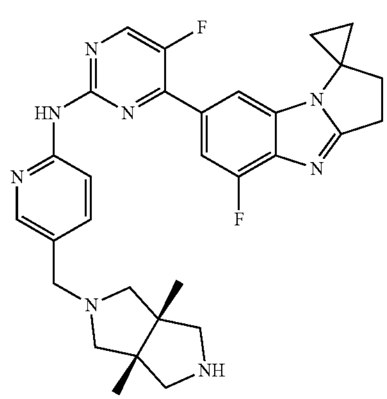 [SMILES: C[C@@]12CNC[C@]1(C)CN(Cc1ccc(Nc3ncc(F)c(-c4cc(F)c5nc6n(c5c4)C4(CC6)CC4)n3)nc1)C2] | N-(5-(((3aR,6aS)-3a,6a-dimethylhexahydropyrrolo[3,4-c]pyrrol-2(1H)-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine | MS-ESI (m/z): 543 [M + 1]⁺ |

TABLE 2-continued

| EXAMPLE | STRUCTURE | NAME | DATA |
|---|---|---|---|
| 139 | 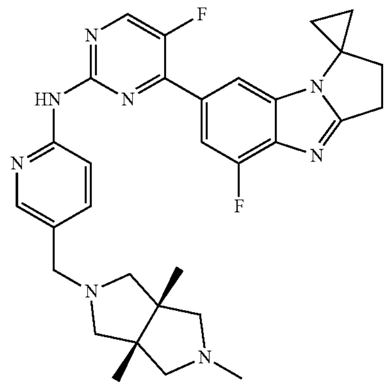 [SMILES: CN1C[C@@]2(C)CN(Cc3ccc(Nc4ncc(F)c(-c5cc(F)c6nc7n(c6c5)C5(CC7)CC5)n4)nc3)C[C@@]2(C)C1] | 5-fluoro-4-(5-fluoro-2,3-dihydrospiro[benzo[d]pyrrolo[1,2-a]imidazole-1,1'-cyclopropan]-7-yl)-N-(5-(((3aR,6aS)-3a,5,6a-trimethylhexahydropyrrolo[3,4-c]pyrrol-2(1H)-yl)methyl)pyridin-2-yl)pyrimidin-2-amine | MS-ESI (m/z): 557 [M + 1]⁺ |
| 140 | 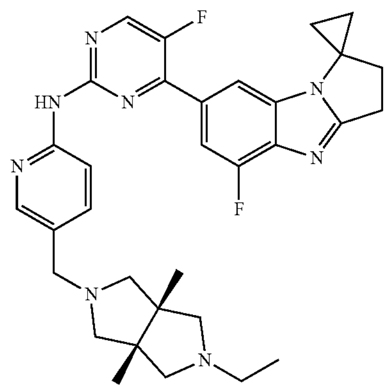 [SMILES: CCN1C[C@@]2(C)CN(Cc3ccc(Nc4ncc(F)c(-c5cc(F)c6nc7n(c6c5)C5(CC7)CC5)n4)nc3)C[C@@]2(C)C1] | N-(5-(((3aR,6aS)-5-ethyl-3a,6a-dimethylhexahydropyrrolo[3,4-c]pyrrol-2(1H)-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine | MS-ESI (m/z): 571 [M + 1]⁺ |
| 141 | 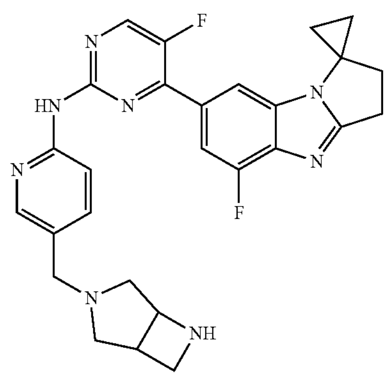 [SMILES: Fc1cnc(Nc2ccc(CN3CC4CNC4C3)cn2)nc1-c1cc(F)c2nc3n(c2c1)C1(CC3)CC1] | N-(5-((3,6-diazabicyclo[3.2.0]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine | MS-ESI (m/z): 501 [M + 1]⁺ |
| 142 | 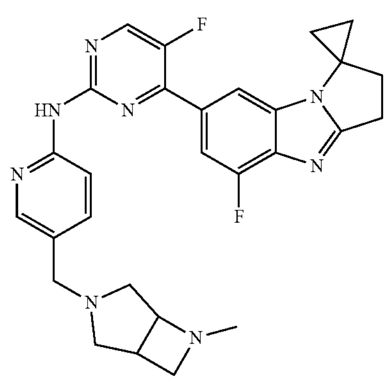 [SMILES: CN1CC2CN(Cc3ccc(Nc4ncc(F)c(-c5cc(F)c6nc7n(c6c5)C5(CC7)CC5)n4)nc3)CC21] | 5-fluoro-4-(5-fluoro-2,3-dihydrospiro[benzo[d]pyrrolo[1,2-a]imidazole-1,1'-cyclopropan]-7-yl)-N-(5-((6-methyl-3,6-diazabicyclo[3.2.0]heptan-3-yl)methyl)pyridin-2-yl)pyrimidin-2-amine | MS-ESI (m/z): 515 [M + 1]⁺ |

TABLE 2-continued

| EXAMPLE | STRUCTURE | NAME | DATA |
|---|---|---|---|
| 143 | 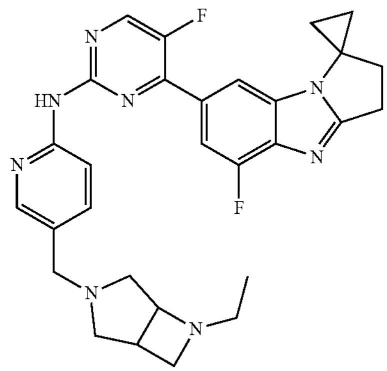 [SMILES: CCN1CC2CN(Cc3ccc(Nc4ncc(F)c(-c5cc(F)c6nc7n(c6c5)C5(CC7)CC5)n4)nc3)CC21] | N-(5-(((6-ethyl-3,6-diazabicyclo[3.2.0]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine | MS-ESI (m/z): 529 [M + 1]+ |
| 144 | 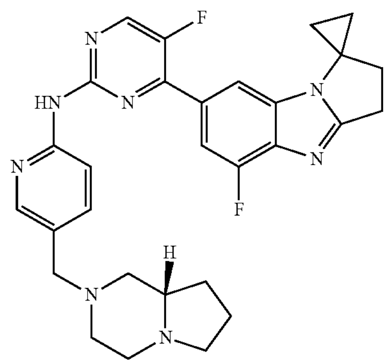 [SMILES: Fc1cnc(Nc2ccc(CN3CCN4CCC[C@H]4C3)cn2)nc1-c1cc(F)c2nc3n(c2c1)C1(CC3)CC1] | (S)-5-fluoro-4-(5-fluoro-2,3-dihydrospiro[benzo[d]pyrrolo[1,2-a]imidazole-1,1'-cyclopropan]-7-yl)-N-(5-((hexahydropyrrolo[1,2-a]pyrazin-2(1H)-yl)methyl)pyridin-2-yl)pyrimidin-2-amine | MS-ESI (m/z): 529 [M + 1]+ |
| 145 | 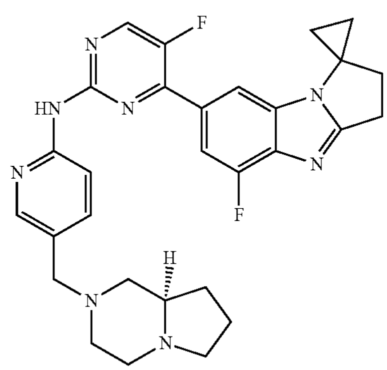 [SMILES: Fc1cnc(Nc2ccc(CN3CCN4CCC[C@@H]4C3)cn2)nc1-c1cc(F)c2nc3n(c2c1)C1(CC3)CC1] | (R)-5-fluoro-4-(5-fluoro-2,3-dihydrospiro[benzo[d]pyrrolo[1,2-a]imidazole-1,1'-cyclopropan]-7-yl)-N-(5-((hexahydropyrrolo[1,2-a]pyrazin-2(1H)-yl)methyl)pyridin-2-yl)pyrimidin-2-amine | MS-ESI (m/z): 529 [M + 1]+ |
| 146 | 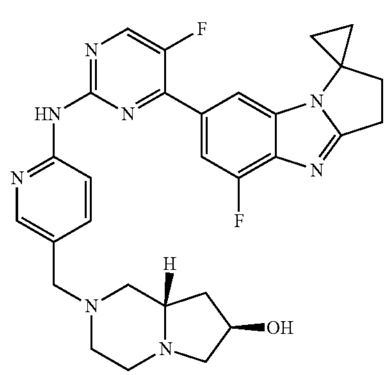 [SMILES: O[C@@H]1C[C@H]2CN(Cc3ccc(Nc4ncc(F)c(-c5cc(F)c6nc7n(c6c5)C5(CC7)CC5)n4)nc3)CCN2C1] | (7R,8aS)-2-((6-((5-fluoro-4-(5-fluoro-2,3-dihydrospiro[benzo[d]pyrrolo[1,2-a]imidazole-1,1'-cyclopropan]-7-yl)pyrimidin-2-yl)amino)pyridin-3-yl)methyl)octahydropyrrolo[1,2-a]pyrazin-7-ol | MS-ESI (m/z): 545 [M + 1]+ |

TABLE 2-continued

| EXAMPLE | STRUCTURE | NAME | DATA |
|---|---|---|---|
| 147 | 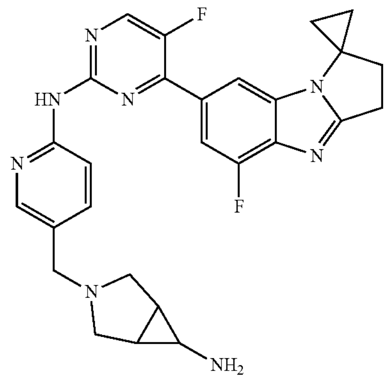 [SMILES: NC1C2CN(Cc3ccc(Nc4ncc(F)c(-c5cc(F)c6nc7n(c6c5)C5(CC7)CC5)n4)nc3)CC12] | 3-((6-((5-fluoro-4-(5-fluoro-2,3-dihydrospiro[benzo[d]pyrrolo[1,2-a]imidazole-1,1'-cyclopropan]-7-yl)pyrimidin-2-yl)amino)pyridin-3-yl)methyl)-3-azabicyclo[3.1.0]hexan-6-amine | MS-ESI (m/z): 501 [M + 1]+ |
| 148 | 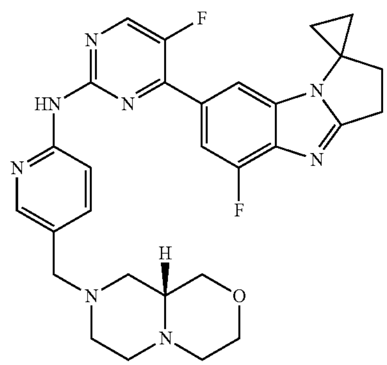 [SMILES: Fc1cnc(Nc2ccc(CN3CCN4CCOC[C@H]4C3)cn2)nc1-c1cc(F)c2nc3n(c2c1)C1(CC3)CC1] | (R)-5-fluoro-4-(5-fluoro-2,3-dihydrospiro[benzo[d]pyrrolo[1,2-a]imidazole-1,1'-cyclopropan]-7-yl)-N-(5-((hexahydropyrazino[2,1-c][1,4]oxazin-8(1H)-yl)methyl)pyridin-2-yl)pyrimidin-2-amine | MS-ESI (m/z): 545 [M + 1]+ |
| 149 | 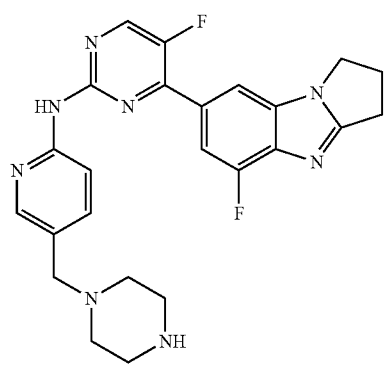 [SMILES: Fc1cnc(Nc2ccc(CN3CCNCC3)cn2)nc1-c1cc(F)c2nc3n(c2c1)CCC3] | 5-fluoro-4-(5-fluoro-2,3-dihydro-1H-benzo[d]pyrrolo[1,2-a]imidazol-7-yl)-N-(5-(piperazin-1-ylmethyl)pyridin-2-yl)pyrimidin-2-amine | MS-ESI (m/z): 463 [M + 1]+ |
| 150 | 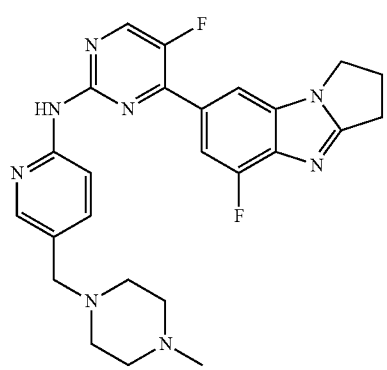 [SMILES: CN1CCN(Cc2ccc(Nc3ncc(F)c(-c4cc(F)c5nc6n(c5c4)CCC6)n3)nc2)CC1] | 5-fluoro-4-(5-fluoro-2,3-dihydro-1H-benzo[d]pyrrolo[1,2-a]imidazol-7-yl)-N-(5-((4-methylpiperazin-1-yl)methyl)pyridin-2-yl)pyrimidin-2-amine | MS-ESI (m/z): 477 [M + 1]+ |

TABLE 2-continued

| EXAMPLE | STRUCTURE | NAME | DATA |
|---|---|---|---|
| 151 | 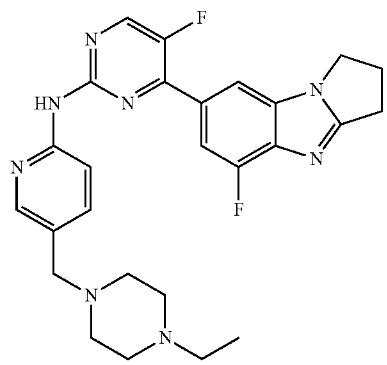 [SMILES: CCN1CCN(Cc2ccc(Nc3ncc(F)c(-c4cc(F)c5nc6n(c5c4)CCC6)n3)nc2)CC1] | N-(5-((4-ethylpiperazin-1-yl)methyl)pyridin-2-yl)-5-fluoro-4-(5-fluoro-2,3-dihydro-1H-benzo[d]pyrrolo[1,2-a]imidazol-7-yl)pyrimidin-2-amine | MS-ESI (m/z): 491 [M + 1]+ |
| 152 | 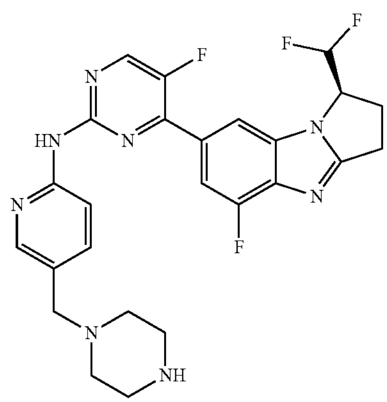 [SMILES: Fc1cnc(Nc2ccc(CN3CCNCC3)cn2)nc1-c1cc(F)c2nc3n(c2c1)[C@@H](C(F)F)CC3] | (R)-4-(1-(difluoromethyl)-5-fluoro-2,3-dihydro-1H-benzo[d]pyrrolo[1,2-a]imidazol-7-yl)-5-fluoro-N-(5-(piperazin-1-ylmethyl)pyridin-2-yl)pyrimidin-2-amine | MS-ESI (m/z): 513 [M + 1]+ |
| 153 | 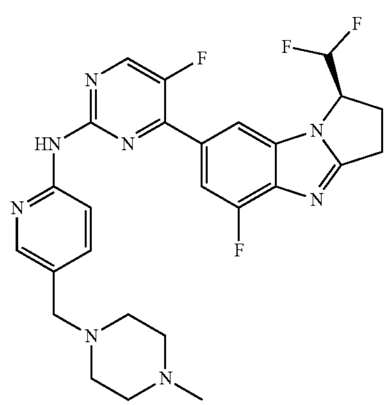 [SMILES: CN1CCN(Cc2ccc(Nc3ncc(F)c(-c4cc(F)c5nc6n(c5c4)[C@@H](C(F)F)CC6)n3)nc2)CC1] | (R)-4-(1-(difluoromethyl)-5-fluoro-2,3-dihydro-1H-benzo[d]pyrrolo[1,2-a]imidazol-7-yl)-5-fluoro-N-(5-((4-methylpiperazin-1-yl)methyl)pyridin-2-yl)pyrimidin-2-amine | MS-ESI (m/z): 527 [M + 1]+ |
| 154 | 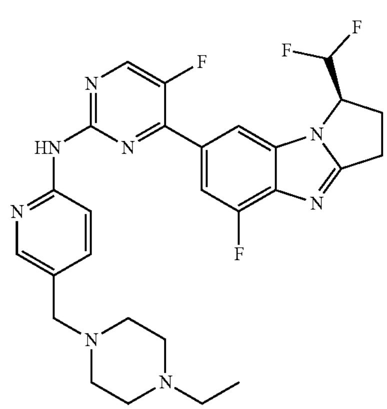 [SMILES: CCN1CCN(Cc2ccc(Nc3ncc(F)c(-c4cc(F)c5nc6n(c5c4)[C@@H](C(F)F)CC6)n3)nc2)CC1] | (R)-4-(1-(difluoromethyl)-5-fluoro-2,3-dihydro-1H-benzo[d]pyrrolo[1,2-a]imidazol-7-yl)-N-(5-((4-ethylpiperazin-1-yl)methyl)pyridin-2-yl)-5-fluoropyrimidin-2-amine | MS-ESI (m/z): 541 [M + 1]+ |

TABLE 2-continued

| EXAMPLE | NAME | DATA |
|---|---|---|
| 155 | (R)-5-fluoro-4-(5-fluoro-1-methyl-2,3-dihydro-1H-benzo[d]pyrrolo[1,2-a]imidazol-7-yl)-N-(5-(piperazin-1-ylmethyl)pyridin-2-yl)pyrimidin-2-amine | MS-ESI (m/z): 477 [M + 1]$^+$ |
| 156 | (S)-5-fluoro-4-(5-fluoro-1-methyl-2,3-dihydro-1H-benzo[d]pyrrolo[1,2-a]imidazol-7-yl)-N-(5-((4-methylpiperazin-1-yl)methyl)pyridin-2-yl)pyrimidin-2-amine | MS-ESI (m/z): 491 [M + 1]$^+$ |
| 157 | (S)-N-(5-((4-ethylpiperazin-1-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine | MS-ESI (m/z): 505 [M + 1]$^+$ |
| 158 | (R)-5-fluoro-4-(5-fluoro-1-(methoxymethyl)-2,3-dihydro-1H-benzo[d]pyrrolo[1,2-a]imidazol-7-yl)-N-(5-(piperazin-1-ylmethyl)pyridin-2-yl)pyrimidin-2-amine | MS-ESI (m/z): 507 [M + 1]$^+$ |

TABLE 2-continued

| EXAMPLE | STRUCTURE | NAME | DATA |
|---|---|---|---|
| 159 | 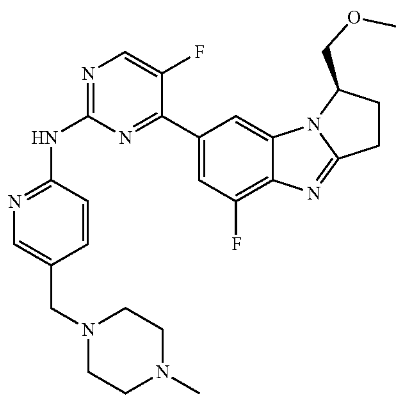 [SMILES: COC[C@H]1CCc2nc3c(F)cc(-c4nc(Nc5ccc(CN6CCN(C)CC6)cn5)ncc4F)cc3n21] | (R)-5-fluoro-4-(5-fluoro-1-(methoxymethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine | MS-ESI (m/z): 521 [M + 1]⁺ |
| 160 | 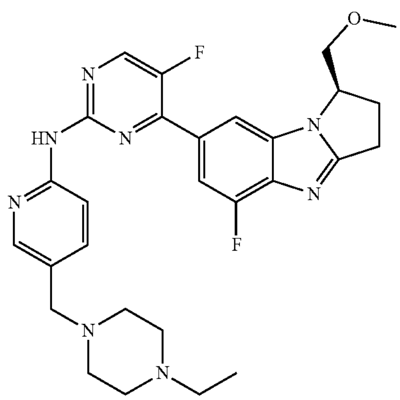 [SMILES: CCN1CCN(Cc2ccc(Nc3ncc(F)c(-c4cc(F)c5nc6n(c5c4)[C@@H](COC)CC6)n3)nc2)CC1] | (R)-N-(5-((4-ethylpiperazin-1-yl)methyl)pyridin-2-yl)-5-fluoro-4-(5-fluoro-1-(methoxymethyl)-2,3-dihydro-1H-benzo[d]pyrrolo[1,2-a]imidazol-7-yl)pyrimidin-2-amine | MS-ESI (m/z): 535 [M + 1]⁺ |
| 161 | 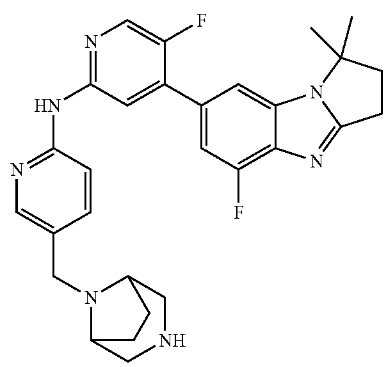 [SMILES: CC1(C)CCc2nc3c(F)cc(-c4cc(Nc5ccc(CN6C7CCC6CNC7)cn5)ncc4F)cc3n21] | N-(5-((3,8-diazabicyclo[3.2.1]octan-8-yl)methyl)pyridin-2-yl)-5-fluoro-4-(5-fluoro-1,1-dimethyl-2,3-dihydro-1H-benzo[d]pyrrolo[1,2-a]imidazol-7-yl)pyridin-2-amine | MS-ESI (m/z): 516 [M + 1]⁺ |
| 162 | 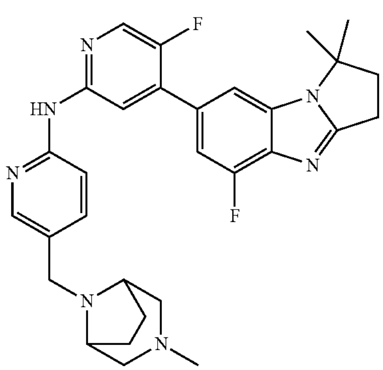 [SMILES: CN1CC2CCC(C1)N2Cc1ccc(Nc2cc(-c3cc(F)c4nc5n(c4c3)C(C)(C)CC5)c(F)cn2)nc1] | 5-fluoro-4-(5-fluoro-1,1-dimethyl-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyridin-2-amine | MS-ESI (m/z): 530 [M + 1]⁺ |

TABLE 2-continued

| EXAMPLE | STRUCTURE | NAME | DATA |
|---|---|---|---|
| 163 | 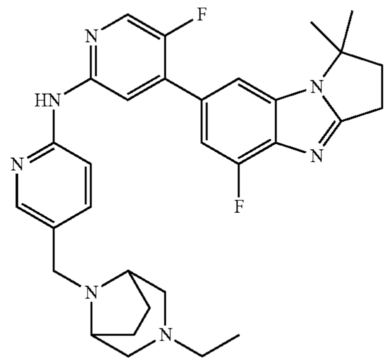 [SMILES: CCN1CC2CCC(C1)N2Cc1ccc(Nc2cc(-c3cc(F)c4nc5n(c4c3)C(C)(C)CC5)c(F)cn2)nc1] | N-(5-((3-ethyl-3,8-diazabicyclo[3.2.1]octan-8-yl)methyl)pyridin-2-yl)-5-fluoro-4-(5-fluoro-1,1-dimethyl-2,3-dihydro-1H-benzo[d]pyrrolo[1,2-a]imidazol-7-yl)pyridin-2-amine | MS-ESI (m/z): 544 [M + 1]+ |
| 164 | 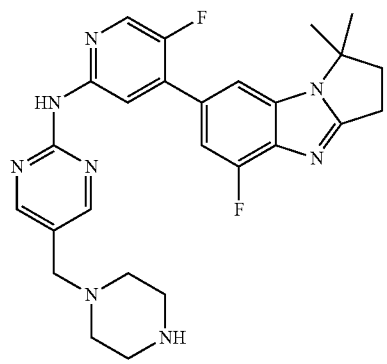 [SMILES: CC1(C)CCc2nc3c(F)cc(-c4cc(Nc5ncc(CN6CCNCC6)cn5)ncc4F)cc3n21] | N-(5-fluoro-4-(5-fluoro-1,1-dimethyl-2,3-dihydro-1H-benzo[d]pyrrolo[1,2-a]imidazol-7-yl)pyridin-2-yl)-5-(piperazin-1-ylmethyl)pyrimidin-2-amine | MS-ESI (m/z): 491 [M + 1]+ |
| 165 | 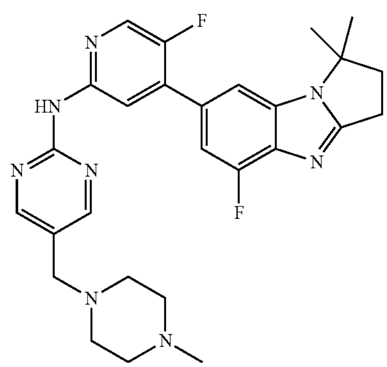 [SMILES: CN1CCN(Cc2cnc(Nc3cc(-c4cc(F)c5nc6n(c5c4)C(C)(C)CC6)c(F)cn3)nc2)CC1] | N-(5-fluoro-4-(5-fluoro-1,1-dimethyl-2,3-dihydro-1H-benzo[d]pyrrolo[1,2-a]imidazol-7-yl)pyridin-2-yl)-5-((4-methylpiperazin-1-yl)methyl)pyrimidin-2-amine | MS-ESI (m/z): 505 [M + 1]+ |
| 166 | 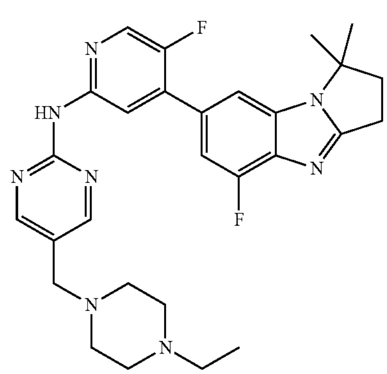 [SMILES: CCN1CCN(Cc2cnc(Nc3cc(-c4cc(F)c5nc6n(c5c4)C(C)(C)CC6)c(F)cn3)nc2)CC1] | 5-((4-ethylpiperazin-1-yl)methyl)-N-(5-fluoro-4-(5-fluoro-1,1-dimethyl-2,3-dihydro-1H-benzo[d]pyrrolo[1,2-a]imidazol-7-yl)pyridin-2-yl)pyrimidin-2-amine | MS-ESI (m/z): 519 [M + 1]+ |

Example 167

N-(5-((3,8-diazabicyclo[3,2,1]octan-8-yl)methyl)pyridin-2-yl)-4-(6,6-dimethyl-7,8-dihydro-6H-pyrrolo[1',2':1,2]imidazo[4,5-b]pyridin-3-yl)-5-fluoropyridin-2-amine (167)

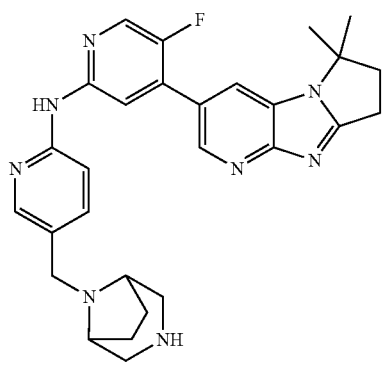

5-bromo-3-fluoropyridin-2-amine (167a)

The title compound 5-bromo-3-fluoropyridin-2-amine (167a) was prepared according to the method described in WO 2011/22473.

5-bromo-3-fluoro-2-nitropyridine (167b)

To a solution of 30% $H_2O_2$ (25 mL) in con.$H_2SO_4$ (50 mL) at 0-5° C. was added dropwise a solution of 5-bromo-3-fluoropyridin-2-amine (1.5 g, 7.85 mmol) in con.$H_2SO_4$ (10 mL). The mixture was stirred at r.t. overnight. The mixture was diluted with ice-water (150 mL), extracted with EA:PE=1:2 (3×50 mL), washed sequentially with 10% aq $Na_2S_2O_4$ (2×50 mL), aq $NaHCO_3$ (50 mL), brine (50 mL), dried and concentrated to give 5-bromo-3-fluoro-2-nitropyridine (167b).

1-(2-amino-5-bromopyridin-3-yl)-5,5-dimethyl pyrrolidin-2-one (167c)

The title compound 1-(2-amino-5-bromopyridin-3-yl)-5,5-dimethylpyrrolidin-2-one (167c) was prepared according to the synthetic method of H-4 by replacing 5-bromo-1,3-difluoro-2-nitrobenzene with 5-bromo-3-fluoro-2-nitropyridine (167b). MS-ESI (m/z): 284/286 [M+1]$^+$.

3-bromo-6,6-dimethyl-7,8-dihydro-6H-pyrrolo[1',2':1,2]imidazo[4,5-b]pyridine (167d)

A solution of 1-(2-amino-5-bromopyridin-3-yl)-5,5-dimethylpyrrolidin-2-one (167c) (700 mg) in acetic acid (8 mL) and PPA (20 g) was stirred at 115° C. for 2-3 h. The reaction mixture was adjusted with $NaHCO_3$ to pH=7-8 and extracted with DCM (3×50 mL). The extracts were washed with saturated brine (100 mL), dried with $Na_2SO_4$ and concentrated. The residue was purified by flash column chromatography on silica gel eluting with EtOAc/PE (4:1) to give the title compound 3-bromo-6,6-dimethyl-7,8-dihydro-6H-pyrrolo[1',2':1,2]imidazo[4,5-b]pyridine (167d). MS-ESI (m/z): 266/268[M+1]$^+$.

3-(2-chloro-5-fluoropyrimidin-4-yl)-6,6-dimethyl-7,8-dihydro-6H-pyrrolo[1',2':1,2]imidazo[4,5-b]pyridine (167e)

The title compound 3-(2-chloro-5-fluoropyrimidin-4-yl)-6,6-dimethyl-7,8-dihydro-6H-pyrrolo[1',2':1,2]imidazo[4,5-b]pyridine (167e) was prepared according to the synthetic method of Intermediate H by replacing 7-bromo-5-fluoro-1,1-dimethyl-2,3-dihydro-1H-benzo[d]pyrrolo[1,2-a]imidazole (H-5) with 3-bromo-6,6-dimethyl-7,8-dihydro-6H-pyrrolo[1',2':1,2]imidazo[4,5-b]pyridine (167d). MS-ESI (m/z): 318 [M+1]$^+$.

N-(5-((3,8-diazabicyclo[3,2,1]octan-8-yl)methyl)pyridin-2-yl)-4-(6,6-dimethyl-7,8-dihydro-6H-pyrrolo[1',2':1,2]imidazo[4,5-b]pyridin-3-yl)-5-fluoropyridin-2-amine (167)

The title compound N-(5-((3,8-diazabicyclo[3.2.1]octan-8-yl)methyl)pyridin-2-yl)-4-(6,6-dimethyl-7,8-dihydro-6H-pyrrolo[1',2':1,2]imidazo[4,5-b]pyridin-3-yl)-5-fluoropyridin-2-amine (167) was prepared according to the synthetic method of 7 by replacing (S)-7-(2-chloro-5-fluoropyrimidin-4-yl)-5-fluoro-1-(methoxymethyl)-2,3-dihydro-1H-benzo[d]pyrrolo[1,2-a]imidazole (Intermediate B) with 3-(2-chloro-5-fluoropyrimidin-4-yl)-6,6-dimethyl-7,8-dihydro-6H-pyrrolo[1',2':1,2]imidazo[4,5-b]pyridine (167e) and replacing tert-butyl 4-((6-aminopyridin-3-yl)methyl)piperazine-1-carboxylate (Intermediate N) with tert-butyl 8-((6-aminopyridin-3-yl)methyl)-3,8-diazabicyclo[3.2.1]octane-3-carboxylate (Intermediate V). MS-ESI (m/z): 499 [M+1]$^+$.

Example 168

4-(6,6-dimethyl-7,8-dihydro-6H-pyrrolo[1',2':1,2]imidazo[4,5-b]pyridin-3-yl)-5-fluoro-N-(5-((3-methyl-3,8-diazabicyclo[3.2.1]octan-8-yl)methyl)pyridin-2-yl)pyridin-2-amine (168)

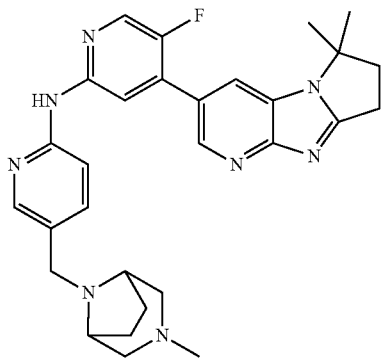

The title compound 4-(6,6-dimethyl-7,8-dihydro-6H-pyrrolo[1',2':1,2]-imidazo[4,5-b]pyridin-3-yl)-5-fluoro-N-(5-((3-methyl-3,8-diazabicyclo[3.2.1]octan-8-yl)methyl)pyridin-2-yl)pyridin-2-amine (168) was prepared according to the synthetic method of 8 by replacing (S)-5-fluoro-4-(5-fluoro-1-(methoxymethyl)-2,3-dihydro-1H-benzo[d]pyrrolo[1,2-a]imidazol-7-yl)-N-(5-(piperazin-1-ylmethyl)pyridin-2-yl)pyrimidin-2-amine (7) with N-(5-((3,8-diazabicyclo[3.2.1]octan-8-yl)methyl)pyridin-2-yl)-4-(6,6- dimethyl-7,8-dihydro-6H-pyrrolo[1',2':1,2]imidazo[4,5-b]pyridin-3-yl)-5-fluoropyridin-2-amine (167). MS-ESI (m/z): 513 [M+1]$^+$.

Example 169

4-(6,6-dimethyl-7,8-dihydro-6H-pyrrolo[1',2':1,2]imidazo[4,5-b]pyridin-3-yl)-N-(5-((3-ethyl-3,8-diazabicyclo[3.2.1]octan-8-yl)methyl)pyridin-2-yl)-5-fluoropyridin-2-amine (169)

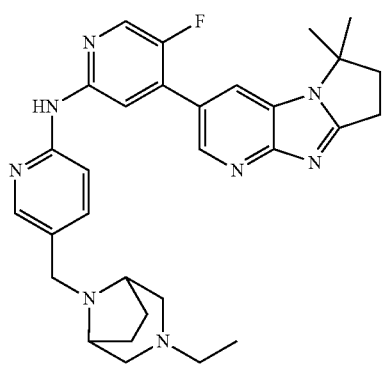

The title compound 4-(6,6-dimethyl-7,8-dihydro-6H-pyrrolo[1',2':1,2]-imidazo[4,5-b]pyridin-3-yl)-N-(5-((3-ethyl-3,8-diazabicyclo[3.2.1]octan-8-yl)methyl)-pyridin-2-yl)-5-fluoropyridin-2-amine (169) was prepared according to the synthetic method of 9 by replacing (S)-5-fluoro-4-(5-fluoro-1-(methoxymethyl)-2,3-dihydro-1H-benzo[d]-pyrrolo[1,2-a]imidazol-7-yl)-N-(5-(piperazin-1-ylmethyl)pyridin-2-yl) pyrimidin-2-amine (7) with N-(5-((3,8-diazabicyclo[3.2.1] octan-8-yl)methyl)pyridin-2-yl)-4-(6,6-dimethyl-7,8-dihydro-6H-pyrrolo[1',2':1,2]imidazo[4,5-b]pyridin-3-yl)-5-fluoropyridin-2-amine (167). MS-ESI (m/z): 527 [M+1]$^+$.

Cell Proliferation Assays

MTS testing kit was purchased from Promega. The DMEM, Fetal bovine serum and Penicillin-Streptomycin were purchased from Gibco. Dimethyl sulfoxide (DMSO) was purchased from Sigma.

To investigate whether a compound is able to inhibit the activity of CDK4/6 in cells, mechanism-based assays using BE(2)-C cell (ATCC® number:CRL-2268) were developed. In the assay, inhibition of CDK4/6 was detected by the inhibition of BE(2)-C cell cells proliferation. BE(2)-C cell cells were cultured in culture flasks to 40-80% confluence in DMEM plus 10% fetal bovine serum. Cells were collected and plated onto 96-well plates at cell density of 3000 cells/well. Plates were incubated overnight at 37° C., with 5% $CO_2$ to adhere. Compounds were added to the plates, the final compound concentrations were 10000, 3333, 1111, 270, 123.5, 41.2, 13.7, 4.6 and 1.5 nM. Place plates at 37° C., with 5% $CO_2$ for 48 h. After removing the medium, 20 µl MTS/100 µl medium mixture solution were added to each well and incubate the plates for exactly 2 hours. The reaction was terminated by adding 25 µl 10% SDS per well. Measure absorbance at 490 nm and 650 nm (reference wavelength). $IC_{50}$ was calculated using GraphPad Prism 5.0.

Select compounds prepared as described above were assayed according to the biological procedures described herein. The results were given in table 3. "++++" stands for $IC_{50}$ value below about 10 nM. "+++" stands for $IC_{50}$ value between greater than about 10 nM to about 100 nM. "++" stands for $IC_{50}$ value between greater than about 100 nM to about µM. "+" stands for $IC_{50}$ value greater than 1 µM.

TABLE 3

| Example | BE(2)-C $IC_{50}$ (nM) |
|---|---|
| 1 | + |
| 2 | ++ |
| 3 | ++ |
| 4 | ++ |
| 5 | ++ |
| 6 | ++ |
| 7 | ++ |
| 8 | ++ |
| 9 | ++ |
| 10 | ++ |
| 11 | +++ |
| 12 | +++ |
| 13 | ++ |
| 14 | ++ |
| 15 | ++ |
| 16 | +++ |
| 17 | +++ |
| 18 | +++ |
| 19 | ++++ |
| 20 | + |
| 21 | ++ |
| 22 | ++ |
| 23 | + |
| 24 | ++ |
| 25 | +++ |
| 26 | ++ |
| 27 | +++ |
| 28 | +++ |
| 29 | ++ |
| 30 | ++ |
| 31 | ++ |
| 32 | ++ |
| 33 | +++ |
| 34 | +++ |
| 35 | ++ |
| 36 | ++ |
| 37 | +++ |
| 38 | ++ |
| 39 | ++ |
| 40 | + |
| 41 | +++ |
| 42 | ++ |
| 43 | +++ |
| 44 | +++ |
| 45 | + |
| 46 | +++ |
| 47 | +++ |
| 48 | ++ |
| 49 | +++ |
| 50 | +++ |
| 51 | ++ |
| 52 | ++ |
| 53 | ++ |
| 54 | ++ |
| 55 | +++ |
| 56 | +++ |
| 57 | ++ |
| 58 | +++ |
| 59 | +++ |
| 60 | +++ |
| 61 | ++ |
| 62 | +++ |
| 63 | +++ |
| 64 | ++ |
| 65 | +++ |
| 66 | +++ |
| 67 | ++ |
| 68 | +++ |
| 69 | +++ |
| 70 | + |
| 71 | +++ |
| 72 | +++ |
| 73 | ++ |

TABLE 3-continued

| Example | BE(2)-C IC$_{50}$ (nM) |
|---|---|
| 74 | +++ |
| 75 | +++ |
| 76 | +++ |
| 77 | +++ |
| 78 | +++ |
| 79 | +++ |
| 80 | +++ |
| 81 | +++ |
| 82 | +++ |
| 83 | +++ |
| 84 | +++ |
| 85 | +++ |
| 86 | ++ |
| 87 | +++ |
| 88 | +++ |
| 89 | ++ |
| 90 | +++ |
| 91 | +++ |
| 92 | ++ |
| 93 | ++ |
| 94 | ++ |
| 95 | + |
| 96 | ++ |
| 97 | +++ |
| 98 | ++ |
| 99 | +++ |
| 100 | +++ |
| 101 | ++ |
| 102 | +++ |
| 103 | +++ |
| 104 | +++ |
| 105 | +++ |
| 106 | +++ |
| 107 | +++ |
| 108 | +++ |
| 109 | +++ |
| 110 | +++ |
| 111 | ++ |
| 112 | ++++ |
| 113 | ++++ |
| 114 | ++ |
| 115 | +++ |
| 116 | +++ |
| 117 | ++ |
| 118 | +++ |
| 119 | +++ |
| 120 | ++ |
| 121 | ++ |
| 122 | +++ |
| 123 | ++ |
| 124 | +++ |
| 125 | +++ |
| 126 | +++ |
| 127 | ++++ |
| 128 | ++++ |
| 129 | +++ |
| 130 | +++ |
| 131 | +++ |
| 132 | ++ |
| 133 | +++ |
| 134 | ++ |
| 135 | + |
| 136 | ++ |
| 137 | +++ |
| 138 | + |
| 139 | + |
| 140 | ++ |
| 141 | + |
| 142 | + |
| 143 | + |
| 144 | +++ |
| 145 | +++ |
| 146 | + |
| 147 | + |
| 148 | +++ |
| 149 | ++ |
| 150 | +++ |
| 151 | +++ |
| 152 | + |
| 153 | + |
| 154 | + |
| 155 | ++ |
| 156 | +++ |
| 157 | +++ |
| 158 | + |
| 159 | + |
| 160 | ++ |
| 161 | ++ |
| 162 | + |
| 163 | + |
| 164 | +++ |
| 165 | ++ |
| 166 | ++ |
| 167 | +++ |
| 168 | ++ |
| 169 | ++ |

CDK Kinase Inhibition Assay

To demonstrate that the compounds exhibit affinity for CDK kinases (CDK1/cyclin B, CDK2/cyclin A, CDK4/cyclin D1 and CDK6/cyclin D1), CDK kinase assays were performed.

Testing compounds were dissolved in 100% DMSO to specific concentration. Compounds were tested in 10-dose mode with 3-fold serial dilution starting at 100 µM. The serial dilution was conducted by epMotion 5070 in DMSO.

Each substrate was prepared in freshly prepared Reaction Buffer (20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO). Each kinase was delivered into the substrate solution and the solution was gently mixed. 0.05 µL Compounds were delivered into 5 µL kinase reaction mixture in a 384 well plate by Acoustic technology (Echo550; nanoliter range), and the mixture was incubated for 20 min at room temperature. The final concentrations of substrates and kinases in each assay were shown in table 4. 0.01 µL of 5 mM ATP with $^{33}$P-ATP (PerkinElmer, Cat# NEG602H001MC, Specific activity 10 Ci/µL) was delivered into the reaction mixture to initiate the reaction, and the final concentration of ATP in the mixture was 10 µM. The resulted solutions were incubated for 2 hours at room temperature, the radioactivity incorporated is determined by the proprietary "HotSpot" platform, which is a miniaturized filter-binding method (using this paper as reference: Anastassiadis et al, 2011 Nature Biotech) IC$_{50}$ value of each compound was generated using GraphPad Prism software.

TABLE 4

| Kinases: | Kinase Vendor | Kinase Cat# | Substrate | Substrate Vendor | Substrate Cat# | Sub in RXN (μM) | Kinase in RXN (nM) |
|---|---|---|---|---|---|---|---|
| CDK1/cyclin B | Invitrogen | PR4768C | Histone H1 | Sigma | H5505 | 20 | 2 |
| CDK2/cyclin A | Invitrogen | PR4448B | Histone H1 | Sigma | H5505 | 20 | 0.3 |
| CDK4/cyclin D1 | Invitrogen | PV4436 | RB Protein | BPS | 40595 | 3 | 12 |
| CDK6/cyclin D1 | Invitrogen | PR8422B | RB Protein | BPS | 40595 | 3 | 5 |

Select compounds prepared as described above were assayed according to the biological procedures described herein. The results were given in table 5.

TABLE 5

| Example | CDK1/ cyclin B | CDK2/ cyclin A | CDK4/ cyclin D1 | CDK6/ cyclin D1 |
|---|---|---|---|---|
| 12 | 403 | 50.5 | <5.00 | <5.00 |
| 39 | 50.5 | 19.2 | <5.00 | <5.00 |

Tumor Growth Inhibition in COLO205 Xenograft Tumors

COLO205 cells were cultured with RPMI-1640 medium containing 10% fetal bovine serum (FBS) at 37° C. in 5% $CO_2$ incubator. Logarithmic growth phase cells were collected. COLO205 cells ($5 \times 10^6$ in 200 μL PBS) were implanted subcutaneously into the left flank region, and tumor growth was monitored. Tumor volume (V) was estimated from the length (l) and width (w) of the tumor using the following formula: $V=1/2 \times l \times w^2$. Treatment started when average tumor size was 100-150 mm³. Measuring subcutaneous tumor volume 2 to 3 times every week. Drug efficacy was assessed as Tumor Growth Inhibition (TGI) and Tumor increment rate T/C (%). TGI was defined as $(1-T/C) \times 100\%$, wherein T/C (%) presented the ratio of the change in mean tumor volume of the treated group and of the control group. Effects of Examples 11-12 on COLO205 tumor volumes are shown in table 6.

TABLE 6

| Group | Dosage (mg/kg) | Average Tumor Volume D0 | Average Tumor Volume D21 | T/C % D21 | TGI % D21 |
|---|---|---|---|---|---|
| Vehicle control | — | 114 ± 2.7 | 1744 ± 207 | — | — |
| 11 | 30 | 110 ± 3.2 | 570 ± 57 | 28% | 72% |
| 12 | 30 | 113 ± 3.4 | 584 ± 86 | 29% | 71% |

What is claimed is:

1. A compound of formula (I):

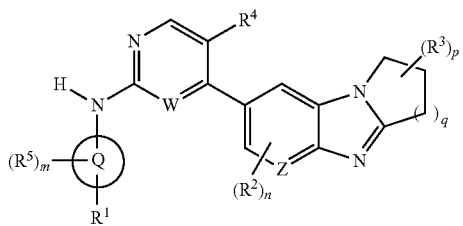

(I)

or a pharmaceutically acceptable salt thereof, wherein:
Q is selected from heteroaryl;
W is selected from N;
Z is selected from N and $CR^6$;
$R^1$ is selected from heterocyclyl and heterocyclyl-$C_{1-4}$ alkyl, wherein alkyl and heterocyclyl are each unsubstituted or substituted with one or more substituents, independently selected from $R^X$;
each $R^2$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, $-NO_2$, $-NR^{A1}R^{B1}$, $-OR^{A1}$, $-SR^{A1}$, $-S(O)_rR^{A1}$, $-S(O)_2OR^{A1}$, $-OS(O)_2R^{B1}$, $-S(O)_rNR^{A1}R^{B1}$, $-O(CR^{C1}R^{D1})_rNR^{A1}R^{B1}$, $-C(O)R^{A1}$, $-CO_2R^{B1}$, $-CO_2(CR^{C1}R^{D1})_rC(O)NR^{A1}R^{B1}$, $-OC(O)R^{A1}$, $-CN$, $-C(O)NR^{A1}R^{B1}$, $-NR^{A1}C(O)R^{B1}$, $-NR^{A1}CO_2R^{B1}$, $-OC(O)NR^{A1}R^{B1}$, $-NR^{A1}C(O)NR^{A1}R^{B1}$, $-NR^{A1}S(O)_rR^{B1}$, and $-CR^{A1}(=N-OR^{B1})$; wherein alkyl, alkenyl, alkynyl, cycloalkyl, heterocyclyl, aryl and heteroaryl are each unsubstituted or substituted with one or more substituents, independently selected from $R^X$;
each $R^3$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, $-NO_2$, $-NR^{A2}R^{B2}$, $-OR^{A2}$, $-SR^{A2}$, $-S(O)_rR^{A2}$, $-S(O)_2OR^{A2}$, $-OS(O)_2R^{B2}$, $-S(O)_rNR^{A2}R^{B2}$, $-O(CR^{C2}R^{D2})_rNR^{A2}R^{B2}$, $-C(O)R^{A2}$, $-C(O)(CR^{C2}R^{D2})_rNR^{A2}R^{B2}$, $-C(O)(CR^{C2}R^{D2})_rOR^{B2}$, $-C(O)(CR^{C2}R^{D2})_rSR^{B2}$, $-C(O)(CR^{C2}R^{D2})_rS(O)_rR^{B2}$, $-CO_2R^{B2}$, $-CO_2(CR^{C2}R^{D2})_rC(O)NR^{A2}R^{B2}$, $-OC(O)R^{A2}$, $-CN$, $-C(O)NR^{A2}R^{B2}$, $-NR^{A2}C(O)R^{B2}$, $-NR^{A2}CO_2R^{B2}$, $-OC(O)NR^{A2}R^{B2}$, $-NR^{A2}C(O)NR^{A2}R^{B2}$, $-NR^{A2}S(O)_rR^{B2}$, and $-CR^{A2}(=N-OR^{B2})$; wherein alkyl, alkenyl, alkynyl, cycloalkyl, heterocyclyl, aryl and heteroaryl are each unsubstituted or substituted with one or more substituents, independently selected from $R^X$;
or two $R^3$ together with the carbon atoms to which they are attached form a cyclic ring of 3 to 7 members containing 0, 1, or 2 additional heteroatoms independently selected from oxygen, sulfur and nitrogen, and optionally substituted with 1 or 2 $R^X$ groups;
$R^4$ is selected from hydrogen, halogen, $C_{1-10}$ alkyl, $C_{2-10}$ alkenyl, $C_{2-10}$ alkynyl, $C_{3-10}$ cycloalkyl, $-NO_2$, $-NR^{A3}R^{B3}$, $-OR^{A3}$, $-SR^{A3}$, $-S(O)_rR^{A3}$, $-S(O)_2OR^{A3}$, $-OS(O)_2R^{B3}$, $-S(O)_rNR^{A3}R^{B3}$, $-P(O)R^{A3}R^{B3}$, $-S(CR^{C3}R^{D3})_rNR^{A3}R^{B3}$, $-C(O)R^{A3}$, $-CO_2R^{B3}$, $-CO_2(CR^{C3}R^{D3})_rC(O)NR^{A3}R^{B3}$, $-OC(O)R^{A3}$, $-CN$, $-C(O)NR^{A3}R^{B3}$, $-NR^{A3}C(O)R^{B3}$, $-NR^{A3}CO_2R^{B3}$, $-OC(O)NR^{A3}R^{B3}$, $-NR^{A3}C(O)NR^{A3}R^{B3}$, $-NR^{A3}S(O)_rR^{B3}$, and $-CR^{A3}(=N-OR^{B3})$; wherein alkyl, alkenyl, alkynyl, and cycloalkyl are each unsubstituted or substituted with one or more substituents, independently selected from $R^X$;
each $R^5$ is independently selected from hydrogen, halogen, $C_{1-10}$ alkyl, $C_{2-10}$ alkenyl, $C_{2-10}$ alkynyl, $C_{3-10}$ cycloalkyl, $-NO_2$, $-NR^{A4}R^{B4}$, $-OR^{A4}$, $-SR^{A4}$, $-S(O)_rR^{A4}$, $-S(O)_2OR^{A4}$, $-OS(O)_2R^{B4}$, $-S(O)_rNR^{A4}R^{B4}$, $-O(CR^{C4}R^{D4})_tNR^{A4}R^{B4}$, $-C(O)R^{A4}$, $-CO_2R^{B4}$, $-CO_2(CR^{C4}R^{D4})_tC(O)NR^{A4}R^{B4}$, $-OC(O)R^{A4}$, $-CN$, $-C(O)NR^{A4}R^{B4}$, $-NR^{A4}C(O)R^{B4}$, $-NR^{A4}CO_2R^{B4}$, $-OC(O)NR^{A4}R^{B4}$, $-NR^{A4}C(O)NR^{A4}R^{B4}$, $-NR^{A4}S(O)_rR^{B4}$, and $-CR^{A4}(=N-OR^{B4})$; wherein alkyl, alkenyl, alkynyl, and cycloalkyl are each unsubstituted or substituted with one or more substituents, independently selected from $R^X$;

each $R^6$ is independently selected from halogen, $C_{1-10}$ alkyl, $C_{2-10}$ alkenyl, $C_{2-10}$ alkynyl, $C_{3-10}$ cycloalkyl, $-NO_2$, $-NR^{A5}R^{B5}$, $-OR^{A5}$, $-SR^{A5}$, $-S(O)_rR^{A5}$, $-S(O)_2OR^{A5}$, $-OS(O)_2R^{B5}$, $-S(O)_rNR^{A5}R^{B5}$, $-(CR^{C5}R^{D5})_tNR^{A5}R^{B5}$, $-(CR^{C5}R^{D5})_tOR^{B5}$, $-(CR^{C5}R^{D5})_tSR^{B5}$, $-(CR^{C5}R^{D5})_tS(O)_rR^{B5}$, $-(CR^{C5}R^{D5})_tCO_2R^{B5}$, $-(CR^{C5}R^{D5})_tC(O)NR^{A5}R^{B5}$, $-(CR^{C5}R^{D5})_tNR^{A5}CO_2R^{B5}$, $-(CR^{C5}R^{D5})_tOC(O)NR^{A5}R^{B5}$, $-(CR^{C5}R^{D5})_tNR^{A5}CONR^{A5}R^{B5}$, $-(CR^{C5}R^{D5})_tNR^{A5}SO_2NR^{A5}R^{B5}$, $-O(CR^{C5}R^{D5})_tNR^{A5}R^{B5}$, $-C(O)R^{A5}$, $-C(O)(CR^{C5}R^{D5})_tNR^{A5}R^{B5}$, $-C(O)(CR^{C5}R^{D5})_tOR^{B5}$, $-C(O)(CR^{C5}R^{D5})_tSR^{B5}$, $-C(O)(CR^{C5}R^{D5})_tS(O)_rR^{B5}$, $-CO_2R^{B5}$, $-CO_2(CR^{C5}R^{D5})_tC(O)NR^{A5}R^{B5}$, $-OC(O)R^{A5}$, $-CN$, $-C(O)NR^{A5}R^{B5}$, $-NR^{A5}C(O)R^{B5}$, $-NR^{A5}CO_2R^{B5}$, $-OC(O)NR^{A5}R^{B5}$, $-NR^{A5}C(O)NR^{A5}R^{B5}$, $-NR^{A5}S(O)_rR^{B5}$, and $-CR^{A5}(=N-OR^{B5})$;

each $R^{A1}$, $R^{A2}$, $R^{A3}$, $R^{A4}$, $R^{A5}$, $R^{B1}$, $R^{B2}$, $R^{B3}$, $R^{B4}$, and $R^{B5}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with one or more substituents, independently selected from $R^X$;

or each "$R^{A1}$ and $R^{B1}$", "$R^{A2}$ and $R^{B2}$", "$R^{A3}$ and $R^{B3}$", "$R^{A4}$ and $R^{B4}$", and "$R^{A5}$ and $R^{B5}$", together with the atom(s) to which they are attached form a heterocyclic ring of 4 to 12 members containing 0, 1, or 2 additional heteroatoms independently selected from oxygen, sulfur and nitrogen, and optionally substituted with 1 or 2 $R^X$ groups;

each $R^{C1}$, $R^{C2}$, $R^{C3}$, $R^{C4}$, $R^{C5}$, $R^{D1}$, $R^{D2}$, $R^{D3}$, $R^{D4}$, and $R^{D5}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl;

each $R^X$ is independently selected from $C_{1-10}$ alkyl, $C_{2-10}$ alkenyl, $C_{2-10}$ alkynyl, $C_{3-10}$ cycloalkyl, halogen, $-NO_2$, $-NR^{a1}R^{b1}$, $-OR^{a1}$, $-SR^{a1}$, $-S(O)_rR^{a1}$, $-S(O)_2OR^{a1}$, $-OS(O)_2R^{b1}$, $-S(O)_rNR^{a1}R^{b1}$, $-(CR^{c1}R^{d1})_tNR^{a1}R^{b1}$, $-(CR^{c1}R^{d1})_tOR^{b1}$, $-(CR^{c1}R^{d1})_tSR^{b1}$, $-(CR^{c1}R^{d1})_tS(O)_rR^{b1}$, $-(CR^{c1}R^{d1})_tCO_2R^{b1}$, $-(CR^{c1}R^{d1})_tC(O)NR^{a1}R^{b1}$, $-(CR^{c1}R^{d1})_tNR^{a1}CO_2R^{b1}$, $-(CR^{c1}R^{d1})_tOC(O)NR^{a1}R^{b1}$, $-(CR^{c1}R^{d1})_tNR^{a1}C(O)_2NR^{a1}R^{b1}$, $-(CR^{c1}R^{d1})_tNR^{a1}SO_2NR^{a1}R^{b1}$, $-O(CR^{c1}R^{d1})_tNR^{a1}R^{b1}$, $-C(O)R^{a1}$, $-C(O)(CR^{c1}R^{d1})_tNR^{a1}R^{b1}$, $-C(O)(CR^{c1}R^{d1})_tOR^{b1}$, $-C(O)(CR^{c1}R^{d1})_tSR^{b1}$, $-C(O)(CR^{c1}R^{d1})_tS(O)_rR^{b1}$, $-CO_2R^{b1}$, $-CO_2(CR^{c1}R^{d1})_tC(O)NR^{a1}R^{b1}$, $-OC(O)R^{a1}$, $-CN$, $-C(O)NR^{a1}R^{b1}$, $-NR^{a1}C(O)R^{b1}$, $-OC(O)NR^{a1}R^{b1}$, $-NR^{a1}C(O)OR^{b1}$, $-NR^{a1}C(O)NR^{a1}R^{b1}$, $-NR^{a1}S(O)_rR^{b1}$, and $-CR^{a1}(=N-OR^{b1})$;

each $R^{a1}$ and each $R^{b1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with one or more substituents, independently selected from $R^Y$;

or $R^{a1}$ and $R^{b1}$ together with the atom(s) to which they are attached form a heterocyclic ring of 4 to 12 members containing 0, 1, or 2 additional heteroatoms independently selected from oxygen, sulfur and nitrogen, and optionally substituted with 1 or 2 $R^Y$ groups;

each $R^{c1}$ and each $R^{d1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl;

$R^Y$ is independently selected from $C_{1-10}$ alkyl, $C_{2-10}$ alkenyl, $C_{2-10}$ alkynyl, $C_{3-10}$ cycloalkyl, halogen, $-NO_2$, $-NR^{a2}R^{b2}$, $-OR^{a2}$, $-SR^{a2}$, $-S(O)_rR^2$, $-S(O)_2OR^{a2}$, $-OS(O)_2R^{b2}$, $-S(O)_rNR^{a2}R^{b2}$, $-(CR^{c2}R^{d2})_tNR^{a2}R^{b2}$, $-(CR^{c2}R^{d2})_tOR^{b2}$, $-(CR^{c2}R^{d2})_tSR^{b2}$, $-(CR^{c2}R^{d2})_tS(O)_rR^{b2}$, $-(CR^{c2}R^{d2})_tCO_2R^{b2}$, $-(CR^{c2}R^{d2})_tC(O)NR^{a2}R^{b2}$, $-(CR^{c2}R^{d2})_tNR^{a2}CO_2R^{b2}$, $-(CR^{c2}R^{d2})_tOC(O)NR^{a2}R^{b2}$, $-(CR^{c2}R^{d2})_tNR^{a2}C(O)NR^{a2}R^{b2}$, $-(CR^{c2}R^{d2})_tNR^{a2}SO_2NR^{a2}R^{b2}$, $-O(CR^{c2}R^{d2})_tNR^{a2}R^{b2}$, $-C(O)R^{a2}$, $-C(O)(CR^{c2}R^{d2})_tOR^{b2}$, $-C(O)(CR^{c2}R^{d2})_tNR^{a2}R^{b2}$, $-C(O)(CR^{c2}R^{d2})_tSR^{b2}$, $-C(O)(CR^{c2}R^{d2})_tS(O)_rR^{b2}$, $-CO_2R^{b2}$, $-CO_2(CR^{c2}R^{d2})_tC(O)NR^{a2}R^{b2}$, $-OC(O)R^{a2}$, $-CN$, $-C(O)NR^{a2}R^{b2}$, $-NR^{a2}C(O)R^{b2}$, $-OC(O)NR^{a2}R^{b2}$, $-NR^{a2}C(O)OR^{b2}$, $-NR^{a2}C(O)NR^{a2}R^{b2}$, $-NR^{a2}S(O)_rR^{b2}$, and $-CR^{a2}(=N-OR^{b2})$;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with one or more substituents, independently selected from CN, halogen, $C_{1-10}$ alkyl, $C_{2-10}$ alkenyl, $C_{2-10}$ alkynyl, and $C_{3-10}$ cycloalkyl;

or $R^{a2}$ and $R^{b2}$ together with the atom(s) to which they are attached form a heterocyclic ring of 4 to 12 members containing 0, 1, or 2 additional heteroatoms independently selected from oxygen, sulfur and nitrogen, and optionally substituted with 1 or 2 substituents, independently selected from CN, halogen, $C_{1-10}$ alkyl, $C_{2-10}$ alkenyl, $C_{2-10}$ alkynyl, and $C_{3-10}$ cycloalkyl;

each $R^{c2}$ and each $R^{d2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl;

m is selected from 0, 1, 2, 3 and 4;

n is selected from 0, 1, and 2;

p is selected from 0, 1, and 2;

q is 1;

each r is independently selected from 1 and 2;

each t is independently selected from 1, 2, and 3.

2. A compound of claim 1 or a pharmaceutically acceptable salt thereof, wherein Q is selected from pyridinyl, pyrimidinyl, pyrazinyl, and pyridazinyl.

3. A compound of claim 2 or a pharmaceutically acceptable salt thereof, wherein Q is selected from pyridinyl and pyrimidinyl.

4. A compound of claim 1 or a pharmaceutically acceptable salt thereof, wherein Z is selected from N and $CR^6$, wherein $R^6$ is selected from halogen.

5. A compound of claim 4 or a pharmaceutically acceptable salt thereof, wherein Z is selected from N and CF.

6. A compound of claim 1 or a pharmaceutically acceptable salt thereof, wherein $R^1$ is selected from heterocyclyl and heterocyclyl-$C_{1-4}$ alkyl, wherein alkyl and heterocyclyl are each unsubstituted or substituted with at least one substituent independently selected from $C_{1-4}$ alkyl, $C_{3-10}$ cycloalkyl, halogen, $-NR^{a1}R^{b1}$, $-OR^{a1}$, $-S(O)_rR^{a1}$, $-S(O)_rNR^{a1}R^{b1}$, $-(CR^{c1}R^{d1})NR^{a1}R^{b1}$, and $-(CR^{c1}R^{d1})_tOR^{b1}$.

7. A compound of claim 6 or a pharmaceutically acceptable salt thereof, wherein $R^1$ is selected from

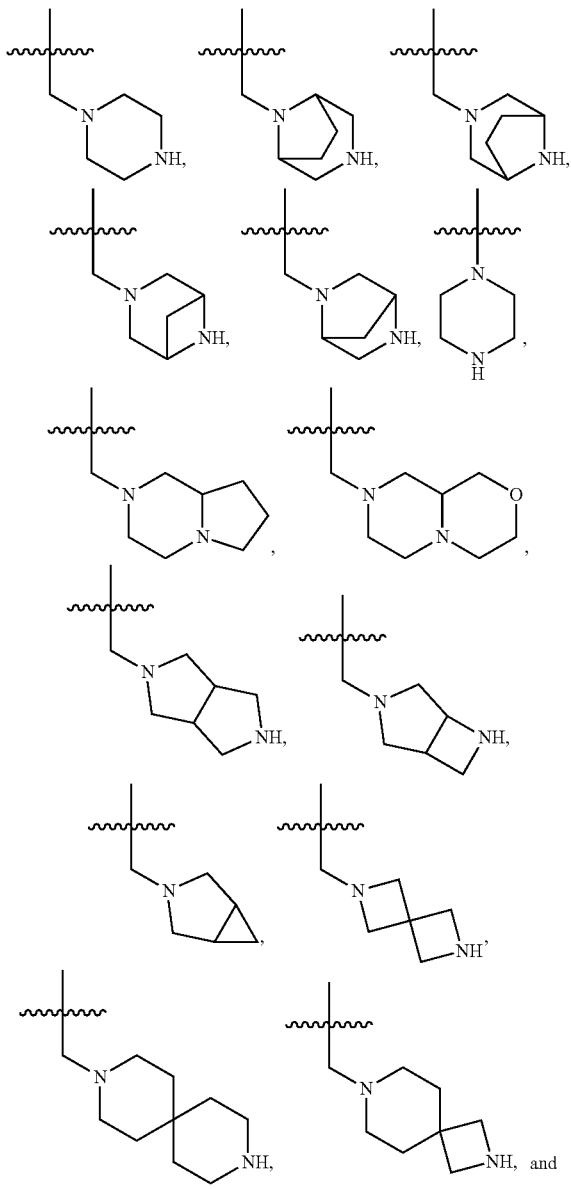

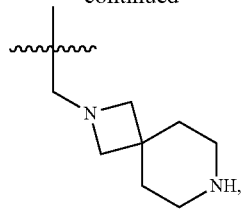

which are each unsubstituted or substituted with at least one substituent independently selected from methyl, ethyl, $-NH_2$ and $-OH$.

8. A compound of claim 1 or a pharmaceutically acceptable salt thereof, wherein $R^2$ is hydrogen.

9. A compound of claim 1 or a pharmaceutically acceptable salt thereof, wherein $R^3$ is selected from $C_{1-10}$ alkyl and $C_{3-10}$ cycloalkyl, or two $R^3$ together with the carbon atoms to which they are attached form a cyclic ring of 3 to 7 members, wherein alkyl and cycloalkyl are each unsubstituted or substituted with at least one substituent independently selected from $R^x$.

10. A compound of claim 9 or a pharmaceutically acceptable salt thereof, wherein $R^3$ is $C_{1-10}$ alkyl or two $R^3$ together with the carbon atoms to which they are attached form a 3-membered cyclic ring, wherein $C_{1-10}$ alkyl is unsubstituted or substituted with at least one substituent independently selected from $R^x$.

11. A compound of claim 10 or a pharmaceutically acceptable salt thereof, wherein $R^3$ is selected from methyl, hydroxymethyl, methoxymethyl, fluoromethyl, difluoromethyl and trifluoromethyl, or two $R^3$ together with the carbon atoms to which they are attached form a 3-membered cyclic ring.

12. A compound of claim 1 or a pharmaceutically acceptable salt thereof, wherein $R^4$ is selected from halogen and CN.

13. A compound of claim 1 or a pharmaceutically acceptable salt thereof, wherein $R^4$ is fluoro.

14. A compound of claim 1 or a pharmaceutically acceptable salt thereof, wherein $R^5$ is hydrogen.

15. A compound of claim 1, selected from
(S)-(5-fluoro-7-(5-fluoro-2-((5-(piperazin-1-ylmethyl)pyridin-2-yl)amino)pyrimidin-4-yl)-2,3-dihydro-1H-benzo[d]pyrrolo[1,2-a]imidazol-1-yl)methanol,
(S)-(5-fluoro-7-(5-fluoro-2-((5-((4-methylpiperazin-1-yl)methyl)pyridin-2-yl)amino)pyrimidin-4-yl)-2,3-dihydro-1H-benzo[d]pyrrolo[1,2-a]imidazol-1-yl)methanol,
(S)-(7-(2-((5-((4-ethylpiperazin-1-yl)methyl)pyridin-2-yl)amino)-5-fluoropyrimidin-4-yl)-5-fluoro-2,3-dihydro-1H-benzo[d]pyrrolo[1,2-a]imidazol-1-yl)methanol,
(S)-5-fluoro-4-(5-fluoro-1-(fluoromethyl)-2,3-dihydro-1H-benzo[d]pyrrolo[1,2-a]imidazol-7-yl)-N-(5-(piperazin-1-ylmethyl)pyridin-2-yl)pyrimidin-2-amine,
(S)-5-fluoro-4-(5-fluoro-1-(fluoromethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine,
(S)—N-(5-((4-ethylpiperazin-1-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine, (S)-5-fluoro-4-(5-fluoro-1-(methoxymethyl)-2,3-dihydro-1H-benzo[d]pyrrolo[1,2-a]imidazol-7-yl)-N-(5-(piperazin-1-ylmethyl)pyridin-2-yl)pyrimidin-2-amine, (S)-5-fluoro-4-(5-fluoro-1-(methoxymethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine, (S)—N-(5-((4-ethylpiperazin-1-yl)methyl)pyridin-2-yl)-5-fluoro-4-(5-fluoro-1-(methoxymethyl)-2,3-dihydro-1H-benzo[d]pyrrolo[1,2-a]imidazol-7-yl)pyrimidin-2-amine, (S)-4-(1-(difluoromethyl)-5-fluoro-2,3-dihydro-1H-benzo[d]pyrrolo[1,2-a]imidazol-7-yl)-5-fluoro-N-(5-(piperazin-1-ylmethyl)pyridin-2-yl)pyrimidin-2-amine, (S)-4-(1-(difluoromethyl)-5-fluoro-2,3-dihydro-1H-benzo[d]pyrrolo[1,2-a]imidazol-7-yl)-5-fluoro-N-(5-((4-methylpiperazin-1-yl)methyl)pyridin-2-yl)pyrimidin-2-amine, (S)-4-(1-(difluoromethyl)-5-fluoro-2,3-dihydro-1H-benzo[d]pyrrolo[1,2-a]imidazol-7-yl)-N-(5-((4-ethylpiperazin-1-yl)methyl)pyridin-2-yl)-5-fluoropyrimidin-2-amine, 5-fluoro-4-(5-fluoro-2,3-dihydrospiro[benzo[d]pyrrolo[1,2-a]imidazole-1,1'-cyclopropan]-7-yl)-N-(5-(piperazin-1-ylmethyl)pyridin-2-yl)pyrimidin-2-amine, 5-fluoro-4-(5-fluoro-2,3-dihydrospiro[benzo[d]pyrrolo[1,2-a]imidazole-1,1'-cyclopropan]-7-yl)-N-(5-((4-methylpiperazin-1-yl)methyl)pyridin-2-yl)pyrimidin-2-amine, N-(5-((4-ethylpiperazin-1-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, (S)-5-fluoro-4-(5-fluoro-1-(trifluoromethyl)-2,3-dihydro-1H-benzo[d]pyrrolo[1,2-a]imidazol-7-yl)-N-(5-(piperazin-1-ylmethyl)pyridin-2-yl)pyrimidin-2-amine, (S)-5-fluoro-4-(5-fluoro-1-(trifluoromethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine, (S)—N-(5-((4-ethylpiperazin-1-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, 5-fluoro-4-((S)-5-fluoro-1-(fluoromethyl)-2,3-dihydro-1H-benzo[d]pyrrolo[1,2-a]imidazol-7-yl)-N-(5-(((R)-hexahydropyrrolo[1,2-a]pyrazin-2(1H)-yl)methyl)pyridin-2-yl)pyrimidin-2-amine, (S)—N-(5-((2,7-diazaspiro[3.5]nonan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine, (S)-5-fluoro-4-(5-fluoro-1-(fluoromethyl)-2,3-dihydro-1H-benzo[d]pyrrolo[1,2-a]imidazol-7-yl)-N-(5-((7-methyl-2,7-diazaspiro[3.5]nonan-2-yl)methyl)pyridin-2-yl)pyrimidin-2-amine, (S)—N-(5-((7-ethyl-2,7-diazaspiro[3.5]nonan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine, (S)—N-(5-((2,6-diazaspiro[3.3]heptan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine, (S)-5-fluoro-4-(5-fluoro-1-(fluoromethyl)-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine, (S)—N-(5-((6-ethyl-2,6-diazaspiro[3.3]heptan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine, 5-fluoro-4-((S)-5-fluoro-1-(fluoromethyl)-2,3-dihydro-1H-benzo[d]pyrrolo[1,2-a]imidazol-7-yl)-N-(5-((hexahydropyrrolo[3,4-c]pyrrol-2(1H)-yl)methyl)pyridin-2-yl)pyrimidin-2-amine, 5-fluoro-4-((S)-5-fluoro-1-(fluoromethyl)-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine, N-(5-((5-ethylhexahydropyrrolo[3,4-c]pyrrol-2(1H)-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine, (S)—N-(5-((3,9-diazaspiro[5.5]undecan-3-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine, (S)-5-fluoro-4-(5-fluoro-1-(fluoromethyl)-2,3-dihydro-1H-benzo[d]pyrrolo[1,2-a]imidazol-7-yl)-N-(5-((9-methyl-3,9-diazaspiro[5.5]undecan-3-yl)methyl)pyridin-2-yl)pyrimidin-2-amine, (S)—N-(5-((9-ethyl-3,9-diazaspiro[5.5]undecan-3-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine, N-(5-((3,8-diazabicyclo[3.2.1]octan-8-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine, 5-fluoro-4-((S)-5-fluoro-1-(fluoromethyl)-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine, N-(5-((3-ethyl-3,8-diazabicyclo[3.2.1]octan-8-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine, N-(5-((3,8-diazabicyclo[3.2.1]octan-3-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine, 5-fluoro-4-((S)-5-fluoro-1-(fluoromethyl)-2,3-dihydro-1H-benzo[d]pyrrolo[1,2-a]imidazol-7-yl)-N-(5-((8-methyl-3,8-diazabicyclo[3.2.1]octan-3-yl)methyl)pyridin-2-yl)pyrimidin-2-amine, N-(5-((8-ethyl-3,8-diazabicyclo[3.2.1]octan-3-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine, (S)-4-(1-(difluoromethyl)-5-fluoro-2,3-dihydro-1H-benzo[d]pyrrolo[1,2-a]imidazol-7-yl)-5-fluoro-N-(5-(piperazin-1-yl)pyridin-2-yl)pyrimidin-2-amine, (S)-4-(1-(difluoromethyl)-5-fluoro-2,3-dihydro-1H-benzo[d]pyrrolo[1,2-a]imidazol-7-yl)-5-fluoro-N-(5-(4-methylpiperazin-1-yl)pyridin-2-yl)pyrimidin-2-amine, (S)-4-(1-(difluoromethyl)-5-fluoro-2,3-dihydro-1H-benzo[d]pyrrolo[1,2-a]imidazol-7-yl)-N-(5-(4-ethylpiperazin-1-yl)pyridin-2-yl)-5-fluoropyrimidin-2-amine, 4-((S)-1-(difluoromethyl)-5-fluoro-2,3-dihydro-1H-benzo[d]pyrrolo[1,2-a]imidazol-7-yl)-5-fluoro-N-(5-(((R)-hexahydropyrrolo[1,2-a]pyrazin-2(1H)-yl)methyl)pyridin-2-yl)pyrimidin-2-amine, (S)—N-(5-((2,7-diazaspiro[3.5]nonan-2-yl)methyl)pyridin-2-yl)-4-(1-(difluoromethyl)-5-fluoro-2,3-dihydro-1H-benzo[d]pyrrolo[1,2-a]imidazol-7-yl)-5-fluoropyrimidin-2-amine, (S)-4-(1-(difluoromethyl)-5-fluoro-2,3-dihydro-1H-benzo[d]pyrrolo[1,2-a]imidazol-7-yl)-5-fluoro-N-(5-((7-methyl-2,7-diazaspiro[3.5]nonan-2-yl)methyl)pyridin-2-yl)pyrimidin-2-amine, (S)-4-(1-(difluoromethyl)-5-fluoro-2,3-dihydro-1H-benzo[d]pyrrolo[1,2-a]imidazol-7-yl)-N-(5-((7-ethyl-2,7-diazaspiro[3.5]nonan-2-yl)methyl)pyridin-2-yl)-5-fluoropyrimidin-2-amine, (S)—N-(5-((2,6-diazaspiro[3.3]heptan-2-yl)methyl)pyridin-2-yl)-4-(1-(difluoromethyl)-5-fluoro-2,3-dihydro-1H-benzo[d]pyrrolo[1,2-a]imidazol-7-yl)-5-fluoropyrimidin-2-amine, (S)-4-(1-(difluoromethyl)-5-fluoro-2,3-dihydro-1H-benzo[d]pyrrolo[1,2-a]imidazol-7-yl)-5-fluoro-N-(5-((6-methyl-2,6-diazaspiro[3.3]heptan-2-yl)methyl)pyridin-2-yl)pyrimidin-2-amine, (S)-4-(1-(difluoromethyl)-5-fluoro-2,3-dihydro-1H-benzo[d]pyrrolo[1,2-a]imidazol-7-yl)-N-(5-((6-ethyl-2,6-diazaspiro[3.3]heptan-2-yl)methyl)pyridin-2-yl)-5-fluoropyrimidin-2-amine, 4-((S)-1-(difluoromethyl)-5-fluoro-2,3-dihydro-1H-benzo[d]pyrrolo[1,2-a]imidazol-7-yl)-5-fluoro-N-(5-((hexahydropyrrolo[3,4-c]pyrrol-2(1H)-yl)methyl)pyridin-2-yl)pyrimidin-2-amine, 4-((S)-1-(difluoromethyl)-5-fluoro-2,3-dihydro-1H-benzo[d]pyrrolo[1,2-a]imidazol-7-yl)-5-fluoro-N-(5-((5-methylhexahydropyrrolo[3,4-c]pyrrol-2(1H)-yl)methyl)pyridin-2-yl)pyrimidin-2-amine, 4-((S)-1-(difluoromethyl)-5-fluoro-2,3-dihydro-1H-benzo[d]pyrrolo[1,2-a]imidazol-7-yl)-N-(5-((5-ethylhexahydropyrrolo[3,4-c]pyrrol-2(1H)-yl)methyl)pyridin-2-yl)-5-fluoropyrimidin-2-amine, (S)—N-(5-((3,9-diazaspiro[5.5]undecan-3-yl)methyl)pyridin-2-yl)-4-(1-(difluoromethyl)-5-fluoro-2,3-dihydro-1H-benzo[d]pyrrolo[1,2-a]imidazol-7-yl)-5-fluoropyrimidin-2-amine, (S)-4-(1-(difluoromethyl)-5-fluoro-2,3-dihydro-1H-benzo[d]pyrrolo[1,2-a]imidazol-7-yl)-5-fluoro-N-(5-((9-methyl-3,9-diazaspiro[5.5]undecan-3-yl)methyl)pyridin-2-yl)pyrimidin-2-amine, (S)-4-(1-(difluoromethyl)-5-fluoro-2,3-dihydro-1H-benzo[d]pyrrolo[1,2-a]imidazol-7-yl)-N-(5-((9-ethyl-3,9-diazaspiro[5.5]undecan-3-yl)methyl)pyridin-2-yl)-5-fluoropyrimidin-2-amine, N-(5-((3,8-diazabicyclo[3.2.1]octan-8-yl)methyl)pyridin-2-yl)-4-((S)-1-(difluoromethyl)-5-fluoro-2,3-dihydro-1H-benzo[d]pyrrolo[1,2-a]imidazol-7-yl)-5-fluoropyrimidin-2-amine, 4-((S)-1-(difluoromethyl)-5-fluoro-2,3-dihydro-1H-benzo[d]pyrrolo[1,2-a]imidazol-7-yl)-5-fluoro-N-(5-((3-methyl-3,8-diazabicyclo[3.2.1]octan-8-yl)methyl)pyridin-2-yl)pyrimidin-2-amine, 4-((S)-1-(difluoromethyl)-5-fluoro-2,3-dihydro-1H-benzo[d]pyrrolo[1,2-a]imidazol-7-yl)-N-(5-((3-ethyl-3,8-diazabicyclo[3.2.1]octan-8-yl)methyl)pyridin-2-yl)-5-fluoropyrimidin-2-amine, N-(5-((3,8-diazabicyclo[3.2.1]octan-3-yl)methyl)pyridin-2-yl)-4-((S)-1-(difluoromethyl)-5-fluoro-2,3-dihydro-1H-benzo[d]pyrrolo[1,2-a]imidazol-7-yl)-5-fluoropyrimidin-2-amine, 4-((S)-1-(difluoromethyl)-5-fluoro-2,3-dihydro-1H-benzo[d]pyrrolo[1,2-a]imidazol-7-yl)-5-fluoro-N-(5-((8-methyl-3,8-diazabicyclo[3.2.1]octan-3-yl)methyl)pyridin-2-yl)pyrimidin-2-amine, 4-((S)-1-(difluoromethyl)-5-fluoro-2,3-dihydro-1H-benzo[d]pyrrolo[1,2-a]imidazol-7-yl)-N-(5-((8-ethyl-3,8-diazabicyclo[3.2.1]octan-3-yl)methyl)pyridin-2-yl)-5-fluoropyrimidin-2-amine, 5-fluoro-4-((S)-5-fluoro-1-(trifluoromethyl)-2,3-dihydro-1H-benzo[d]pyrrolo[1,2-a]imidazol-7-yl)-N-(5-(((R)-hexahydropyrrolo[1,2-a]pyrazin-2(1H)-yl)methyl)pyridin-2-yl)pyrimidin-2-amine, (S)—N-(5-((2,7-diazaspiro[3.5]nonan-2-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, (S)-5-fluoro-4-(5-fluoro-1-(trifluoromethyl)-2,3-dihydro-1H-benzo[d]pyrrolo[1,2-a]imidazol-7-yl)-N-(5-((7-methyl-2,7-diazaspiro[3.5]nonan-2-yl)methyl)pyridin-2-yl)pyrimidin-2-amine, (S)—N-(5-((7-ethyl-2,7-diazaspiro[3.5]nonan-2-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, (S)—N-(5-((2,7-diazaspiro[3.5]nonan-7-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, (S)-5-fluoro-4-(5-fluoro-1-(trifluoromethyl)-2,3-dihydro-1H-benzo[d]pyrrolo[1,2-a]imidazol-7-yl)-N-(5-((2-methyl-2,7-diazaspiro[3.5]nonan-7-yl)methyl)pyridin-2-yl)pyrimidin-2-amine, (S)—N-(5-((2-ethyl-2,7-diazaspiro[3.5]nonan-7-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, (S)—N-(5-((2,6-diazaspiro[3.3]heptan-2-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, (S)-5-fluoro-4-(5-fluoro-1-(trifluoromethyl)-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine, (S)—N-(5-((6-ethyl-2,6-diazaspiro[3.3]heptan-2-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, (S)—N-(5-((3,9-diazaspiro[5.5]undecan-3-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, (S)-5-fluoro-4-(5-fluoro-1-(trifluoromethyl)-2,3-dihydro-1H-benzo[d]pyrrolo[1,2-a]imidazol-7-yl)-N-(5-((9-methyl-3,9-diazaspiro[5.5]undecan-3-yl)methyl)pyridin-2-yl)pyrimidin-2-amine, (S)—N-(5-((9-ethyl-3,9-diazaspiro[5.5]undecan-3-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine, 5-fluoro-4-((S)-5-fluoro-1-(trifluoromethyl)-2,3-dihydro-1H-benzo[d]pyrrolo[1,2-a]imidazol-7-yl)-N-(5-((hexahydropyrrolo[3,4-c]pyrrol-2(1H)-yl)methyl)pyridin-2-yl)pyrimidin-2-amine, 5-fluoro-4-((S)-5-fluoro-1-(trifluoromethyl)-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine, N-(5-((5-ethylhexahydropyrrolo[3,4-c]pyrrol-2(1H)-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine, N-(5-((3,8-diazabicyclo[3.2.1]octan-8-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine, 5-fluoro-4-((S)-5-fluoro-1-(trifluoromethyl)-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine, N-(5-((3-ethyl-3,8-diazabicyclo[3.2.1]octan-8-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine, N-(5-((3,8-diazabicyclo[3.2.1]octan-3-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine, 5-fluoro-4-((S)-5-fluoro-1-(trifluoromethyl)-2,3-dihydro-1H-benzo[d]pyrrolo[1,2-a]imidazol-7-yl)-N-(5-((8-methyl-3,8-diazabicyclo[3.2.1]octan-3-yl)methyl)pyridin-2-yl)pyrimidin-2-amine, N-(5-((8-ethyl-3,8-diazabicyclo[3.2.1]octan-3-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine, (R)-5-fluoro-4-(5-fluoro-1-methyl-2,3-dihydro-1H-benzo[d]pyrrolo[1,2-a]imidazol-7-yl)-N-(5-(piperazin-1-ylmethyl)pyridin-2-yl)pyrimidin-2-amine, (R)-5-fluoro-4-(5-fluoro-1-methyl-2,3-dihydro-1H-benzo[d]pyrrolo[1,2-a]imidazol-7-yl)-N-(5-((4-methylpiperazin-1-yl)methyl)pyridin-2-yl)pyrimidin-2-amine, (R)—N-(5-((4-ethylpiperazin-1-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, 5-fluoro-4-((R)-5-fluoro-1-methyl-2,3-dihydro-1H-benzo[d]pyrrolo[1,2-a]imidazol-7-yl)-N-(5-(((R)-hexahydropyrrolo[1,2-a]pyrazin-2(1H)-yl)methyl)pyridin-2-yl)pyrimidin-2-amine, (R)—N-(5-((2,7-diazaspiro[3.5]nonan-7-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, (R)-5-fluoro-4-(5-fluoro-1-methyl-2,3-dihydro-1H-benzo[d]pyrrolo[1,2-a]imidazol-7-yl)-N-(5-((2-methyl-2,7-diazaspiro[3.5]nonan-7-yl)methyl)pyridin-2-yl)pyrimidin-2-amine, (R)—N-(5-((2-ethyl-2,7-diazaspiro[3.5]nonan-7-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, (R)—N-(5-((2,7-diazaspiro[3.5]nonan-2-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, (R)-5-fluoro-4-(5-fluoro-1-methyl-2,3-dihydro-1H-benzo[d]pyrrolo[1,2-a]imidazol-7-yl)-N-(5-((7-methyl-2,7-diazaspiro[3.5]nonan-2-yl)methyl)pyridin-2-yl)pyrimidin-2-amine, (R)—N-(5-((7-ethyl-2,7-diazaspiro[3.5]nonan-2-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, (R)—N-(5-((3,9-diazaspiro[5.5]undecan-3-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, (R)-5-fluoro-4-(5-fluoro-1-methyl-2,3-dihydro-1H-benzo[d]pyrrolo[1,2-a]imidazol-7-yl)-N-(5-((9-methyl-3,9-diazaspiro[5.5]undecan-3-yl)methyl)pyridin-2-yl)pyrimidin-2-amine, (R)—N-(5-((9-ethyl-3,9-diazaspiro[5.5]undecan-3-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, (R)—N-(5-((2,6-diazaspiro[3.3]heptan-2-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, (R)-5-fluoro-4-(5-fluoro-1-methyl-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine, (R)—N-(5-((6-ethyl-2,6-diazaspiro[3.3]heptan-2-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, 5-fluoro-4-((R)-5-fluoro-1-methyl-2,3-dihydro-1H-benzo[d]pyrrolo[1,2-a]imidazol-7-yl)-N-(5-((hexahydropyrrolo[3,4-c]pyrrol-2(1H)-yl)methyl)pyridin-2-yl)pyrimidin-2-amine, 5-fluoro-4-((R)-5-fluoro-1-methyl-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine, N-(5-((5-ethylhexahydropyrrolo[3,4-c]pyrrol-2(1H)-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine, N-(5-((3,8-diazabicyclo[3.2.1]octan-8-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine, 5-fluoro-4-((R)-5-fluoro-1-methyl-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine, N-(5-((3-ethyl-3,8-diazabicyclo[3.2.1]octan-8-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine, N-(5-((3,8-diazabicyclo[3.2.1]octan-3-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine, 5-fluoro-4-((R)-5-fluoro-1-methyl-2,3-dihydro-1H-benzo[d]pyrrolo[1,2-a]imidazol-7-yl)-N-(5-((8-methyl-3,8-diazabicyclo[3.2.1]octan-3-yl)methyl)pyridin-2-yl)pyrimidin-2-amine, N-(5-((8-ethyl-3,8-diazabicyclo[3.2.1]octan-3-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-(piperazin-1-ylmethyl)pyridin-2-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((4-methylpiperazin-1-yl)methyl)pyridin-2-yl)pyrimidin-2-amine, N-(5-((4-ethylpiperazin-1-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, (R)-5-fluoro-4-(5-fluoro-1,1-dimethyl-2,3-dihydro-1H-benzo[d]pyrrolo[1,2-a]imidazol-7-yl)-N-(5-((hexahydropyrrolo[1,2-a]pyrazin-2(1H)-yl)methyl)pyridin-2-yl)pyrimidin-2-amine, N-(5-((2,7-diazaspiro[3.5]nonan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((7-methyl-2,7-diazaspiro[3.5]nonan-2-yl)methyl)pyridin-2-yl)pyrimidin-2-amine, N-(5-((7-ethyl-2,7-diazaspiro[3.5]nonan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, N-(5-((2,7-diazaspiro[3.5]nonan-7-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((2-methyl-2,7-diazaspiro[3.5]nonan-7-yl)methyl)pyridin-2-yl)pyrimidin-2-amine, N-(5-((2-ethyl-2,7-diazaspiro[3.5]nonan-7-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, N-(5-((2,6-diazaspiro[3.3]heptan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine, N-(5-((6-ethyl-2,6-diazaspiro[3.3]heptan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, N-(5-((3,9-diazaspiro[5.5]undecan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((9-methyl-3,9-diazaspiro[5.5]undecan-3-yl)methyl)pyridin-2-yl)pyrimidin-2-amine, N-(5-((9-ethyl-3,9-diazaspiro[5.5]undecan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((hexahydropyrrolo[3,4-c]pyrrol-2(1H)-yl)methyl)pyridin-2-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine, N-(5-((5-ethylhexahydropyrrolo[3,4-c]pyrrol-2(1H)-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, N-(5-((3,8-diazabicyclo[3.2.1]octan-8-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine, N-(5-((3-ethyl-3,8-diazabicyclo[3.2.1]octan-8-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, N-(5-((3,8-diazabicyclo[3.2.1]octan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, 5-fluoro-4-(5-fluoro-1,1-dimethyl-2,3-dihydro-1H-benzo[d]pyrrolo[1,2-a]imidazol-7-yl)-N-(5-((8-methyl-3,8-diazabicyclo[3.2.1]octan-3-yl)methyl)pyridin-2-yl)pyrimidin-2-amine, N-(5-((8-ethyl-3,8-diazabicyclo[3.2.1]octan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine, N-(5-((3,6-diazabicyclo[3.1.1]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, 5-fluoro-4-(5-fluoro-2,3-dihydrospiro[benzo[d]pyrrolo[1,2-a]imidazole-1,1'-cyclopropan]-7-yl)-N-(5-((6-methyl-3,6-diazabicyclo[3.1.1]heptan-3-yl)methyl)pyridin-2-yl)pyrimidin-2-amine, N-(5-((6-ethyl-3,6-diazabicyclo[3.1.1]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, N-(5-(((1S,4S)-2,5-diazabicyclo[2.2.1]heptan-2-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, 5-fluoro-4-(5-fluoro-2,3-dihydrospiro[benzo[d]pyrrolo[1,2-a]imidazole-1,1'-cyclopropan]-7-yl)-N-(5-(((1S,4S)-5-methyl-2,5-diazabicyclo[2.2.1]heptan-2-yl)methyl)pyridin-2-yl)pyrimidin-2-amine, N-(5-(((1S,4S)-5-ethyl-2,5-diazabicyclo[2.2.1]heptan-2-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, N-(5-(((3aR,6aS)-3a,6a-dimethylhexahydropyrrolo[3,4-c]pyrrol-2(1H)-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, 5-fluoro-4-(5-fluoro-2,3-dihydrospiro[benzo[d]pyrrolo[1,2-a]imidazole-1,1'-cyclopropan]-7-yl)-N-(5-(((3aR, 6aS)-3a,5,6a-trimethylhexahydropyrrolo[3,4-c]pyrrol-2(1H)-yl)methyl)pyridin-2-yl)pyrimidin-2-amine, N-(5-(((3aR,6aS)-5-ethyl-3a,6a-dimethylhexahydropyrrolo[3,4-c]pyrrol-2(11)-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, N-(5-(((3,6-diazabicyclo[3.2.0]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, 5-fluoro-4-(5-fluoro-2,3-dihydrospiro[benzo[d]pyrrolo[1,2-a]imidazole-1,1'-cyclopropan]-7-yl)-N-(5-((6-methyl-3,6-diazabicyclo[3.2.0]heptan-3-yl)methyl)pyridin-2-yl)pyrimidin-2-amine, N-(5-((6-ethyl-3,6-diazabicyclo[3.2.0]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, (S)-5-fluoro-4-(5-fluoro-2,3-dihydrospiro[benzo[d]pyrrolo[1,2-a]imidazole-1,1'-cyclopropan]-7-yl)-N-(5-((hexahydropyrrolo[1,2-a]pyrazin-2(1H)-yl)methyl)pyridin-2-yl)pyrimidin-2-amine, (R)-5-fluoro-4-(5-fluoro-2,3-dihydrospiro[benzo[d]pyrrolo[1,2-a]imidazole-1,1'-cyclopropan]-7-yl)-N-(5-((hexahydropyrrolo[1,2-a]pyrazin-2(1H)-yl)methyl)pyridin-2-yl)pyrimidin-2-amine, (7R,8aS)-2-((6-((5-fluoro-4-(5-fluoro-2,3-dihydrospiro[benzo[d]pyrrolo[1,2-a]imidazole-1,1'-cyclopropan]-7-yl)pyrimidin-2-yl)amino)pyridin-3-yl)methyl)octahydropyrrolo[1,2-a]pyrazin-7-ol, 3-((6-((5-fluoro-4-(5-fluoro-2,3-dihydrospiro[benzo[d]pyrrolo[1,2-a]imidazole-1,1'-cyclopropan]-7-yl)pyrimidin-2-yl)amino)pyridin-3-yl)methyl)-3-azabicyclo[3.1.0]hexan-6-amine, (R)-5-fluoro-4-(5-fluoro-2,3-dihydrospiro[benzo[d]pyrrolo[1,2-a]imidazole-1,1'-cyclopropan]-7-yl)-N-(5-((hexahydropyrazino[2,1-c][1,4]oxazin-8(1H)-yl)methyl)pyridin-2-yl)pyrimidin-2-amine, 5-fluoro-4-(5-fluoro-2,3-dihydro-1H-benzo[d]pyrrolo[1,2-a]imidazol-7-yl)-N-(5-(piperazin-1-ylmethyl)pyridin-2-yl)pyrimidin-2-amine, 5-fluoro-4-(5-fluoro-2,3-dihydro-1H-benzo[d]pyrrolo[1,2-a]imidazol-7-yl)-N-(5-((4-methylpiperazin-1-yl)methyl)pyridin-2-yl)pyrimidin-2-amine, N-(5-((4-ethylpiperazin-1-yl)methyl)pyridin-2-yl)-5-fluoro-4-(5-fluoro-2,3-dihydro-1H-benzo[d]pyrrolo[1,2-a]imidazol-7-yl)pyrimidin-2-amine, (R)-4-(1-(difluoromethyl)-5-fluoro-2,3-dihydro-1H-benzo[d]pyrrolo[1,2-a]imidazol-7-yl)-5-fluoro-N-(5-(piperazin-1-ylmethyl)pyridin-2-yl)pyrimidin-2-amine, (R)-4-(1-(difluoromethyl)-5-fluoro-2,3-dihydro-1H-benzo[d]pyrrolo[1,2-a]imidazol-7-yl)-5-fluoro-N-(5-((4-methylpiperazin-1-yl)methyl)pyridin-2-yl)pyrimidin-2-amine, (R)-4-(1-(difluoromethyl)-5-fluoro-2,3-dihydro-1H-benzo[d]pyrrolo[1,2-a]imidazol-7-yl)-N-(5-((4-ethylpiperazin-1-yl)methyl)pyridin-2-yl)-5-fluoropyrimidin-2-amine, (S)-5-fluoro-4-(5-fluoro-1-methyl-2,3-dihydro-1H-benzo[d]pyrrolo[1,2-a]imidazol-7-yl)-N-(5-(piperazin-1-ylmethyl)pyridin-2-yl)pyrimidin-2-amine, (S)-5-fluoro-4-(5-fluoro-1-methyl-2,3-dihydro-1H-benzo[d]pyrrolo[1,2-a]imidazol-7-yl)-N-(5-((4-methylpiperazin-1-yl)methyl)pyridin-2-yl)pyrimidin-2-amine, (S)—N-(5-((4-ethylpiperazin-1-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine, (R)-5-fluoro-4-(5-fluoro-1-(methoxymethyl)-2,3-dihydro-1H-benzo[d]pyrrolo[1,2-a]imidazol-7-yl)-N-(5-(piperazin-1-ylmethyl)pyridin-2-yl)pyrimidin-2-amine, (R)-5-fluoro-4-(5-fluoro-1-(methoxymethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine, (R)—N-(5-((4-ethylpiperazin-1-yl)methyl)pyridin-2-yl)-5-fluoro-4-(5-fluoro-1-(methoxymethyl)-2,3-dihydro-1H-benzo[d]pyrrolo[1,2-a]imidazol-7-yl)pyrimidin-2-amine, or pharmaceutically acceptable salts thereof.

16. A pharmaceutical composition, comprising a compound of claim 1 or a pharmaceutically acceptable salt thereof, and at least one pharmaceutically acceptable carrier.

\* \* \* \* \*